US010047155B2

(12) United States Patent
Chen et al.

(10) Patent No.: US 10,047,155 B2
(45) Date of Patent: Aug. 14, 2018

(54) ANTIBODIES TARGETING BONE MORPHOGENETIC PROTEIN 9 (BMP9) AND METHODS THEREFOR

(71) Applicant: NOVARTIS AG, Basel (CH)

(72) Inventors: Zijun Chen, Shanghai (CN); Sujun Deng, Shanghai (CN); Yun He, Shanghai (CN); Dagang Huang, Shanghai (CN); Markus Kugler, Planegg (DE); Qian Li, Shanghai (CN); Chris Xiangyang Lu, Shanghai (CN); Xiao Luo, Shanghai (CN); Yongqiang Shan, Shanghai (CN); Kathrin Ulrike Tissot-Daguette, Planegg (DE); Jing Wu, Shanghai (CN)

(73) Assignee: NOVARTIS AG, Basel (CH)

(*) Notice: Subject to any disclaimer, the term of this patent is extended or adjusted under 35 U.S.C. 154(b) by 70 days.

(21) Appl. No.: 15/165,150

(22) Filed: May 26, 2016

(65) Prior Publication Data

US 2016/0355583 A1 Dec. 8, 2016

(30) Foreign Application Priority Data

Jun. 5, 2015 (WO) ................ PCT/CN2015/080887

(51) Int. Cl.

| | |
|---|---|
| ***C07K 16/22*** | (2006.01) |
| ***A61K 39/395*** | (2006.01) |
| ***A61K 38/18*** | (2006.01) |
| ***C12N 15/13*** | (2006.01) |
| ***C12N 15/63*** | (2006.01) |
| ***C12N 15/09*** | (2006.01) |
| ***A61K 45/06*** | (2006.01) |
| ***A61K 31/155*** | (2006.01) |
| ***A61K 31/355*** | (2006.01) |
| ***A61K 31/4439*** | (2006.01) |
| ***A61K 31/4725*** | (2006.01) |
| ***A61K 31/497*** | (2006.01) |
| ***A61K 31/513*** | (2006.01) |
| ***A61K 31/522*** | (2006.01) |
| ***A61K 31/575*** | (2006.01) |
| ***A61K 31/675*** | (2006.01) |
| ***A61K 31/7072*** | (2006.01) |
| *A61K 39/00* | (2006.01) |

(52) U.S. Cl.

CPC ........... *C07K 16/22* (2013.01); *A61K 31/155* (2013.01); *A61K 31/355* (2013.01); *A61K 31/4439* (2013.01); *A61K 31/4725* (2013.01); *A61K 31/497* (2013.01); *A61K 31/513* (2013.01); *A61K 31/522* (2013.01); *A61K 31/575* (2013.01); *A61K 31/675* (2013.01); *A61K 31/7072* (2013.01); *A61K 38/1875* (2013.01); *A61K 39/3955* (2013.01); *A61K 45/06* (2013.01); *C12N 15/09* (2013.01); *C12N 15/63* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/55* (2013.01); *C07K 2317/73* (2013.01); *C07K 2317/76* (2013.01); *C07K 2317/90* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 5,661,007 A | 8/1997 | Wozney et al. | |
| 6,034,061 A | 3/2000 | Rosen et al. | |
| 6,034,062 A | 3/2000 | Thies et al. | |
| 6,287,816 B1 | 9/2001 | Rosen et al. | |
| 7,615,383 B2 | 11/2009 | Devaux et al. | |
| 7,968,690 B2 | 6/2011 | Pons | |
| 8,318,135 B2 | 11/2012 | O'Connor-McCourt et al. | |
| 8,969,040 B2 * | 3/2015 | Shimizu ................ | C07K 16/18 424/133.1 |
| 2012/0046227 A1 | 2/2012 | Berasi et al. | |
| 2012/0183543 A1 | 7/2012 | Buckler et al. | |
| 2013/0202594 A1 | 8/2013 | Bhatt et al. | |
| 2013/0209490 A1 * | 8/2013 | Buckler ............ | A61K 38/1875 424/158.1 |
| 2013/0281371 A1 | 10/2013 | Kumar et al. | |
| 2014/0044721 A1 | 2/2014 | Paris et al. | |
| 2014/0056902 A1 | 2/2014 | Shimizu et al. | |
| 2014/0227254 A1 | 8/2014 | Seehra et al. | |

FOREIGN PATENT DOCUMENTS

| | | |
|---|---|---|
| CN | 1844391 A | 10/2006 |
| EP | 0592562 B1 | 4/1994 |
| EP | 0764208 B1 | 3/1997 |

(Continued)

OTHER PUBLICATIONS

Andrieux, Joris et al., "Bone morphogenetic protein antagonist gene NOG is involved in myeloproliferative disease associated with myelofrisosis," Cancer Genetics and Cytogenetics 178(1):11-16 (Sep. 21, 2007).

Zeisberg and Kalluri, "The role of epithelial-to-mesenchymal transition in renal fibrosis," Journal of Molecular Medicine 82(3):175-181 (Mar. 1, 2004).

Klahr, Saulo, "The bone morphogenetic proteins (BMPs). Their role in renal fibrosis and renal function," Journal of Nephrology 16(2):179-185 (Mar. 1, 2003).

Tobin and Celeste, "Bone morphogenetic proteins and growth differentiation factors as drug targets in cardiovascular and metabolic disease," Drug Discovery Today 11(9-10):405-411 (May 1, 2006).

Ruiz-Ortega et al., "TGF-beta signaling in vascular fibrosis," Cardiovascular Research 74(2):196-206 (May 2007).

(Continued)

*Primary Examiner* — Xiaozhen Xie

(74) *Attorney, Agent, or Firm* — Adam Poulin-Kerstien

(57) ABSTRACT

The present invention relates to isolated antibodies and antigen-binding fragments thereof which bind human BMP9 and compositions and methods of use thereof.

34 Claims, 11 Drawing Sheets

(56) References Cited

FOREIGN PATENT DOCUMENTS

| | | | |
|---|---|---|---|
| EP | 1571159 | A1 | 7/2005 |
| EP | 2868667 | A1 | 5/2015 |
| JP | 2008-225462 | A | 9/1996 |
| JP | 2006-241060 | A | 9/2006 |
| JP | 2007-526758 | A | 9/2007 |
| JP | 2009-506791 | A | 2/2009 |
| WO | 93/00432 | A1 | 7/1993 |
| WO | 2005/035762 | A1 | 4/2005 |
| WO | 2006/016110 | A1 | 2/2006 |
| WO | 2007/034753 | A1 | 3/2007 |
| WO | 2007/146968 | A2 | 12/2007 |
| WO | 2007/147647 | A1 | 12/2007 |
| WO | 2008/048519 | A2 | 4/2008 |
| WO | 2008/057461 | A2 | 5/2008 |
| WO | 2008/113185 | A1 | 9/2008 |
| WO | 2008/151078 | A1 | 12/2008 |
| WO | 2009/139891 | A2 | 11/2009 |
| WO | 2010126169 | A1 | 11/2010 |
| WO | 2012/031273 | A2 | 3/2012 |
| WO | 2013/164689 | A2 | 11/2013 |
| WO | 2013/166943 | A1 | 11/2013 |
| WO | 2014/051109 | A1 | 4/2014 |
| WO | 2014/009633 | A1 | 6/2014 |

OTHER PUBLICATIONS

Liu, Youhua, "Renal fibrosis: New insights into the pathogenesis and therapeutics" Kidney International 69(2):213-217 (Jan. 2006).

Verrecchia et al., "Transforming growth factor-beta and fibrosis," World Journal of Gastroenterology 13(22):3056-3065 (Jun. 14, 2007).

Breitkopf, K et al., "279 Bone Morphogenetic protein (BMP)-9: A New Member of the TGF-beta Superfamily which is Secreted by Activated Hepatic Stellate Cells," Journal of Hepatology, vol. 50: S110, (Apr. 1, 2009).

Henderson et al., "Hepatic fibrogenesis: from within and outwith," Toxicology. Dec. 30, 2008;254(3):130-5.

David et al., "Identification of BMP9 and BMP10 as functional activators of the orphan activin receptor-like kinase 1 (ALK1) in endothelial cells," Blood. Mar. 1, 2007;109(5):1953-61.

Gressner et al., "Molecular mechanisms of liver fibrogenesis—a homage to the role of activated fat-storing cells," Digestion. 1995;56(5):335-46.

Friedman, "Hepatic stellate cells: protean, multifunctional, and enigmatic cells of the liver," Physiol Rev. Jan. 2008;88(1):125-72.

Friedman, "Hepatic fibrosis—overview," Toxicology. Dec. 30, 2008;254(3):120-9.

Ismail et al., "Reversal of liver fibrosis," Saudi J Gastroenterol. Jan. 2009;15(1):72-9.

Miller et al., "Bone morphogenetic protein-9. An autocrine/paracrine cytokine in the liver," J Biol Chem. Jun. 16, 2000;275(24):17937-45.

Korff et al., "Cyclic stretch controls the expression of CD40 in endothelial cells by changing their transforming growth factor-beta1 response," Circulation. Nov. 13, 2007;116(20):2288-97.

Yao et al., "Activin-like kinase receptor 1 (ALK1) in atherosclerotic lesions and vascular mesenchymal cells," Cardiovasc Res. May 1, 2007;74(2):279-89.

Scharpfenecker et al., "BMP-9 signals via ALK1 and inhibits bFGF-induced endothelial cell proliferation and VEGF-stimulated angiogenesis," J Cell Sci. Mar. 15, 2007;120(Pt 6):964-72.

van Meeteren et al., "Anti-human activin receptor-like kinase 1 (ALK1) antibody attenuates bone morphogenetic protein 9 (BMP9)-induced ALK1 signaling and interferes with endothelial cell sprouting," J Biol Chem. May 25, 2012;287(22):18551-61.

Early Edition of article published as: Yoshimatsu et al., "Bone morphogenetic protein-9 inhibits lymphatic vessel formation via activin receptor-like kinase 1 during development and cancer progression," Proc Natl Acad Sci U S A. Nov. 19, 2013;110(47):18940-5 (6 pages).

Ricard et al., "BMP9 and BMP10 are critical for postnatal retinal vascular remodeling," Blood. Jun. 21, 2012;119(25):6162-71.

International Search Report and Written Opinion from related PCT/IB2016/053095 dated Jan. 3, 2017.

* cited by examiner

CCl4+Ctr IgG
CCl4+2B11G2-AM0100
1 2 3 4 5 1 2 3 4 5 6 7 8 9 10
IB: pSmad1/5
IB: GAPDH
p-smad1/5/GAPDH
1.5
1.0
0.5
0.0
***
CCl4+Ctr IgG
CCl4+2B11G2-AM4405

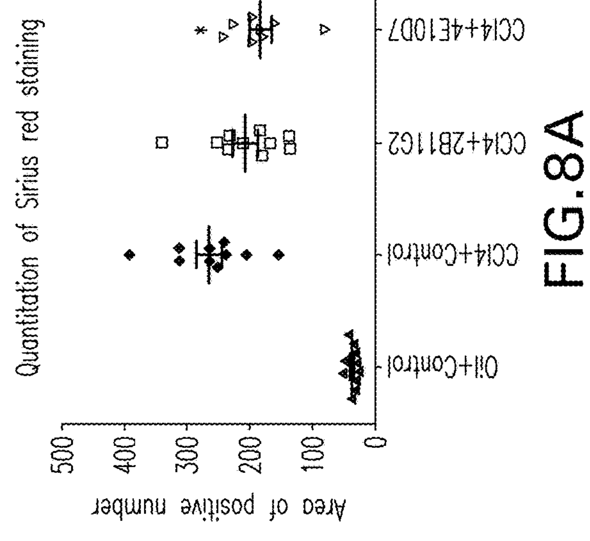
FIG.8A
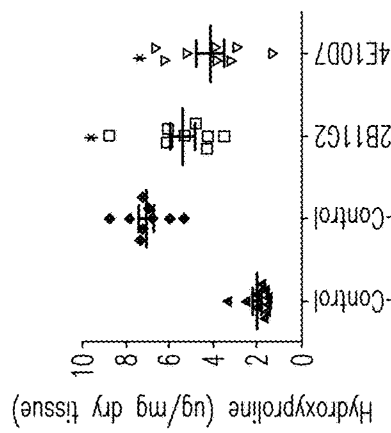
FIG.8B
ALT (U/L)
3000
2000
1000
0
Oil+Control
CCl4+Control
CCl4+2B11G2
CCl4+4E10D7
FIG.8C
Liver weight
Liver weight (g)
2.5
2.0
1.5
1.0
0.5
0
Oil+Control
CCl4+Control
CCl4+2B11G2
CCl4+4E10D7
FIG.8D
Id1
Id1 mRNA level
40
30
20
10
0
Oil+Control
CCl4+Control
CCl4+2B11G2
CCl4+4E10D7
FIG.8E

ANTIBODIES TARGETING BONE MORPHOGENETIC PROTEIN 9 (BMP9) AND METHODS THEREFOR

RELATED APPLICATIONS

This application claims priority to PCT Application No. PCT/CN2015/080887, filed Jun. 5, 2015. The entire contents of this application are incorporated herein by reference.

SEQUENCE LISTING

The instant application contains a Sequence Listing which has been submitted electronically in ASCII format and is hereby incorporated by reference in its entirety. Said ASCII copy, created on May 4, 2016, is named PAT056928-US-NP_SL.txt and is 163,925 bytes in size.

INTRODUCTION

The present invention relates to antibodies and antigen-binding fragments thereof which bind human BMP9, and compositions and methods of use thereof.

BACKGROUND OF THE INVENTION

Fibrosis is a pathological process that refers to the aberrant formation or development of excess fibrous connective tissue by cells in an organ or tissue. Although processes related to fibrosis can occur as part of normal tissue formation or repair, dysregulation of these processes can lead to altered cellular composition and excess connective tissue deposition that progressively impairs tissue or organ function.

Fibrotic liver disease, including cirrhosis, affects more than 100 million people worldwide and causes more than 1 million deaths each year. Portal vein hypertension, one of the main consequences of fibrotic liver disease and cirrhosis, is responsible for many of the diseases' complications. Existing therapies for liver diseases, including fibrotic liver disease, including cirrhosis, can have low efficacy and undesirable side effects. Moreover, there are currently no wholly effective treatments or cures for liver disease, including fibrotic liver diseases, including cirrhosis. Accordingly, there is a great need for moieties which can inhibit, prevent or reverse liver disease, including fibrotic liver diseases and cirrhosis, including its consequences such as portal vein hypertension, and can therefore be used to treat or prevent liver disease, e.g., liver fibrosis, cirrhosis or portal vein hypertension, in a subject, as well as methods for diagnosing the debilitating diseases.

SUMMARY OF THE INVENTION

The present invention provides isolated BMP9-binding molecules (e.g., BMP9-binding antibodies or antigen-binding fragments thereof), pharmaceutical compositions comprising such molecules, methods of making such molecules and compositions, and methods of use thereof in treating disease, for example, liver disease, for example, liver fibrosis, cirrhosis and portal vein hypertension.

In one aspect, the invention provides an isolated antibody or antigen-binding fragment thereof to BMP9 comprising any 1, 2, 3, 4, 5, or 6 CDRs of any of the antibodies in Table 1.

In one aspect, the invention provides an isolated antibody or antigen-binding fragment thereof to BMP9 comprising the 6 CDRs of BMP9-1, as described in Table 1.

In one aspect, the invention provides an isolated antibody or antigen-binding fragment thereof to BMP9 comprising the 6 CDRs of BMP9-2, as described in Table 1.

In one aspect, the invention provides an isolated antibody or antigen-binding fragment thereof to BMP9 comprising the 6 CDRs of BMP9-3, as described in Table 1.

In one aspect, the invention provides an isolated antibody or antigen-binding fragment thereof to BMP9 comprising the 6 CDRs of BMP9-4, as described in Table 1.

In one aspect, the invention provides an isolated antibody or antigen-binding fragment thereof to BMP9 comprising the 6 CDRs of BMP9-5, as described in Table 1.

In one aspect, the invention provides an isolated antibody or antigen-binding fragment thereof to BMP9 comprising the 6 CDRs of BMP9-6, as described in Table 1.

In one aspect, the invention provides an isolated antibody or antigen-binding fragment thereof to BMP9 comprising the 6 CDRs of BMP9-7, as described in Table 1.

In one aspect, the invention provides an isolated antibody or antigen-binding fragment thereof to BMP9 comprising the 6 CDRs of BMP9-8, as described in Table 1.

In one aspect, the invention provides an isolated antibody or antigen-binding fragment thereof to BMP9 comprising the 6 CDRs of BMP9-9, as described in Table 1.

In one aspect of the present invention, the isolated antibody or antigen-binding fragment thereof binds human BMP9 and comprises:

the HCDR1, HCDR2, and HCDR3 sequences of SEQ ID NOs: 1, 2 and 3, respectively, and the LCDR1, LCDR2, and LCDR3 sequences of SEQ ID NOs: 11, 12 and 13, respectively.

In one aspect of the present invention, the isolated antibody or antigen-binding fragment thereof binds human BMP9 and comprises:

the HCDR1, HCDR2, and HCDR3 sequences of SEQ ID NOs: 4, 5 and 6, respectively, and the LCDR1, LCDR2, and LCDR3 sequences of SEQ ID NOs: 14, 15 and 16, respectively.

In one aspect of the present invention, the isolated antibody or antigen-binding fragment thereof binds human BMP9 and comprises:

the HCDR1, HCDR2, and HCDR3 sequences of SEQ ID NOs: 21, 22 and 23, respectively, and the LCDR1, LCDR2, and LCDR3 sequences of SEQ ID NOs: 31, 32 and 33, respectively.

In one aspect of the present invention, the isolated antibody or antigen-binding fragment thereof binds human BMP9 and comprises:

the HCDR1, HCDR2, and HCDR3 sequences of SEQ ID NOs: 24, 25 and 26, respectively, and the LCDR1, LCDR2, and LCDR3 sequences of SEQ ID NOs: 34, 35 and 36, respectively.

In one aspect of the present invention, the isolated antibody or antigen-binding fragment thereof binds human BMP9 and comprises:

the HCDR1, HCDR2, and HCDR3 sequences of SEQ ID NOs: 41, 42 and 43, respectively, and the LCDR1, LCDR2, and LCDR3 sequences of SEQ ID NOs: 51, 52 and 53, respectively.

In one aspect of the present invention, the isolated antibody or antigen-binding fragment thereof binds human BMP9 and comprises:

the HCDR1, HCDR2, and HCDR3 sequences of SEQ ID NOs: 44, 45 and 46, respectively, and the LCDR1, LCDR2, and LCDR3 sequences of SEQ ID NOs: 54, 55 and 56, respectively.

In one aspect of the present invention, the isolated antibody or antigen-binding fragment thereof binds human BMP9 and comprises:

the HCDR1, HCDR2, and HCDR3 sequences of SEQ ID NOs: 61, 62 and 63, respectively, and the LCDR1, LCDR2, and LCDR3 sequences of SEQ ID NOs: 71, 72 and 73, respectively.

In one aspect of the present invention, the isolated antibody or antigen-binding fragment thereof binds human BMP9 and comprises:

the HCDR1, HCDR2, and HCDR3 sequences of SEQ ID NOs: 64, 65 and 66, respectively, and the LCDR1, LCDR2, and LCDR3 sequences of SEQ ID NOs: 74, 75 and 76, respectively.

In one aspect of the present invention, the isolated antibody or antigen-binding fragment thereof binds human BMP9 and comprises:

the HCDR1, HCDR2, and HCDR3 sequences of SEQ ID NOs: 81, 82 and 83, respectively, and the LCDR1, LCDR2, and LCDR3 sequences of SEQ ID NOs: 91, 92 and 93, respectively.

In one aspect of the present invention, the isolated antibody or antigen-binding fragment thereof binds human BMP9 and comprises:

the HCDR1, HCDR2, and HCDR3 sequences of SEQ ID NOs: 84, 85 and 86, respectively, and the LCDR1, LCDR2, and LCDR3 sequences of SEQ ID NOs: 94, 95 and 96, respectively.

In one aspect of the present invention, the isolated antibody or antigen-binding fragment thereof binds human BMP9 and comprises:

the HCDR1, HCDR2, and HCDR3 sequences of SEQ ID NOs: 101, 102 and 103, respectively, and the LCDR1, LCDR2, and LCDR3 sequences of SEQ ID NOs: 111, 112 and 113, respectively.

In one aspect of the present invention, the isolated antibody or antigen-binding fragment thereof binds human BMP9 and comprises:

the HCDR1, HCDR2, and HCDR3 sequences of SEQ ID NOs: 104, 105 and 106, respectively, and the LCDR1, LCDR2, and LCDR3 sequences of SEQ ID NOs: 114, 115 and 116, respectively.

In one aspect of the present invention, the isolated antibody or antigen-binding fragment thereof binds human BMP9 and comprises:

the HCDR1, HCDR2, and HCDR3 sequences of SEQ ID NOs: 121, 122 and 123, respectively, and the LCDR1, LCDR2, and LCDR3 sequences of SEQ ID NOs: 131, 132 and 133, respectively.

In one aspect of the present invention, the isolated antibody or antigen-binding fragment thereof binds human BMP9 and comprises:

the HCDR1, HCDR2, and HCDR3 sequences of SEQ ID NOs: 124, 125 and 126, respectively, and the LCDR1, LCDR2, and LCDR3 sequences of SEQ ID NOs: 134, 135 and 136, respectively.

In one aspect of the present invention, the isolated antibody or antigen-binding fragment thereof binds human BMP9 and comprises:

the HCDR1, HCDR2, and HCDR3 sequences of SEQ ID NOs: 141, 142 and 143, respectively, and the LCDR1, LCDR2, and LCDR3 sequences of SEQ ID NOs: 151, 152 and 153, respectively.

In one aspect of the present invention, the isolated antibody or antigen-binding fragment thereof binds human BMP9 and comprises:

the HCDR1, HCDR2, and HCDR3 sequences of SEQ ID NOs: 144, 145 and 146, respectively, and the LCDR1, LCDR2, and LCDR3 sequences of SEQ ID NOs: 154, 155 and 156, respectively.

In one aspect of the present invention, the isolated antibody or antigen-binding fragment thereof binds human BMP9 and comprises:

the HCDR1, HCDR2, and HCDR3 sequences of SEQ ID NOs: 161, 162 and 163, respectively, and the LCDR1, LCDR2, and LCDR3 sequences of SEQ ID NOs: 171, 172 and 173, respectively.

In one aspect of the present invention, the isolated antibody or antigen-binding fragment thereof binds human BMP9 and comprises:

the HCDR1, HCDR2, and HCDR3 sequences of SEQ ID NOs: 164, 165 and 166, respectively, and the LCDR1, LCDR2, and LCDR3 sequences of SEQ ID NOs: 174, 175 and 176, respectively.

In one aspect of the present invention, the isolated monoclonal antibodies or antigen-binding fragments thereof that bind human BMP9 comprise at least one complementarity determining (CDR) sequence having at least 90%, 95%, 97%, 98% or at least 99% sequence identity to any one or more of:

(a) the HCDR1, HCDR2, and HCDR3 sequences of SEQ ID NOs: 1, 2 and 3, respectively, and the LCDR1, LCDR2, and LCDR3 sequences of SEQ ID NOs: 11, 12 and 13, respectively;

(b) the HCDR1, HCDR2, and HCDR3 sequences of SEQ ID NOs: 4, 5 and 6, respectively, and the LCDR1, LCDR2, and LCDR3 sequences of SEQ ID NOs: 14, 15 and 16, respectively;

(c) the HCDR1, HCDR2, and HCDR3 sequences of SEQ ID NOs: 21, 22 and 23, respectively, and the LCDR1, LCDR2, and LCDR3 sequences of SEQ ID NOs: 31, 32 and 33, respectively;

(d) the HCDR1, HCDR2, and HCDR3 sequences of SEQ ID NOs: 24, 25 and 26, respectively, and the LCDR1, LCDR2, and LCDR3 sequences of SEQ ID NOs: 34, 35 and 36, respectively;

(e) the HCDR1, HCDR2, and HCDR3 sequences of SEQ ID NOs: 41, 42 and 43, respectively, and the LCDR1, LCDR2, and LCDR3 sequences of SEQ ID NOs: 51, 52 and 53, respectively;

(f) the HCDR1, HCDR2, and HCDR3 sequences of SEQ ID NOs: 44, 45 and 46, respectively, and the LCDR1, LCDR2, and LCDR3 sequences of SEQ ID NOs: 54, 55 and 56, respectively;

(g) the HCDR1, HCDR2, and HCDR3 sequences of SEQ ID NOs: 61, 62 and 63, respectively, and the LCDR1, LCDR2, and LCDR3 sequences of SEQ ID NOs: 71, 72 and 73, respectively;

(h) the HCDR1, HCDR2, and HCDR3 sequences of SEQ ID NOs: 64, 65 and 66, respectively, and the LCDR1, LCDR2, and LCDR3 sequences of SEQ ID NOs: 74, 75 and 76, respectively;

(i) the HCDR1, HCDR2, and HCDR3 sequences of SEQ ID NOs: 81, 82 and 83, respectively, and the LCDR1, LCDR2, and LCDR3 sequences of SEQ ID NOs: 91, 92 and 93, respectively;

(j) the HCDR1, HCDR2, and HCDR3 sequences of SEQ ID NOs: 84, 85 and 86, respectively, and the LCDR1, LCDR2, and LCDR3 sequences of SEQ ID NOs: 94, 95 and 96, respectively;

(k) the HCDR1, HCDR2, and HCDR3 sequences of SEQ ID NOs: 101, 102 and 103, respectively, and the LCDR1, LCDR2, and LCDR3 sequences of SEQ ID NOs: 111, 112 and 113, respectively;

(l) the HCDR1, HCDR2, and HCDR3 sequences of SEQ ID NOs: 104, 105 and 106, respectively, and the LCDR1, LCDR2, and LCDR3 sequences of SEQ ID NOs: 114, 115 and 116, respectively;

(m) the HCDR1, HCDR2, and HCDR3 sequences of SEQ ID NOs: 121, 122 and 123, respectively, and the LCDR1, LCDR2, and LCDR3 sequences of SEQ ID NOs: 131, 132 and 133, respectively;

(n) the HCDR1, HCDR2, and HCDR3 sequences of SEQ ID NOs: 124, 125 and 126, respectively, and the LCDR1, LCDR2, and LCDR3 sequences of SEQ ID NOs: 134, 135 and 136, respectively;

(o) the HCDR1, HCDR2, and HCDR3 sequences of SEQ ID NOs: 141, 142 and 143, respectively, and the LCDR1, LCDR2, and LCDR3 sequences of SEQ ID NOs: 151, 152 and 153, respectively;

(p) the HCDR1, HCDR2, and HCDR3 sequences of SEQ ID NOs: 144, 145 and 146, respectively, and the LCDR1, LCDR2, and LCDR3 sequences of SEQ ID NOs: 154, 155 and 156, respectively;

(q) the HCDR1, HCDR2, and HCDR3 sequences of SEQ ID NOs: 161, 162 and 163, respectively, and the LCDR1, LCDR2, and LCDR3 sequences of SEQ ID NOs: 171, 172 and 173, respectively; or (r) the HCDR1, HCDR2, and HCDR3 sequences of SEQ ID NOs: 164, 165 and 166, respectively, and the LCDR1, LCDR2, and LCDR3 sequences of SEQ ID NOs: 174, 175 and 176, respectively.

In one aspect, the invention relates to an antibody or antigen binding fragment thereof comprising the VH and VL amino acid sequences of BMP9-1, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-1, as described in Table 1, and/or a VL amino acid sequence having at least 90%, at least 95%, at least 96%, at least 97%, at least 98% or at least 99% sequence identity to the VL amino acid sequence of BMP9-1, as described in Table 1.

In one aspect, the invention relates to an antibody or antigen binding fragment thereof comprising the VH and VL amino acid sequences of BMP9-2, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-2, as described in Table 1, and/or a VL amino acid sequence having at least 90%, at least 95%, at least 96%, at least 97%, at least 98% or at least 99% sequence identity to the VL amino acid sequence of BMP9-2, as described in Table 1.

In one aspect, the invention relates to an antibody or antigen binding fragment thereof comprising the VH and VL amino acid sequences of BMP9-3, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-3, as described in Table 1, and/or a VL amino acid sequence having at least 90%, at least 95%, at least 96%, at least 97%, at least 98% or at least 99% sequence identity to the VL amino acid sequence of BMP9-3, as described in Table 1.

In one aspect, the invention relates to an antibody or antigen binding fragment thereof comprising the VH and VL amino acid sequences of BMP9-4, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-4, as described in Table 1, and/or a VL amino acid sequence having at least 90%, at least 95%, at least 96%, at least 97%, at least 98% or at least 99% sequence identity to the VL amino acid sequence of BMP9-4, as described in Table 1.

In one aspect, the invention relates to an antibody or antigen binding fragment thereof comprising the VH and VL amino acid sequences of BMP9-5, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-5, as described in Table 1, and/or a VL amino acid sequence having at least 90%, at least 95%, at least 96%, at least 97%, at least 98% or at least 99% sequence identity to the VL amino acid sequence of BMP9-5, as described in Table 1.

In one aspect, the invention relates to an antibody or antigen binding fragment thereof comprising the VH and VL amino acid sequences of BMP9-6, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-6, as described in Table 1, and/or a VL amino acid sequence having at least 90%, at least 95%, at least 96%, at least 97%, at least 98% or at least 99% sequence identity to the VL amino acid sequence of BMP9-6, as described in Table 1.

In one aspect, the invention relates to an antibody or antigen binding fragment thereof comprising the VH and VL amino acid sequences of BMP9-7, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-7, as described in Table 1, and/or a VL amino acid sequence having at least 90%, at least 95%, at least 96%, at least 97%, at least 98% or at least 99% sequence identity to the VL amino acid sequence of BMP9-7, as described in Table 1.

In one aspect, the invention relates to an antibody or antigen binding fragment thereof comprising the VH and VL amino acid sequences of BMP9-8, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-8, as described in Table 1, and/or a VL amino acid sequence having at least 90%, at least 95%, at least 96%, at least 97%, at least 98% or at least 99% sequence identity to the VL amino acid sequence of BMP9-8, as described in Table 1.

In one aspect, the invention relates to an antibody or antigen binding fragment thereof comprising the VH and VL amino acid sequences of BMP9-9, as described in Table 1. In another aspect, the invention relates to an isolated antibody or antigen binding fragment thereof comprising a VH amino acid sequence having at least 90%, at least 95%, at least 96%, at least 97%, at least 98% or at least 99% sequence identity to the VH amino acid sequence of BMP9-9, as described in Table 1, and/or a VL amino acid sequence having at least 90%, at least 95%, at least 96%, at least 97%, at least 98% or at least 99% sequence identity to the VL amino acid sequence of BMP9-9, as described in Table 1.

In one aspect, the invention relates to an isolated antibody or antigen-binding fragment thereof, described in Table 1.

In one aspect, the invention relates to an isolated antibody or antigen-binding fragment thereof that includes: a VH sequence of SEQ ID NO: 7; a VH sequence of SEQ ID NO: 27; a VH sequence of SEQ ID NO: 47; a VH sequence of SEQ ID NO: 67; a VH sequence of SEQ ID NO: 87; a VH sequence of SEQ ID NO: 107; a VH sequence of SEQ ID NO: 127; a VH sequence of SEQ ID NO: 147; or a VH sequence of SEQ ID NO: 167.

In one aspect, the invention relates to an isolated antibody or antigen-binding fragment that includes: a VL sequence of SEQ ID NO: 17; a VL sequence of SEQ ID NO: 37; a VL sequence of SEQ ID NO: 57; a VL sequence of SEQ ID NO: 77; a VL sequence of SEQ ID NO: 97; a VL sequence of SEQ ID NO: 117; a VL sequence of SEQ ID NO: 137; a VL sequence of SEQ ID NO: 157; or a VL sequence of SEQ ID NO: 177.

In one aspect, the invention relates to an isolated antibody or antigen-binding fragment that includes: a VH sequence of SEQ ID NO: 7 and a VL sequence of SEQ ID NO: 17; a VH sequence of SEQ ID NO: 27 and a VL sequence of SEQ ID NO: 37; a VH sequence of SEQ ID NO: 47 and VL sequence of SEQ ID NO: 57; a VH sequence of SEQ ID NO: 67 and a VL sequence of SEQ ID NO: 77; a VH sequence of SEQ ID NO: 87 and a VL sequence of SEQ ID NO: 97; a VH sequence of SEQ ID NO: 107 and a VL sequence of SEQ ID NO: 117; a VH sequence of SEQ ID NO: 127 and a VL sequence of SEQ ID NO: 137; a VH sequence of SEQ ID NO: 147 and VL sequence of SEQ ID NO: 157; or a VH sequence of SEQ ID NO: 167 and a VL sequence of SEQ ID NO: 177.

In one aspect, the invention relates to an isolated antibody or antigen-binding fragment that includes: a heavy chain sequence of SEQ ID NO: 9; a heavy chain sequence of SEQ ID NO: 29; a heavy chain sequence of SEQ ID NO: 49; a heavy chain sequence of SEQ ID NO: 69; a heavy chain sequence of SEQ ID NO: 89; a heavy chain sequence of SEQ ID NO: 109; a heavy chain sequence of SEQ ID NO: 129; a heavy chain sequence of SEQ ID NO: 149; or a heavy chain sequence of SEQ ID NO: 169.

In one aspect, the invention relates to an isolated antibody or antigen-binding fragment that includes: a light chain sequence of SEQ ID NO: 19; a light chain sequence of SEQ ID NO: 39; a light chain sequence of SEQ ID NO: 59; a light chain sequence of SEQ ID NO: 79; a light chain sequence of SEQ ID NO: 99; a light chain sequence of SEQ ID NO: 119; a light chain sequence of SEQ ID NO: 139; a light chain sequence of SEQ ID NO: 159; or a light chain sequence of SEQ ID NO: 179.

In one aspect, the invention relates to an isolated antibody or antigen-binding fragment that includes: a heavy chain sequence of SEQ ID NO: 9; and a light chain sequence of SEQ ID NO: 19; a heavy chain sequence of SEQ ID NO: 29; and a light chain sequence of SEQ ID NO: 39; a heavy chain sequence of SEQ ID NO: 49; and a light chain sequence of SEQ ID NO: 59; a heavy chain sequence of SEQ ID NO: 69; and a light chain sequence of SEQ ID NO: 79; a heavy chain sequence of SEQ ID NO: 89; and a light chain sequence of SEQ ID NO: 99; a heavy chain sequence of SEQ ID NO: 109; and a light chain sequence of SEQ ID NO: 119; a heavy chain sequence of SEQ ID NO: 129; and a light chain sequence of SEQ ID NO: 139; a heavy chain sequence of SEQ ID NO: 149; and a light chain sequence of SEQ ID NO: 159; or a heavy chain sequence of SEQ ID NO: 169; and a light chain sequence of SEQ ID NO: 179.

The invention also includes antibodies and antigen-binding fragments thereof which bind BMP9 having a light chain having at least 90%, at least 95%, at least 96%, at least 97%, at least 98% or at least 99% sequence identity to a heavy chain sequence of SEQ ID NO: 9; a heavy chain sequence of SEQ ID NO: 29; a heavy chain sequence of SEQ ID NO: 49; a heavy chain sequence of SEQ ID NO: 69; a heavy chain sequence of SEQ ID NO: 89; a heavy chain sequence of SEQ ID NO: 109; a heavy chain sequence of SEQ ID NO: 129; a heavy chain sequence of SEQ ID NO: 149; or a heavy chain sequence of SEQ ID NO: 169, and/or a light chain having at least 90%, at least 95%, at least 96%, at least 97%, at least 98% or at least 99% sequence identity to a light chain sequence of SEQ ID NO: 19; a light chain sequence of SEQ ID NO: 39; a light chain sequence of SEQ ID NO: 59; a light chain sequence of SEQ ID NO: 79; a light chain sequence of SEQ ID NO: 99; a light chain sequence of SEQ ID NO: 119; a light chain sequence of SEQ ID NO: 139; a light chain sequence of SEQ ID NO: 159; or a light chain sequence of SEQ ID NO: 179.

In one aspect, including in any of the previous aspects, the invention relates to an isolated antibody or antigen-binding fragment thereof, that binds human BMP9 with a KD of ≤1 nM.

In one aspect, including in any of the previous aspects, the invention relates to an isolated antibody or antigen-binding fragment thereof, that binds human BMP9 with a KD of ≤500 pM.

In one aspect, including in any of the previous aspects, the invention relates to an isolated antibody or antigen-binding fragment thereof, wherein the antibody or antigen-binding fragment thereof binds human BMP9 with a KD of ≤200 pM.

In one aspect, including in any of the previous aspects, the invention relates to an isolated antibody or antigen-binding fragment thereof, wherein the antibody or antigen-binding fragment thereof binds human BMP9 with a KD of ≤100 pM.

In one aspect, including in any of the previous aspects, the invention relates to an isolated antibody or antigen-binding fragment thereof, wherein the antibody or antigen-binding fragment thereof binds human BMP9 with a KD of ≤50 pM.

In one aspect, including in any of the previous aspects, the invention relates to an isolated antibody or antigen-binding fragment thereof, wherein the antibody or antigen-binding fragment thereof binds human BMP9 with a KD of ≤20 pM.

In one aspect, including in any of the previous aspects, the invention relates to an isolated antibody or antigen-binding fragment thereof, wherein the antibody or antigen-binding fragment thereof has at least about 100-fold greater affinity for human BMP9 than for human BMP10.

In one aspect, including in any of the previous aspects, the invention relates to an isolated antibody or antigen-binding fragment thereof, wherein the antibody or antigen-binding fragment thereof has at least about 100-fold greater affinity for human BMP9 than for human BMP7.

In one aspect, including in any of the previous aspects, the invention relates to an isolated antibody or antigen-binding fragment thereof, wherein the antibody or antigen-binding fragment thereof has at least about 100-fold greater affinity for human BMP9 than for human BMP2.

In one aspect, including in any of the previous aspects, the invention relates to an isolated antibody or antigen-binding fragment thereof, wherein the antibody or antigen-binding fragment thereof has at least about 100-fold greater affinity for human BMP9 than for human BMP2, human BMP7 and human BMP10.

In one aspect, including in any of the previous aspects, the invention relates to an isolated antibody or antigen-binding fragment thereof, wherein the antibody or antigen-binding fragment thereof has at least about 1000-fold greater affinity for human BMP9 than for human BMP10.

In one aspect, including in any of the previous aspects, the invention relates to an isolated antibody or antigen-binding fragment thereof, wherein the antibody or antigen-binding fragment thereof has at least about 1000-fold greater affinity for human BMP9 than for human BMP7.

In one aspect, including in any of the previous aspects, the invention relates to an isolated antibody or antigen-binding fragment thereof, wherein the antibody or antigen-binding fragment thereof has at least about 1000-fold greater affinity for human BMP9 than for human BMP2.

In one aspect, including in any of the previous aspects, the invention relates to an isolated antibody or antigen-binding fragment thereof, wherein the antibody or antigen-binding fragment thereof has at least about 1000-fold greater affinity for human BMP9 than for human BMP2, human BMP7 and human BMP10.

In one aspect, including in any of the previous aspects, the invention relates to an isolated antibody or antigen-binding fragment thereof, wherein the antibody or antigen-binding fragment thereof binds to cyno BMP9, rat BMP9 and/or mouse BMP9 with a KD≤1 nM.

In one aspect, including in any of the previous aspects, the invention relates to an isolated antibody or antigen-binding fragment thereof, wherein the antibody or antigen-binding fragment thereof binds to cyno BMP9, rat BMP9 and/or mouse BMP9 with a KD≤0.5 nM.

In one aspect, including in any of the previous aspects, the invention relates to an isolated antibody or antigen-binding fragment thereof, wherein the antibody or antigen-binding fragment thereof binds to cyno BMP9, rat BMP9 and/or mouse BMP9 with a KD≤0.2 nM.

In one aspect, including in any of the previous aspects, the invention relates to an isolated antibody or antigen-binding fragment, wherein the antibody or antigen-binding fragment thereof binds to cyno BMP9, rat BMP9 and/or mouse BMP9 with a KD≤0.05 nM.

In one aspect, including in any of the previous aspects, the invention relates to an isolated antibody or antigen-binding fragment thereof, which (a) has at least about has at least about 1000-fold greater affinity for human BMP9 than for human BMP10, for human BMP7 and for human BMP2; and (b) binds to human BMP9, cyno BMP9, rat BMP9 and murine BMP9 with an KD≤1 nM. In any of the previous aspects reciting a KD, the KD may be measured by a MSD-SET assay, e.g., as described herein.

In one aspect, including in any of the previous aspects, the invention relates to an isolated antibody or antigen-binding fragment thereof which binds to human BMP9 and has no detectable binding to human BMP10 in a Biacore assay.

In one aspect, including in any of the previous aspects, the invention relates to an isolated antibody or antigen-binding fragment thereof, wherein the isolated antibody or antigen-binding fragment inhibits binding of human BMP9 to a human BMP Type I receptor, e.g., human ALK1, human ALK2 and/or human ALK3.

In one aspect, including in any of the previous aspects, the invention relates to an isolated antibody or antigen-binding fragment thereof, wherein the isolated antibody or antigen-binding fragment inhibits binding of human BMP9 to a human BMP Type II receptor, e.g., human ActRIIB, ActRIIA and/or BMPRII.

In one aspect, including in any of the previous aspects, the invention relates to an isolated antibody or antigen-binding fragment thereof, wherein the isolated antibody or antigen-binding fragment inhibits binding of human BMP9 to a human BMP Type I receptor, e.g., human ALK1, human ALK2 and/or human ALK3; and inhibits binding of human BMP9 to a human BMP Type II receptor, e.g., human ActRIIB, ActRIIA and/or BMPRII. Said inhibition of both human BMP Type I receptor and human BMP Type II receptor binding to human BMP9 need not be simultaneous.

In any of the preceding aspects, inhibition of binding of human BMP9 to the BMP Type I and/or BMP Type II receptor occurs at an isolated antibody or antigen-binding fragment thereof concentration less than $1\times10^{-7}$M, $1\times10^{-8}$ M or $1\times10^{-9}$ M. In one aspect, inhibition of binding of human BMP9 to the BMP Type I and/or BMP Type II receptor occurs at an isolated antibody or antigen-binding fragment thereof concentration less than $1\times10^{-9}$ M, as measured in a blocking ELISA assay, e.g., as described herein.

In one aspect, including in any of the previous aspects, the invention relates to an isolated antibody or antigen-binding fragment thereof, wherein the isolated antibody or antigen-binding fragment thereof exhibits at least about a 50% reduction in BMP9-induced ID1 expression in liver cell lines or primary liver cells in vitro or in vivo, e.g., in as assay described herein.

In one aspect, including in any of the previous aspects, the invention relates to an isolated antibody or antigen-binding fragment thereof, wherein the isolated antibody or antigen-binding fragment thereof reduces the activity of human BMP9 in vitro, e.g., in an assay described herein.

In one aspect, including in any of the previous aspects, the invention relates to an isolated antibody or antigen-binding fragment thereof, wherein the isolated antibody or antigen-binding fragment thereof reduces the activity of human BMP9 in vitro, as measured in a HEKT-BRE-Luc reporter gene assay, e.g., as described herein.

In one aspect, including in any of the previous aspects, the invention relates to an isolated antibody or antigen-binding fragment thereof, wherein the isolated antibody or antigen-binding fragment thereof reduces the activity of human BMP9 in vivo.

In one aspect, including in any of the previous aspects, the invention relates to an isolated antibody or antigen-binding fragment thereof which cross-blocks an antibody or isolated antigen-binding fragment thereof of any of the previous aspects. In embodiments, the antibody or antigen-binding fragment thereof cross-blocks an antibody or antigen-binding fragment thereof of any of the previous aspects, e.g., as described herein, at a concentration of less than about 500 nM, less than about 200 nM, less than about 100 nM, less than about 10 nM, or less than about 1 nM.

In one aspect, including in any of the previous aspects, the invention relates to an isolated antibody or antigen binding fragment thereof, (a) which has at least about has at least about 1000-fold greater affinity for human BMP9 than for human BMP10, human BMP7 and human BMP2, and (b) binds to human BMP9, cyno BMP9, rat BMP9 and murine BMP9 with an KD less than 1 nM. In embodiments, the antibody or antigen-binding fragment thereof is monoclonal.

In embodiments, the antibody or antigen-binding fragment thereof is chimeric, humanized or fully human.

In one aspect, including in any of the previous aspects, the invention relates to an isolated antibody or antigen-binding fragment thereof, which has an IC50 of less than 200 pM as measured in a HEK293T-BRE-Luc assay, as described herein. In one aspect, including in any of the previous aspects, the invention relates to an isolated antibody or antigen-binding fragment thereof, which has an IC50 of less than 100 pM as measured in a HEK293T-BRE-Luc assay, as described herein. In embodiments, the antibody or antigen-binding fragment thereof is monoclonal. In embodiments, the antibody or antigen-binding fragment thereof is chimeric, humanized or fully human.

In one aspect, including in any of the previous aspects, the invention relates to an isolated antibody or antigen-binding fragment thereof, which has an IC50 of less than about 200 pM as measured in a HEK293T-BRE-Luc assay, as described herein. In one aspect, including in any of the previous aspects, the invention relates to an isolated antibody or antigen-binding fragment thereof, which has an IC50 of less than or equal to about 100 pM as measured in a HEK293T-BRE-Luc assay, as described herein. In embodiments, the antibody or antigen-binding fragment thereof is monoclonal. In embodiments, the antibody or antigen-binding fragment thereof is chimeric, humanized or fully human.

In one aspect, the invention relates to an isolated antibody or antigen-binding fragment thereof, which binds to the mature fragment of human BMP9 at an epitope including human BMP9 mature fragment amino acid residues 21-25, 43-60, 86 and 96 of SEQ ID NO: 215.

In one aspect, the invention relates to an isolated antibody or antigen-binding fragment thereof, which binds to the mature fragment of human BMP9 at an epitope within human BMP9 mature fragment amino acid residues 21-25, 43-60, 86 and 96 of SEQ ID NO: 215.

In one aspect, the invention relates to an isolated antibody or antigen-binding fragment thereof, which binds to the mature fragment of human BMP9 at an epitope comprising amino acid residues 21-25, 43-60, 86 and 96 of SEQ ID NO: 215. In some aspects, the binding includes direct interactions between amino acids of the isolated antibody or antigen-binding fragment thereof and amino acid residues G21, W22, S24, W25, F43, P44, L45, A46, D47, D48, K53, I56, L60, L63, Y86 and K96 of SEQ ID NO: 215.

In one aspect, the invention relates to an isolated antibody or antigen-binding fragment thereof, which binds to the mature fragment of human BMP9, and comprises a) the amino acid residues Y32, D50, S91, D92, T93, S94, and L96 in the light chain variable region; and b) the amino acid residues W47, I50, L52, H56, H58, I102, W103, and S104 in the heavy chain variable region.

In one aspect, the invention relates to an isolated antibody or antigen-binding fragment thereof, which binds to the mature fragment of human BMP9 at an epitope consisting of amino acid residues 21-25, 43-60, 86 and 96 of SEQ ID NO: 215. In some aspects, the binding includes direct interactions between amino acids of the isolated antibody or antigen-binding fragment thereof and amino acid residues G21, W22, S24, W25, F43, P44, L45, A46, D47, D48, K53, I56, L60, L63, Y86 and K96 of SEQ ID NO: 215.

In one aspect, the invention provides an isolated antibody or antigen-binding fragment thereof, which binds to the mature fragment of human BMP9 at an epitope consisting of amino acid residues G21, W22, S24, W25, F43, P44, L45, A46, D47, D48, K53, I56, L60, L63, Y86 and K96 of SEQ ID NO: 215.

In one aspect, the invention provides an isolated antibody or antigen-binding fragment thereof, which binds to the mature fragment of human BMP9 at an epitope comprising amino acid residues G21, W22, S24, W25, F43, P44, L45, A46, D47, D48, K53, I56, L60, L63, Y86 and K96 of SEQ ID NO: 215.

In one aspect, the invention relates to an isolated antibody or antigen-binding fragment thereof, which binds to the mature fragment of human BMP9 at an epitope within human BMP9 mature fragment amino acid residues 83-85 and 95-100 of SEQ ID NO: 215.

In one aspect, the invention relates to an isolated antibody or antigen-binding fragment thereof, which binds to the mature fragment of human BMP9 at an epitope comprising amino acid residues S83, L85, L95, Y97, H98 and E100 of SEQ ID NO: 215. In some aspects, the binding includes direct interactions between amino acids of the isolated antibody or antigen-binding fragment thereof and amino acid residues amino acid residues S83, L85, L95, Y97, H98 and E100 of SEQ ID NO: 215.

In one aspect, the invention relates to an isolated antibody or antigen-binding fragment thereof, which binds to the mature fragment of human BMP9 at an epitope consisting of amino acid residues S83, L85, L95, Y97, H98 and E100 of SEQ ID NO: 215. In some aspects, the binding includes direct interactions between amino acids of the isolated antibody or antigen-binding fragment thereof and amino acid residues amino acid residues S83, L85, L95, Y97, H98 and E100 of SEQ ID NO: 215.

In one aspect, the invention relates to an isolated antibody or antigen-binding fragment thereof, comprising the HCDR1, HCDR2, and HCDR3 sequences of SEQ ID NOs: 184, 185 and 186, respectively, and the LCDR1, LCDR2, and LCDR3 sequences of SEQ ID NOs: 192, 193 and 194, respectively, for example a murine or humanized isolated antibody or antigen-binding fragment thereof.

In one aspect, the invention relates to an isolated antibody or antigen-binding fragment thereof, that is B211G2, as described in Table 3. In some aspects, the invention relates to a humanized antibody derived from B211G2.

In one aspect, the invention relates to an isolated antibody or antigen-binding fragment thereof, comprising the HCDR1, HCDR2, and HCDR3 sequences of SEQ ID NOs: 200, 201, and 202, respectively, and the LCDR1, LCDR2, and LCDR3 sequences of SEQ ID NOs: 208, 209, and 210, respectively, for example a murine or humanized isolated antibody or antigen-binding fragment thereof.

In one aspect, the invention relates to an isolated antibody or antigen-binding fragment thereof, that is 4E10D7, as described in Table 3. In some aspects, the invention relates to a humanized antibody derived from 4E10D7.

In one aspect, the antibodies and antigen-binding fragments thereof of the invention that specifically bind to BMP9 are isolated monoclonal antibodies. In one aspect, the antibodies and antigen-binding fragments thereof of the invention that specifically bind to BMP9 are isolated human monoclonal antibodies. In one aspect, the antibodies and antigen-binding fragments thereof of the invention that specifically bind to BMP9 are humanized monoclonal antibodies. In one aspect, the antibodies and antigen-binding fragments thereof of the invention that specifically bind to BMP9 are isolated chimeric antibodies. In one aspect, the antibodies and antigen-binding fragments thereof of the invention comprise a human heavy chain constant region and a human light chain constant region.

In one aspect of the present invention, the isolated antibody or antigen-binding fragment thereof that specifically binds to BMP9 is a single chain antibody.

In one aspect of the present invention, the isolated antibody or antigen-binding fragment thereof that specifically binds to BMP9 is a Fab fragment.

In one aspect of the present invention, the isolated antibody or antigen-binding fragment thereof that specifically binds to BMP9 is a scFv.

In one aspect, the antibodies and antigen-binding fragments thereof of the invention are an IgG, or are derived from an IgG. In one aspect of the present invention, the IgG is an IgG1, IgG2, IgG3, or IgG4.

In one aspect of the present invention, the isolated antibodies or antigen-binding fragments thereof comprise a framework in which amino acids have been substituted into the antibody framework from the respective human VH or VL germline sequences. In one aspect, the amino acids substituted into the antibody framework are from, or derived from B211G2. In one aspect, the amino acids substituted into the antibody framework are from, or derived from 4E10D7. In some aspects, the amino acids substituted into the antibody framework comprise CDR amino acids.

In one aspect of the present invention, the isolated antibody or antigen-binding fragment thereof is a component of an immunoconjugate. In one aspect, the immunoconjugate can comprise the isolated antibody or antigen-binding fragment thereof and any of the following, as non-limiting examples: an enzyme, toxin, hormone, growth factor, or drug.

In one aspect of the present invention, the isolated antibody or antigen-binding fragment thereof has altered effector function through mutation of the Fc region.

In one aspect of the present invention, the isolated antibody or antigen-binding fragment thereof inhibits BMP9 activity, e.g., BMP9-induced Smad1/5/8 phosphorylation or Id1 expression in liver cells (e.g., liver cell lines and/or primary liver cells in vitro or in vivo). In such aspects, primary liver cells include any cell type present in the liver, for example, hepatocytes. In one aspect of the present invention, the isolated antibody or antigen-binding fragment thereof inhibits BMP9 activity, e.g., BMP9-induced Smad1/5/8 phosphorylation or Id1 expression in liver cells (e.g., liver cell lines and/or primary liver cells in vitro or in vivo) by at least about 50%. For example, the isolated antibody or antigen-binding fragment thereof inhibits BMP9 activity, e.g., BMP9-induced Smad1/5/8 phosphorylation or Id1 expression in liver cells (e.g., liver cell lines and/or primary liver cells in vitro or in vivo) by at least about 50, 60, 70, 80, 90 or 100%. BMP9 activity can be measured, as non-limiting examples, by measuring the amount of smad1/5/8 phosphorylation, or of Id1 mRNA or protein levels.

In one aspect of the present invention, the isolated antibody or antigen-binding fragment thereof reduces the activity of human BMP9 in vitro. In one aspect of the present invention, the isolated antibody or antigen-binding fragment thereof reduces the activity of human BMP9 in vitro, as measured in a HEK293T-BRE-Luc reporter gene assay, for example as described herein.

In one aspect, the invention provides an isolated antibody or antigen-binding fragment thereof of any of the previous aspects, for example, as described herein, e.g., in Table 1, and an additional therapeutic agent. The additional therapeutic agent may be present in a composition that includes an isolated antibody or antigen-binding fragment thereof, or may be present in a separate composition.

In one aspect of the present invention, the additional therapeutic agent reduces the activity of BMP9.

In one aspect of the present invention, the additional therapeutic agent is a siRNA, antibody or antigen-binding fragment thereof, soluble BMP9 receptor, protein or small molecule.

In one aspect, the additional therapeutic agent is selected from the group consisting of: an antiviral agent, an anti-inflammatory agent, an anti-fibrotic agent, an anti-steatotic agent, an anti-apoptotic, a hepatoprotective agent, and combinations thereof.

In one aspect, the additional therapeutic agent is selected from the group consisting of: tenofovir, entecavir, lamivudine, telbuvudine, adefovir, pegylated interferon, sofusbuvir, telaprevir, daclatsivir, simeprevir, ledasprevir, corticosteroid, GFT-505, cenicriviroc, vitamin E, pioglitazone, metformin, obeticholic acid, GR-MD-02, and combinations thereof.

In another aspect, the present invention provides a composition comprising an isolated antibody or antigen-binding fragment thereof, including of any of the previous aspects, for example, as described herein, e.g., in Table 1, and a pharmaceutically acceptable carrier. The compositions may optionally further include an additional therapeutic agent, for example, as described herein.

In one aspect, the isolated antibody or antigen-binding fragment thereof of the present invention, for example, as described in Table 1, can be administered to a patient in need thereof in conjunction with a therapeutic method or procedure, such as described herein or known in the art. The isolated antibody or antigen-binding fragment thereof can be administered before, after or coincident with a method or procedure. The isolated antibody or antigen-binding fragment thereof can be administered adjunctively to another therapeutic method or procedure.

In one aspect, the invention provides a method of reducing the activity of BMP9 in a cell. The method may include the step of contacting a cell with an isolated antibody or antigen-binding fragment thereof of the present invention, e.g., as described herein, e.g., in Table 1.

In one aspect, the invention provides a method of inhibiting BMP9 in a patient in need thereof. The method may include the step of administering to the patient a therapeutically effective amount of an isolated antibody or antigen-binding fragment thereof of the present invention, e.g., as described herein, e.g., in Table 1. In some aspects, the patient has liver disease. In some aspects the liver disease is treated with the isolated antibody or antigen-binding fragment thereof of the present invention. In some aspects, the liver disease is associated with one or more of factors such as hepatitis C virus ("HCV") infection; hepatitis B virus ("HBV") infection; autoimmune hepatitis; alcohol exposure; toxin exposure; drug exposure; liver trauma; biliary obstruction; primary biliary cirrhosis; alagille syndrome; chronic hepatic congestion; nonalcoholic steatohepatitis (NASH); primary sclerosing cholangitis; hemochromatosis; alpha 1-antitrypsin deficiency; and Wilson disease. In some aspects, the liver disease is liver fibrosis, portal vein hypertension, nonalcoholic steatohepatitis (NASH), fatty liver disease, and cirrhosis, or combinations thereof. In some aspects, the liver disease is liver fibrosis. In some aspects the liver disease is portal vein hypertension. In some aspects, the liver disease is nonalcoholic steatohepatitis (NASH). In some aspects, the liver disease is fatty liver disease. In some aspects, the liver disease is cirrhosis.

In some aspects, the invention relates to a method of treating a patient in need thereof, or a method of reducing BMP9 activity in a patient, that includes administering an antibody or antigen-binding fragment thereof of the present invention together with an additional therapeutic agent. In some aspects, the additional therapeutic agent reduces the activity of BMP9. In some aspects, the additional therapeutic agent is a siRNA, antibody or antigen-binding fragment thereof, soluble receptor, protein, or small molecule. In some aspects, the additional therapeutic agent is selected from the group consisting of: an antiviral agent, an anti-inflammatory agent, an anti-fibrotic agent, an anti-steatotic agent, an anti-apoptotic, a hepatoprotective agent, and combinations thereof. In some aspects, the additional therapeutic agent is selected from the group consisting of: tenofovir, entecavir, lamivudine, telbuvudine, adefovir, pegylated interferon, sofusbuvir, telaprevir, daclatsivir, simeprevir, ledasprevir, corticosteroid, GFT-505, cenicriviroc, vitamin E, pioglitazone, metformin, obeticholic acid, GR-MD-02, and combinations thereof. In some aspects, the isolated antibody or antigen-binding fragment thereof of the present invention and the additional therapeutic agent are administered simultaneously or sequentially. In some aspects, the isolated antibody or antigen-binding fragment thereof is administered adjunctively to administration of the additional therapeutic agent.

In one aspect, the invention provides an isolated polynucleotide, for example, one or more nucleic acid molecules, that include sequence encoding an antibody or antigen-binding fragment thereof of the present invention, including of any of the previous aspects.

In one aspect, the present invention includes nucleic acid, e.g., one or more polynucleotides, encoding any of the antibodies or antigen-binding fragments thereof described herein. In one aspect, the present invention provides nucleic acid, e.g., one or more polynucleotides, which encodes a VH or a VL sequence of an antibody or antigen-binding fragment thereof which binds human BMP9, wherein the antibody or antigen-binding fragment thereof includes:

(a) the HCDR1, HCDR2, and HCDR3 sequences of SEQ ID NOs: 1, 2 and 3, respectively, and the LCDR1, LCDR2, and LCDR3 sequences of SEQ ID NOs: 11, 12 and 13, respectively;

(b) the HCDR1, HCDR2, and HCDR3 sequences of SEQ ID NOs: 4, 5 and 6, respectively, and the LCDR1, LCDR2, and LCDR3 sequences of SEQ ID NOs: 14, 15 and 16, respectively;

(c) the HCDR1, HCDR2, and HCDR3 sequences of SEQ ID NOs: 21, 22 and 23, respectively, and the LCDR1, LCDR2, and LCDR3 sequences of SEQ ID NOs: 31, 32 and 33, respectively;

(d) the HCDR1, HCDR2, and HCDR3 sequences of SEQ ID NOs: 24, 25 and 26, respectively, and the LCDR1, LCDR2, and LCDR3 sequences of SEQ ID NOs: 34, 35 and 36, respectively;

(e) the HCDR1, HCDR2, and HCDR3 sequences of SEQ ID NOs: 41, 42 and 43, respectively, and the LCDR1, LCDR2, and LCDR3 sequences of SEQ ID NOs: 51, 52 and 53, respectively;

(f) the HCDR1, HCDR2, and HCDR3 sequences of SEQ ID NOs: 44, 45 and 46, respectively, and the LCDR1, LCDR2, and LCDR3 sequences of SEQ ID NOs: 54, 55 and 56, respectively;

(g) the HCDR1, HCDR2, and HCDR3 sequences of SEQ ID NOs: 61, 62 and 63, respectively, and the LCDR1, LCDR2, and LCDR3 sequences of SEQ ID NOs: 71, 72 and 73, respectively;

(h) the HCDR1, HCDR2, and HCDR3 sequences of SEQ ID NOs: 64, 65 and 66, respectively, and the LCDR1, LCDR2, and LCDR3 sequences of SEQ ID NOs: 74, 75 and 76, respectively;

(i) the HCDR1, HCDR2, and HCDR3 sequences of SEQ ID NOs: 81, 82 and 83, respectively, and the LCDR1, LCDR2, and LCDR3 sequences of SEQ ID NOs: 91, 92 and 93, respectively;

(j) the HCDR1, HCDR2, and HCDR3 sequences of SEQ ID NOs: 84, 85 and 86, respectively, and the LCDR1, LCDR2, and LCDR3 sequences of SEQ ID NOs: 94, 95 and 96, respectively;

(k) the HCDR1, HCDR2, and HCDR3 sequences of SEQ ID NOs: 101, 102 and 103, respectively, and the LCDR1, LCDR2, and LCDR3 sequences of SEQ ID NOs: 111, 112 and 113, respectively;

(l) the HCDR1, HCDR2, and HCDR3 sequences of SEQ ID NOs: 104, 105 and 106, respectively, and the LCDR1, LCDR2, and LCDR3 sequences of SEQ ID NOs: 114, 115 and 116, respectively;

(m) the HCDR1, HCDR2, and HCDR3 sequences of SEQ ID NOs: 121, 122 and 123, respectively, and the LCDR1, LCDR2, and LCDR3 sequences of SEQ ID NOs: 131, 132 and 133, respectively;

(n) the HCDR1, HCDR2, and HCDR3 sequences of SEQ ID NOs: 124, 125 and 126, respectively, and the LCDR1, LCDR2, and LCDR3 sequences of SEQ ID NOs: 134, 135 and 136, respectively;

(o) the HCDR1, HCDR2, and HCDR3 sequences of SEQ ID NOs: 141, 142 and 143, respectively, and the LCDR1, LCDR2, and LCDR3 sequences of SEQ ID NOs: 151, 152 and 153, respectively;

(p) the HCDR1, HCDR2, and HCDR3 sequences of SEQ ID NOs: 144, 145 and 146, respectively, and the LCDR1, LCDR2, and LCDR3 sequences of SEQ ID NOs: 154, 155 and 156, respectively;

(q) the HCDR1, HCDR2, and HCDR3 sequences of SEQ ID NOs: 161, 162 and 163, respectively, and the LCDR1, LCDR2, and LCDR3 sequences of SEQ ID NOs: 171, 172 and 173, respectively; or (r) the HCDR1, HCDR2, and HCDR3 sequences of SEQ ID NOs: 164, 165 and 166, respectively, and the LCDR1, LCDR2, and LCDR3 sequences of SEQ ID NOs: 174, 175 and 176, respectively.

In one aspect, the present invention provides nucleic acid, e.g., one or more polynucleotides, which encodes an isolated antibody or antigen-binding fragment thereof, for example, those described in Table 1, wherein the isolated antibody or antigen-binding fragment thereof includes any one of: a VH sequence of SEQ ID NO: 7; a VH sequence of SEQ ID NO: 27; a VH sequence of SEQ ID NO: 47; a VH sequence of SEQ ID NO: 67; a VH sequence of SEQ ID NO: 87; a VH sequence of SEQ ID NO: 107; a VH sequence of SEQ ID NO: 127; a VH sequence of SEQ ID NO: 147; or a VH sequence of SEQ ID NO: 167;

In some aspects, the invention provides nucleic acid, e.g., one or more polynucleotides, which encodes an isolated antibody or antigen-binding fragment thereof, for example, those described in Table 1, wherein the isolated antibody or antigen-binding fragment thereof includes any one of: a VL sequence of SEQ ID NO: 17; a VL sequence of SEQ ID NO: 37; a VL sequence of SEQ ID NO: 57; a VL sequence of SEQ ID NO: 77; a VL sequence of SEQ ID NO: 97; a VL sequence of SEQ ID NO: 117; a VL sequence of SEQ ID NO: 137; a VL sequence of SEQ ID NO: 157; or a VL sequence of SEQ ID NO: 177.

In some aspects, the invention provides nucleic acid, e.g., one or more polynucleotides, which encodes an isolated antibody or antigen-binding fragment thereof, for example, those described in Table 1, wherein the isolated antibody or antigen-binding fragment thereof includes any one of: a VH sequence of SEQ ID NO: 7 and a VL sequence of SEQ ID NO: 17; a VH sequence of SEQ ID NO: 27 and a VL sequence of SEQ ID NO: 37; a VH sequence of SEQ ID NO: 47 and VL sequence of SEQ ID NO: 57; a VH sequence of SEQ ID NO: 67 and a VL sequence of SEQ ID NO: 77; a VH sequence of SEQ ID NO: 87 and a VL sequence of SEQ ID NO: 97; a VH sequence of SEQ ID NO: 107 and a VL sequence of SEQ ID NO: 117; a VH sequence of SEQ ID NO: 127 and a VL sequence of SEQ ID NO: 137; a VH sequence of SEQ ID NO: 147 and VL sequence of SEQ ID NO: 157; or a VH sequence of SEQ ID NO: 167 and a VL sequence of SEQ ID NO: 177.

In some aspects, the invention provides nucleic acid, e.g., one or more polynucleotides, which encodes an isolated antibody or antigen-binding fragment thereof, for example, those described in Table 1, wherein the isolated antibody or antigen-binding fragment thereof includes any one of: a heavy chain sequence of SEQ ID NO: 9; a heavy chain sequence of SEQ ID NO: 29; a heavy chain sequence of SEQ ID NO: 49; a heavy chain sequence of SEQ ID NO: 69; a heavy chain sequence of SEQ ID NO: 89; a heavy chain sequence of SEQ ID NO: 109; a heavy chain sequence of SEQ ID NO: 129; a heavy chain sequence of SEQ ID NO: 149; or a heavy chain sequence of SEQ ID NO: 169.

In some aspects, the invention provides nucleic acid, e.g., one or more polynucleotides, which encodes an isolated antibody or antigen-binding fragment thereof, for example, those described in Table 1, wherein the isolated antibody or antigen-binding fragment thereof includes any one of: a light chain sequence of SEQ ID NO: 19; a light chain sequence of SEQ ID NO: 39; a light chain sequence of SEQ ID NO: 59; a light chain sequence of SEQ ID NO: 79; a light chain sequence of SEQ ID NO: 99; a light chain sequence of SEQ ID NO: 119; a light chain sequence of SEQ ID NO: 139; a light chain sequence of SEQ ID NO: 159; or a light chain sequence of SEQ ID NO: 179.

In some aspects, the invention provides nucleic acid, e.g., one or more polynucleotides, which encodes an isolated antibody or antigen-binding fragment thereof, for example, those described in Table 1, wherein the isolated antibody or antigen-binding fragment thereof includes any one of: a heavy chain sequence of SEQ ID NO: 9; and a light chain sequence of SEQ ID NO: 19; a heavy chain sequence of SEQ ID NO: 29; and a light chain sequence of SEQ ID NO: 39; a heavy chain sequence of SEQ ID NO: 49; and a light chain sequence of SEQ ID NO: 59; a heavy chain sequence of SEQ ID NO: 69; and a light chain sequence of SEQ ID NO: 79; a heavy chain sequence of SEQ ID NO: 89; and a light chain sequence of SEQ ID NO: 99; a heavy chain sequence of SEQ ID NO: 109; and a light chain sequence of SEQ ID NO: 119; a heavy chain sequence of SEQ ID NO: 129; and a light chain sequence of SEQ ID NO: 139; a heavy chain sequence of SEQ ID NO: 149; and a light chain sequence of SEQ ID NO: 159; or a heavy chain sequence of SEQ ID NO: 169; and a light chain sequence of SEQ ID NO: 179.

In some aspects, the invention provides nucleic acid, e.g., one or more polynucleotides, which encodes an isolated antibody or antigen-binding fragment thereof, for example, those described in Table 1, wherein the nucleic acid comprises any one of: a heavy chain sequence of SEQ ID NO: 10; a VH sequence of SEQ ID NO: 8; a light chain sequence of SEQ ID NO: 20; a VL sequence of SEQ ID NO: 18; a heavy chain sequence of SEQ ID NO: 30; a VH sequence of SEQ ID NO: 28; a light chain sequence of SEQ ID NO: 40; a VL sequence of SEQ ID NO: 38; a heavy chain sequence of SEQ ID NO: 50; a VH sequence of SEQ ID NO: 48; a light chain sequence of SEQ ID NO: 60; a VL sequence of SEQ ID NO: 58; a heavy chain sequence of SEQ ID NO: 70; a VH sequence of SEQ ID NO: 68; a light chain sequence of SEQ ID NO: 80; a VL sequence of SEQ ID NO: 78; a heavy chain sequence of SEQ ID NO: 90; a VH sequence of SEQ ID NO: 88; a light chain sequence of SEQ ID NO: 100; a VL sequence of SEQ ID NO: 98; a heavy chain sequence of SEQ ID NO: 110; a VH sequence of SEQ ID NO: 108; a light chain sequence of SEQ ID NO: 120; a VL sequence of SEQ ID NO: 118; a heavy chain sequence of SEQ ID NO: 130; a VH sequence of SEQ ID NO: 128; a light chain sequence of SEQ ID NO: 140; a VL sequence of SEQ ID NO: 138; a heavy chain sequence of SEQ ID NO: 150; a VH sequence of SEQ ID NO: 148; a light chain sequence of SEQ ID NO: 160; a VL sequence of SEQ ID NO: 158; a heavy chain sequence of SEQ ID NO: 170; a VH sequence of SEQ ID NO: 168; a light chain sequence of SEQ ID NO: 180; or a VL sequence of SEQ ID NO: 178.

In some aspects, the invention provides nucleic acid, e.g., one or more polynucleotides, which encodes an isolated antibody or antigen-binding fragment thereof, for example, those described in Table 1, wherein the nucleic acid comprises any one of: a VH sequence of SEQ ID NO: 8 and the VL sequence of SEQ ID NO: 18; a VH sequence of SEQ ID NO: 28 and the VL sequence of SEQ ID NO: 38; a VH sequence of SEQ ID NO: 48 and the VL sequence of SEQ ID NO: 58; a VH sequence of SEQ ID NO: 68 and the VL sequence of SEQ ID NO: 78; a VH sequence of SEQ ID NO: 88 and the VL sequence of SEQ ID NO: 98; a VH sequence of SEQ ID NO: 108 and the VL sequence of SEQ ID NO: 118; a VH sequence of SEQ ID NO: 128 and the VL sequence of SEQ ID NO: 138; a VH sequence of SEQ ID NO: 148 and the VL sequence of SEQ ID NO: 158; or a VH sequence of SEQ ID NO: 168 and the VL sequence of SEQ ID NO: 178.

In some aspects the invention provides nucleic acid, e.g., one or more polynucleotides, encoding an isolated antibody or antigen-binding fragment thereof, wherein the encoded isolated antibody or antigen-binding fragment thereof includes an amino acid sequence having at least 90%, 95%, 96%, 97%, 98% or 99% sequence identity to a VL sequence, a VH sequence, a light chain sequence, or a heavy chain sequence set forth in Table 1.

In one aspect, the present invention provides nucleic acid, e.g., one or more polynucleotides, which encodes an isolated antibody or antigen-binding fragment thereof described in Table 1, wherein the nucleic acid includes a sequence selected from the group consisting of:

The heavy chain sequence of SEQ ID NO: 10;
the heavy chain sequence of SEQ ID NO: 30;
the heavy chain sequence of SEQ ID NO: 50;
the heavy chain sequence of SEQ ID NO: 70;
the heavy chain sequence of SEQ ID NO: 90;
the heavy chain sequence of SEQ ID NO: 110;
the heavy chain sequence of SEQ ID NO: 130;
the heavy chain sequence of SEQ ID NO: 150;
the heavy chain sequence of SEQ ID NO: 170;
the light chain sequence of SEQ ID NO: 20;
the light chain sequence of SEQ ID NO: 40;
the light chain sequence of SEQ ID NO: 60;
the light chain sequence of SEQ ID NO: 80;
the light chain sequence of SEQ ID NO: 100;

the light chain sequence of SEQ ID NO: 120;
the light chain sequence of SEQ ID NO: 140;
the light chain sequence of SEQ ID NO: 160;
the light chain sequence of SEQ ID NO: 180;
the VH sequence of SEQ ID NO: 8;
the VH sequence of SEQ ID NO: 28;
the VH sequence of SEQ ID NO: 48;
the VH sequence of SEQ ID NO: 68;
the VH sequence of SEQ ID NO: 88;
the VH sequence of SEQ ID NO: 108;
the VH sequence of SEQ ID NO: 128;
the VH sequence of SEQ ID NO: 148;
the VH sequence of SEQ ID NO: 168;
the VL sequence of SEQ ID NO: 18;
the VL sequence of SEQ ID NO: 38;
the VL sequence of SEQ ID NO: 58;
the VL sequence of SEQ ID NO: 78;
the VL sequence of SEQ ID NO: 98;
the VL sequence of SEQ ID NO: 118;
the VL sequence of SEQ ID NO: 138;
the VL sequence of SEQ ID NO: 158; and
the VL sequence of SEQ ID NO: 178.

The aspects of the invention relating to nucleic acid contemplate embodiments where the nucleic acid is disposed on a single continuous polynucleotide, for example a single continuous polynucleotide encoding 1) a light chain or VL of an antibody or antigen-binding fragment thereof of the present invention and 2) a heavy chain or VH of an antibody or antigen-binding fragment thereof of the present invention. The invention also contemplates embodiments where the nucleic acid is disposed on two or more continuous polynucleotides, for example, one polynucleotide encoding a light chain or VL of an antibody or antigen-binding fragment thereof of the present invention and another polynucleotide encoding a heavy chain or VH of an antibody or antigen-binding fragment thereof of the present invention.

The present invention also provides a vector that includes nucleic acids or polynucleotides, for example, those described herein. The present invention also provides a cell, for example, a host cell, that includes such nucleic acids or polynucleotides. In one aspect of the present invention, the isolated host cells include a vector comprising such nucleic acids or polynucleotides.

In one aspect, the present invention provides an isolated host cell comprising (1) a recombinant nucleic acid segment encoding a heavy chain of the antibodies of the invention, and (2) a second recombinant nucleic acid segment encoding a light chain of the antibodies of the invention; wherein said DNA segments are respectively operably linked to a first and a second promoter, and are capable of being expressed in said host cell. In another aspect of the present invention, the isolated host cells comprises a recombinant DNA segment encoding a heavy chain, and a light chain of the antibodies of the invention, respectively, wherein said DNA segment is operably linked to a promoter, and is capable of being expressed in said host cells. In one aspect, the host cells are a non-human mammalian cell line. In one aspect, the host cells are a human cell line. In one aspect, the antibody or antigen-binding fragment thereof is a human monoclonal antibody, or an antigen-binding fragment thereof. In one aspect, the antibody or antigen-binding fragment thereof is a humanized monoclonal antibody, or an antigen-binding fragment thereof.

The present invention provides the use of an antibody or antigen-binding fragment thereof to BMP9, a polynucleotide, a vector, or a host cell, as described herein, in the manufacture of a medicament. The present invention provides for use of an antibody or antigen-binding fragment thereof, e.g., as described herein, in the manufacture of a medicament, for example, in the manufacture of a medicament for use in a therapy, for example, in the manufacture of a medicament for treating a subject having liver disease. The present invention provides for use of an antibody or antigen-binding fragment thereof, e.g., as described herein, in the manufacture of a medicament for use in reducing the activity of BMP9 in a patient in need thereof. The present invention provides an antibody or antigen-binding fragment thereof to BMP9, as described herein, for use as a medicament. The present invention provides an antibody or antigen-binding fragment thereof to BMP9, as described herein, for use in a therapy. The present invention provides an antibody or antigen-binding fragment thereof, as described herein, for use in treating a fibrotic condition. The present invention provides an antibody or antigen-binding fragment thereof, as described herein, for use in treating a liver disease, including liver disease associated with one or more of factors selected from the group consisting of hepatitis C virus ("HCV") infection; hepatitis B virus ("HBV") infection; autoimmune hepatitis; alcohol exposure; toxin exposure; drug exposure; liver trauma; biliary obstruction; primary biliary cirrhosis; alagille syndrome; chronic hepatic congestion; nonalcoholic steatohepatitis (NASH); primary sclerosing cholangitis; hemochromatosis; alpha 1-antitrypsin deficiency; or Wilson disease. The present invention provides an antibody or antigen-binding fragment thereof, as described herein, for use in treating liver fibrosis, portal vein hypertension, nonalcoholic steatohepatitis (NASH), fatty liver disease, or cirrhosis.

In one aspect, the present invention provides an isolated antibody or antigen-binding fragment thereof which binds human BMP9, e.g., as described herein, for use in reducing the activity of BMP9 in a patient in need thereof.

In one aspect, the present invention provides an isolated antibody or antigen-binding fragment thereof which binds human BMP9, which includes a CDR, e.g., one or more CDRs, listed in Table 1. For example, said isolated antibody or antigen-binding fragment thereof which binds human BMP9 may include 2, 3, 4, 5, or 6 CDRs listed in Table 1, for example 6 CDRs (e.g., HCDR1, HCDR2, HCDR3, LCDR1, LCDR2 and LCDR3) of an antibody listed in Table 1.

In one aspect, the present invention provides an isolated antibody or antigen-binding fragment thereof which binds human BMP9, listed in Table 1.

In one aspect, the present invention provides an isolated antibody or antigen-binding fragment thereof which binds human BMP9, that includes a VH amino acid sequence having at least 90%, at least 95%, at least 96%, at least 97%, at least 98% or at least 99% sequence identity to a VH amino acid sequence described in Table 1.

In one aspect, the present invention provides an isolated antibody or antigen-binding fragment thereof which binds human BMP9, that includes a VL amino acid sequence having at least 90%, at least 95%, at least 96%, at least 97%, at least 98% or at least 99% sequence identity to a VL amino acid sequence described in Table 1.

In one aspect, the present invention provides an isolated antibody or antigen-binding fragment thereof which binds human BMP9, that includes a VH amino acid sequence having at least 90%, at least 95%, at least 96%, at least 97%, at least 98% or at least 99% sequence identity to a VH amino acid sequence described in Table 1, and a VL amino acid sequence having at least 90%, at least 95%, at least 96%, at least 97%, at least 98% or at least 99% sequence identity to a VL amino acid sequence described in Table 1.

In one aspect, the present invention provides an isolated antibody or antigen-binding fragment thereof which binds human BMP9, comprising a light chain amino acid sequence having at least 90%, at least 95%, at least 96%, at least 97%, at least 98% or at least 99% sequence identity to a light chain amino acid sequence described in Table 1.

In one aspect, the present invention provides an isolated antibody or antigen-binding fragment thereof which binds human BMP9, that includes a heavy chain amino acid sequence having at least 90%, at least 95%, at least 96%, at least 97%, at least 98% or at least 99% sequence identity to a heavy chain amino acid sequence described in Table 1.

In one aspect, the present invention provides an isolated antibody or antigen-binding fragment thereof which binds human BMP9, that includes a light chain amino acid sequence having at least 90%, at least 95%, at least 96%, at least 97%, at least 98% or at least 99% sequence identity to a light chain amino acid sequence described in Table 1, and a heavy chain amino acid sequence having at least 90%, at least 95%, at least 96%, at least 97%, at least 98% or at least 99% sequence identity to a heavy chain amino acid sequence described in Table 1.

In one aspect, the present invention provides an isolated polynucleotide encoding an antibody or antigen-binding fragment thereof of any of the preceding aspects.

In one aspect, the present invention provides an isolated polynucleotide encoding an antibody or antigen-binding fragment thereof which binds human BMP9 which includes a CDR listed in Table 1. Said antibody or antigen-binding fragment thereof which binds human BMP9 may include 2, 3, 4, 5, or 6 CDRs listed in Table 1, for example 6 CDRs (e.g., HCDR1, HCDR2, HCDR3, LCDR1, LCDR2 and LCDR3) of an antibody listed in Table 1.

Definitions

Unless defined otherwise, all technical and scientific terms used herein have the same meaning as commonly understood by those of ordinary skill in the art to which this invention pertains.

"BMP9", as used herein, means the refers to the art known member of the TGFβ/BMP superfamily that is known to be a potent inducer of osteoblast differentiation of mesenchymal stem cells (see Tang et al. (2008) J Cell Mol Med. [PMID: 19175684]) protein Bone Morphogenetic Protein 9 (BMP9) (also referenced interchangeably herein as "BMP9", "BMP-9", "growth differentiation factor 2", "GDF-2", "GDF2," and "Growth/differentiation factor 2 precursor") or a gene or nucleic acid encoding BMP9. BMP9 has also been shown to be involved in the regulation of glucose metabolism, capable of reducing glycemia in diabetic mice, a differentiation factor for cholinergic neurons in the central nervous system, and to induce the expression of a hormone (hepcidin) that plays a role in iron homeostasis (David et al. 2008. Circ Res. April 25; 102(8):914-22).

Representative BMP9 sequences, include, but are not limited to, the sequences set forth below.

BMP9/Growth Differentiation Factor 2 [*Homo sapiens*] (NP_057288).
(SEQ ID NO: 213)

```
MCPGALWVALPLLSLLAGSLQGKPLQSWGRGSAGGNAHSPLGVPGGGLPE

HTFNLKMFLENVKVDFLRSLNLSGVPSQDKTRVEPPQYMIDLYNRYTSDKSTTPA

SNIVRSFSMEDAISITATEDFPFQKHILLFNISIPRHEQITRAELRLYVSCQNHVDPSH

DLKGSVVIYDVLDGTDAWDSATETKTFLVSQDIQDEGWETLEVSSAVKRWVRSD

STKSKNKLEVTVESHRKGCDTLDISVPPGSRNLPFFVVFSNDHSSGTKETRLELRE

MISHEQESVLKKLSKDGSTEAGESSHEEDTDGHVAAGSTLARRKRSAGAGSHCQ

KTSLRVNFEDIGWDSWIIAPKEYEAYECKGGCFFPLADDVTPTKHAIVQTLVHLK

FPTKVGKACCVPTKLSPISVLYKDDMGVPTLKYHYEGMSVAECGCR
```

BMP9/Growth Differentiation Factor 2 [*Homo sapiens*] (AF188285)
(SEQ ID NO: 214)

```
cggtccagcc cggcagcggg tgagagtagg tgctggccaa gacggttcct tcagagcaaa

cagcagggag atgccggccc gctccttccc agctcctccc cgtgcccgct aacacagcac

ggccgcctgc agtctcctct ctgggtgatt gcgcgggcct aagatgtgtc ctggggcact

gtgggtggcc ctgcccctgc tgtccctgct ggctggctcc ctacagggga agccactgca

gagctgggga cgagggtctg ctgggggaaa cgcccacagc ccactggggg tgcctggagg

tgggctgcct gagcacacct tcaacctgaa gatgtttctg gagaacgtga aggtggattt

cctgcgcagc cttaacctga gtggggtccc ttcgcaggac aaaaccaggg tggagccgcc

gcagtacatg attgacctgt acaacaggta cacgtccgat aagtcgacta cgccagcgtc

caacattgtg cggagcttca gcatggaaga tgccatctcc ataactgcca cagaggactt

cccccttccag aagcacatct tgctcttcaa catctccatt cctaggcatg agcagatcac

cagagctgag ctccgactct atgtctcctg tcaaaatcac gtggacccct ctcatgacct

gaaaggaagc gtggtcattt atgatgttct ggatggaaca gatgcctggg atagtgctac
```

-continued

```
agagaccaaa accttcctgg tgtcccagga cattcaggat gagggctggg agaccttgga

agtgtccagc gccgtgaagc gctgggtccg gtccgactcc accaagagca aaaataagct

ggaagtgact gtggagagcc acaggaaggg ctgcgacacg ctggacatca gtgtcccccc

aggttccaga aacctgccct tctttgttgt cttctccaat gaccacagca gtggaaccaa

ggagaccagg ctggagctga gggagatgat cagccatgaa caagagagcg tgctcaagaa

gctgtccaag gacggctcca cagaggcagg tgagagcagt cacgaggagg acacggatgg

ccacgtggct gcggggtcga ctttagccag gcggaaaagg agcgccgggg ctggcagcca

ctgtcaaaag acctccctgc gggtaaactt cgaggacatc ggctgggaca gctggatcat

tgcacccaag gagtatgaag cctacgagtg taagggcggc tgcttcttcc ccttggctga

cgatgtgacg ccgacgaaac acgctatcgt gcagaccctg gtgcatctca agttccccac

aaaggtgggc aaggcctgct gtgtgcccac caaactgagc cccatctccg tcctctacaa

ggatgacatg gaggtgccca ccctcaagta ccattacgag ggcatgagcg tggcagagtg

tgggtgcagg tagtatctgc ctgcggggct ggggaggcag gccaaagggg ctccacatga

gaggtcctgc atgcccctgg gcacaacaag gactgattca atctgcatgc cagcctggag

gaggaaaggg agcctgctct ccctccccac accccaccca aagcatacac cgctgagctc

aactgccagg gaaggctaag gaaatgggga tttgagcaca acaggaaagc ctgggagggt

tgttgggatg caaggaggtg atgaaaagga gacaggggga aaaataatcc atagtcagca

gaaaacaaca gcagtgagcc agaggagcac aggcgggcag gtcactgcag agactgatgg

aagttagaga ggtggaggag gccagctcac tccaaaaccc ttggggagta gagggaagga

gcaggccgcg tgtcacaccc atcattgtat gttatttccc acaacccagt tggaggggca

tggcttccaa tttagagacc cg
```

Mature Fragment of BMP9/Growth Differentiation Factor 2 [*Homo sapiens*]
(Amino acids from NP_057288) (SEQ ID NO: 215):
SAGAGSHCQKTSLRVNFEDIGWDSWIIAPKEYEAYECKGGCFFPLADDVTPTKHAIVQTL
VHLKFPTKVGKACCVPTKLSPISVLYKDDMGVPTLKYHYEGMSVAECGCR The murine and other animal BMP9 molecules are known in the art (see, for example, NP_062379 for murine BMP9 and NP_001099566 for rat BMP9).

As described herein, an antibody antigen-binding fragment thereof which binds to BMP9 binds to BMP9 protein. As used herein "huBMP9" refers to human BMP9 or a fragment thereof.

"BMP2", as used herein, means the protein Bone Morphogenetic Protein 2 (BMP2) or a gene or nucleic acid encoding BMP2. BMP2 is also known as: BDA2; and BMP2A; External IDs OMIM: 112261 MGI: 88177 HomoloGene: 926 GeneCards: BMP2 Gene. Species: Human; Entrez: 650; Ensembl: ENSG00000125845; UniProt: P12643; RefSeq (mRNA): NM_001200; RefSeq (protein): NP_001191; Location (UCSC): Chr 20: 6.75-6.76 Mb. Species: Mouse; Entrez: 12156; Ensembl: ENSMUSG00000027358; UniProt: P21274; RefSeq (mRNA): NM 007553; RefSeq (protein): NP_031579; Location (UCSC): Chr 2: 133.55-133.56 Mb. As described herein, an antibody antigen-binding fragment thereof which binds to BMP2 binds to BMP2 protein.

"BMP7", as used herein, means the protein Bone Morphogenetic Protein 7 (BMP7) or a gene or nucleic acid encoding BMP7. BMP7 is also known as: osteogenic protein-1; OP-1; External IDs OMIM: 112267 MGI: 103302 HomoloGene: 20410 GeneCards: BMP7 Gene. Species: Human; Entrez: 655; Ensembl: ENSG00000101144; UniProt: P18075; RefSeq (mRNA): NM_001719; RefSeq (protein): NP_001710; Location (UCSC): Chr 20: 55.74-55.84 Mb. Species: Mouse; Entrez: 12162; Ensembl: ENSMUSG00000008999; UniProt: P23359; RefSeq (mRNA): NM_007557; RefSeq (protein): NP_031583; Location (UCSC): Chr 2: 172.87-172.94 Mb. As described herein, an antibody antigen-binding fragment thereof which binds to BMP7 binds to BMP7 protein.

"BMP10", as used herein, means the art known member of the TGFβ/BMP superfamily Bone Morphogenetic Protein 10 (BMP10) (also referenced interchangeably herein as "BMP10", "BMP-10". "MGC126783", and "Bone morphogenetic protein 10 precursor") or a gene or nucleic acid encoding BMP10. It has been suggested that BMP10 is an essential component in modulating cardiomyocyte proliferation and maturation during cardiac ventricular development. (Chen et al., (2004) Development. 131(9):2219-31 and Neubaus et al., (1999) Mech Dev., 80(2): 181-4). A representative BMP10 sequence, includes, but is not limited to, the sequence set forth below.

Bone Morphogenetic Protein 10 Preproprotein [*Homo sapiens*] (NP_055297)
(SEQ ID NO: 216)

MGSLVLTLCALFCLAAYLVSGSPIMNLEQSPLEEDMSLFGDVFSEQDGVDFNTLL

QSMKDEFLKTLNLSDIPTQDSAKVDPPEYMLELYNKFATDRTSMPSANIIRSFKNE

DLFSQPVSFNVSIPHHEEVIMAELRLYTLVQRDRMIYDGVDRKITTFEVLESKGDN

EGERNMLVLVSGEIYGTNSEWETFDVTDAIRRWQKSGSSTHQLEVHIESKHDEAE

DASSGRLEIDTSAQNKHNPLLIVFSDDQSSDKERKEELNEMISHEQLPELDNLGLD

SFSSGPGEEALLQMRSNITYDSTARIRRNAKGNYCKRTPLYIDFKEIGWDSWIIAPP

GYEAYECRGVCNYPLAEHLTPTKHAIIQALVHLKNSQKASKACCVPTKLEPISILY

LDKGVVTYKFKYEGMAVSECGCR

Bone Morphogenitic Protein 10 [*Homo sapiens*] (NM_014482)
(SEQ ID NO: 217)

ggggagagga agagtggtag ggggagggag agagagagga agagtttcca aacttgtctc cagtgacagg agacatttac gttccacaag ataaaactgc cacttagagc ccagggaagc taaaccttcc tggcttggcc taggagctcg agcggagtca tgggctctct ggtcctgaca ctgtgcgctc ttttctgcct ggcagcttac ttggtttctg gcagccccat catgaaccta gagcagtctc ctctggaaga agatatgtcc ctctttggtg atgttttctc agagcaagac ggtgtcgact ttaacacact gctccagagc atgaaggatg agtttcttaa gacactaaac ctctctgaca tccccacgca ggattcagcc aaggtggacc caccagagta catgttggaa ctctacaaca aatttgcaac agatcggacc tccatgccct ctgccaacat cattaggagt ttcaagaatg aagatctgtt ttcccagccg gtcagtttta atgggctccg aaaatacccc ctcctcttca atgtgtccat tcctcaccat gaagaggtca tcatggctga acttaggcta tacacactgg tgcaaaggga tcgtatgata tacgatggag tagaccggaa aattaccatt tttgaagtgc tggagagcaa aggggataac gagggagaaa gaaacatgct ggtcctggtg tctggggaga tatatggaac caacagtgag tgggagactt ttgatgtcac agatgccatc agacgttggc aaaagtcagg ctcatccacc caccagctgg aggcccacat tgagagcaaa cacgatgaag ctgaggatgc cagcagtgga cggctagaaa tagataccag tgcccagaat aagcataacc ctttgctcat cgtgttttct gatgaccaaa gcagtgacaa ggagaggaag gaggaactga atgaaatgat ttcccatgag caacctccag agctggacaa cttgggcctg gatagctttt ccagtggacc tggggaagag gctttgttgc agatgagatc aaacatcatc tatgactcca ctgcccgaat cagaaggaac gccaaaggaa actactgtaa gaggaccccg ctctacatcg acttcaagga gattgggtgg gactcctgga tcatcgctcc gcctggatac gaagcctatg aatgccgtgg tgtttgtaac taccccctgg cagagcatct cacacccaca aagcatgcaa ttatccaggc cttggtccac ctcaagaatt cccagaaagc ttccaaagcc tgctgtgtgc ccacaaagct agagcccatc tccatcctct atttagacaa aggcgtcgtc acctacaagt ttaaatacga aggcatggcc gtctccgaat gtggctgtag atagaagaag agtcctatgg cttatttaat aactgtaaat gtgtatattt ggtgttccta tttaatgaga ttatttaata agggtgtaca gtaatagagg cttgctgcct tcaggaaatg gacaggtcag tttgttgtag gaaatgcata tttt The murine and other animal BMP10 molecules are known in the art (see, for example, NP_033886 for murine BMP10). As described herein, an antibody antigen-binding fragment thereof which binds to BMP10 binds to BMP10 protein.

"Smad" refers to a family of intracellular proteins that transduce extracellular signals from transforming growth factor beta ligands to the nucleus, where they activate downstream gene transcription (See, e.g., Heldin C H (1997), *Nature* 390 (6659): 465-71; Attisano L (1998) *Curr.*

*Opin. Cell Biol.* 10 (2): 188-94; Massagué J (1998), *Annu. Rev. Biochem.* 67: 753-91; Attisano L (2002) *Science* 296 (5573): 1646-7; Whitman M (1998) *Genes Dev.* 12 (16): 2445-62; Wrana J L (2000) Sci. STKE 2000 (23): RE1; Wharton K, (2009), *Development* 136 (22): 3691-7). The receptor-regulated Smads (R-SMAD) include Smad1, Smad2, Smad3, Smad5 and Smad8/9. The term "smad" includes the gene for an Smad, e.g., the gene for Smad1, Smad5 or Smad8, or an Smad protein, e.g., Smad1, Smad5 or Smad8. Without being bound by theory, it is believed that Smad1, Smad5 and Smad8 are preferentially activated by the BMP subfamily of ligands, including BMP9. Multiple members of the Smad family are referred to together by their numbers. Thus, for example, "Smad1/5/8" refers to Smad1, Smad5 and/or Smad8. "Smad1/5" refers to Smad1 and/or Smad5. Again, without being bound by theory, it is believed that signaling through Smad leads to phosphorylation of Smad protein. "pSmad" refers to phosphorylated Smad protein.

"Id1" means the gene Id1 or the protein Id1 (See, e.g., Benezra R, *Cell* 61 (1): 49-59; Hara E (1994) *J Biol Chem* 269 (3): 2139-45; Ruzinova M B (2003) *Trends in Cell Biology* 13 (8): 410-8; Perk J (2005) *Nat Rev Cancer* 5 (8): 603-614; Korchynskyi O (2002). *J Biol Chem.,* 277 (7): 4883-91). DNA-binding protein inhibitor 1 (Id1) is a helix-loop-helix (HLH) protein that can form heterodimers with, e.g., members of the basic HLH family of transcription factors. Without being bound by theory, Id1 is a well know target gene for BMP signaling pathway, including BMP9.

As used herein, the term "fibrosis" refers to the aberrant formation or development of excess fibrous connective tissue by cells in an organ or tissue. Although processes related to fibrosis can occur as part of normal tissue formation or repair, dysregulation of these processes can lead to altered cellular composition and excess connective tissue deposition that progressively impairs to tissue or organ function. There are several types of fibrosis, for example, cystic fibrosis of the pancreas and lungs, injection fibrosis, which can occur as a complication of intramuscular injections, especially in children, endomyocardial fibrosis, idiopathic pulmonary fibrosis of the lung, mediastinal fibrosis, myelofibrosis, retroperitoneal fibrosis, progressive massive fibrosis, a complication of coal workers' pneumoconiosis, and nephrogenic systemic fibrosis.

As used herein, the terms "fibrotic disorder", "fibrotic condition," and "fibrotic disease," are used interchangeably to refer to a disorder, condition or disease characterized by fibrosis. Examples of fibrotic disorders include, but are not limited to vascular fibrosis, pulmonary fibrosis (e.g., idiopathic pulmonary fibrosis), pancreatic fibrosis, liver fibrosis (e.g., "fibrotic liver disease", e.g., cirrhosis), renal fibrosis, musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), progressive systemic sclerosis (PSS), chronic graft versus-host disease, Peyronie's disease, post-cystoscopic urethral stenosis, idiopathic and pharmacologically induced retroperitoneal fibrosis, mediastinal fibrosis, progressive massive fibrosis, proliferative fibrosis and neoplastic fibrosis.

As used herein, the terms "fibrotic liver disease" and "liver fibrosis" are used interchangeably, and refer to a disease of the liver characterized by the aberrant formation or development of excess fibrous connective tissue (e.g., extracelluar matrix ("ECM") proteins including collagen) by cells in the liver. Without being bound by any particular theory, it is believed that activated hepatic stellate cells, portal fibroblasts and myofibroblasts are the major fibrogenic cells (i.e., ECM-producing cells) in the liver. Liver fibrosis leads to portal vein hypertension. Advanced liver fibrosis results in cirrhosis, liver failure.

Fibrotic liver diseases, including those that result in cirrhosis and/or portal vein hypertension, that may be treated with the antibodies or antigen-binding fragments thereof of the invention may be caused by, for example, hepatitis C virus ("HCV") infection; hepatitis B virus ("HBV") infection; autoimmune hepatitis; alcohol, toxin or drug exposure; liver trauma; biliary obstruction; primary biliary cirrhosis; alagille syndrome; chronic hepatic congestion, including from cardiac disease or hepatic outflow obstruction; nonalcoholic steatohepatitis (NASH); primary sclerosing cholangitis; hemochromatosis; alpha 1-antitrypsin deficiency; and Wilson disease.

As used herein, the terms "BMP9 antibody," "anti-BMP9 antibody," "BMP9-binding antibody", "BMP9 antagonist antibody" and the like (and antigen-binding fragments thereof) include antibodies (and antigen-binding fragments thereof) which bind to the protein BMP9.

As used herein, the term "cell" refers to any cell prone to undergoing a fibrotic response, including, but not limited to, individual cells, tissues, and cells within tissues and organs. The term cell, as used herein, includes the cell itself, as well as the extracellular matrix (ECM) surrounding a cell. For example, inhibition of the fibrotic response of a cell, includes, but is not limited to the inhibition of the fibrotic response of one or more cells within the lung (or lung tissue); one or more cells within the liver (or liver tissue); one or more cells within the kidney (or renal tissue); one or more cells within muscle tissue; one or more cells within the heart (or cardiac tissue); one or more cells within the pancreas; one or more cells within the skin; one or more cells within the bone, one or more cells within the vasculature, one or more stem cells, or one or more cells within the eye.

As used herein, the term "Epithelial-Mesenchymal Transition" (EMT) refers to the conversion from an epithelial to a mesenchymal phenotype, which is a normal process of embryonic development. EMT is also the process whereby injured epithelial cells that function as ion and fluid transporters become matrix remodeling mesenchymal cells. In carcinomas, this transformation results in altered cell morphology, the expression of mesenchymal proteins and increased invasiveness. The criteria for defining EMT in vitro involve the loss of epithelial cell polarity, the separation into individual cells and subsequent dispersion after the acquisition of cell motility (See Vincent-Salomon et al., Breast Cancer Res. 2003; 5(2): 101-106). Classes of molecules that change in expression, distribution, and/or function during EMT, and that are causally involved, include growth factors (e.g., transforming growth factor (TGF)-β, wnts), transcription factors (e.g., snails, SMAD, LEF, and nuclear β-catenin), molecules of the cell-to-cell adhesion axis (cadherins, catenins), cytoskeletal modulators (Rho family), and extracellular proteases (matrix metalloproteinases, plasminogen activators) (see Thompson et al., Cancer Research 65, 5991-5995, Jul. 15, 2005).

The term "antibody" and the like, as used herein, include whole antibodies and any antigen-binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "antigen-binding fragment", "antigen-binding fragment thereof," "antigen binding portion" of an antibody, and the like, as used herein, refer to one or more fragments of an intact antibody that retain the ability to specifically bind to a given antigen (e.g., BMP9). Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F $(ab)_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8 (10):1057-1062; and U.S. Pat. No. 5,641,870).

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with one antigenic determinant and not with a different antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

Specific binding between two entities means a binding with an equilibrium constant (KA or $K_A$) of at least $1\times10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, $10^{13}$ $M^{-1}$, or $10^{14}$ $M^{-1}$. The phrase "specifically (or selectively) binds" to an antibody (e.g., BMP9-binding antibody) refers to a binding reaction that is determinative of the presence of a cognate antigen (e.g., a human BMP9 protein) in a heterogeneous population of proteins and other biologics. In addition to the equilibrium constant (KA) noted above, an BMP9-binding antibody of the invention typically also has a dissociation rate constant (Kd or $K_{off}$) of about $1\times10^{-2}$ $s^{-1}$, $1\times10^{-3}$ $s^{-1}$, or lower, and binds to BMP9 with an affinity that is at least two-fold greater than its affinity for binding to a non-specific antigen (e.g., BMP2, BMP10 or BMP7). The phrases "an antibody recognizing an antigen" and "an antibody specific for an antigen" are used interchangeably herein with the term "an antibody which binds specifically to an antigen".

The term "chimeric antibody" (or antigen-binding fragment thereof) is an antibody molecule (or antigen-binding fragment thereof) in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In one embodiment, the term "conservative sequence modifications" are used to refer to amino acid modifications that do not significantly affect or alter the binding characteristics of the antibody containing the amino acid sequence.

The term "blocks" as used herein refers to stopping or preventing an interaction or a process, e.g., stopping ligand-dependent or ligand-independent signaling.

The term "recognize" as used herein refers to an antibody antigen-binding fragment thereof that finds and interacts (e.g., binds) with its conformational epitope.

The terms "cross-block", "cross-blocked", "cross-blocking", "compete", "cross compete" and related terms are used interchangeably herein to mean the ability of an antibody or other binding agent to interfere with the binding of other antibodies or binding agents to BMP9 in a standard competitive binding assay.

The ability or extent to which an antibody or other binding agent is able to interfere with the binding of another antibody or binding molecule to BMP9, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach. Although the techniques are expected to produce substantially similar results, measurement by the Biacore technique is considered definitive.

The term "neutralizes" means that an antibody, upon binding to its target, reduces the activity, level or stability of the target; e.g., a BMP9 antibody, upon binding to BMP9 neutralizes BMP9 by at least partially reducing an activity, level or stability of BMP9, such as signaling or its role in phosphorylation of Smad1/5/8 and/or fibrosis, e.g., liver fibrosis.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational."

The term "linear epitope" refers to an epitope with all of the points of interaction between the protein and the interacting molecule (such as an antibody) occur linearally along the primary amino acid sequence of the protein (continuous).

As used herein, the term "high affinity" for an IgG antibody refers to an antibody having a KD of $10^{-8}$ M or less, $10^{-9}$ M or less, or $10^{-10}$ M, or $10^{-11}$M or less for a target antigen, e.g., BMP9. However, "high affinity" binding can vary for other antibody isotypes. For example, "high affinity" binding for an IgM isotype refers to an antibody having a KD of $10^{-7}$ M or less, or $10^{-8}$ M or less.

The term "human antibody" (or antigen-binding fragment thereof), as used herein, is intended to include antibodies (and antigen-binding fragments thereof) having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies and antigen-binding fragments thereof of the invention may include amino acid residues not encoded by human sequences (e.g., mutations introduced by random or site-specific mutagenesis in vitro or by somatic mutation in vivo).

The phrases "monoclonal antibody" or "monoclonal antibody composition" (or antigen-binding fragment thereof) as used herein refers to polypeptides, including antibodies, antibody fragments, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The term "human monoclonal antibody" (or antigen-binding fragment thereof) refers to antibodies (and antigen-binding fragments thereof) displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The phrase "recombinant human antibody" (or antigen-binding fragment thereof), as used herein, includes all human antibodies (and antigen-binding fragments thereof) that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In one embodiment, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "humanized" antibody (or antigen-binding fragment thereof), as used herein, is an antibody (or antigen-binding fragment thereof) that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, 96%, 97%, 98% or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. Optionally, the identity exists over a region that is at least 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length Win the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (N) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P (N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" (or antigen-binding fragment thereof), as used herein, refers to an antibody (or antigen-binding fragment thereof) that is substantially free of other antibodies having different antigenic specificities (e.g., an isolated antibody that specifically binds BMP9 is substantially free of antibodies that specifically bind antigens other than BMP9). Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to after the Fc function, for example, to enhance or reduce effector functions or binding to Fc receptors.

The term "Kassoc", "Ka" or "$K_{on}$", as used herein, is intended to refer to the association rate of a particular antibody-antigen interaction, whereas the term "Kdis", "Kd," or "$K_{off}$", as used herein, is intended to refer to the dissociation rate of a particular antibody-antigen interaction. In one embodiment, the term "KD", as used herein, is intended to refer to the dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system. Where the dissociation constant is less than about $10^{-9}$ M, solution equilibrium kinetic exclusion KD measurement (MSD-SET) is a preferred method for determining the KD of an antibody (see, e.g., Friquet, B., Chaffotte, A. F., Djavadi-Ohaniance, L., and Goldberg, M. E. (1985). Measurements of the true affinity constant in solution of antigen-antibody complexes by enzyme-linked immunosorbent assay. J Immnunol Meth 77, 305-319; herein incorporated by reference).

The term "IC50," as used herein, refers to the concentration of an antibody or an antigen-binding fragment thereof, which induces an inhibitory response, either in an in vitro or an in vivo assay, which is 50% of the maximal response, i.e., halfway between the maximal response and the baseline.

The term "effector function" refers to an activity of an antibody molecule that is mediated by binding through a domain of the antibody other than the antigen-binding domain, usually mediated by binding of effector molecules. Effector function includes complement-mediated effector function, which is mediated by, for example, binding of the C1 component of the complement to the antibody. Activation of complement is important in the opsonisation and lysis of cell pathogens. The activation of complement also stimulates the inflammatory response and may also be involved in autoimmune hypersensitivity. Effector function also includes Fc receptor (FcR)-mediated effector function, which may be triggered upon binding of the constant domain of an antibody to an Fc receptor (FcR). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. An effector function of an antibody may be altered by altering, e.g., enhancing or reducing, the affinity of the antibody for an effector molecule such as an Fc receptor or a complement component. Binding affinity will generally be varied by modifying the effector molecule binding site, and in this case it is appropriate to locate the site of interest and modify at least part of the site in a suitable way. It is also envisaged that an alteration in the binding site on the antibody for the effector molecule need not alter significantly the overall binding affinity but may alter the geometry of the interaction rendering the effector mechanism ineffective as in non-productive binding. It is further envisaged that an effector function may also be altered by modifying a site not directly involved in effector molecule binding, but otherwise involved in performance of the effector function.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody" (or antigen-binding fragment thereof), as used herein, includes all human antibodies (and antigen-binding fragments thereof) that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In one embodiment, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "treat," "treated," "treating," and "treatment," include the administration of compositions or antibodies to prevent or delay the onset of the symptoms, complications, or biochemical indicia of a disease (e.g., liver fibrosis), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease. Treatment can be measured by the therapeutic measures described herein. The methods of "treatment" of the present invention include administration of a BMP9 antibody or antigen binding fragment thereof to a subject in order to cure, reduce the severity of, or ameliorate one or more symptoms of a fibrotic disease or condition, in order to prolong the health or survival of a subject beyond that expected in the absence of such treatment. For example, "treatment" includes the alleviation of a fibrotic disease symptom (e.g., shortness of breath, fatigue, cough, weight loss, loss of appetite associated with pulmonary fibrosis or anorexia, fatigue, weight loss, portal vein hypertension and ascites associated with liver fibrosis) in a subject by at least 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% or more.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

BRIEF DESCRIPTION OF THE FIGURES

FIG. 8. In vivo efficacy study in 2 week $CCl_4$ liver fibrosis mouse model with mouse anti-BMP9 antibodies (2B11G2 and 4E10D7). Quantitation of Sirius red staining (a), liver hydroxyproline content (b), liver function (c), liver weight (d) of different treatment groups are shown in comparison to untreated and negative controls. e. mRNA expression of ID1 were detected by quantitative PCR. *P<0.05.

FIG. 9. PK assay in normal mice (a) and ANIT rat model (b).

FIG. 10. Total anti-BMP6 concentration after single dose administration of antibody BMP9-2 in cynomolgus monkey (each line represents data from a single monkey).

FIG. 11. Total anti-BMP6 concentration during multiple-dose study of antibody BMP9-2 (MOR022962) in cynomolgus monkey.

DETAILED DESCRIPTION OF THE INVENTION

The present invention provides antibodies and antigen-binding fragments thereof that specifically bind to BMP9 protein, and pharmaceutical compositions, production methods, and methods of use of such antibodies and compositions.

BMP9 Antibodies and Antigen-Binding Fragments Thereof

The present invention provides antibodies and antigen-binding fragments thereof that specifically bind to human BMP9.

BMP9 signaling plays a role in the pathogenesis of liver fibrosis/cirrhosis and portal vein hypertension. BMP9 expression, serum levels, and signaling are increased in fibrotic conditions, e.g., in cirrhotic liver tissue. Without being bound by any particular theory, this disclosure suggests a BMP9 antagonist antibody as an anti-fibrotic therapy is expected to benefit patients with chronic liver disease and/or portal vein hypertension, e.g., with liver fibrosis, e.g., Nonalcoholic steatohepatitis- (NASH-), viral infection (e.g., HBV- or HCV-)-, alcohol, toxin-, or immune-induced liver fibrosis or cirrhosis.

Examples of such anti-human BMP9 antibodies are Antibodies BMP9-1, BMP9-2, BMP9-3, BMP9-4, BMP9-5, BMP9-6, BMP9-7, BMP9-8 and BMP9-9 whose sequences are listed in Table 1.

Antibodies BMP9-1, BMP9-2, BMP9-3, BMP9-4, BMP9-5, BMP9-6, BMP9-7, BMP9-8 and BMP9-9 all bind with high affinity to human BMP9, with high selectivity over human BMP7, human BMP10 and human BMP2. These antibodies also inhibit Smad1/5/8 phosphorylation and Id1 induction, and protect livers from BMP9-induced damage in an in vivo mouse model.

The BMP9 antagonist antibodies disclosed herein represent a novel therapeutic approach to safely improve or prevent the progression of liver diseases, e.g., liver fibrosis, cirrhosis or portal vein hypertension. Without being bound by any particular theory, this disclosure suggests that this may occur through the inhibition of BMP9 signaling.

Figures 1A, 1B:
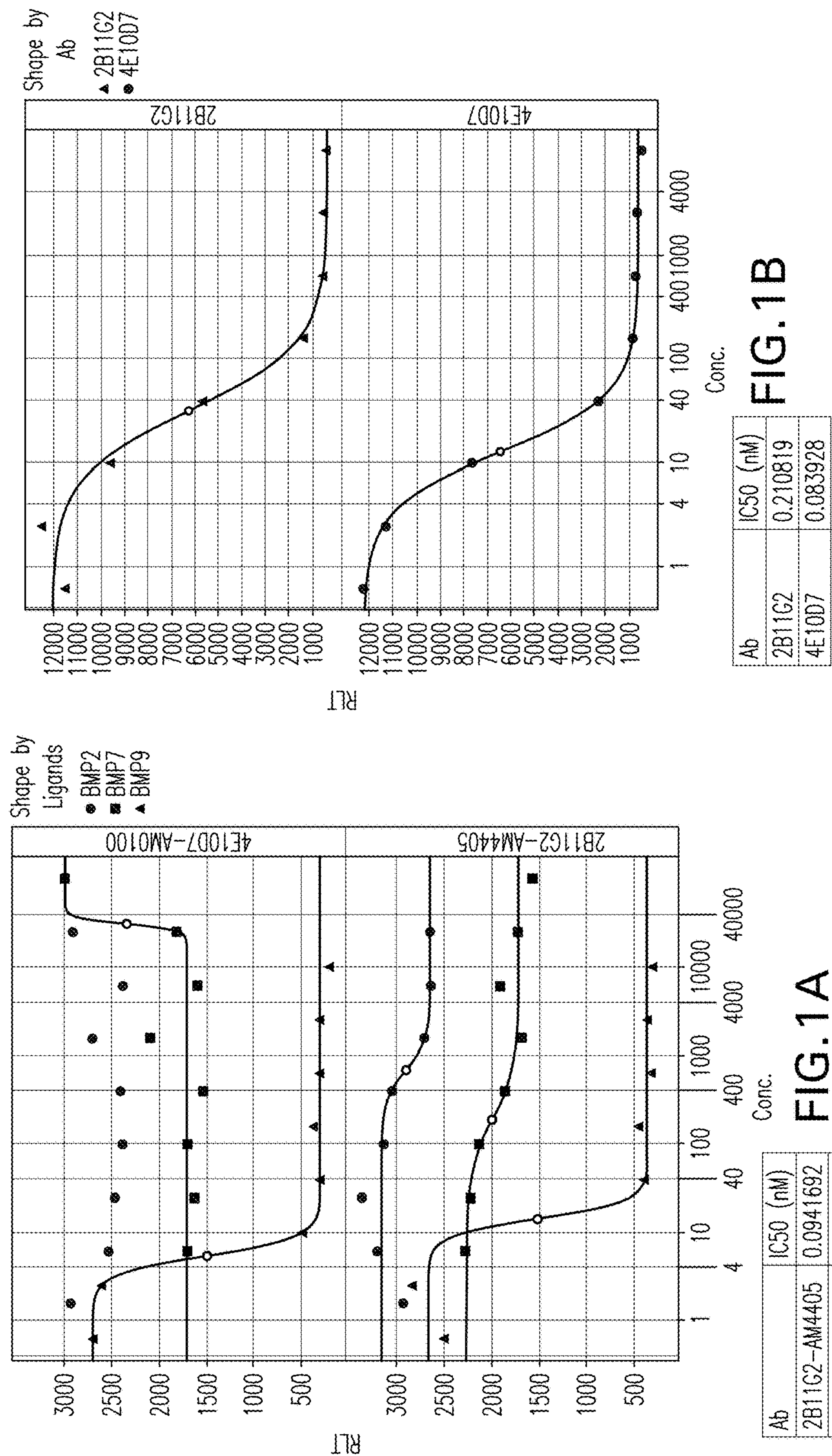
FIG. 1: In vitro activity test of anti-BMP9 antibodies generated by the hybridoma approach in an RGA assay a. Reducing curves and IC50 of hybridoma-generated BMP9 antibodies on human BMP2-, BMP7- and BMP9-induced RGA activity; b. Reducing curves and IC50 of hybridoma-generated BMP9 antibodies on rat BMP9-induced RGA activity.
Figures 2A, 2B:
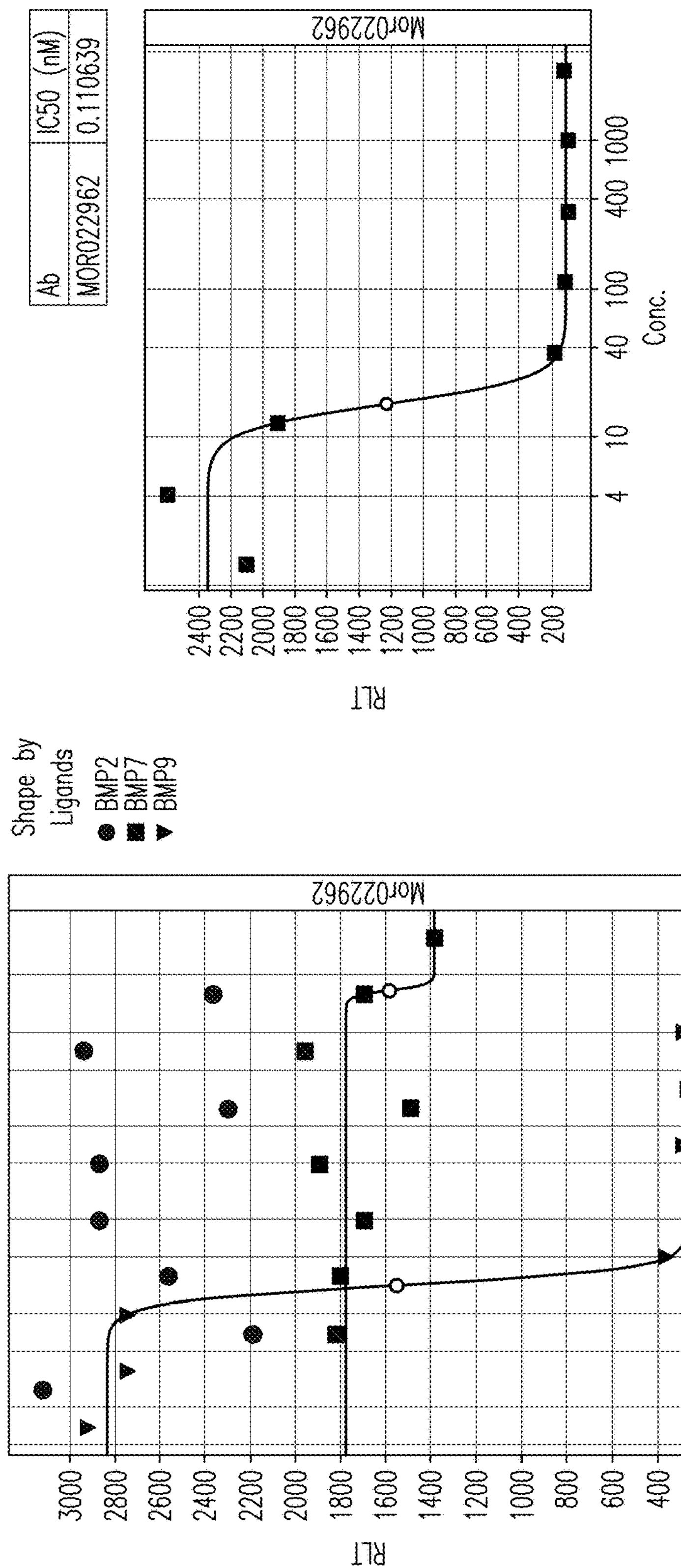
FIG. 2: In vitro activity test of anti-BMP9 antibodies generated by the phage display approach in an RGA assay a. Reducing curves and IC50 of phage display-generated BMP9 antibodies on human BMP2-, BMP7- and BMP9-induced RGA activity; b. Reducing curves and IC50 of phage display-generated BMP9 antibodies on rat BMP9-induced RGA activity.

In one embodiment, the present invention provides isolated antibodies or antigen-binding fragments thereof that bind with a 100-, 500- or 1000-fold higher affinity for human BMP9 protein, than to any of: human BMP2, BMP10 or human BMP7 protein. Specificity to BMP9 without binding to BMP7 is important: knock-out mice for BMP7 die after birth with kidney, eye and bone defects. As well, BMP7 is important in preventing progression of chronic heart disease associated with fibrosis. Therefore, cross-reactivity of an anti-BMP9 antibody with BMP7 is not desirable. Antibodies provided herein are specific to BMP9 over BMP7; See, for example, Table 5 and Table 7. FIG. 1*a* and FIG. 2*a* also show evidence for binding specificity to human BMP9 over human BMP2 and BMP7 proteins.

Antibodies of the invention include, but are not limited to, the human and humanized monoclonal antibodies isolated as described herein, including in the Examples.

Examples of such anti-human BMP9 antibodies are antibodies BMP9-1, BMP9-2, BMP9-3, BMP9-4, BMP9-5, BMP9-6, BMP9-7, BMP9-8 and BMP9-9 whose sequences are listed in Table 1.

Antibody BMP9-2 binds with high affinity for human BMP9 in an ELISA binding assay, and does not bind human BMP2, human BMP7 or human BMP10 (i.e., is selective, e.g., greater than 1000-fold, e.g., greater than 10,000-fold, for binding to human BMP9), i.e., has no detectable activity against human BMP2, BMP7 or BMP10. Antibody BMP9-2 also inhibits BMP9 binding to both ALKI and ActRIIB receptors in vitro. Binding of BMP9 to ALKI is inhibited maximally 59% and binding to ActRIIB is inhibited maximally 85%, as measured by competition ELISA. As well, a single 10 mg/kg treatment in mice led to suppression of $CCl_4$-induced pSmad1/5/8 (as measured by IHC and Western blot). As well, a single 10 mg/kg injection of Antibody BMP9-2 led to a decrease in BMP9-induced Id1 production and led to a rescue of BMP9-induced liver weight decrease.

Antibodies BMP9-1, BMP9-3 and BMP9-4 all show high specificity for human BMP9 protein compared to human BMP2, BMP10 or BMP7 protein. Additional details regarding the generation and characterization of the antibodies described herein are provided in the Examples.

The present invention provides antibodies that specifically bind BMP9 (e.g., human BMP9 protein), said antibodies comprising a VH domain listed in Table 1. The present invention also provides antibodies that specifically bind to BMP9 protein, said antibodies comprising a VH CDR having an amino acid sequence of any one of the VH CDRs listed in Table 1. In particular, the invention provides antibodies that specifically bind to BMP9 protein, said antibodies comprising (or alternatively, consisting of) one, two, three, four, five or more VH CDRs having an amino acid sequence of any of the VH CDRs listed in Table 1.

The invention also provides antibodies and antigen-binding fragments thereof that specifically bind to BMP9, said antibodies or antigen-binding fragments thereof comprising (or alternatively, consisting of) a VH amino acid sequence listed in Table 1, wherein no more than about 10 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP9, said antibodies or antigen-binding fragments thereof comprising (or alternatively, consisting of) a VH amino acid sequence listed in Table 1, wherein no more than 10 amino acids in a framework sequence (for example, a sequence which is not a CDR) have been mutated (wherein a mutation is, as various non-limiting examples, an addition, substitution or deletion).

The invention also provides antibodies and antigen-binding fragments thereof that specifically bind to BMP9, said antibodies or antigen-binding fragments thereof comprising (or alternatively, consisting of) a VH amino acid sequence listed in Table 1, wherein no more than about 20 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP9, said antibodies or antigen-binding fragments thereof comprising (or alternatively, consisting of) a VH amino acid sequence listed in Table 1, wherein no more than 20 amino acids in a framework sequence (for example, a sequence which is not a CDR) have been mutated (wherein a mutation is, as various non-limiting examples, an addition, substitution or deletion).

The invention also provides antibodies and antigen-binding fragments thereof that specifically bind to BMP9, said antibodies or antigen-binding fragments thereof comprising (or alternatively, consisting of) a VL amino acid sequence listed in Table 1, wherein no more than about 10 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP9, said antibodies or antigen-binding fragments thereof comprising (or alternatively, consisting of) a VL amino acid sequence listed in Table 1, wherein no more than 10 amino acids in a framework sequence (for example, a sequence which is not a CDR) have been mutated (wherein a mutation is, as various non-limiting examples, an addition, substitution or deletion).

The invention also provides antibodies and antigen-binding fragments thereof that specifically bind to BMP9, said antibodies or antigen-binding fragments thereof comprising (or alternatively, consisting of) a VL amino acid sequence listed in Table 1, wherein no more than about 20 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP9, said antibodies or antigen-binding fragments thereof comprising (or alternatively, consisting of) a VL amino acid sequence listed in Table 1, wherein no more than 20 amino acids in a framework sequence (for example, a sequence which is not a CDR) have been mutated (wherein a mutation is, as various non-limiting examples, an addition, substitution or deletion).

The present invention provides antibodies and antigen-binding fragments thereof that specifically bind to BMP9 protein, said antibodies or antigen-binding fragments thereof comprising a VL domain listed in Table 1. The present invention also provides antibodies and antigen-binding fragments thereof that specifically bind to BMP9 protein, said antibodies or antigen-binding fragments thereof comprising a VL CDR having an amino acid sequence of any one of the VL CDRs listed in Table 1. In particular, the invention provides antibodies and antigen-binding fragments thereof that specifically bind to BMP9 protein, said antibodies or antigen-binding fragments thereof comprising (or alternatively, consisting of) one, two, three or more VL CDRs having an amino acid sequence of any of the VL CDRs listed in Table 1.

Other antibodies and antigen-binding fragments thereof of the invention include amino acids that have been mutated, yet have at least 60, 70, 80, 90, 91, 92, 93, 94, 95, 96, 97, 98 or 99 percent identity in the CDR regions with the CDR regions depicted in the sequences described in Table 1. In one aspect, other antibodies and antigen-binding fragments thereof of the invention includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies and antigen-binding fragments thereof that specifically bind to BMP9 protein. Such nucleic acid sequences can be optimized for expression in mammalian cells (for example, Table 1 shows example nucleic acid sequences for the heavy chain and light chain of Antibodies BMP9-1, BMP9-2, BMP9-3, BMP9-5, BMP9-6, BMP9-7, BMP9-8 and BMP9-9).

TABLE 1

Examples of BMP9 Antibodies of the Present Invention

| Convention | Sequence Name | Sequence | SEQ ID NO: |
|---|---|---|---|
| | | Antibody BMP9-4: AM4405 | |
| (Kabat) | HCDR1 | SYNMH | 61 |
| (Kabat) | HCDR2 | LIYPGNAVTSYSQKFKD | 62 |
| (Kabat) | HCDR3 | DDYFRGGSYAMDY | 63 |
| (Chothia) | HCDR1 | GYTFRSY | 64 |
| (Chothia) | HCDR2 | YPGNAV | 65 |
| (Chothia) | HCDR3 | DDYFRGGSYAMDY | 66 |
| | VH | QVQLVQSGAEVKKPGASVKVSCKASGYTF RSYNMHWVRQAPGQGLEWMGLIYPGNAV TSYSQKFKDRVTMTVDKSTSTAYMELSSLR SEDTAVYYCAKDDYFRGGSYAMDYWGQG TTVTVSS | 67 |
| | DNA VH | CAAGTCCAGCTCGTCCAGTCCGGGGCCG AAGTCAAGAAGCCCGGAGCCAGCGTGAA AGTGTCCTGCAAGGCGTCAGGCTATACCT TCCGGTCGTACAACATGCACTGGGTCAGA CAGGCCCCAGGACAGGGGCTGGAATGGA TGGGCCTGATCTACCCGGGAAACGCTGTG ACTAGCTACTCCCAAAAGTTCAAGGATCG CGTGACGATGACCGTGGATAAGTCCACCT CAACCGCGTACATGGAGCTGTCCTCGCTG AGGTCGGAGGACACCGCAGTGTACTACT GCGCCAAGGACGACTACTTCCGGGGCGG TTCCTACGCCATGGACTACTGGGGACAGG GCACCACTGTGACTGTGTCCAGC | 68 |
| | Heavy Chain | QVQLVQSGAEVKKPGASVKVSCKASGYTF RSYNMHWVRQAPGQGLEWMGLIYPGNAV TSYSQKFKDRVTMTVDKSTSTAYMELSSLR SEDTAVYYCAKDDYFRGGSYAMDYWGQG TTVTVSSASTKGPSVFPLAPSSKSTSGGTAA LGCLVKDYFPEPVTVSWNSGALTSGVHTFP AVLQSSGLYSLSSVVTVPSSSLGTQTYICNV NHKPSNTKVDKRVEPKSCDKTHTCPPCPAP ELLGGPSVFLFPPKPKDTLMISRTPEVTCVV VDVSHEDPEVKFNWYVDGVEVHNAKTKP REEQYNSTYRVVSVLTVLHQDWLNGKEYK CKVSNKALPAPIEKTISKAKGQPREPQVYTL PPSREEMTKNQVSLTCLVKGFYPSDIAVEW ESNGQPENNYKTTPPVLDSDGSFFLYSKLT VDKSRWQQGNVFSCSVMHEALHNHYTQK SLSLSPGK | 69 |
| | DNA Heavy Chain | CAAGTCCAGCTCGTCCAGTCCGGGGCCG AAGTCAAGAAGCCCGGAGCCAGCGTGAA AGTGTCCTGCAAGGCGTCAGGCTATACCT TCCGGTCGTACAACATGCACTGGGTCAGA CAGGCCCCAGGACAGGGGCTGGAATGGA TGGGCCTGATCTACCCGGGAAACGCTGTG ACTAGCTACTCCCAAAAGTTCAAGGATCG CGTGACGATGACCGTGGATAAGTCCACCT | 70 |

TABLE 1-continued

Examples of BMP9 Antibodies of the Present Invention

| Convention | Sequence Name | Sequence | SEQ ID NO: |
|---|---|---|---|
| | | CAACCGCGTACATGGAGCTGTCCTCGCTG AGGTCGGAGGACACCGCAGTGTACTACT GCGCCAAGGACGACTACTTCCGGGGCGG TTCCTACGCCATGGACTACTGGGGACAGG GCACCACTGTGACTGTGTCCAGCGCTAGC ACCAAGGGCCCAAGTGTGTTTCCCCTGGC CCCCAGCAGCAAGTCTACTTCCGGCGGA ACTGCTGCCCTGGGTTGCCTGGTGAAGGA CTACTTCCCCGAGCCCGTGACAGTGTCCT GGAACTCTGGGGCTCTGACTTCCGGCGTG CACACCTTCCCCGCCGTGCTGCAGAGCAG CGGCCTGTACAGCCTGAGCAGCGTGGTG ACAGTGCCCTCCAGCTCTCTGGGAACCCA GACCTATATCTGCAACGTGAACCACAAG CCCAGCAACACCAAGGTGGACAAGAGAG TGGAGCCCAAGAGCTGCGACAAGACCCA CACCTGCCCCCCCTGCCCAGCTCCAGAAC TGCTGGGAGGGCCTTCCGTGTTCCTGTTC CCCCCCAAGCCCAAGGACACCCTGATGA TCAGCAGGACCCCCGAGGTGACCTGCGT GGTGGTGGACGTGTCCCACGAGGACCCA GAGGTGAAGTTCAACTGGTACGTGGACG GCGTGGAGGTGCACAACGCCAAGACCAA GCCCAGAGAGGAGCAGTACAACAGCACC TACAGGGTGGTGTCCGTGCTGACCGTGCT GCACCAGGACTGGCTGAACGGCAAAGAA TACAAGTGCAAAGTCTCCAACAAGGCCC TGCCAGCCCCAATCGAAAAGACAATCAG CAAGGCCAAGGGCCAGCCACGGGAGCCC CAGGTGTACACCCTGCCCCCCAGCCGGG AGGAGATGACCAAGAACCAGGTGTCCCT GACCTGTCTGGTGAAGGGCTTCTACCCCA GCGATATCGCCGTGGAGTGGGAGAGCAA CGGCCAGCCCGAGAACAACTACAAGACC ACCCCCCCAGTGCTGGACAGCGACGGCA GCTTCTTCCTGTACAGCAAGCTGACCGTG GACAAGTCCAGGTGGCAGCAGGGCAACG TGTTCAGCTGCAGCGTGATGCACGAGGCC CTGCACAACCACTACACCCAGAAGTCCCT GAGCCTGAGCCCCGGCAAG | |
| (Kabat) | LCDR1 | RASQSIRNNLH | 71 |
| (Kabat) | LCDR2 | YASQSIR | 72 |
| (Kabat) | LCDR3 | QQSHSWPYT | 73 |
| (Chothia) | LCDR1 | SQSIRNN | 74 |
| (Chothia) | LCDR2 | YAS | 75 |
| (Chothia) | LCDR3 | SHSWPY | 76 |
| | VL | EIVLTQSPDFQSVTPKEKVTITCRASQSIRNN LHWYQQKPDQSPKLLIKYASQSIRGVPSRF SGSGSGTDFTLTINSLEAEDAATYYCQQSH SWPYTFGGGTKVEIK | 77 |
| | DNA VL | GAAATTGTGCTGACCCAGAGCCCGGACTT CCAATCCGTGACTCCCAAGGAGAAGGTC ACAATCACGTGCAGAGCATCGCAGTCCA TCCGGAACAACTTGCACTGGTATCAACAG AAGCCCGACCAGTCCCCTAAGCTGCTGAT TAAGTACGCCAGCCAGTCGATCAGGGGG GTGCCATCACGGTTTAGCGGATCCGGATC AGGCACCGACTTCACTCTGACCATCAACT CCCTGGAGGCTGAAGATGCGGCCACCTA CTACTGCCAGCAGTCCCATTCGTGGCCGT ACACTTTCGGCGGCGGTACCAAAGTGGA AATCAAG | 78 |
| | Light Chain | EIVLTQSPDFQSVTPKEKVTITCRASQSIRNN LHWYQQKPDQSPKLLIKYASQSIRGVPSRF SGSGSGTDFTLTINSLEAEDAATYYCQQSH SWPYTFGGGTKVEIKRTVAAPSVFIFPPSDE QLKSGTASVVCLLNNFYPREAKVQWKVDN ALQSGNSQESVTEQDSKDSTYSLSSTLTLSK | 79 |

TABLE 1-continued

Examples of BMP9 Antibodies of the Present Invention

| Convention | Sequence Name | Sequence | SEQ ID NO: |
|---|---|---|---|
| | | ADYEKHKVYACEVTHQGLSSPVTKSFNRGEC | |
| | DNA Light Chain | GAAATTGTGCTGACCCAGAGCCCGGACTTCCAATCCGTGACTCCCAAGGAGAAGGTCACAATCACGTGCAGAGCATCGCAGTCCATCCGGAACAACTTGCACTGGTATCAACAGAAGCCCGACCAGTCCCCTAAGCTGCTGATTAAGTACGCCAGCCAGTCGATCAGGGGGGTGCCATCACGGTTTAGCGGATCCGGATCAGGCACCGACTTCACTCTGACCATCAACTCCCTGGAGGCTGAAGATGCGGCCACCTACTACTGCCAGCAGTCCCATTCGTGGCCGTACACTTTCGGCGGCGGTACCAAAGTGGAAATCAAGCGTACGGTGGCCGCTCCCAGCGTGTTCATCTTCCCCCCCAGCGACGAGCAGCTGAAGAGCGGCACCGCCAGCGTGGTGTGCCTGCTGAACAACTTCTACCCCCGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAGAAGCATAAGGTGTACGCCTGCGAGGTGACCCACCAGGGCCTGTCCAGCCCCGTGACCAAGAGCTTCAACAGGGGCGAGTGC | 80 |
| | | Antibody BMP9-1: AM0100 | |
| (Kabat) | HCDR1 | RYWMH | 1 |
| (Kabat) | HCDR2 | EINPSQGGTNYNEKFKS | 2 |
| (Kabat) | HCDR3 | GSNYGGLVY | 3 |
| (Chothia) | HCDR1 | GYTFTRY | 4 |
| (Chothia) | HCDR2 | NPSQGG | 5 |
| (Chothia) | HCDR3 | GSNYGGLVY | 6 |
| | VH | QVQLVQSGAEVKKPGASVKVSCKASGYTFTRYWMHWVRQAPGQGLEWMGEINPSQGGTNYNEKFKSRVTMTVDKSISTAYMELSRLRSDDTAVYYCAIGSNYGGLVYWGQGTLVTVSS | 7 |
| | DNA VH | CAAGTCCAGTTGGTCCAATCGGGCGCAGAAGTGAAAAAGCCGGGAGCCTCAGTGAAGGTGTCCTGCAAAGCGTCCGGCTATACTTTCACGCGCTACTGGATGCACTGGGTCAGACAGGCCCCGGGACAGGGTCTGGAATGGATGGGAGAGATTAATCCCAGCCAGGGAGGCACCAACTACAACGAGAAGTTCAAGTCCCGGGTCACCATGACCGTGGATAAGAGCATCAGCACTGCCTACATGGAGCTGTCCAGGCTGCGGTCGGACGACACCGCCGTGTACTACTGCGCCATCGGGTCAAACTACGGCGGACTGGTGTACTGGGGCCAGGGGACCCTCGTGACTGTGTCCTCG | 8 |
| | Heavy Chain | QVQLVQSGAEVKKPGASVKVSCKASGYTFTRYWMHWVRQAPGQGLEWMGEINPSQGGTNYNEKFKSRVTMTVDKSISTAYMELSRLRSDDTAVYYCAIGSNYGGLVYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 9 |

TABLE 1-continued

| Examples of BMP9 Antibodies of the Present Invention | | | |
|---|---|---|---|
| Convention | Sequence Name | Sequence | SEQ ID NO: |
| | DNA Heavy Chain | CAAGTCCAGTTGGTCCAATCGGGCGCAG<br>AAGTGAAAAAGCCGGGAGCCTCAGTGAA<br>GGTGTCCTGCAAAGCGTCCGGCTATACTT<br>TCACGCGCTACTGGATGCACTGGGTCAGA<br>CAGGCCCCGGGACAGGGTCTGGAATGGA<br>TGGGAGAGATTAATCCCAGCCAGGGAGG<br>CACCAACTACAACGAGAAGTTCAAGTCC<br>CGGGTCACCATGACCGTGGATAAGAGCA<br>TCAGCACTGCCTACATGGAGCTGTCCAGG<br>CTGCGGTCGGACGACACCGCCGTGTACTA<br>CTGCGCCATCGGGTCAAACTACGGCGGA<br>CTGGTGTACTGGGGCCAGGGGACCCTCGT<br>GACTGTGTCCTCGGCTAGCACCAAGGGCC<br>CAAGTGTGTTTCCCCTGGCCCCCAGCAGC<br>AAGTCTACTTCCGGCGGAACTGCTGCCCT<br>GGGTTGCCTGGTGAAGGACTACTTCCCCG<br>AGCCCGTGACAGTGTCCTGGAACTCTGGG<br>GCTCTGACTTCCGGCGTGCACACCTTCCC<br>CGCCGTGCTGCAGAGCAGCGGCCTGTAC<br>AGCCTGAGCAGCGTGGTGACAGTGCCCT<br>CCAGCTCTCTGGGAACCCAGACCTATATC<br>TGCAACGTGAACCACAAGCCCAGCAACA<br>CCAAGGTGGACAAGAGAGTGGAGCCCAA<br>GAGCTGCGACAAGACCCACACCTGCCCC<br>CCCTGCCCAGCTCCAGAACTGCTGGGAG<br>GGCCTTCCGTGTTCCTGTTCCCCCCCAAG<br>CCCAAGGACACCCTGATGATCAGCAGGA<br>CCCCCGAGGTGACCTGCGTGGTGGTGGA<br>CGTGTCCCACGAGGACCCAGAGGTGAAG<br>TTCAACTGGTACGTGGACGGCGTGGAGG<br>TGCACAACGCCAAGACCAAGCCCAGAGA<br>GGAGCAGTACAACAGCACCTACAGGGTG<br>GTGTCCGTGCTGACCGTGCTGCACCAGGA<br>CTGGCTGAACGGCAAAGAATACAAGTGC<br>AAAGTCTCCAACAAGGCCCTGCCAGCCC<br>CAATCGAAAAGACAATCAGCAAGGCCAA<br>GGGCCAGCCACGGGAGCCCCAGGTGTAC<br>ACCCTGCCCCCCAGCCGGGAGGAGATGA<br>CCAAGAACCAGGTGTCCCTGACCTGTCTG<br>GTGAAGGGCTTCTACCCCAGCGATATCGC<br>CGTGGAGTGGGAGAGCAACGGCCAGCCC<br>GAGAACAACTACAAGACCACCCCCCCAG<br>TGCTGGACAGCGACGGCAGCTTCTTCCTG<br>TACAGCAAGCTGACCGTGGACAAGTCCA<br>GGTGGCAGCAGGGCAACGTGTTCAGCTG<br>CAGCGTGATGCACGAGGCCCTGCACAAC<br>CACTACACCCAGAAGTCCCTGAGCCTGA<br>GCCCCGGCAAG | 10 |
| (Kabat) | LCDR1 | RASESLDNYGISFMN | 11 |
| (Kabat) | LCDR2 | AASNQGS | 12 |
| (Kabat) | LCDR3 | QQSKEVPRT | 13 |
| (Chothia) | LCDR1 | SESLDNYGISF | 14 |
| (Chothia) | LCDR2 | AAS | 15 |
| (Chothia) | LCDR3 | SKEVPR | 16 |
| | VL | EIVLTQSPATLSLSPGERATLSCRASESLDN<br>YGISFMNWFQQKPGQAPRFLIYAASNQGSG<br>IPARFSGSGSGTDFTLTISSLQPEDTAVYFCQ<br>QSKEVPRTFGGGTKVEIK | 17 |
| | DNA VL | GAAATTGTGCTGACCCAGTCCCCCGCGAC<br>GCTGTCACTGTCCCCTGGGGAGCGGGCTA<br>CCTTGTCCTGCCGCGCCTCCGAATCGCTC<br>GACAACTACGGCATCAGCTTCATGAACTG<br>GTTCCAGCAAAAGCCGGGACAGGCCCCA<br>CGGTTCCTGATCTACGCCGCATCGAACCA<br>GGGTTCAGGGATTCCCGCGAGGTTCTCGG<br>GATCTGGATCCGGCACCGACTTCACTCTG<br>ACAATCAGCAGCCTGCAGCCTGAAGATA | 18 |

TABLE 1-continued

Examples of BMP9 Antibodies of the Present Invention

| Convention | Sequence Name | Sequence | SEQ ID NO: |
|---|---|---|---|
| | | CCGCCGTGTACTTCTGCCAACAGTCCAAG<br>GAGGTCCCGCGGACTTTTGGCGGAGGCA<br>CCAAAGTGGAGATCAAG | |
| | Light Chain | EIVLTQSPATLSLSPGERATLSCRASESLDN<br>YGISFMNWFQQKPGQAPRFLIYAASNQGSG<br>IPARFSGSGSGTDFTLTISSLQPEDTAVYFCQ<br>QSKEVPRTFGGGTKVEIKRTVAAPSVFIFPP<br>SDEQLKSGTASVVCLLNNFYPREAKVQWK<br>VDNALQSGNSQESVTEQDSKDSTYSLSSTL<br>TLSKADYEKHKVYACEVTHQGLSSPVTKSF<br>NRGEC | 19 |
| | DNA Light Chain | GAAATTGTGCTGACCCAGTCCCCCGCGAC<br>GCTGTCACTGTCCCCTGGGGAGCGGGCTA<br>CCTTGTCCTGCCGCGCCTCCGAATCGCTC<br>GACAACTACGGCATCAGCTTCATGAACTG<br>GTTCCAGCAAAAGCCGGGACAGGCCCCA<br>CGGTTCCTGATCTACGCCGCATCGAACCA<br>GGGTTCAGGGATTCCCGCGAGGTTCTCGG<br>GATCTGGATCCGGCACCGACTTCACTCTG<br>ACAATCAGCAGCCTGCAGCCTGAAGATA<br>CCGCCGTGTACTTCTGCCAACAGTCCAAG<br>GAGGTCCCGCGGACTTTTGGCGGAGGCA<br>CCAAAGTGGAGATCAAGCGTACGGTGGC<br>CGCTCCCAGCGTGTTCATCTTCCCCCCCA<br>GCGACGAGCAGCTGAAGAGCGGCACCGC<br>CAGCGTGGTGTGCCTGCTGAACAACTTCT<br>ACCCCCGGGAGGCCAAGGTGCAGTGGAA<br>GGTGGACAACGCCCTGCAGAGCGGCAAC<br>AGCCAGGAGAGCGTCACCGAGCAGGACA<br>GCAAGGACTCCACCTACAGCCTGAGCAG<br>CACCCTGACCCTGAGCAAGGCCGACTAC<br>GAGAAGCATAAGGTGTACGCCTGCGAGG<br>TGACCCACCAGGGCCTGTCCAGCCCCGTG<br>ACCAAGAGCTTCAACAGGGGCGAGTGC | 20 |
| | | Antibody BMP9-2: MOR022962 | |
| (Kabat) | HCDR1 | SYAMS | 21 |
| (Kabat) | HCDR2 | ITLGTGHTHYADSVKG | 22 |
| (Kabat) | HCDR3 | GSYIIWSALDY | 23 |
| (Chothia) | HCDR1 | GFTFSSY | 24 |
| (Chothia) | HCDR2 | LGTGH | 25 |
| (Chothia) | HCDR3 | GSYIIWSALDY | 26 |
| | VH | QVQLLESGGGLVQPGGSLRLSCAASGFTFS<br>SYAMSWVRQAPGKGLEWVSITLGTGHTHY<br>ADSVKGRFTISRDNSKNTLYLQMNSLRAED<br>TAVYYCARGSYIIWSALDYWGQGTLVTVS<br>S | 27 |
| | DNA VH | CAAGTCCAGCTGCTCGAATCTGGCGGCG<br>GACTGGTGCAGCCCGGAGGCAGCCTGCG<br>GCTGTCGTGTGCCGCCTCCGGATTCACCT<br>TCTCATCCTACGCCATGTCCTGGGTCCGC<br>CAGGCACCGGGGAAGGGACTGGAATGGG<br>TGTCGATCACCCTGGGAACCGGGCACACT<br>CATTATGCGGACTCCGTGAAAGGGCGCTT<br>CACCATTTCCCGGGACAACAGCAAGAAC<br>ACTCTGTACTTGCAAATGAACTCCCTGAG<br>AGCCGAGGATACCGCTGTGTACTACTGCG<br>CGAGGGGCTCCTACATCATCTGGAGCGCC<br>CTGGACTACTGGGGACAGGGTACTCTCGT<br>GACCGTGTCGAGC | 28 |
| | Heavy Chain | QVQLLESGGGLVQPGGSLRLSCAASGFTFS<br>SYAMSWVRQAPGKGLEWVSITLGTGHTHY<br>ADSVKGRFTISRDNSKNTLYLQMN<br>TAVYYCARGSYIIWSALDYWGQGTLVTVS<br>SASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPSN<br>TKVDKRVEPKSCDKTHTCPPCPAPELLGGP<br>SVFLFPPKPKDTLMISRTPEVTCVVVDVSHE | 29 |

TABLE 1-continued

Examples of BMP9 Antibodies of the Present Invention

| Convention | Sequence Name | Sequence | SEQ ID NO: |
|---|---|---|---|
| | | DPEVKFNWYVDGVEVHNAKTKPREEQYN<br>STYRVVSVLTVLHQDWLNGKEYKCKVSN<br>KALPAPIEKTISKAKGQPREPQVYTLPPSRE<br>EMTKNQVSLTCLVKGFYPSDIAVEWESNG<br>QPENNYKTTPPVLDSDGSFFLYSKLTVDKS<br>RWQQGNVFSCSVMHEALHNHYTQKSLSLS<br>PGK | |
| | DNA Heavy Chain | CAAGTCCAGCTGCTCGAATCTGGCGGCG<br>GACTGGTGCAGCCCGGAGGCAGCCTGCG<br>GCTGTCGTGTGCCGCCTCCGGATTCACCT<br>TCTCATCCTACGCCATGTCCTGGGTCCGC<br>CAGGCACCGGGGAAGGGACTGGAATGGG<br>TGTCGATCACCCTGGGAACCGGGCACACT<br>CATTATGCGGACTCCGTGAAAGGGCGCTT<br>CACCATTTCCCGGGACAACAGCAAGAAC<br>ACTCTGTACTTGCAAATGAACTCCCTGAG<br>AGCCGAGGATACCGCTGTGTACTACTGCG<br>CGAGGGGCTCCTACATCATCTGGAGCGCC<br>CTGGACTACTGGGGACAGGGTACTCTCGT<br>GACCGTGTCGAGCGCTAGCACCAAGGGC<br>CCAAGTGTGTTTCCCCTGGCCCCCAGCAG<br>CAAGTCTACTTCCGGCGGAACTGCTGCCC<br>TGGGTTGCCTGGTGAAGGACTACTTCCCC<br>GAGCCCGTGACAGTGTCCTGGAACTCTGG<br>GGCTCTGACTTCCGGCGTGCACACCTTCC<br>CCGCCGTGCTGCAGAGCAGCGGCCTGTA<br>CAGCCTGAGCAGCGTGGTGACAGTGCCC<br>TCCAGCTCTCTGGGAACCCAGACCTATAT<br>CTGCAACGTGAACCACAAGCCCAGCAAC<br>ACCAAGGTGGACAAGAGAGTGGAGCCCA<br>AGAGCTGCGACAAGACCCACACCTGCCC<br>CCCCTGCCCAGCTCCAGAACTGCTGGGAG<br>GGCCTTCCGTGTTCCTGTTCCCCCCCAAG<br>CCCAAGGACACCCTGATGATCAGCAGGA<br>CCCCCGAGGTGACCTGCGTGGTGGTGGA<br>CGTGTCCCACGAGGACCCAGAGGTGAAG<br>TTCAACTGGTACGTGGACGGCGTGGAGG<br>TGCACAACGCCAAGACCAAGCCCAGAGA<br>GGAGCAGTACAACAGCACCTACAGGGTG<br>GTGTCCGTGCTGACCGTGCTGCACCAGGA<br>CTGGCTGAACGGCAAAGAATACAAGTGC<br>AAAGTCTCCAACAAGGCCCTGCCAGCCC<br>CAATCGAAAAGACAATCAGCAAGGCCAA<br>GGGCCAGCCACGGGAGCCCCAGGTGTAC<br>ACCCTGCCCCCCAGCCGGGAGGAGATGA<br>CCAAGAACCAGGTGTCCCTGACCTGTCTG<br>GTGAAGGGCTTCTACCCCAGCGATATCGC<br>CGTGGAGTGGGAGAGCAACGGCCAGCCC<br>GAGAACAACTACAAGACCACCCCCCCAG<br>TGCTGGACAGCGACGGCAGCTTCTTCCTG<br>TACAGCAAGCTGACCGTGGACAAGTCCA<br>GGTGGCAGCAGGGCAACGTGTTCAGCTG<br>CAGCGTGATGCACGAGGCCCTGCACAAC<br>CACTACACCCAGAAGTCCCTGAGCCTGA<br>GCCCCGGCAAG | 30 |
| (Kabat) | LCDR1 | RASQDIRSYLN | 31 |
| (Kabat) | LCDR2 | DASNLQS | 32 |
| (Kabat) | LCDR3 | QQSDTSPLT | 33 |
| (Chothia) | LCDR1 | SQDIRSY | 34 |
| (Chothia) | LCDR2 | DAS | 35 |
| (Chothia) | LCDR3 | SDTSPL | 36 |
| | VL | DIQMTQSPSSLSASVGDRVTITCRASQDIRS<br>YLNWYQQKPGKAPKLLIYDASNLQSGVPS<br>RFSGSGSGTDFTLTISSLQPEDFATYYCQQS<br>DTSPLTFGQGTKVEIK | 37 |
| | DNA VL | GACATCCAGATGACTCAGTCACCGTCATC<br>GCTGTCCGCCTCCGTGGGAGATCGGGTCA<br>CCATTACCTGTCGGGCATCCCAAGACATC<br>AGAAGCTACCTGAACTGGTATCAGCAGA | 38 |

TABLE 1-continued

Examples of BMP9 Antibodies of the Present Invention

| Convention | Sequence Name | Sequence | SEQ ID NO: |
| --- | --- | --- | --- |
| | | AGCCTGGGAAGGCCCCCAAGCTGCTCAT<br>CTACGACGCGAGCAACCTCCAGTCTGGA<br>GTGCCCAGCCGCTTCTCCGGTTCGGGGTC<br>CGGCACTGACTTTACCCTGACCATTTCGT<br>CCCTGCAACCGGAGGATTTCGCTACCTAC<br>TACTGCCAGCAGTCCGACACAAGCCCACT<br>GACGTTCGGCCAGGGCACCAAAGTGGAA<br>ATCAAG | |
| | Light Chain | DIQMTQSPSSLSASVGDRVTITCRASQDIRS<br>YLNWYQQKPGKAPKLLIYDASNLQSGVPS<br>RFSGSGSGTDFTLTISSLQPEDFATYYCQQS<br>DTSPLTFGQGTKVEIKRTVAAPSVFIFPPSDE<br>QLKSGTASVVCLLNNFYPREAKVQWKVDN<br>ALQSGNSQESVTEQDSKDSTYSLSSTLTLSK<br>ADYEKHKVYACEVTHQGLSSPVTKSFNRG<br>EC | 39 |
| | DNA Light Chain | GACATCCAGATGACTCAGTCACCGTCATC<br>GCTGTCCGCCTCCGTGGGAGATCGGGTCA<br>CCATTACCTGTCGGGCATCCCAAGACATC<br>AGAAGCTACCTGAACTGGTATCAGCAGA<br>AGCCTGGGAAGGCCCCCAAGCTGCTCAT<br>CTACGACGCGAGCAACCTCCAGTCTGGA<br>GTGCCCAGCCGCTTCTCCGGTTCGGGGTC<br>CGGCACTGACTTTACCCTGACCATTTCGT<br>CCCTGCAACCGGAGGATTTCGCTACCTAC<br>TACTGCCAGCAGTCCGACACAAGCCCACT<br>GACGTTCGGCCAGGGCACCAAAGTGGAA<br>ATCAAGCGTACGGTGGCCGCTCCCAGCGT<br>GTTCATCTTCCCCCCCAGCGACGAGCAGC<br>TGAAGAGCGGCACCGCCAGCGTGGTGTG<br>CCTGCTGAACAACTTCTACCCCCGGGAGG<br>CCAAGGTGCAGTGGAAGGTGGACAACGC<br>CCTGCAGAGCGGCAACAGCCAGGAGAGC<br>GTCACCGAGCAGGACAGCAAGGACTCCA<br>CCTACAGCCTGAGCAGCACCCTGACCCTG<br>AGCAAGGCCGACTACGAGAAGCATAAGG<br>TGTACGCCTGCGAGGTGACCCACCAGGG<br>CCTGTCCAGCCCCGTGACCAAGAGCTTCA<br>ACAGGGGCGAGTGC | 40 |
| Antibody BMP9-3: MOR023795 | | | |
| (Kabat) | HCDR1 | TYWIG | 41 |
| (Kabat) | HCDR2 | IIYPEGSYTTYSPSFQG | 42 |
| (Kabat) | HCDR3 | GKRVDASSFDY | 43 |
| (Chothia) | HCDR1 | GYSFTTY | 44 |
| (Chothia) | HCDR2 | YPEGSY | 45 |
| (Chothia) | HCDR3 | GKRVDASSFDY | 46 |
| | VH | EVQLVQSGAEVKKPGESLKISCKGSGYSFT<br>TYWIGWVRQMPGKGLEWMGIIYPEGSYTT<br>YSPSFQGQVTISADKSISTAYLQWSSLKASD<br>TAMYYCARGKRVDASSFDYWGQGTLVTV<br>SS | 47 |
| | DNA VH | GAAGTGCAGCTCGTGCAGTCCGGAGCGG<br>AAGTGAAAAAGCCGGGAGAATCCCTGAA<br>GATTAGCTGCAAGGGGTCGGGGTACTCA<br>TTCACGACTTACTGGATCGGCTGGGTCCG<br>GCAGATGCCCGGAAAGGGACTGGAGTGG<br>ATGGGCATCATCTACCCGGAGGGCAGCT<br>ACACCACCTACTCCCCATCGTTTCAAGGA<br>CAGGTCACCATTTCCGCCGATAAGTCAAT<br>CAGCACCGCCTACCTCCAATGGTCGAGCC<br>TGAAGGCCTCCGACACTGCTATGTACTAT<br>TGCGCGAGAGGGAAGCGCGTGGACGCCT<br>CCTCCTTCGACTACTGGGGCCAGGGCACT<br>CTGGTCACCGTGTCCTCG | 48 |
| | Heavy Chain | EVQLVQSGAEVKKPGESLKISCKGSGYSFT<br>TYWIGWVRQMPGKGLEWMGIIYPEGSYTT<br>YSPSFQGQVTISADKSISTAYLQWSSLKASD<br>TAMYYCARGKRVDASSFDYWGQGTLVTV | 49 |

TABLE 1-continued

| Examples of BMP9 Antibodies of the Present Invention | | | |
|---|---|---|---|
| Convention | Sequence Name | Sequence | SEQ ID NO: |
| | | SSASTKGPSVFPLAPSSKSTSGGTAALGCLV<br>KDYFPEPVTVSWNSGALTSGVHTFPAVLQS<br>SGLYSLSSVVTVPSSSLGTQTYICNVNHKPS<br>NTKVDKRVEPKSCDKTHTCPPCPAPELLGG<br>PSVFLFPPKPKDTLMISRTPEVTCVVVDVSH<br>EDPEVKFNWYVDGVEVHNAKTKPREEQY<br>NSTYRVVSVLTVLHQDWLNGKEYKCKVS<br>NKALPAPIEKTISKAKGQPREPQVYTLPPSR<br>EEMTKNQVSLTCLVKGFYPSDIAVEWESN<br>GQPENNYKTTPPVLDSDGSFFLYSKLTVDK<br>SRWQQGNVFSCSVMHEALHNHYTQKSLSL<br>SPGK | |
| | DNA Heavy Chain | GAAGTGCAGCTCGTGCAGTCCGGAGCGG<br>AAGTGAAAAAGCCGGGAGAATCCCTGAA<br>GATTAGCTGCAAGGGGTCGGGGTACTCA<br>TTCACGACTTACTGGATCGGCTGGGTCCG<br>GCAGATGCCCGGAAAGGGACTGGAGTGG<br>ATGGGCATCATCTACCCGGAGGGCAGCT<br>ACACCACCTACTCCCCATCGTTTCAAGGA<br>CAGGTCACCATTTCCGCCGATAAGTCAAT<br>CAGCACCGCCTACCTCCAATGGTCGAGCC<br>TGAAGGCCTCCGACACTGCTATGTACTAT<br>TGCGCGAGAGGGAAGCGCGTGGACGCCT<br>CCTCCTTCGACTACTGGGGCCAGGGCACT<br>CTGGTCACCGTGTCCTCGGCTAGCACCAA<br>GGGCCCAAGTGTGTTTCCCCTGGCCCCCA<br>GCAGCAAGTCTACTTCCGGCGGAACTGCT<br>GCCCTGGGTTGCCTGGTGAAGGACTACTT<br>CCCCGAGCCCGTGACAGTGTCCTGGAACT<br>CTGGGGCTCTGACTTCCGGCGTGCACACC<br>TTCCCCGCCGTGCTGCAGAGCAGCGGCCT<br>GTACAGCCTGAGCAGCGTGGTGACAGTG<br>CCCTCCAGCTCTCTGGGAACCCAGACCTA<br>TATCTGCAACGTGAACCACAAGCCCAGC<br>AACACCAAGGTGGACAAGAGAGTGGAGC<br>CCAAGAGCTGCGACAAGACCCACACCTG<br>CCCCCCCTGCCCAGCTCCAGAACTGCTGG<br>GAGGGCCTTCCGTGTTCCTGTTCCCCCCC<br>AAGCCCAAGGACACCCTGATGATCAGCA<br>GGACCCCCGAGGTGACCTGCGTGGTGGT<br>GGACGTGTCCCACGAGGACCCAGAGGTG<br>AAGTTCAACTGGTACGTGGACGGCGTGG<br>AGGTGCACAACGCCAAGACCAAGCCCAG<br>AGAGGAGCAGTACAACAGCACCTACAGG<br>GTGGTGTCCGTGCTGACCGTGCTGCACCA<br>GGACTGGCTGAACGGCAAAGAATACAAG<br>TGCAAAGTCTCCAACAAGGCCCTGCCAG<br>CCCCAATCGAAAAGACAATCAGCAAGGC<br>CAAGGGCCAGCCACGGGAGCCCCAGGTG<br>TACACCCTGCCCCCCAGCCGGGAGGAGA<br>TGACCAAGAACCAGGTGTCCCTGACCTGT<br>CTGGTGAAGGGCTTCTACCCCAGCGATAT<br>CGCCGTGGAGTGGGAGAGCAACGGCCAG<br>CCCGAGAACAACTACAAGACCACCCCCC<br>CAGTGCTGGACAGCGACGGCAGCTTCTTC<br>CTGTACAGCAAGCTGACCGTGGACAAGT<br>CCAGGTGGCAGCAGGGCAACGTGTTCAG<br>CTGCAGCGTGATGCACGAGGCCCTGCAC<br>AACCACTACACCCAGAAGTCCCTGAGCCT<br>GAGCCCCGGCAAG | 50 |
| (Kabat) | LCDR1 | SGSSSNIGDNYVS | 51 |
| (Kabat) | LCDR2 | RNNKRPS | 52 |
| (Kabat) | LCDR3 | SSTDKEHLV | 53 |
| (Chothia) | LCDR1 | SSSNIGDNY | 54 |
| (Chothia) | LCDR2 | RNN | 55 |
| (Chothia) | LCDR3 | TDKEHL | 56 |
| | VL | QSVLTQPPSVSGAPGQRVTISCSGSSSNIGD<br>NYVSWYQQLPGTAPKLLIYRNNKRPSGVP | 57 |

TABLE 1-continued

| Convention | Sequence Name | Sequence | SEQ ID NO: |
|---|---|---|---|
| | | Examples of BMP9 Antibodies of the Present Invention | |
| | | DRFSGSKSGTSASLAITGLQAEDEADYYCS STDKEHLVFGGGTKLTVL | |
| | DNA VL | CAATCAGTGCTGACCCAGCCCCCGAGCGT GTCCGGTGCCCCTGGACAGCGGGTCACC ATCTCCTGTTCCGGCTCCTCAAGCAATAT TGGCGACAACTATGTGTCGTGGTACCAGC AGCTGCCGGGGACGGCCCCTAAGCTGCT GATCTACCGGAACAACAAAAGGCCATCC GGCGTGCCGGATAGATTCTCGGGCTCGA AGTCCGGAACTAGCGCCAGCCTGGCAAT CACCGGGCTGCAGGCTGAAGATGAGGCG GACTACTACTGCTCCTCTACCGACAAGGA ACACCTGGTGTTCGGAGGAGGAACCAAG CTGACTGTGCTG | 58 |
| | Light Chain | QSVLTQPPSVSGAPGQRVTISCSGSSSNIGD NYVSWYQQLPGTAPKLLIYRNNKRPSGVP DRFSGSKSGTSASLAITGLQAEDEADYYCS STDKEHLVFGGGTKLTVLGQPKAAPSVTLF PPSSEELQANKATLVCLISDFYPGAVTVAW KADSSPVKAGVETTTPSKQSNNKYAASSYL SLTPEQWKSHRSYSCQVTHEGSTVEKTVAP TECS | 59 |
| | DNA Light Chain | CAATCAGTGCTGACCCAGCCCCCGAGCGT GTCCGGTGCCCCTGGACAGCGGGTCACC ATCTCCTGTTCCGGCTCCTCAAGCAATAT TGGCGACAACTATGTGTCGTGGTACCAGC AGCTGCCGGGGACGGCCCCTAAGCTGCT GATCTACCGGAACAACAAAAGGCCATCC GGCGTGCCGGATAGATTCTCGGGCTCGA AGTCCGGAACTAGCGCCAGCCTGGCAAT CACCGGGCTGCAGGCTGAAGATGAGGCG GACTACTACTGCTCCTCTACCGACAAGGA ACACCTGGTGTTCGGAGGAGGAACCAAG CTGACTGTGCTGGGACAGCCTAAGGCTGC CCCCAGCGTGACCCTGTTCCCCCCCAGCA GCGAGGAGCTGCAGGCCAACAAGGCCAC CCTGGTGTGCCTGATCAGCGACTTCTACC CAGGCGCCGTGACCGTGGCCTGGAAGGC CGACAGCAGCCCCGTGAAGGCCGGCGTG GAGACCACCACCCCCAGCAAGCAGAGCA ACAACAAGTACGCCGCCAGCAGCTACCT GAGCCTGACCCCCGAGCAGTGGAAGAGC CACAGGTCCTACAGCTGCCAGGTGACCC ACGAGGGCAGCACCGTGGAAAAGACCGT GGCCCCAACCGAGTGCAGC | 60 |
| | | Antibody BMP9-5: AM1900 | |
| (Kabat) | HCDR1 | RYWMH | 81 |
| (Kabat) | HCDR2 | EINPSQGGTNYNEKFKS | 82 |
| (Kabat) | HCDR3 | GANYGGLVY | 83 |
| (Chothia) | HCDR1 | GYTFTRY | 84 |
| (Chothia) | HCDR2 | NPSQGG | 85 |
| (Chothia) | HCDR3 | GANYGGLVY | 86 |
| | VH | QVQLVQSGAEVKKPGASVKVSCKASGYTF TRYWMHWVRQAPGQGLEWMGEINPSQGG TNYNEKFKSRVTMTVDKSISTAYMELSRLR SDDTAVYYCAIGANYGGLVYWGQGTLVT VSS | 87 |
| | DNA VH | CAAGTCCAGCTCGTCCAATCGGGCGCCG AAGTGAAAAAGCCGGGAGCCTCCGTGAA GGTGTCCTGCAAGGCGTCCGGTTATACTT TCACGCGCTACTGGATGCACTGGGTCAGA CAGGCTCCGGGACAGGGACTGGAATGGA TGGGAGAGATTAACCCCTCCCAGGGAGG CACCAACTACAACGAGAAGTTCAAGTCC CGGGTCACCATGACCGTGGATAAGTCCAT CAGCACTGCCTACATGGAGCTGTCCCGCC TGCGGTCGGACGACACCGCCGTGTACTAC TGCGCCATCGGGGCGAACTACGGCGGAC | 88 |

TABLE 1-continued

Examples of BMP9 Antibodies of the Present Invention

| Convention | Sequence Name | Sequence | SEQ ID NO: |
|---|---|---|---|
| | | TGGTGTACTGGGGCCAGGGGACTCTCGTG ACTGTGTCCTCG | |
| | Heavy Chain | QVQLVQSGAEVKKPGASVKVSCKASGYTF TRYWMHWVRQAPGQGLEWMGEINPSQGG TNYNEKFKSRVTMTVDKSISTAYMELSRLR SDDTAVYYCAIGANYGGLVYWGQGTLVT VSSASTKGPSVFPLAPSSKSTSGGTAALGCL VKDYFPEPVTVSWNSGALTSGVHTFPAVL QSSGLYSLSSVVTVPSSSLGTQTYICNVNHK PSNTKVDKRVEPKSCDKTHTCPPCPAPELL GGPSVFLFPPKPKDTLMISRTPEVTCVVVD VSHEDPEVKFNWYVDGVEVHNAKTKPREE QYNSTYRVVSVLTVLHQDWLNGKEYKCK VSNKALPAPIEKTISKAKGQPREPQVYTLPP SREEMTKNQVSLTCLVKGFYPSDIAVEWES NGQPENNYKTTPPVLDSDGSFFLYSKLTVD KSRWQQGNVFSCSVMHEALHNHYTQKSLS LSPGK | 89 |
| | DNA Heavy Chain | CAAGTCCAGCTCGTCCAATCGGGCGCCG AAGTGAAAAAGCCGGGAGCCTCCGTGAA GGTGTCCTGCAAGGCGTCCGGTTATACTT TCACGCGCTACTGGATGCACTGGGTCAGA CAGGCTCCGGGACAGGGACTGGAATGGA TGGGAGAGATTAACCCCTCCCAGGGAGG CACCAACTACAACGAGAAGTTCAAGTCC CGGGTCACCATGACCGTGGATAAGTCCAT CAGCACTGCCTACATGGAGCTGTCCCGCC TGCGGTCGGACGACACCGCCGTGTACTAC TGCGCCATCGGGGCGAACTACGGCGGAC TGGTGTACTGGGGCCAGGGGACTCTCGTG ACTGTGTCCTCGGCTAGCACCAAGGGCCC AAGTGTGTTTCCCCTGGCCCCCAGCAGCA AGTCTACTTCCGGCGGAACTGCTGCCCTG GGTTGCCTGGTGAAGGACTACTTCCCCGA GCCCGTGACAGTGTCCTGGAACTCTGGGG CTCTGACTTCCGGCGTGCACACCTTCCCC GCCGTGCTGCAGAGCAGCGGCCTGTACA GCCTGAGCAGCGTGGTGACAGTGCCCTCC AGCTCTCTGGGAACCCAGACCTATATCTG CAACGTGAACCACAAGCCCAGCAACACC AAGGTGGACAAGAGAGTGGAGCCCAAGA GCTGCGACAAGACCCACACCTGCCCCCCC TGCCCAGCTCCAGAACTGCTGGGAGGGC CTTCCGTGTTCCTGTTCCCCCCCAAGCCC AAGGACACCCTGATGATCAGCAGGACCC CCGAGGTGACCTGCGTGGTGGTGGACGT GTCCCACGAGGACCCAGAGGTGAAGTTC AACTGGTACGTGGACGGCGTGGAGGTGC ACAACGCCAAGACCAAGCCCAGAGAGGA GCAGTACAACAGCACCTACAGGGTGGTG TCCGTGCTGACCGTGCTGCACCAGGACTG GCTGAACGGCAAAGAATACAAGTGCAAA GTCTCCAACAAGGCCCTGCCAGCCCCAAT CGAAAAGACAATCAGCAAGGCCAAGGGC CAGCCACGGGAGCCCCAGGTGTACACCC TGCCCCCCAGCCGGGAGGAGATGACCAA GAACCAGGTGTCCCTGACCTGTCTGGTGA AGGGCTTCTACCCCAGCGATATCGCCGTG GAGTGGGAGAGCAACGGCCAGCCCGAGA ACAACTACAAGACCACCCCCCCAGTGCT GGACAGCGACGGCAGCTTCTTCCTGTACA GCAAGCTGACCGTGGACAAGTCCAGGTG GCAGCAGGGCAACGTGTTCAGCTGCAGC GTGATGCACGAGGCCCTGCACAACCACT ACACCCAGAAGTCCCTGAGCCTGAGCCC CGGCAAG | 90 |
| (Kabat) | LCDR1 | RASESLDNYGISFMN | 91 |
| (Kabat) | LCDR2 | AASNQGS | 92 |
| (Kabat) | LCDR3 | QQSKEVPRT | 93 |
| (Chothia) | LCDR1 | SESLDNYGISF | 94 |

TABLE 1-continued

Examples of BMP9 Antibodies of the Present Invention

| Convention | Sequence Name | Sequence | SEQ ID NO: |
|---|---|---|---|
| (Chothia) | LCDR2 | AAS | 95 |
| (Chothia) | LCDR3 | SKEVPR | 96 |
| | VL | EIVLTQSPATLSLSPGERATLSCRASESLDN YGISFMNWFQQKPGQAPRFLIYAASNQGSG IPARFSGSGSGTDFTLTISSLQPEDTAVYFCQ QSKEVPRTFGGGTKVEIK | 97 |
| | DNA VL | GAAATTGTGCTGACCCAGTCCCCCGCGAC GCTGTCACTGTCCCCTGGGGAGCGGGCTA CCTTGTCCTGCCGCGCCTCCGAATCGCTC GACAACTACGGCATCAGCTTCATGAACTG GTTCCAGCAAAAGCCGGGACAGGCCCCA CGGTTCCTGATCTACGCCGCATCGAACCA GGGTTCAGGGATTCCCGCGAGGTTCTCGG GATCTGGATCCGGCACCGACTTCACTCTG ACAATCAGCAGCCTGCAGCCTGAAGATA CCGCCGTGTACTTCTGCCAACAGTCCAAG GAGGTCCCGCGGACTTTTGGCGGAGGCA CCAAAGTGGAGATCAAG | 98 |
| | Light Chain | EIVLTQSPATLSLSPGERATLSCRASESLDN YGISFMNWFQQKPGQAPRFLIYAASNQGSG IPARFSGSGSGTDFTLTISSLQPEDTAVYFCQ QSKEVPRTFGGGTKVEIKRTVAAPSVFIFPP SDEQLKSGTASVVCLLNNFYPREAKVQWK VDNALQSGNSQESVTEQDSKDSTYSLSSTL TLSKADYEKHKVYACEVTHQGLSSPVTKSF NRGEC | 99 |
| | DNA Light Chain | GAAATTGTGCTGACCCAGTCCCCCGCGAC GCTGTCACTGTCCCCTGGGGAGCGGGCTA CCTTGTCCTGCCGCGCCTCCGAATCGCTC GACAACTACGGCATCAGCTTCATGAACTG GTTCCAGCAAAAGCCGGGACAGGCCCCA CGGTTCCTGATCTACGCCGCATCGAACCA GGGTTCAGGGATTCCCGCGAGGTTCTCGG GATCTGGATCCGGCACCGACTTCACTCTG ACAATCAGCAGCCTGCAGCCTGAAGATA CCGCCGTGTACTTCTGCCAACAGTCCAAG GAGGTCCCGCGGACTTTTGGCGGAGGCA CCAAAGTGGAGATCAAGCGTACGGTGGC CGCTCCCAGCGTGTTCATCTTCCCCCCCA GCGACGAGCAGCTGAAGAGCGGCACCGC CAGCGTGGTGTGCCTGCTGAACAACTTCT ACCCCCGGGAGGCCAAGGTGCAGTGGAA GGTGGACAACGCCCTGCAGAGCGGCAAC AGCCAGGAGAGCGTCACCGAGCAGGACA GCAAGGACTCCACCTACAGCCTGAGCAG CACCCTGACCCTGAGCAAGGCCGACTAC GAGAAGCATAAGGTGTACGCCTGCGAGG TGACCCACCAGGGCCTGTCCAGCCCCGTG ACCAAGAGCTTCAACAGGGGCGAGTGC | 100 |
| | | Antibody BMP9-6: MOR022965 | |
| (Kabat) | HCDR1 | SYAIS | 101 |
| (Kabat) | HCDR2 | HIIPHWGHARYAQKFQG | 102 |
| (Kabat) | HCDR3 | SASSLPHFHWFDY | 103 |
| (Chothia) | HCDR1 | GGTFSSY | 104 |
| (Chothia) | HCDR2 | IPHWGH | 105 |
| (Chothia) | HCDR3 | SASSLPHFHWFDY | 106 |
| | VH | QVQLVQSGAEVKKPGSSVKVSCKASGGTF SSYAISWVRQAPGQGLEWMGHIIPHWGHA RYAQKFQGRVTITADESTSTAYMELSSLRS EDTAVYYCARSASSLPHFHWFDYWGQGTL VTVSS | 107 |
| | DNA VH | CAAGTCCAACTCGTGCAGTCTGGAGCAG AAGTCAAGAAGCCGGGCTCAAGCGTGAA GGTGTCCTGCAAAGCCAGCGGAGGGACC TTCTCCTCCTATGCCATCTCATGGGTCAG ACAGGCCCCGGGCCAGGGCCTGGAATGG ATGGGTCACATCATCCCCCATTGGGGACA | 108 |

TABLE 1-continued

Examples of BMP9 Antibodies of the Present Invention

| Convention | Sequence Name | Sequence | SEQ ID NO: |
|---|---|---|---|
| | | CGCGCGCTACGCCCAGAAGTTTCAGGGC CGCGTGACTATTACCGCGGACGAAAGCA CTTCCACCGCCTACATGGAGCTGTCCTCC CTGCGGTCGGAGGACACCGCAGTGTACT ACTGCGCCCGGTCGGCTTCGTCCCTGCCA CACTTCCACTGGTTCGATTACTGGGGACA GGGAACCCTGGTCACTGTGTCCAGC | |
| | Heavy Chain | QVQLVQSGAEVKKPGSSVKVSCKASGGTF SSYAISWVRQAPGQGLEWMGHIIPHWGHA RYAQKFQGRVTITADESTSTAYMELSSLRS EDTAVYYCARSASSLPHFHWFDYWGQGTL VTVSSASTKGPSVFPLAPSSKSTSGGTAALG CLVKDYFPEPVTVSWNSGALTSGVHTFPAV LQSSGLYSLSSVVTVPSSSLGTQTYICNVNH KPSNTKVDKRVEPKSCDKTHTCPPCPAPEL LGGPSVFLFPPKPKDTLMISRTPEVTCVVVD VSHEDPEVKFNWYVDGVEVHNAKTKPREE QYNSTYRVVSVLTVLHQDWLNGKEYKCK VSNKALPAPIEKTISKAKGQPREPQVYTLPP SREEMTKNQVSLTCLVKGFYPSDIAVEWES NGQPENNYKTTPPVLDSDGSFFLYSKLTVD KSRWQQGNVFSCSVMHEALHNHYTQKSLS LSPGK | 109 |
| | DNA Heavy Chain | CAAGTCCAACTCGTGCAGTCTGGAGCAG AAGTCAAGAAGCCGGGCTCAAGCGTGAA GGTGTCCTGCAAAGCCAGCGGAGGGACC TTCTCCTCCTATGCCATCTCATGGGTCAG ACAGGCCCCGGGCCAGGGCCTGGAATGG ATGGGTCACATCATCCCCCATTGGGGACA CGCGCGCTACGCCCAGAAGTTTCAGGGC CGCGTGACTATTACCGCGGACGAAAGCA CTTCCACCGCCTACATGGAGCTGTCCTCC CTGCGGTCGGAGGACACCGCAGTGTACT ACTGCGCCCGGTCGGCTTCGTCCCTGCCA CACTTCCACTGGTTCGATTACTGGGGACA GGGAACCCTGGTCACTGTGTCCAGCGCTA GCACCAAGGGCCCAAGTGTGTTTCCCCTG GCCCCCAGCAGCAAGTCTACTTCCGGCGG AACTGCTGCCCTGGGTTGCCTGGTGAAGG ACTACTTCCCCGAGCCCGTGACAGTGTCC TGGAACTCTGGGGCTCTGACTTCCGGCGT GCACACCTTCCCCGCCGTGCTGCAGAGCA GCGGCCTGTACAGCCTGAGCAGCGTGGT GACAGTGCCCTCCAGCTCTCTGGGAACCC AGACCTATATCTGCAACGTGAACCACAA GCCCAGCAACACCAAGGTGGACAAGAGA GTGGAGCCCAAGAGCTGCGACAAGACCC ACACCTGCCCCCCCTGCCCAGCTCCAGAA CTGCTGGGAGGGCCTTCCGTGTTCCTGTT CCCCCCCAAGCCCAAGGACACCCTGATG ATCAGCAGGACCCCCGAGGTGACCTGCG TGGTGGTGGACGTGTCCCACGAGGACCC AGAGGTGAAGTTCAACTGGTACGTGGAC GGCGTGGAGGTGCACAACGCCAAGACCA AGCCCAGAGAGGAGCAGTACAACAGCAC CTACAGGGTGGTGTCCGTGCTGACCGTGC TGCACCAGGACTGGCTGAACGGCAAAGA ATACAAGTGCAAAGTCTCCAACAAGGCC CTGCCAGCCCCAATCGAAAAGACAATCA GCAAGGCCAAGGGCCAGCCACGGGAGCC CCAGGTGTACACCCTGCCCCCCAGCCGGG AGGAGATGACCAAGAACCAGGTGTCCCT GACCTGTCTGGTGAAGGGCTTCTACCCCA GCGATATCGCCGTGGAGTGGGAGAGCAA CGGCCAGCCCGAGAACAACTACAAGACC ACCCCCCCAGTGCTGGACAGCGACGGCA GCTTCTTCCTGTACAGCAAGCTGACCGTG GACAAGTCCAGGTGGCAGCAGGGCAACG TGTTCAGCTGCAGCGTGATGCACGAGGCC CTGCACAACCACTACACCCAGAAGTCCCT GAGCCTGAGCCCCGGCAAG | 110 |
| (Kabat) | LCDR1 | RASQDINNYLN | 111 |
| (Kabat) | LCDR2 | AASRLQS | 112 |

TABLE 1-continued

| Examples of BMP9 Antibodies of the Present Invention | | | |
|---|---|---|---|
| Convention | Sequence Name | Sequence | SEQ ID NO: |
| (Kabat) | LCDR3 | QQRDTTPWT | 113 |
| (Chothia) | LCDR1 | SQDINNY | 114 |
| (Chothia) | LCDR2 | AAS | 115 |
| (Chothia) | LCDR3 | RDTTPW | 116 |
| | VL | DIQMTQSPSSLSASVGDRVTITCRASQDINNYLNWYQQKPGKAPKLLIYAASRLQSGVPSRFSGSGSGTDFTLTISSLQPEDFATYYCQQRDTTPWTFGQGTKVEIK | 117 |
| | DNA VL | GATATCCAGATGACTCAGTCCCCATCCTCCCTGTCGGCCTCCGTGGGCGATCGGGTCACTATTACGTGCCGCGCCAGCCAGGACATTAACAACTACCTGAACTGGTATCAACAGAAGCCGGGGAAGGCCCCTAAGCTGCTGATCTACGCTGCAAGCCGGTTGCAGTCAGGAGTGCCCTCAAGGTTCTCCGGTTCCGGATCGGGCACCGACTTCACCCTGACCATCAGCAGCCTCCAGCCGGAGGACTTTGCGACCTACTACTGTCAGCAAAGAGACACCACCCCCTGGACATTCGGACAGGGCACCAAAGTGGAAATCAAG | 118 |
| | Light Chain | DIQMTQSPSSLSASVGDRVTITCRASQDINNYLNWYQQKPGKAPKLLIYAASRLQSGVPSRFSGSGSGTDFTLTISSLQPEDFATYYCQQRDTTPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 119 |
| | DNA Light Chain | GATATCCAGATGACTCAGTCCCCATCCTCCCTGTCGGCCTCCGTGGGCGATCGGGTCACTATTACGTGCCGCGCCAGCCAGGACATTAACAACTACCTGAACTGGTATCAACAGAAGCCGGGGAAGGCCCCTAAGCTGCTGATCTACGCTGCAAGCCGGTTGCAGTCAGGAGTGCCCTCAAGGTTCTCCGGTTCCGGATCGGGCACCGACTTCACCCTGACCATCAGCAGCCTCCAGCCGGAGGACTTTGCGACCTACTACTGTCAGCAAAGAGACACCACCCCCTGGACATTCGGACAGGGCACCAAAGTGGAAATCAAGCGTACGGTGGCCGCTCCCAGCGTGTTCATCTTCCCCCCCAGCGACGAGCAGCTGAAGAGCGGCACCGCCAGCGTGGTGTGCCTGCTGAACAACTTCTACCCCCGGGAGGCCAAGGTGCAGTGGAAGGTGGACAACGCCCTGCAGAGCGGCAACAGCCAGGAGAGCGTCACCGAGCAGGACAGCAAGGACTCCACCTACAGCCTGAGCAGCACCCTGACCCTGAGCAAGGCCGACTACGAGAAGCATAAGGTGTACGCCTGCGAGGTGACCCACCAGGGCCTGTCCAGCCCCGTGACCAAGAGCTTCAACAGGGGCGAGTGC | 120 |
| Antibody BMP9-7: MOR023787 | | | |
| (Kabat) | HCDR1 | SAWMS | 121 |
| (Kabat) | HCDR2 | HIKSKTYGGTIDYAAPVKG | 122 |
| (Kabat) | HCDR3 | VGGYYGYGYAFAY | 123 |
| (Chothia) | HCDR1 | GFTFSSA | 124 |
| (Chothia) | HCDR2 | KSKTYGGT | 125 |
| (Chothia) | HCDR3 | VGGYYGYGYAFAY | 126 |
| | VH | QVQLVESGGGLVKPGGSLRLSCAASGFTFSSAWMSWVRQAPGKGLEWVGHIKSKTYGGTIDYAAPVKGRFTISRDDSKNTLYLQMNSLKTEDTAVYYCARVGGYYGYGYAFAYWGQGTLVTVSS | 127 |

TABLE 1-continued

| Examples of BMP9 Antibodies of the Present Invention | | | |
|---|---|---|---|
| Convention | Sequence Name | Sequence | SEQ ID NO: |
| | DNA VH | CAAGTCCAGCTCGTCGAATCCGGTGGCG GACTCGTGAAGCCGGGAGGATCCCTGCG GCTGTCCTGCGCCGCCTCCGGGTTCACTT TTTCCTCCGCATGGATGTCATGGGTCCGC CAGGCCCCCGGGAAGGGTCTGGAATGGG TCGGGCACATCAAGTCAAAGACCTACGG CGGCACCATTGACTACGCCGCCCCAGTGA AAGGAAGGTTCACTATCTCGCGGGACGA CAGCAAGAACACCCTGTATCTGCAAATG AACAGCCTCAAGACCGAGGATACTGCGG TGTACTACTGCGCAAGAGTGGGCGGATA CTACGGTTACGGCTACGCTTTCGCGTACT GGGGACAGGGCACCCTCGTGACCGTGTC GAGC | 128 |
| | Heavy Chain | QVQLVESGGGLVKPGGSLRLSCAASGFTFS SAWMSWVRQAPGKGLEWVGHIKSKTYGG TIDYAAPVKGRFTISRDDSKNTLYLQMNSL KTEDTAVYYCARVGGYYGYGYAFAYWGQ GTLVTVSSASTKGPSVFPLAPSSKSTSGGTA ALGCLVKDYFPEPVTVSWNSGALTSGVHT FPAVLQSSGLYSLSSVVTVPSSSLGTQTYIC NVNHKPSNTKVDKRVEPKSCDKTHTCPPCP APELLGGPSVFLFPPKPKDTLMISRTPEVTC VVVDVSHEDPEVKFNWYVDGVEVHNAKT KPREEQYNSTYRVVSVLTVLHQDWLNGKE YKCKVSNKALPAPIEKTISKAKGQPREPQV YTLPPSREEMTKNQVSLTCLVKGFYPSDIA VEWESNGQPENNYKTTPPVLDSDGSFFLYS KLTVDKSRWQQGNVFSCSVMHEALHNHY TQKSLSLSPGK | 129 |
| SEQ ID NO: | DNA Heavy Chain | CAAGTCCAGCTCGTCGAATCCGGTGGCG GACTCGTGAAGCCGGGAGGATCCCTGCG GCTGTCCTGCGCCGCCTCCGGGTTCACTT TTTCCTCCGCATGGATGTCATGGGTCCGC CAGGCCCCCGGGAAGGGTCTGGAATGGG TCGGGCACATCAAGTCAAAGACCTACGG CGGCACCATTGACTACGCCGCCCCAGTGA AAGGAAGGTTCACTATCTCGCGGGACGA CAGCAAGAACACCCTGTATCTGCAAATG AACAGCCTCAAGACCGAGGATACTGCGG TGTACTACTGCGCAAGAGTGGGCGGATA CTACGGTTACGGCTACGCTTTCGCGTACT GGGGACAGGGCACCCTCGTGACCGTGTC GAGCGCTAGCACCAAGGGCCCAAGTGTG TTTCCCCTGGCCCCCAGCAGCAAGTCTAC TTCCGGCGGAACTGCTGCCCTGGGTTGCC TGGTGAAGGACTACTTCCCCGAGCCCGTG ACAGTGTCCTGGAACTCTGGGGCTCTGAC TTCCGGCGTGCACACCTTCCCCGCCGTGC TGCAGAGCAGCGGCCTGTACAGCCTGAG CAGCGTGGTGACAGTGCCCTCCAGCTCTC TGGGAACCCAGACCTATATCTGCAACGTG AACCACAAGCCCAGCAACACCAAGGTGG ACAAGAGAGTGGAGCCCAAGAGCTGCGA CAAGACCCACACCTGCCCCCCCTGCCCAG CTCCAGAACTGCTGGGAGGGCCTTCCGTG TTCCTGTTCCCCCCCAAGCCCAAGGACAC CCTGATGATCAGCAGGACCCCCGAGGTG ACCTGCGTGGTGGTGGACGTGTCCCACGA GGACCCAGAGGTGAAGTTCAACTGGTAC GTGGACGGCGTGGAGGTGCACAACGCCA AGACCAAGCCCAGAGAGGAGCAGTACAA CAGCACCTACAGGGTGGTGTCCGTGCTGA CCGTGCTGCACCAGGACTGGCTGAACGG CAAAGAATACAAGTGCAAAGTCTCCAAC AAGGCCCTGCCAGCCCCAATCGAAAAGA CAATCAGCAAGGCCAAGGGCCAGCCACG GGAGCCCCAGGTGTACACCCTGCCCCCCA GCCGGGAGGAGATGACCAAGAACCAGGT GTCCCTGACCTGTCTGGTGAAGGGCTTCT ACCCCAGCGATATCGCCGTGGAGTGGGA GAGCAACGGCCAGCCCGAGAACAACTAC AAGACCACCCCCCCAGTGCTGGACAGCG ACGGCAGCTTCTTCCTGTACAGCAAGCTG | 130 |

TABLE 1-continued

| Examples of BMP9 Antibodies of the Present Invention | | | |
|---|---|---|---|
| Convention | Sequence Name | Sequence | SEQ ID NO: |
| | | ACCGTGGACAAGTCCAGGTGGCAGCAGG GCAACGTGTTCAGCTGCAGCGTGATGCAC GAGGCCCTGCACAACCACTACACCCAGA AGTCCCTGAGCCTGAGCCCCGGCAAG | |
| (Kabat) | LCDR1 | SGDNIGDKYVS | 131 |
| (Kabat) | LCDR2 | DDNKRPS | 132 |
| (Kabat) | LCDR3 | SSTASKSFNV | 133 |
| (Chothia) | LCDR1 | DNIGDKY | 134 |
| (Chothia) | LCDR2 | DDN | 135 |
| (Chothia) | LCDR3 | TASKSFN | 136 |
| | VL | SYELTQPLSVSVALGQTARITCSGDNIGDK YVSWYQQKPGQAPVLVIYDDNKRPSGIPER FSGSNSGNTATLTISRAQAGDEADYYCSST ASKSFNVFGGGTKLTVL | 137 |
| | DNA VL | AGCTACGAACTCACCCAGCCTCTGTCCGT GTCCGTCGCGCTGGGACAGACTGCTCGCA TCACTTGCTCCGGCGACAACATCGGGGAC AAATACGTGTCGTGGTACCAGCAGAAGC CGGGCCAAGCCCCCGTGCTGGTCATCTAT GACGATAACAAGCGGCCATCGGGCATTC CGGAGAGATTCAGCGGTTCCAACAGCGG AAACACTGCCACCCTGACCATCAGCAGG GCACAGGCCGGGGATGAGGCCGACTACT ACTGCTCATCCACCGCCTCCAAGTCATTC AATGTGTTCGGAGGCGGCACCAAGCTGA CCGTGCTC | 138 |
| | Light Chain | SYELTQPLSVSVALGQTARITCSGDNIGDK YVSWYQQKPGQAPVLVIYDDNKRPSGIPER FSGSNSGNTATLTISRAQAGDEADYYCSST ASKSFNVFGGGTKLTVLGQPKAAPSVTLFP PSSEELQANKATLVCLISDFYPGAVTVAWK ADSSPVKAGVETTTPSKQSNNKYAASSYLS LTPEQWKSHRSYSCQVTHEGSTVEKTVAPT ECS | 139 |
| | DNA Light Chain | AGCTACGAACTCACCCAGCCTCTGTCCGT GTCCGTCGCGCTGGGACAGACTGCTCGCA TCACTTGCTCCGGCGACAACATCGGGGAC AAATACGTGTCGTGGTACCAGCAGAAGC CGGGCCAAGCCCCCGTGCTGGTCATCTAT GACGATAACAAGCGGCCATCGGGCATTC CGGAGAGATTCAGCGGTTCCAACAGCGG AAACACTGCCACCCTGACCATCAGCAGG GCACAGGCCGGGGATGAGGCCGACTACT ACTGCTCATCCACCGCCTCCAAGTCATTC AATGTGTTCGGAGGCGGCACCAAGCTGA CCGTGCTCGGTCAACCTAAGGCTGCCCCC AGCGTGACCCTGTTCCCCCCCAGCAGCGA GGAGCTGCAGGCCAACAAGGCCACCCTG GTGTGCCTGATCAGCGACTTCTACCCAGG CGCCGTGACCGTGGCCTGGAAGGCCGAC AGCAGCCCCGTGAAGGCCGGCGTGGAGA CCACCACCCCCAGCAAGCAGAGCAACAA CAAGTACGCCGCCAGCAGCTACCTGAGC CTGACCCCCGAGCAGTGGAAGAGCCACA GGTCCTACAGCTGCCAGGTGACCCACGA GGGCAGCACCGTGGAAAAGACCGTGGCC CCAACCGAGTGCAGC | 140 |
| Antibody BMP9-8: MOR023793 | | | |
| (Kabat) | HCDR1 | SYYMN | 141 |
| (Kabat) | HCDR2 | WINPVQGNTNYAQKFQG | 142 |
| (Kabat) | HCDR3 | NYFDV | 143 |
| (Chothia) | HCDR1 | GYTFTSY | 144 |
| (Chothia) | HCDR2 | NPVQGN | 145 |

TABLE 1-continued

Examples of BMP9 Antibodies of the Present Invention

| Convention | Sequence Name | Sequence | SEQ ID NO: |
|---|---|---|---|
| (Chothia) | HCDR3 | NYFDV | 146 |
| | VH | QVQLVQSGAEVKKPGASVKVSCKASGYTF TSYYMNWVRQAPGQGLEWMGWINPVQG NTNYAQKFQGRVTMTRDTSISTAYMELSR LRSEDTAVYYCARNYFDVWGQGTLVTVSS | 147 |
| | DNA VH | CAAGTCCAGCTCGTCCAATCCGGTGCTGA AGTCAAGAAGCCGGGAGCCAGCGTGAAA GTGTCCTGCAAGGCCTCCGGGTACACCTT CACCTCCTACTACATGAACTGGGTCAGAC AGGCCCCGGGCCAGGGCCTGGAGTGGAT GGGATGGATCAATCCAGTGCAGGGAAAC ACTAACTACGCGCAGAAGTTCCAGGGTC GCGTGACCATGACTCGGGACACTAGCATT TCCACGGCCTACATGGAGCTGTCAAGGCT GCGGTCGGAAGATACCGCGGTGTATTACT GCGCCCGCAACTACTTCGACGTGTGGGG ACAGGGAACCCTTGTGACCGTGTCCAGC | 148 |
| | Heavy Chain | QVQLVQSGAEVKKPGASVKVSCKASGYTF TSYYMNWVRQAPGQGLEWMGWINPVQG NTNYAQKFQGRVTMTRDTSISTAYMELSR LRSEDTAVYYCARNYFDVWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPSN TKVDKRVEPKSCDKTHTCPPCPAPELLGGP SVFLFPPKPKDTLMISRTPEVTCVVVDVSHE DPEVKFNWYVDGVEVHNAKTKPREEQYN STYRVVSVLTVLHQDWLNGKEYKCKVSN KALPAPIEKTISKAKGQPREPQVYTLPPSRE EMTKNQVSLTCLVKGFYPSDIAVEWESNG QPENNYKTTPPVLDSDGSFFLYSKLTVDKS RWQQGNVFSCSVMHEALHNHYTQKSLSLS PGK | 149 |
| | DNA Heavy Chain | CAAGTCCAGCTCGTCCAATCCGGTGCTGA AGTCAAGAAGCCGGGAGCCAGCGTGAAA GTGTCCTGCAAGGCCTCCGGGTACACCTT CACCTCCTACTACATGAACTGGGTCAGAC AGGCCCCGGGCCAGGGCCTGGAGTGGAT GGGATGGATCAATCCAGTGCAGGGAAAC ACTAACTACGCGCAGAAGTTCCAGGGTC GCGTGACCATGACTCGGGACACTAGCATT TCCACGGCCTACATGGAGCTGTCAAGGCT GCGGTCGGAAGATACCGCGGTGTATTACT GCGCCCGCAACTACTTCGACGTGTGGGG ACAGGGAACCCTTGTGACCGTGTCCAGC GCTAGCACCAAGGGCCCAAGTGTGTTTCC CCTGGCCCCCAGCAGCAAGTCTACTTCCG GCGGAACTGCTGCCCTGGGTTGCCTGGTG AAGGACTACTTCCCCGAGCCCGTGACAGT GTCCTGGAACTCTGGGGCTCTGACTTCCG GCGTGCACACCTTCCCCGCCGTGCTGCAG AGCAGCGGCCTGTACAGCCTGAGCAGCG TGGTGACAGTGCCCTCCAGCTCTCTGGGA ACCCAGACCTATATCTGCAACGTGAACCA CAAGCCCAGCAACACCAAGGTGGACAAG AGAGTGGAGCCCAAGAGCTGCGACAAGA CCCACACCTGCCCCCCCTGCCCAGCTCCA GAACTGCTGGGAGGGCCTTCCGTGTTCCT GTTCCCCCCCAAGCCCAAGGACACCCTGA TGATCAGCAGGACCCCCGAGGTGACCTG CGTGGTGGTGGACGTGTCCCACGAGGAC CCAGAGGTGAAGTTCAACTGGTACGTGG ACGGCGTGGAGGTGCACAACGCCAAGAC CAAGCCCAGAGAGGAGCAGTACAACAGC ACCTACAGGGTGGTGTCCGTGCTGACCGT GCTGCACCAGGACTGGCTGAACGGCAAA GAATACAAGTGCAAAGTCTCCAACAAGG CCCTGCCAGCCCCAATCGAAAAGACAAT CAGCAAGGCCAAGGGCCAGCCACGGGAG CCCCAGGTGTACACCCTGCCCCCCAGCCG GGAGGAGATGACCAAGAACCAGGTGTCC CTGACCTGTCTGGTGAAGGGCTTCTACCC CAGCGATATCGCCGTGGAGTGGGAGAGC AACGGCCAGCCCGAGAACAACTACAAGA | 150 |

TABLE 1-continued

Examples of BMP9 Antibodies of the Present Invention

| Convention | Sequence Name | Sequence | SEQ ID NO: |
|---|---|---|---|
| | | CCACCCCCCCAGTGCTGGACAGCGACGG CAGCTTCTTCCTGTACAGCAAGCTGACCG TGGACAAGTCCAGGTGGCAGCAGGGCAA CGTGTTCAGCTGCAGCGTGATGCACGAG GCCCTGCACAACCACTACACCCAGAAGT CCCTGAGCCTGAGCCCCGGCAAG | |
| (Kabat) | LCDR1 | RASQTISNFLA | 151 |
| (Kabat) | LCDR2 | AASNLQS | 152 |
| (Kabat) | LCDR3 | QQLYAESIT | 153 |
| (Chothia) | LCDR1 | SQTISNF | 154 |
| (Chothia) | LCDR2 | AAS | 155 |
| (Chothia) | LCDR3 | LYAESI | 156 |
| | VL | DIQMTQSPSSLSASVGDRVTITCRASQTISN FLAWYQQKPGKAPKLLIYAASNLQSGVPSR FSGSGSGTDFTLTISSLQPEDFAVYYCQQLY AESITFGQGTKVEIK | 157 |
| | DNA VL | GATATCCAGATGACCCAGAGCCCATCATC CCTGTCGGCCTCCGTGGGCGACAGAGTG ACCATTACTTGCCGGGCATCACAGACGAT CTCCAACTTTCTGGCCTGGTATCAGCAGA AGCCGGGGAAGGCGCCCAAGCTGCTCAT CTACGCTGCCTCCAACCTCCAATCCGGAG TGCCTAGCCGGTTCAGCGGCTCGGGATCC GGGACTGACTTCACCCTGACTATCTCGAG CCTGCAGCCGGAGGACTTCGCGGTGTACT ACTGTCAGCAACTGTACGCCGAATCCATC ACATTCGGACAGGGCACCAAAGTGGAGA TTAAG | 158 |
| | Light Chain | DIQMTQSPSSLSASVGDRVTITCRASQTISN FLAWYQQKPGKAPKLLIYAASNLQSGVPSR FSGSGSGTDFTLTISSLQPEDFAVYYCQQLY AESITFGQGTKVEIKRTVAAPSVFIFPPSDEQ LKSGTASVVCLLNNFYPREAKVQWKVDNA LQSGNSQESVTEQDSKDSTYSLSSTLTLSKA DYEKHKVYACEVTHQGLSSPVTKSFNRGE C | 159 |
| | DNA Light Chain | GATATCCAGATGACCCAGAGCCCATCATC CCTGTCGGCCTCCGTGGGCGACAGAGTG ACCATTACTTGCCGGGCATCACAGACGAT CTCCAACTTTCTGGCCTGGTATCAGCAGA AGCCGGGGAAGGCGCCCAAGCTGCTCAT CTACGCTGCCTCCAACCTCCAATCCGGAG TGCCTAGCCGGTTCAGCGGCTCGGGATCC GGGACTGACTTCACCCTGACTATCTCGAG CCTGCAGCCGGAGGACTTCGCGGTGTACT ACTGTCAGCAACTGTACGCCGAATCCATC ACATTCGGACAGGGCACCAAAGTGGAGA TTAAGCGTACGGTGGCCGCTCCCAGCGTG TTCATCTTCCCCCCCAGCGACGAGCAGCT GAAGAGCGGCACCGCCAGCGTGGTGTGC CTGCTGAACAACTTCTACCCCCGGGAGGC CAAGGTGCAGTGGAAGGTGGACAACGCC CTGCAGAGCGGCAACAGCCAGGAGAGCG TCACCGAGCAGGACAGCAAGGACTCCAC CTACAGCCTGAGCAGCACCCTGACCCTGA GCAAGGCCGACTACGAGAAGCATAAGGT GTACGCCTGCGAGGTGACCCACCAGGGC CTGTCCAGCCCCGTGACCAAGAGCTTCAA CAGGGGCGAGTGC | 160 |
| | | Antibody BMP9-9: MOR023796 | |
| (Kabat) | HCDR1 | DYAIH | 161 |
| (Kabat) | HCDR2 | GIIPFFGTAYYAQKFQG | 162 |
| (Kabat) | HCDR3 | RIVSDSVAVQYRHAFDP | 163 |
| (Chothia) | HCDR1 | GGTFSDY | 164 |

TABLE 1-continued

Examples of BMP9 Antibodies of the Present Invention

| Convention | Sequence Name | Sequence | SEQ ID NO: |
|---|---|---|---|
| (Chothia) | HCDR2 | IPFFGT | 165 |
| (Chothia) | HCDR3 | RIVSDSVAVQYRHAFDP | 166 |
| | VH | QVQLVQSGAEVKKPGSSVKVSCKASGGTF SDYAIHWVRQAPGQGLEWMGGIIPFFGTA YYAQKFQGRVTITADESTSTAYMELSSLRS EDTAVYYCARRIVSDSVAVQYRHAFDPWG QGTLVTVSS | 167 |
| | DNA VH | CAAGTGCAACTCGTCCAGTCTGGTGCCGA AGTCAAGAAGCCAGGATCCTCGGTGAAA GTGTCCTGCAAGGCCTCCGGGGGAACCTT TTCCGACTACGCCATCCACTGGGTCCGCC AAGCACCGGGACAGGGCCTGGAATGGAT GGGTGGCATTATCCCCTTCTTCGGGACTG CTTACTATGCGCAGAAGTTCCAGGGAAG AGTGACGATTACCGCCGACGAGAGCACC TCCACCGCCTACATGGAACTGAGCTCACT GAGGTCGGAGGATACTGCGGTGTACTAC TGCGCCCGCCGGATCGTGTCGGATTCCGT GGCCGTGCAGTACCGGCATGCCTTCGACC CGTGGGGCCAGGGAACCCTGGTCACTGT GTCATCC | 168 |
| | Heavy Chain | QVQLVQSGAEVKKPGSSVKVSCKASGGTF SDYAIHWVRQAPGQGLEWMGGIIPFFGTA YYAQKFQGRVTITADESTSTAYMELSSLRS EDTAVYYCARRIVSDSVAVQYRHAFDPWG QGTLVTVSSASTKGPSVFPLAPSSKSTSGGT AALGCLVKDYFPEPVTVSWNSGALTSGVH TFPAVLQSSGLYSLSSVVTVPSSSLGTQTYI CNVNHKPSNTKVDKRVEPKSCDKTHTCPP CPAPELLGGPSVFLFPPKPKDTLMISRTPEV TCVVVDVSHEDPEVKFNWYVDGVEVHNA KTKPREEQYNSTYRVVSVLTVLHQDWLNG KEYKCKVSNKALPAPIEKTISKAKGQPREP QVYTLPPSREEMTKNQVSLTCLVKGFYPSD IAVEWESNGQPENNYKTTPPVLDSDGSFFL YSKLTVDKSRWQQGNVFSCSVMHEALHN HYTQKSLSLSPGK | 169 |
| | DNA Heavy Chain | CAAGTGCAACTCGTCCAGTCTGGTGCCGA AGTCAAGAAGCCAGGATCCTCGGTGAAA GTGTCCTGCAAGGCCTCCGGGGGAACCTT TTCCGACTACGCCATCCACTGGGTCCGCC AAGCACCGGGACAGGGCCTGGAATGGAT GGGTGGCATTATCCCCTTCTTCGGGACTG CTTACTATGCGCAGAAGTTCCAGGGAAG AGTGACGATTACCGCCGACGAGAGCACC TCCACCGCCTACATGGAACTGAGCTCACT GAGGTCGGAGGATACTGCGGTGTACTAC TGCGCCCGCCGGATCGTGTCGGATTCCGT GGCCGTGCAGTACCGGCATGCCTTCGACC CGTGGGGCCAGGGAACCCTGGTCACTGT GTCATCCGCTAGCACCAAGGGCCCAAGT GTGTTTCCCCTGGCCCCCAGCAGCAAGTC TACTTCCGGCGGAACTGCTGCCCTGGGTT GCCTGGTGAAGGACTACTTCCCCGAGCCC GTGACAGTGTCCTGGAACTCTGGGGCTCT GACTTCCGGCGTGCACACCTTCCCCGCCG TGCTGCAGAGCAGCGGCCTGTACAGCCT GAGCAGCGTGGTGACAGTGCCCTCCAGC TCTCTGGGAACCCAGACCTATATCTGCAA CGTGAACCACAAGCCCAGCAACACCAAG GTGGACAAGAGAGTGGAGCCCAAGAGCT GCGACAAGACCCACACCTGCCCCCCCTGC CCAGCTCCAGAACTGCTGGGAGGGCCTTC CGTGTTCCTGTTCCCCCCCAAGCCCAAGG ACACCCTGATGATCAGCAGGACCCCCGA GGTGACCTGCGTGGTGGTGGACGTGTCCC ACGAGGACCCAGAGGTGAAGTTCAACTG GTACGTGGACGGCGTGGAGGTGCACAAC GCCAAGACCAAGCCCAGAGAGGAGCAGT ACAACAGCACCTACAGGGTGGTGTCCGT GCTGACCGTGCTGCACCAGGACTGGCTG AACGGCAAAGAATACAAGTGCAAAGTCT CCAACAAGGCCCTGCCAGCCCCAATCGA | 170 |

TABLE 1-continued

| Examples of BMP9 Antibodies of the Present Invention | | | |
|---|---|---|---|
| Convention | Sequence Name | Sequence | SEQ ID NO: |
| | | AAAGACAATCAGCAAGGCCAAGGGCCAG CCACGGGAGCCCCAGGTGTACACCCTGC CCCCCAGCCGGGAGGAGATGACCAAGAA CCAGGTGTCCCTGACCTGTCTGGTGAAGG GCTTCTACCCCAGCGATATCGCCGTGGAG TGGGAGAGCAACGGCCAGCCCGAGAACA ACTACAAGACCACCCCCCCAGTGCTGGA CAGCGACGGCAGCTTCTTCCTGTACAGCA AGCTGACCGTGGACAAGTCCAGGTGGCA GCAGGGCAACGTGTTCAGCTGCAGCGTG ATGCACGAGGCCCTGCACAACCACTACA CCCAGAAGTCCCTGAGCCTGAGCCCCGG CAAG | |
| (Kabat) | LCDR1 | SGSSSNIGSNYVY | 171 |
| (Kabat) | LCDR2 | GNNNRPS | 172 |
| (Kabat) | LCDR3 | NAWDTKAYVWV | 173 |
| (Chothia) | LCDR1 | SSSNIGSNY | 174 |
| (Chothia) | LCDR2 | GNN | 175 |
| (Chothia) | LCDR3 | WDTKAYVW | 176 |
| | VL | QSVLTQPPSVSGAPGQRVTISC<u>SGSSSNIGS NYVY</u>WYQQLPGTAPKLLIY<u>GNNNRPS</u>GVP DRFSGSKSGTSASLAITGLQAEDEADYYC<u>N AWDTKAYVWV</u>FGGGTKLTVL | 177 |
| | DNA VL | CAGTCTGTGCTGACTCAGCCTCCGAGCGT GTCAGGAGCACCGGGACAGAGAGTGACC ATCTCCTGTTCGGGGTCCAGCTCGAACAT TGGCTCCAACTACGTGTACTGGTATCAGC AGCTCCCCGGTACCGCGCCCAAGCTGTTG ATCTACGGCAACAACAACCGGCCTAGCG GCGTGCCGGATAGGTTCTCGGGTTCAAAA TCCGGGACGTCCGCTTCCCTGGCCATCAC TGGCCTGCAAGCGGAGGACGAAGCCGAC TACTACTGCAATGCCTGGGACACCAAGG CCTACGTCTGGGTGTTCGGAGGAGGCACT AAGCTGACCGTGCTG | 178 |
| | Light Chain | QSVLTQPPSVSGAPGQRVTISCSGSSSNIGS NYVYWYQQLPGTAPKLLIYGNNNRPSGVP DRFSGSKSGTSASLAITGLQAEDEADYYCN AWDTKAYVWVFGGGTKLTVLGQPKAAPS VTLFPPSSEELQANKATLVCLISDFYPGAVT VAWKADSSPVKAGVETTTPSKQSNNKYAA SSYLSLTPEQWKSHRSYSCQVTHEGSTVEK TVAPTECS | 179 |
| | DNA Light Chain | CAGTCTGTGCTGACTCAGCCTCCGAGCGT GTCAGGAGCACCGGGACAGAGAGTGACC ATCTCCTGTTCGGGGTCCAGCTCGAACAT TGGCTCCAACTACGTGTACTGGTATCAGC AGCTCCCCGGTACCGCGCCCAAGCTGTTG ATCTACGGCAACAACAACCGGCCTAGCG GCGTGCCGGATAGGTTCTCGGGTTCAAAA TCCGGGACGTCCGCTTCCCTGGCCATCAC TGGCCTGCAAGCGGAGGACGAAGCCGAC TACTACTGCAATGCCTGGGACACCAAGG CCTACGTCTGGGTGTTCGGAGGAGGCACT AAGCTGACCGTGCTGGGACAGCCTAAGG CTGCCCCCAGCGTGACCCTGTTCCCCCCC AGCAGCGAGGAGCTGCAGGCCAACAAGG CCACCCTGGTGTGCCTGATCAGCGACTTC TACCCAGGCGCCGTGACCGTGGCCTGGA AGGCCGACAGCAGCCCCGTGAAGGCCGG CGTGGAGACCACCACCCCCAGCAAGCAG AGCAACAACAAGTACGCCGCCAGCAGCT ACCTGAGCCTGACCCCCGAGCAGTGGAA GAGCCACAGGTCCTACAGCTGCCAGGTG ACCCACGAGGGCAGCACCGTGGAAAAGA CCGTGGCCCCAACCGAGTGCAGC | 180 |

Other antibodies and antigen-binding fragments thereof of the invention include those wherein the amino acids or nucleic acids encoding the amino acids have been mutated, yet have at least 60, 70, 80, 90 or 95 percent identity to the sequences described in Table 1. In one embodiment, it include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

In another specific embodiment, the present invention provides an isolated antibody or antigen-binding fragment thereof, which binds human BMP9 and comprises the HCDR1, HCDR2, and HCDR3 sequences of SEQ ID NOs: 1, 2, and 3, respectively, and the LCDR1, LCDR2, and LCDR3 sequences of SEQ ID NOs: 11, 12, and 13, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 4, 5, and 6, respectively, and the LCDR1, LCDR2, and LCDR3 sequences of SEQ ID NOs: 14, 15, and 16, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 21, 22, and 23, respectively, and the LCDR1, LCDR2, and LCDR3 sequences of SEQ ID NOs: 31, 32, and 33, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 24, 25, and 26, respectively, and the LCDR1, LCDR2, and LCDR3 sequences of SEQ ID NOs: 34, 35, and 36, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 41, 42, and 43, respectively, and the LCDR1, LCDR2, and LCDR3 sequences of SEQ ID NOs: 51, 52, and 53, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 44, 45, and 46, respectively, and the LCDR1, LCDR2, and LCDR3 sequences of SEQ ID NOs: 54, 55, and 56, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 61, 62, and 63, respectively, and the LCDR1, LCDR2, and LCDR3 sequences of SEQ ID NOs: 71, 72, and 73, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 64, 65, and 66, respectively, and the LCDR1, LCDR2, and LCDR3 sequences of SEQ ID NOs: 74, 75, and 76, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 81, 82, and 83, respectively, and the LCDR1, LCDR2, and LCDR3 sequences of SEQ ID NOs: 91, 92, and 93, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 84, 85, and 86, respectively, and the LCDR1, LCDR2, and LCDR3 sequences of SEQ ID NOs: 94, 95, and 96, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 101, 102, and 103, respectively, and the LCDR1, LCDR2, and LCDR3 sequences of SEQ ID NOs: 111, 112, and 113, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 104, 105, and 106, respectively, and the LCDR1, LCDR2, and LCDR3 sequences of SEQ ID NOs: 114, 115, and 116, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 121, 122, and 123, respectively, and the LCDR1, LCDR2, and LCDR3 sequences of SEQ ID NOs: 131, 132, and 133, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 124, 125, and 126, respectively, and the LCDR1, LCDR2, and LCDR3 sequences of SEQ ID NOs: 134, 135, and 136, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 141, 142, and 143, respectively, and the LCDR1, LCDR2, and LCDR3 sequences of SEQ ID NOs: 151, 152, and 153, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 144, 145, and 146, respectively, and the LCDR1, LCDR2, and LCDR3 sequences of SEQ ID NOs: 154, 155, and 156, respectively.

In another specific embodiment, the present invention provides an isolated antibody or antigen-binding fragment thereof, which binds human BMP9 and comprises the HCDR1, HCDR2, and HCDR3 sequences of SEQ ID NOs: 161, 162, and 163, respectively, and the LCDR1, LCDR2, and LCDR3 sequences of SEQ ID NOs: 171, 172, and 173, respectively.

In another specific embodiment, the present invention provides an isolated antibody or antigen-binding fragment thereof, which binds human BMP9 and comprises the HCDR1, HCDR2, and HCDR3 sequences of SEQ ID NOs:

164, 165, and 166, respectively, and the LCDR1, LCDR2, and LCDR3 sequences of SEQ ID NOs: 174, 175, and 176, respectively.

Since each of these antibodies can bind to BMP9, the VH, VL, full length light chain, and full length heavy chain sequences (amino acid sequences and the nucleotide sequences encoding the amino acid sequences) can be "mixed and matched" to create other BMP9-binding antibodies and antigen-binding fragments thereof of the invention. Such "mixed and matched" BMP9-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

In another aspect, the present invention provides BMP9-binding antibodies that comprise the heavy chain and light chain CDR1s, CDR2s and CDR3s as described in Table 1, or combinations thereof. The CDR regions are delineated using the Kabat system (Kabat et al. 1991 Sequences of Proteins of Immunological Interest, Fifth Edition, U.S. Department of Health and Human Services, NIH Publication No. 91-3242), or using the Chothia system (Chothia et al. 1987 J. Mol. Biol. 196: 901-917; and Al-Lazikani et al. 1997 J. Mol. Biol. 273: 927-948). Other methods for delineating the CDR regions may alternatively be used. For example, the CDR definitions of both Kabat and Chothia may be combined such that, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Given that each of these antibodies can bind to BMP9 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other BMP9-binding binding molecules of the invention. Such "mixed and matched" BMP9-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence (s). Likewise, when VL CDR sequences are mixed and matched, the CDR1, CDR2 and/or CDR3 sequence from a particular VL sequence should be replaced with a structurally similar CDR sequence (s). It will be readily apparent to the ordinarily skilled artisan that novel VH and VL sequences can be created by mutating one or more VH and/or VL CDR region sequences with structurally similar sequences from the CDR sequences shown herein for monoclonal antibodies of the present invention.

Accordingly, the present invention provides an isolated monoclonal antibody or antigen binding region thereof comprising a heavy chain variable region CDR1 comprising an amino acid sequence selected from any of SEQ ID NOs: 1, 21, 41, 61, 81, 101, 121, 141, 161, 4, 24, 44, 64, 84, 104, 124, 144, and 164; a heavy chain variable region CDR2 comprising an amino acid sequence selected from any of SEQ ID NOs: 2, 22, 42, 62, 82, 102, 122, 142, 162, 5, 25, 45, 65, 85, 105, 125, 145, and 165; a heavy chain variable region CDR3 comprising an amino acid sequence selected from any of SEQ ID NOs: 3, 23, 43, 63, 83, 103, 123, 143, 163, 6, 26, 46, 66, 86, 106, 126, 146, and 166; a light chain variable region CDR1 comprising an amino acid sequence selected from any of SEQ ID NOs: 11, 31, 51, 71, 91, 111, 131, 151, 171, 14, 34, 54, 74, 94, 114, 134, 154, and 174; a light chain variable region CDR2 comprising an amino acid sequence selected from any of SEQ ID NOs: 12, 32, 52, 72, 92, 112, 132, 152, 172, 15, 35, 55, 75, 95, 115, 135, 155, and 175; and a light chain variable region CDR3 comprising an amino acid sequence selected from any of SEQ ID NOs: 13, 33, 53, 73, 93, 113, 133, 153, 173, 16, 36, 56, 76, 96, 116, 136, 156, and 176; wherein the antibody specifically binds BMP9.

In one embodiment, an antibody that specifically binds to BMP9 is an antibody that is described in Table 1. In one embodiment, an antibody that specifically binds to BMP9 is BMP9-1. In one embodiment, an antibody that specifically binds to BMP9 is BMP9-2. In one embodiment, an antibody that specifically binds to BMP9 is BMP9-3. In one embodiment, an antibody that specifically binds to BMP9 is BMP9-4. In one embodiment, an antibody that specifically binds to BMP9 is BMP9-5. In one embodiment, an antibody that specifically binds to BMP9 is BMP9-6. In one embodiment, an antibody that specifically binds to BMP9 is BMP9-7. In one embodiment, an antibody that specifically binds to BMP9 is BMP9-8. In one embodiment, an antibody that specifically binds to BMP9 is BMP9-9.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

BMP Family Members and Liver Fibrosis

In one embodiment, the invention provides an antibody or binding fragment thereof that specifically binds to BMP9. In one embodiment, the antibody or binding fragment thereof is described in Table 1.

In one embodiment, the antibody or binding fragment thereof specifically binds to BMP9 but not to other BMP proteins (such as BMP2, BMP10 or BMP7).

In humans and mice, BMP9 is expressed in the liver, and it is believed that BMP9 signaling plays a role in the pathogenesis of liver disease, e.g., liver fibrosis, cirrhosis or portal vein hypertension. Without being bound to any theory, it is believed that BMP9 signaling leads to Smad1/5/8 phosphorylation, which in turn leads to activation of Id1. Activation of Id1 leads to hepatocyte apoptosis, HSC activation and HSC-EC cross-talk, which leads to liver fibrosis. It has been shown that activation of BMP9 expression in the liver causes hepatocyte cell death and activation of hepatic stellate cells, hepatic fibrosis and induction of fibrotic marker genes (e.g., αSMA, vimentin and Colla1), and severe liver damage. As described herein, including in the Examples, it has been surprisingly and unexpectedly shown that the BMP9 antibodies of the present invention are highly specific for BMP9 (as compared to BMP2, BMP10 and/or BMP7) and inhibit BMP9 in vitro and in vivo, including inhibiting BMP9-induced liver disease, including BMP9-induced liver fibrosis.

Various types of antibodies and antigen-binding fragments thereof to BMP9 are described below.

Homologous Antibodies

In yet another embodiment, the present invention provides an antibody or an antigen-binding fragment thereof comprising amino acid sequences that are homologous to the sequences described in Table 1, and said antibody binds to BMP9, and retains the desired functional properties of those antibodies described in Table 1.

For example, the invention provides an isolated monoclonal antibody (or a functional antigen-binding fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ ID NOs: 7, 27, 47, 67, 87, 107, 127, 147 and 167; the light chain variable region comprises an amino acid sequence that is at least 80%, at least 90%, or at least 95% identical to an amino acid sequence selected from the group consisting of SEQ ID NOs: 17, 37, 57, 77, 97, 107, 117, 137, 157 and 177; the antibody specifically binds to BMP9 protein, and the antibody inhibits BMP9-induced Smad1/5/8 phosphorylation, BMP9-induced Id1 induction, BMP9 induction of fibrotic markers, and/or BMP9-induced liver damage, wherein any of the assays is known in the art. In a specific example, such antibodies have an $IC_{50}$ value in a BRE-Luc reporter gene assay (as described herein) of less than 500 pM. In a specific example, such antibodies significantly inhibit Smad1/5/8 phosphorylation upon single injection of a 10 mg/kg dose in a $CCl_4$ mouse model, e.g., a $CCl_4$ mouse model as described herein. In a specific example, such antibodies significantly inhibit BMP9 induction of Id1 upon single injection of a 10 mg/kg dose in a mouse HDI model, e.g., in a mouse HDI model as described herein. In a specific example, such antibodies significantly protect liver tissue from BMP9-induced damage, e.g., fibrosis.

In one embodiment, the VH and/or VL amino acid sequences may be 50%, 60%, 70%, 80%, 90%, 95%, 96%, 97%, 98% or 99% identical to the sequences set forth in Table 1. In one embodiment, the VH and/or VL amino acid sequences may be identical except an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 7, 27, 47, 67, 87, 107, 127, 147 or 167; and 17, 37, 57, 77, 97, 107, 117, 137, 157 or 177 respectively, followed by testing of the encoded altered antibody for retained function using the functional assays described herein.

In one embodiment, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 9, 29, 49, 69, 89, 109, 129, 149 or 169 and full length light chains of any of SEQ ID NOs: 19, 39, 59, 79, 99, 119, 139, 159, or 179 respectively, can be obtained by mutagenesis (e.g., site-directed or PCR-mediated mutagenesis) of nucleic acid molecules encoding such polypeptides respectively, followed by testing of the encoded altered antibody for retained function using the functional assays described herein.

In one embodiment, the full length heavy chain and/or full length light chain nucleotide sequences may be 60%, 70%, 80%, 90%, 95%, 96%, 97%, 98% or 99% identical to the sequences set forth in Table 1.

In one embodiment, the variable regions of heavy chain and/or light chain nucleotide sequences may be 60%, 70%, 80%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In one embodiment, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the BMP9- binding antibodies and antigen-binding fragments thereof of the invention. Accordingly, the invention provides an isolated monoclonal antibody, or a functional antigen-binding fragment thereof, consisting of a heavy chain variable region comprising CDR1, CDR2, and CDR3 sequences and a light chain variable region comprising CDR1, CDR2, and CDR3 sequences, wherein: a heavy chain variable region CDR1 comprising an amino acid sequence selected from any of SEQ ID NOs: 1, 4, 21, 24, 41, 44, 61, 64, 81, 84, 101, 104, 121, 124, 141, 144, 161 and 164 or conservative variants thereof; a heavy chain variable region CDR2 comprising an amino acid sequence selected from any of SEQ ID NOs: 2, 5, 22, 25, 42, 45, 62, 65, 82, 85, 102, 105, 122, 125, 142, 145, 162 and 165 or conservative variants thereof; a heavy chain variable region CDR3 comprising an amino acid sequence selected from any of SEQ ID NOs: 3, 6, 23, 26, 43, 46, 63, 66, 83, 86, 103, 106, 123, 126, 143, 146, 163 and 166 or conservative variants thereof; a light chain variable region CDR1 comprising an amino acid sequence selected from any of SEQ ID NOs: 11, 14, 31, 34, 51, 54, 71, 74, 91, 94, 111, 114, 131, 134, 151, 154, 171 and 174 or conservative variants thereof; a light chain variable region CDR2 comprising an amino acid sequence selected from any of SEQ ID NOs: 12, 15, 32, 35, 52, 55, 72, 75, 92, 95, 112, 115, 132, 135, 152, 155, 172 and 175 or conservative variants thereof; and a light chain variable region CDR3 comprising an amino acid sequence selected from any of SEQ ID NOs: 13, 16, 33, 36, 53, 56, 73, 76, 93, 96, 113, 116, 133, 136, 153, 156, 173 and 176 or conservative variants thereof; the antibody or the antigen-binding fragment thereof specifically binds to BMP9, and the antibody inhibits BMP9-induced Smad1/5/8 phosphorylation, BMP9-induced Id1 induction, BMP9 induction of fibrotic markers, and/or BMP9-induced liver damage, wherein any of the assays is known in the art. In a specific example, the antibody specifically binds to BMP9 protein, and the antibody inhibits BMP9-induced Smad1/5/8 phosphorylation, BMP9-induced Id1 induction, BMP9 induction of fibrotic markers, and/or BMP9-induced liver damage, wherein any of the assays is known in the art. In a specific example, such antibodies have an $IC_{50}$ value in a BRE-Luc reporter gene assay (as described herein) of less than 500 pM. In a specific example, such antibodies significantly inhibit Smad1/5/8 phosphorylation upon single injection of a 10 mg/kg dose in a $CCl_4$ mouse model, e.g., a $CCl_4$ mouse model as described herein. In a specific example, such antibodies significantly inhibit BMP9 induction of Id1 upon single injection of a 10 mg/kg dose in a mouse HDI model, e.g., in a mouse HDI model as described herein. In a specific example, such antibodies significantly protect liver tissue from BMP9-induced damage, e.g., fibrosis.

In one embodiment, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the BMP9-binding antibodies and antigen-binding fragments thereof of the invention. Accordingly, the invention provides an isolated monoclonal antibody optimized for expression in a mammalian cell consisting of a full length heavy chain and a full length light chain wherein: the full length heavy chain has amino acid sequences selected from the group of SEQ ID NOs: 9, 29, 49, 69, 89, 109, 129, 149, 169, and conservative modifications thereof; and the full length light chain has amino acid sequences selected from the group of SEQ ID NOs: 19, 39, 59, 79, 99, 119, 139, 159, 179, and conservative modifications thereof; the antibody specifically binds to BMP9; and the antibody inhibits BMP9-induced Smad1/5/8 phosphorylation, BMP9-induced Id1 induction, BMP9 induction of fibrotic markers, and/or BMP9-induced liver damage, wherein any of the assays is known in the art. In a specific example, the antibody specifically binds to BMP9 protein, and the antibody inhibits BMP9-induced Smad1/5/8 phosphorylation, BMP9-induced Id1 induction, BMP9 induction of fibrotic markers, and/or BMP9-induced liver damage, wherein any of the assays is known in the art. In a specific example, such antibodies have an $IC_{50}$ value in a BRE-Luc reporter gene assay (as described herein) of less than 500 pM. In a specific example, such antibodies significantly inhibit Smad1/5/8 phosphorylation upon single injection of a 10 mg/kg dose in a $CCl_4$ mouse model, e.g., a $CCl_4$ mouse model as described herein. In a specific example, such antibodies significantly inhibit BMP9 induction of Id1 upon single injection of a 10 mg/kg dose in a mouse HDI model, e.g., in a mouse HDI model as described herein. In a specific example, such antibodies significantly protect liver tissue from BMP9-induced damage, e.g., fibrosis.

Antibodies that Bind to the Same Epitope

The present invention provides antibodies that bind to the same epitope as do the BMP9-binding antibodies listed in Table 1. Additional antibodies can therefore be identified based on their ability to cross-compete (e.g., to competitively inhibit the binding of, in a statistically significant manner) with other antibodies and antigen-binding fragments thereof of the invention in BMP9 binding assays. The ability of a test antibody to inhibit the binding of antibodies and antigen-binding fragments thereof of the present invention to BMP9 protein demonstrates that the test antibody can compete with that antibody for binding to BMP9; such an antibody may, according to non-limiting theory, bind to the same or a related (e.g., a structurally similar or spatially proximal) epitope on BMP9 as the antibody with which it competes. In a certain embodiment, the antibody that binds to the same epitope on BMP9 as the antibodies and antigen-binding fragments thereof of the present invention is a human monoclonal antibody. Such human monoclonal antibodies can be prepared and isolated as described herein. In a certain embodiment, the antibody that binds to the same epitope on BMP9 as the antibodies and antigen-binding fragments thereof of the present invention is a mouse monoclonal antibody. Such mouse monoclonal antibodies are listed in Table 3. In certain embodiments the antibody that binds to the same epitope on BMP9 as the antibodies and antigen-binding fragments thereof of the present invention, is a humanized monoclonal antibody derived from the mouse monoclonal antibodies listed in Table 3. In a certain embodiment, the antibody that binds to the same epitope on BMP9 as the antibodies and antigen-binding fragments thereof of the present invention is a humanized monoclonal antibody. Such humanized monoclonal antibodies can be prepared and isolated as described herein.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 2003/48731. As will be appreciated by one of skill in the art, practically anything to which an antibody can specifically bind could be an epitope. An epitope can comprises those residues to which the antibody binds.

Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids BMP9 such as by, e.g., hydrogen/deuterium exchange, x-ray crystallography and two-dimensional nuclear magnetic resonance See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region (s), for example to alter the effector function (s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germine antibody gene sequences or rearranged antibody sequences. For example, germine DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference. For example, germline DNA sequences for human heavy and light chain variable region genes and rearranged antibody sequences can be found in "IMGT" database (available on the Internet at www.imgt.org; see Lefranc, M. P. et al., 1999 Nucleic Acids Res. 27:209-212; the contents of each of which are expressly incorporated herein by reference.)

An example of framework sequences for use in the antibodies and antigen-binding fragments thereof of the invention are those that are structurally similar to the framework sequences used by selected antibodies and antigen-binding fragments thereof of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation (s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to BMP9. Such frameworks or scaffolds include the 5 main idiotypes of human immunoglobulins, antigen-binding fragments thereof, and include immunoglobulins of other animal species, preferably having humanized aspects. Single heavy-chain antibodies such as those identified in camelids are of particular interest in this regard.

Novel frameworks, scaffolds and fragments continue to be discovered and developed by those skilled in the art.

In one aspect, the invention pertains to a method of generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target BMP9 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (SciI Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity for those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel alpha-helices and a beta-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris *Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The human BMP9-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric BMP9-binding antibodies described above as the reference antibody, this method can be readily employed to generate human antibodies that bind to human BMP9 with the same binding specificity and the same or better binding affinity. In addition, such human BMP9-binding antibodies can also be commercially obtained from companies which customarily produce human antibodies, e.g., KaloBios, Inc. (Mountain View, Calif.).

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies and antigen-binding fragments thereof of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for BMP9. In one embodiment herein, the camelid antibody or nanobody is naturally produced in the camelid animal, i.e., is produced by the camelid following immunization with BMP9 or a peptide fragment thereof, using techniques described herein for other antibodies. Alternatively, the BMP9-binding camelid nanobody is engineered, i.e., produced by selection for example from a library of phage displaying appropriately mutagenized camelid nanobody proteins using panning procedures with BMP9 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising an BMP9-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for BMP9 and a second binding specificity for a second target epitope. For example, the second target epitope is another epitope of BMP9 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F (ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poijak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45 (3-4):128-30; Wu et al., 1996 Immunotechnology, 2 (1):21-36). scDb can be expressed in bacteria in soluble, active monomeric form (see Holliger and Winter, 1997 Cancer Immunol. Immunother., 45 (34): 128-30; Wu et al., 1996 Immunotechnology, 2 (1):21-36; Pluckthun and Pack, 1997 Immunotechnology, 3 (2): 83-105; Ridgway et al., 1996 Protein Eng., 9 (7):617-21). A diabody can be fused to Fc to generate a "di-diabody" (see Lu et al., 2004 J. Biol. Chem., 279 (4):2856-65).

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F (ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies and antigen-binding fragments thereof of the invention binding to BMP9. The antigen-binding portions can be linked together via protein fusion or covalent or non covalent linkage. Alternatively, methods of linkage has been described for the bispecific molecules. Tetravalent compounds can be obtained for example by cross-linking antibodies and antigen-binding fragments thereof of the invention with an antibody or antigen-binding fragment that binds to the constant regions of the antibodies and antigen-binding fragments thereof of the invention, for example the Fc or hinge region.

Trimerizing domain are described for example in Borean patent EP 1 012 280B1. Pentamerizing modules are described for example in PCT/EP97/05897.

Antibodies with Extended Half Life

The present invention provides for antibodies that specifically bind to BMP9 which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies and antigen-binding fragments thereof of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, antigen-binding fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In one embodiment, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies and antigen-binding fragments thereof of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

Antibody Conjugates

The present invention provides antibodies or antigen-binding fragments thereof that specifically bind to BMP9 recombinantly fused or chemically conjugated (including both covalent and non-covalent conjugations) to a heterologous protein or polypeptide (or antigen-binding fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F $(ab)_2$ fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies and antigen-binding fragments thereof of the invention (e.g., antibodies and antigen-binding fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16 (2):76-82; Hansson, et al., 1999, J. Mol. Biol. 287:265-76; and Lorenzo and Blasco, 1998, Biotechniques 24 (2):308-313 (each of these patents and publications are hereby incorporated by reference in its entirety). Antibodies and antigen-binding fragments thereof, or the encoded antibodies and antigen-binding fragments thereof, may be altered by being subjected to random mutagenesis by error-prone PCR, random nucleotide insertion or other methods prior to recombination. A polynucleotide encoding an antibody antigen-binding fragment thereof that specifically binds to BMP9 may be recombined with one or more components, motifs, sections, parts, domains, fragments, etc. of one or more heterologous molecules.

Moreover, the antibodies and antigen-binding fragments thereof can be fused to marker sequences, such as a peptide to facilitate purification. In one embodiment, the marker amino acid sequence is a hexa-histidine peptide (SEQ ID NO: 218), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 218) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In one embodiment, antibodies and antigen-binding fragments thereof of the present invention antigen-binding fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149 Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

The present invention further encompasses uses of antibodies and antigen-binding fragments thereof conjugated to a therapeutic moiety. An antibody antigen-binding fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody antigen-binding fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In one embodiment, the macrocyclic chelator is 1,4,7,10-tetraazacyclododecane-N,N',N'',N'''-tetraacetic acid (DOTA) which can be attached to the antibody via a linker molecule.

Such linker molecules are commonly known in the art and described in Denardo et al., 1998, Clin Cancer Res. 4 (10):2483-90; Peterson et al., 1999, Bioconjug. Chem. 10 (4):553-7; and Zimmerman et al., 1999, Nucl. Med. Biol. 26 (8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention

Nucleic Acids Encoding the Antibodies

The invention provides substantially purified nucleic acid molecules which encode polypeptides comprising segments or domains of the BMP9-binding antibody chains described above. Some of the nucleic acids of the invention comprise the nucleotide sequence encoding the heavy chain variable region shown in any of SEQ ID NOs: 7, 27, 47, 67, 87, 107, 127, 147, or 167, and/or the nucleotide sequence encoding the light chain variable region shown in any of SEQ ID NOs: 17, 37, 57, 77, 97, 117, 137, 157, or 177. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting BMP9 antigen binding capacity.

Also provided in the invention are polynucleotides which encode at least one CDR region and usually all three CDR regions from the heavy or light chain of the BMP9-binding antibody set forth in Table 1. Some other polynucleotides encode all or substantially all of the variable region sequence of the heavy chain and/or the light chain of the BMP9-binding antibody set forth in Table 1. Because of the degeneracy of the code, a variety of nucleic acid sequences will encode each of the immunoglobulin amino acid sequences.

The nucleic acid molecules of the invention can encode both a variable region and a constant region of the antibody. Some of the nucleic acid sequences of the invention comprise nucleotides encoding a mature heavy chain variable region sequence that is substantially identical (e.g., at least 80%, 90%, or 99%) to the mature heavy chain variable region sequence set forth in any of SEQ ID NOs: 7, 27, 47, 67, 87, 107, 127, 147, or 167. Some of the nucleic acid sequences of the invention comprise nucleotide encoding a mature light chain variable region sequence that is substantially identical (e.g., at least 80%, 90%, or 99%) to the mature light chain variable region sequence set forth in any of SEQ ID NOs: 17, 37, 57, 77, 97, 117, 137, 157, and 177.

The polynucleotide sequences can be produced by de novo solid-phase DNA synthesis or by PCR mutagenesis of an existing sequence (e.g., sequences as described in the Examples below) encoding an BMP9-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Manila et al., Nucleic Acids Res. 19:967, 1991; and Eckert et al., PCR Methods and Applications 1:17, 1991.

Also provided in the invention are expression vectors and host cells for producing the BMP9-binding antibodies described above. Various expression vectors can be employed to express the polynucleotides encoding the BMP9-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the BMP9-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an BMP9-binding antibody chain antigen-binding fragment. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an BMP9-binding antibody chain antigen-binding fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted BMP9-binding antibody sequences. More often, the inserted BMP9-binding antibody sequences are linked to a signal sequences before inclusion in the vector. Vectors to be used to receive sequences encoding BMP9-binding antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The host cells for harboring and expressing the BMP9-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express BMP9-binding polypeptides of the invention. Insect cells in combination with baculovirus vectors can also be used.

In one embodiment, mammalian host cells are used to express and produce the BMP9-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express BMP9-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

In a certain embodiment, the antibodies of the invention are humanized monoclonal antibodies. Chimeric or humanized antibodies and antigen-binding fragments thereof of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against BMP9 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see e.g., Lonberg, et al., 1994 Nature 368 (6474): 856-859). Accordingly, the mice exhibit reduced expression of mouse IgM or K, and in response to immunization, the introduced human heavy and light chain transgenes undergo class switching and somatic mutation to generate high affinity human IgG-kappa monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise BMP9-binding antibodies and antigen-binding fragments thereof of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise BMP9-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise BMP9-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies and antigen-binding fragments thereof of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In one embodiment, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc-gamma receptor by modifying one or more amino acids. This approach is described further in PCT Publication WO 00/42072 by Presta. Moreover, the binding sites on human IgG1 for Fc-gamma RI, Fc-gamma RII, Fc-gamma RIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lecl3 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the BMP9-binding antibodies having VH and VL sequences or full length heavy and light chain sequences shown herein can be used to create new BMP9-binding antibodies by modifying full length heavy chain and/or light chain sequences, VH and/or VL sequences, or the constant region (s) attached thereto. Thus, in another aspect of the invention, the structural features of BMP9-binding antibody of the invention are used to create structurally related BMP9-binding antibodies that retain at least one functional property of the antibodies and antigen-binding fragments thereof of the invention, such as binding to human BMP9 and also inhibiting one or more functional properties of BMP9 (e.g., inhibits BMP9-induced Smad1/5/8 phosphorylation, BMP9-induced Id1 induction, BMP9 induction of fibrotic markers, and/or BMP9-induced liver damage, wherein any of the assays is known in the art, e.g., inhibits Smad1/5/8 phosphorylation as measured by a HUVEC assay followed by Western-Blotting (as described herein), or CFSCs assay followed by cellomics scan (as described herein); e.g., inhibit BMP9 induction of Id1 upon single injection of a 10 mg/kg dose in a mouse HDI model, e.g., in a mouse HDI model as described herein).

For example, one or more CDR regions of the antibodies and antigen-binding fragments thereof of the present invention, or mutations thereof, can be combined recombinantly with known framework regions and/or other CDRs to create additional, recombinantly-engineered, BMP9-binding antibodies and antigen-binding fragments thereof of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence (s) is used as the starting material to create a "second generation" sequence (s) derived from the original sequence (s) and then the "second generation" sequence (s) is prepared and expressed as a protein.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence (s) is one that retains one, some or all of the functional properties of the BMP9-binding antibodies described herein, which functional properties include, but are not limited to, specifically binding to human BMP9 protein and/or inhibiting one or more functional properties of BMP9 (e.g., inhibits BMP9-induced Smad1/5/8 phosphorylation, BMP9-induced Id1 induction, BMP9 induction of fibrotic markers, and/or BMP9-induced liver damage, wherein any of the assays is known in the art, e.g., inhibits Smad1/5/8 phosphorylation as measured by a HUVEC assay followed by Western-Blotting (as described herein), or CFSCs assay followed by cellomics scan (as described herein); e.g., inhibit BMP9 induction of Id1 upon single injection of a 10 mg/kg dose in a mouse HDI model, e.g., in a mouse HDI model as described herein).

The functional properties of the altered antibodies can be assessed using standard assays available in the art and/or described herein, such as those set forth in the Examples (e.g., ELISAs).

In one embodiment of the methods of engineering antibodies and antigen-binding fragments thereof of the invention, mutations can be introduced randomly or selectively along all or part of an BMP9-binding antibody coding sequence and the resulting modified BMP9-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies of the Invention

The antibodies and antigen-binding fragments thereof of the invention can be characterized by various functional assays. For example, they can be characterized by their ability to inhibit BMP9.

The ability of an antibody to bind to BMP9 can be detected by labelling the antibody of interest directly, or the antibody may be unlabeled and binding detected indirectly using various sandwich assay formats known in the art.

In one embodiment, the BMP9-binding antibodies and antigen-binding fragments thereof of the invention block or compete with binding of a reference BMP9-binding antibody to BMP9 polypeptide. These can be fully human or humanized BMP9-binding antibodies described above. They can also be other human, mouse, chimeric or humanized BMP9-binding antibodies which bind to the same epitope as the reference antibody. The capacity to block or compete with the reference antibody binding indicates that BMP9-binding antibody under test binds to the same or similar epitope as that defined by the reference antibody, or to an epitope which is sufficiently proximal to the epitope bound by the reference BMP9-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as BMP9 polypeptide. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of an antibody with a reference antibody for binding to a particular protein, in this case, BMP9. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using 1-125 label (see Morel et al., Molec. Immunol. 25:7-15, 1988); solid phase direct biotin-avidin EIA (Cheung et al., Virology 176:546-552, 1990); and direct labeled RIA (Moldenhauer et al., Scand. J. Immunol. 32:77-82, 1990). Typically, such an assay involves the use of purified antigen bound to a solid surface or cells bearing either of these, an unlabelled test BMP9-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected BMP9-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using BMP9 polypeptide coated-ELISA plates. Biotinylated MAb binding can be detected with a strep-avidin-alkaline phosphatase probe. To determine the isotype of a purified BMP9-binding antibody, isotype ELISAs can be performed. For example, wells of microtiter plates can be coated with 1 μg/ml of anti-human IgG overnight at 4 degrees C. After blocking with 1% BSA, the plates are reacted with 1 μg/ml or less of the monoclonal BMP9-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal BMP9-binding antibodies to live cells expressing BMP9 polypeptide, flow cytometry can be used. Briefly, cell lines expressing BMP9 (grown under standard growth conditions) can be mixed with various concentrations of BMP9-binding antibody in PBS containing 0.1% BSA and 10% fetal calf serum, and incubated at 37 degrees C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

BMP9-binding antibodies and antigen-binding fragments thereof of the invention can be further tested for reactivity with BMP9 polypeptide or antigenic fragment by Western blotting. Briefly, purified BMP9 polypeptides or fusion proteins, or cell extracts from cells expressing BMP9 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Examples of functional assays are also described in the Example section below.

Prophylactic and Therapeutic Uses

The present invention provides methods of treating a disease or disorder associated with increased BMP9 activity by administering to a subject in need thereof an effective amount of any antibody or antigen-binding fragment thereof of the invention. In a specific embodiment, the present invention provides a method of treating liver fibrosis by administering to a subject in need thereof an effective amount of an antibody or antigen-binding fragment thereof of the invention. In a specific embodiment, the present invention provides a method of treating cirrhosis by administering to a subject in need thereof an effective amount of an antibody or antigen-binding fragment thereof of the invention. In a specific embodiment, the present invention provides a method of treating portal vein hypertension by administering to a subject in need thereof an effective amount of an antibody or antigen-binding fragment thereof of the invention.

The antibodies or antigen-binding fragments thereof of the invention can be used, inter alia, to treat, e.g., prevent, delay or reverse progression of, liver disease, e.g., liver fibrosis. The antibodies or antigen-binding fragment thereof of the invention can be used, inter alia, to treat, e.g., prevent, delay or reverse progression of, cirrhosis. The antibodies or antigen-binding fragment thereof of the invention can be used, inter alia, to treat, e.g., to prevent, delay or reverse progression of, portal vein hypertension. The antibodies or antigen-binding fragments thereof can also be used in combination with other therapies for the treatment of liver fibrosis, cirrhosis and/or portal vein hypertension in patients. The antibodies or antigen-binding fragment thereof of the invention can be used, inter alia, to treat, e.g., prevent, delay or reverse progression of end stage liver disease, for example, varices, jaundice, ascites, hepatic encephalopathy, hepatorenal syndrome, spontaneous bacterial peritonitis, and hepato-pulmonary syndrome.

In one embodiment, the present invention provides methods of treating a BMP9 related disease or disorder by administering to a subject in need thereof an effective amount of the antibodies and antigen-binding fragments thereof of the invention. Examples of known BMP9 related diseases or disorders for which the antibodies, or antigen-binding fragments thereof, may be useful include: angiogenesis, including inhibition of tumor angiogenesis; anemia, including renal anemia and cancer-induced anemia; ectopic ossification disease; vascular disease, including artherosclerosis, hypertension and heart disease. In addition, examples of known BMP9 related diseases or disorders for which the antibodies, or antigen-binding fragments thereof, may be useful include fibrotic liver diseases, including those that result in cirrhosis and/or portal vein hypertension, including fibrotic liver disease caused by, for example, hepatitis C virus ("HCV") infection; hepatitis B virus ("HBV") infection; autoimmune hepatitis; alcohol, toxin or drug exposure; liver trauma; biliary obstruction; primary biliary cirrhosis; alagille syndrome; chronic hepatic congestion, including from cardiac disease or hepatic outflow obstruction; nonalcoholic steatohepatitis (NASH); primary sclerosing cholangitis; hemochromatosis; alpha 1-antitrypsin deficiency; and Wilson disease.

In a specific embodiment, the present invention provides methods of treating a BMP9 related disease or disorder by administering to a subject in need thereof an effective amount of the antibodies and antigen-binding fragments thereof of the invention, wherein said disease or disorder is a liver disease, e.g., liver fibrosis, cirrhosis or portal vein hypertension.

In a specific embodiment, the present invention provides methods of treating a liver disease, e.g., liver fibrosis, cirrhosis or portal vein hypertension by administering to a subject in need thereof an effective amount of a composition comprising an antibody of the present invention. In a specific embodiment, the present invention provides methods of treating a liver disease, e.g., liver fibrosis or cirrhosis by administering to a subject in need thereof an effective amount of a composition comprising an antibody of the present invention.

In a specific embodiment, the present invention provides methods of treating portal vein hypertension.

In one embodiment, the isolated antibody or antigen-binding fragment thereof described in Table 1 can be administered to a patient in need thereof in conjunction with a therapeutic method or procedure, such as described herein or known in the art. Such a method or procedure includes, as non-limiting examples: co-administration with anti-viral therapies for hepatitis B or C, anti-inflammatory agents, anti-steatotic agents, anti-apoptotic or hepatoprotective or other anti-fibrotic agents.

For example, the antibody or antigen-binding fragment thereof of the present invention, including those described in Table 1, may be used in combination with "standard" anti-fibrotic agents. For example, the antibody or antigen-binding fragment thereof can be administered in combination with (i.e., together with or linked to (i.e., an immunoconjugate)) cytotoxins, immunosuppressive agents, radiotoxic agents, and/or therapeutic antibodies. Particular co-therapeutics contemplated by the present invention include, but are not limited to, steroids (e.g., corticosteroids, such as Prednisone), immune-suppressing and/or anti-inflammatory agents (e.g., gamma-interferon, cyclophosphamide, azathioprine, methotrexate, penicillamine, cyclosporine, colchicines, antithymocyte globulin, mycophenolate mofetil, and hydroxychloroquine), cytotoxic drugs, calcium channel blockers (e.g., nifedipine), angiotensin converting enzyme inhibitors (ACE) inhibitors, para-aminobenzoic acid (PABA), dimethyl sulfoxide, transforming growth factor-beta (TGF-β) inhibitors, interleukin-5 (IL-5) inhibitors, and pan caspase inhibitors.

Additional anti-fibrotic agents that may be used in combination with, the isolated antibody or antigen-binding fragment thereof of the invention, including those in Table 1, include, but are not limited to, lectins (as described in, for example, U.S. Pat. No. 7,026,283, the entire contents of which is incorporated herein by reference), as well as the anti-fibrotic agents described by Wynn et al (Journal Clin. Invest. Vol 117 Number 3, March 2007, p 524, the entire contents of which is incorporated herein by reference). For example, additional anti-fibrotic agents and therapies include, but are not limited to, various anti-inflammatory/immunosuppressive/cytotoxic drugs (including colchicine, azathioprine, cyclophosphamide, prednisone, thalidomide, pentoxifylline, and theophylline). TGF-β signaling modifiers (including relaxin, SMAD7, HGF, and BMP7, as well as TGF-β1, TGFβRI, TGFβRII, EGR-1, and CTGF inhibitors) (e.g., perfenidone, F-351, F-200 and F-573), cytokine and cytokine receptor antagonists (inhibitors of IL-1β, IL-5, IL-6, IL-13, IL-21, IL-4R, IL-13Rβ1, GM-CSF, TNF-α, oncostatin M, WISP-1, and PDGFs), cytokines and chemokines (IFN-γ, IFN-α/β, IL-12, IL-10, HGF, CXCL10, and CXCL11), chemokine antagonists (inhibitors of CXCL1, CXCL2, CXCL12, CCL2, CCL3, CCL6, CCL17, and CCL18), chemokine receptor antagonists (inhibitors of CCR2, CCR3, CCR5, CCR7, CXCR2, and CXCR4), TLR antagonists (inhibitors of TLR3, TLR4, and TLR9), Angiogenesis antagonists (VEGF-specific antibodies and adenosine deaminase replacement therapy), Antihypertensive drugs (beta blockers and inhibitors of ANG II, ACE, and aldosterone), Vasoactive substances (ET-1 receptor antagonists and bosetan), Inhibitors of the enzymes that synthesize and process collagen (inhibitors of prolyl hydroxylase), B cell antagonists (rituximab), Integrin/adhesion molecule antagonists (molecules that block α1β1 and αvβ6 integrins, as well as inhibitors of integrin linked kinase, and antibodies specific for ICAM-1 and VCAM-1), proapoptotic drugs that target myofibroblasts, MMP inhibitors (inhibitors of MMP2, MMP9, and MMP12), and TIMP inhibitors (antibodies specific for TIMP-1).

The antibody or antigen-binding fragment thereof of the present invention, including those described in Table 1, may be used in combination with "standard" anti-diabetic agents, e.g., metformin, to treat diabetes-associated NASH fibrosis. Other anti-diabetic agents that may be used in combination with the antibody or antigen-binding fragment thereof of the present invention, including those described in Table 1, are known in the art, and include sulfonylureas (e.g., glyburide, glipizide and glimepiride), meglitinides (e.g., repaglinide and nateglinide), thiazolidinediones (e.g., rosiglitazone and pioglitazone), DPP-4 inhibitors (e.g., sitagliptin, saxagliptin, and linagliptin), GLP-1 receptor agonists (e.g., exenatide and liraglutide), SGLT2 inhibitors (e.g., canagliflozin and dapagliflozin), and insulin.

The antibody or antigen-binding fragment thereof of the present invention, including those described in Table 1, may be used in combination with "standard" anti-viral agents, e.g., HBV- and HCV-antivirals, to treat HBV- and/or HCV-associated fibrosis. Other anti-viral agents that may be used in combination with the antibody or antigen-binding fragment thereof of the present invention, including those described in Table 1, are known in the art, and include interferons (e.g., IFN alfa-2b, IFN alfa-2a, PEG-Intron and IFN alfacon-1), interferons combined with ribavirin, protease inhibitors (e.g., ledipasvir, sofosbuvir, boceprivir or telaprevir, tenofovir, daclatsivir, simeprevir, ledasprevir), and other antivirals (e.g., lamivudine, adefovir, telbivudine, and entecavir).

The antibody or antigen-binding fragment thereof of the present invention, including those described in Table 1, may be used in combination with "standard" anti-inflammatory agents, e.g., corticosteroids, GFT-505, and cenicriviroc, and combinations thereof.

The antibody or antigen-binding fragment thereof of the present invention, including those described in Table 1, may be used in combination with "standard" anti-steatotic agents, for example, vitamin E, pioglitazone, metformin, obeticholic acid, and combinations thereof.

The antibody or antigen-binding fragment thereof of the present invention, including those described in Table 1, may be used in combination with "standard" anti-apoptotic or hepatoprotective agents, for example, obeticholic acid, GFT-505, GR-MD-02, and combinations thereof.

As will be appreciated by the skilled artisan, the combination therapies involving the antibodies or antigen-binding fragments thereof of the present invention, including those described in Table 1, may include combination therapies involving multiple classes of the agents described above, for example, may involve one or more antiviral agents and one or more additional anti-fibrotic agents.

When the therapeutic agents of the present invention are administered together with another agent or agents, the two (or more) can be administered sequentially in any order or simultaneously. In some aspects, an antibody of the present invention is administered to a subject who is also receiving therapy with a second agent or method. In other aspects, the binding molecule is administered in conjunction with surgical treatments.

Suitable agents for combination treatment with BMP9-binding antibodies include agents known in the art that inhibit or reduce the expression, level, stability and/or activity of BMP9. Such agents include antibodies, siRNAs, soluble BMP9 receptors, proteins, and small molecules to BMP9.

Various antibodies to BMP9 are known in the art, including, inter alia, those described in the literature or are commercially available, for example, monoclonal mouse IgG2b clone 360107 (R&D systems MAB3209), and those described in, for example, US2014/0056902.

Various siRNAs to BMP9 are known in the art.

Additional inhibitors of BMP9 are known, including for example, soluble BMP receptors such as soluble fragments of ALKI, and ActRIIb. Any of these can be used in combination with any antibody or antigen-binding fragment thereof disclosed herein.

A combination therapy regimen may be additive, or it may produce synergistic results (e.g., reductions in BMP9 activity more than expected for the combined use of the two agents). In one embodiment, the present invention provide a combination therapy for preventing and/or treating liver disease, e.g., fibrosis, portal vein hypertension or cirrhosis, or another BMP9 related disease as described above with BMP9-binding antibody of the invention and an anti-fibrosis agent or method, as described above.

Diagnostic Uses

In one aspect, the invention encompasses diagnostic assays for determining BMP9 and/or nucleic acid expression as well as BMP9 function, in the context of a biological sample (e.g., blood, serum, cells, tissue) or from individual is afflicted with a disease or disorder, or is at risk of developing a disorder associated with liver disease, e.g., liver fibrosis, cirrhosis or portal vein hypertension.

Diagnostic assays, such as competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antibodies and BMP9-binding antibodies results in the bound BMP9, preferably the BMP9 epitopes of the invention, being a measure of antibodies in the serum sample, most particularly, neutralising antibodies in the serum sample.

A significant advantage of the assay is that measurement is made of neutralising antibodies directly (i.e., those which interfere with binding of BMP9, specifically, epitopes). Such an assay, particularly in the form of an ELISA test has considerable applications in the clinical environment and in routine blood screening.

In the clinical diagnosis or monitoring of patients with disorders associated with liver disease, e.g., liver fibrosis, cirrhosis or portal vein hypertension, the detection of elevated levels of BMP9 protein or mRNA, e.g., in the liver, in comparison to the levels in a corresponding biological sample from a normal subject is indicative of a patient with disorders associated with liver disease, e.g., liver fibrosis, cirrhosis or portal vein hypertension.

In vivo diagnostic or imaging is described in US2006/0067935. Briefly, these methods generally comprise administering or introducing to a patient a diagnostically effective amount of BMP9 binding molecule that is operatively attached to a marker or label that is detectable by non-invasive methods. The antibody-marker conjugate is allowed sufficient time to localize and bind to BMP9. The patient is then exposed to a detection device to identify the detectable marker, thus forming an image of the location of the BMP9 binding molecules in the tissue of a patient. The presence of BMP9 binding antibody or an antigen-binding fragment thereof is detected by determining whether an antibody-marker binds to a component of the tissue. Detection of an increased level in BMP9 proteins or a combination of protein in comparison to a normal individual without liver disease, e.g., liver fibrosis, cirrhosis or portal vein hypertension is indicative of a predisposition for and/or on set of disorders associated with liver disease, e.g., liver fibrosis, cirrhosis or portal vein hypertension. These aspects of the invention are also for use in tissue imaging methods and combined diagnostic and treatment methods.

The invention also pertains to the field of predictive medicine in which diagnostic assays, prognostic assays, pharmacogenomics, and monitoring clinical trials are used for prognostic (predictive) purposes to thereby treat an individual prophylactically.

The invention also provides for prognostic (or predictive) assays for determining whether an individual is at risk of developing a disorder associated with dysregulation of BMP9 pathway activity. For example, mutations in BMP9 gene can be assayed in a biological sample. Such assays can be used for prognostic or predictive purpose to thereby prophylactically treat an individual prior to the onset of a disorder characterized by or associated with BMP9, nucleic acid expression or activity.

Another aspect of the invention provides methods for determining BMP9 nucleic acid expression or BMP9 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention provides a method of monitoring the influence of agents (e.g., drugs) on the expression or activity of BMP9 in clinical trials.

Pharmaceutical Compositions

The invention provides pharmaceutical compositions comprising the BMP9-binding antibody or binding fragment thereof formulated together with a pharmaceutically acceptable carrier. The compositions can additionally contain one or more other therapeutical agents that are suitable for treating or preventing a BMP9-associated disease (e.g., liver disease, e.g., liver fibrosis, cirrhosis or portal vein hypertension). Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the BMP9-binding antibody is employed in the pharmaceutical compositions of the invention. The BMP9-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies and antigen-binding fragments thereof of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. An exemplary treatment regime entails systemic administration once per every two weeks or once a month or once every 3 to 6 months. For intravitreal administration with an antibody, the dosage ranges from about 0.0001 to about 10 mg. An exemplary treatment regime entails systemic administration once per every two weeks or once a month or once every 3 to 6 months.

Antibody is usually administered on multiple occasions. Intervals between single dosages can be weekly, monthly or yearly. Intervals can also be irregular as indicated by measuring blood levels of BMP9-binding antibody in the patient. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1: Generation of Recombinant BMP9

DNA sequence encoding full length hBMP9 protein was cloned an expression vector and confirmed by DNA sequencing. hBMP9 construct was transiently transfected into 293F cell line and the cells were further optimized for hBMP9 protein production. The final production was carried out at 10 L scale and multiple runs. Final harvests were collected when cell viability was >80%. Cell debris in the final harvest were removed by centrifugation and filtration processes. The target hBMP9 protein was purified by using cation exchange chromatography and anion exchange chromatography. Ultrafiltration was used to concentrate hBMP9 protein and to exchange buffer. Quantitation of the protein was determined by Lowry method. Purified hBMP9 protein was analyzed by SDS-PAGE, Western blot and HPLC.

Example 2: Generation of Anti-BMP9 Antibodies by Hybridoma Technology

Mice Immunization and Fusion

Ten BALB/c mice were immunized with recombinant protein human BMP9 (huBMP9) by a repetitive procedure involving 4 injections either subcutaneously or interperitoneally of 25-50 ug huBMP9. Spleens of immunized mice were harvested, and isolated splenocytes were fused to myeloma cells (P3Ag8.653 cell line) to create hybridoma clones. Supernatant from hybridoma clones was tested with binding ELISA as the primary screening assay to identify positive clones binding to BMP9. Supernatant of positive clones identified from primary screening binding assay was then tested in blocking ELISA to identify positive clones that can inhibit the interactions between BMP9 and its receptors. Four different recombinant BMP9 receptors were used: human Alk1-Fc (R&D system, 370-AL-100); human BMPRII-Fc (R&D system, 811-BR-100); human ActRIIA-Fc (R&D system, 340-R2-100); human ActRIIB-Fc (R&D system).

Two clones were selected for humanization based upon their ability to bind huBMP9 with high affinity, as verified by Biacore, and for their ability to block specific BMP9 receptor interactions. The 2B11G2 inhibits binding of human BMP9 and human Alk1, whereas the 4E10D7 antibody can inhibit the binding of human BMP9 and human BMPRII. Thus, 2B11G2 is classified as an inhibitor of Type I receptor interactions, while 4E10D7 is classified as an inhibitor of Type II receptor interactions.

Binding properties and sequences of mouse hybridoma antibodies 2B11G2 and 4E10D7 are shown in Tables 2 and 3, respectively.

TABLE 2

Kinetic parameters of the mouse hybridoma anti-BMP9 monoclonal antibodies determined by Biacore. Kinetic data were fitted with a bivalent model and parameters $K_{a1}$ and $K_{d1}$ were used to determine KD.

| Antibody | Inhibitor SubType | $ka_1$ (1/Ms) | $kd_1$ (1/s) | $K_D$ (M) |
|---|---|---|---|---|
| 2B11G2 | Type I | 2508 | 1.66E−04 | 6.62E−08 |
| 4E10D7 | Type II | 2.81E+05 | 6.17E−04 | 2.20E−09 |

TABLE 3

Examples of murine antibodies that bind human BMP9.

| Convention | Sequence Name | Sequence | SEQ ID NO: |
|---|---|---|---|
| | | Mouse Antibody 2B11G2 | |
| (Kabat) | HCDR1 | SYNMH | 181 |
| (Kabat) | HCDR2 | VIYPGNGVTSYSQKFKD | 182 |
| (Kabat) | HCDR3 | DDYFYGGSYAMDY | 183 |
| (Chothia) | HCDR1 | GYTFPSY | 184 |
| (Chothia) | HCDR2 | YPGNGV | 185 |
| (Chothia) | HCDR3 | DDYFYGGSYAMDY | 186 |
| | VH | QAYLQQSGAELVRPGASVKMSCKASGYTF PSYNMHWVKQTPRQGLEWIGVIYPGNGVT SYSQKFKDKATLTVDKSSSTAYMQLSSLTS EDSAVYFCAKDDYFYGGSYAMDYWGQGT SVTVSS | 187 |
| | DNA VH | caggcttatctacagcagtctggggctgagctggtgaggcctgggg cctcagtgaagatgtcctgcaaggcttctggctacacatttcccagtt acaatatgcactgggtaaagcagacacctagacagggcctggaat ggattggagttatttatccaggaaatggtgttacttcctacagtcagaa gttcaaggacaaggccacactgactgtagacaaatcttccagcaca gcctacatgcagctcagcagcctgacatctgaggactctgcggtcta tttctgtgcaaaagacgattatttctacggtggtagctatgctatggact actggggtcaaggaacctcagtcaccgtctcctca | 188 |
| (Kabat) | LCDR1 | RASQSISNNLH | 189 |
| (Kabat) | LCDR2 | YASQSIS | 190 |
| (Kabat) | LCDR3 | QQSHSWPYT | 191 |
| (Chothia) | LCDR1 | SQSISNN | 192 |
| (Chothia) | LCDR2 | YAS | 193 |
| (Chothia) | LCDR3 | SHSWPY | 194 |
| | VL | DIVLTQSPATLSVTPGDSVSLSCRASQSISN NLHWYQQISHESPRLLIKYASQSISGIPSRFS GSGSGTDFTLSINSMETEDFGMFFCQQSHS WPYTFGGGTKLEIK | 195 |
| | DNA VL | gatattgtgctaactcagtctccagccaccctgtctgtgactccagga gatagcgtcagtctttcctgcagggccagccaaagtattagcaacaa cctacactggtatcagcaaatatcacatgagtctccaaggcttctcat caagtatgcctcccagtccatctctggcatcccctccaggttcagtgg cagtggatcagggacagatttcactctcagtatcaacagtatggaga ctgaagattttggaatgtttttctgtcaacagagtcacagctggcctta cacgttcggaggggggaccaagctggaaataaaa | 196 |
| | | Mouse Antibody 4E10D7 | |
| (Kabat) | HCDR1 | RYWMH | 197 |
| (Kabat) | HCDR2 | EINPSNGGTNYNEKFKS | 198 |
| (Kabat) | HCDR3 | GSNYGGFVY | 199 |
| (Chothia) | HCDR1 | GYTFTRY | 200 |
| (Chothia) | HCDR2 | NPSNGG | 201 |
| (Chothia) | HCDR3 | GSNYGGFVY | 202 |
| | VH | QVQLQQPGAEAVKPGASVKLSCKASGYTF TRYWMHWVKQRPGQGLEWIGEINPSNGGT NYNEKFKSKATLTVDKSSSTAYMQLSSLTS EDFAVYYCTMGSNYGGFVYWGQGTLVTV SA | 203 |
| | DNA VH | caggtccaactgcagcagcctggggctgaggctgtgaagcctggg gcttcagtgaagttgtcctgcaaggcttctggctacaccttcaccagg tattggatgcactgggtgaagcagaggcctggacaaggccttgagt ggattggagagattaatcctagcaatggtggtactaactacaatgag aagttcaagagcaaggccacactgactgtagacaaatcctccagca cagcctacatgcaactcagcagcctgacatctgaggattttgcggtc tattactgtacaatggggagtaactacgggggttttgtttactggggc caagggactctggtcactgtctctgca | 204 |
| (Kabat) | LCDR1 | RASESLDNYGISFMN | 205 |
| (Kabat) | LCDR2 | AASNQGS | 206 |
| (Kabat) | LCDR3 | QQSKEVPRT | 207 |
| (Chothia) | LCDR1 | SESLDNYGISF | 208 |
| (Chothia) | LCDR2 | AAS | 209 |
| (Chothia) | LCDR3 | SKEVPR | 210 |
| | VL | DIVLTQSPASLAVSLGQRATISCRASESLDN YGISFMNWFQQKPGQPPKFLIYAASNQGSG VPARFSGSGSGTDFSLNIHPLEEDDTAMYF CQQSKEVPRTFGGGTKLEIK | 211 |
| | DNA VL | gacattgtgctgacccaatctccagcttctttggctgtgtctctagggc agagggccaccatctcctgcagagccagcgaaagtcttgataattat ggcattagttttatgaattggttccaacagaaaccaggacagccacc caaattcctcatctatgctgcatccaaccaaggaagcggggtccctg ccaggtttagtggcagtgggtctgggacagacttcagcctcaacatc | 212 |

TABLE 3-continued

| Examples of murine antibodies that bind human BMP9. | | | |
|---|---|---|---|
| Convention | Sequence Name | Sequence | SEQ ID NO: |
| | | catcctttggaggaggatgatactgcaatgtatttctgtcagcaaagt aaggaggttcctcggacgttcggtggaggcaccaaactggaaatc aaa | |

Design of 2B11G2 Humanized Antibodies

The humanized antibodies derived from 2B11G2 mouse antibody were designed by CDR grafting. Briefly, humanization was generated by grafting the amino acid sequence of VH CDR or VL CDR of a non-human animal antibody (referred as "donor") to the framework regions of VH or VL of a human antibody (referred as "acceptor").

Human germline sequence 1-46 (VBASE VH1 1-46; IMGT IGHV1-46*01) was selected as acceptor framework for humanizing 2B11G2 VH; CDRs of 2B11G2 VH were grafted into acceptor framework to generate first humanized sequence of 2B11G2 VH named 2B11G2_VH1_Hz0. Positions 71, 73, 78, 94 (in Chothia numbering convention) in heavy chain frameworks were mutated to corresponding mouse donor residue to generate sequence 2B11G2_VH1_Hz1. Potential post-translational modification (PTM) NG site in CDR2 of 2B11G2_VH1_Hz0 and 2B11G2_VH1_Hz1 was removed by substituting NG to QG in sequence 2B11G2_VH1_Hz0_N55Q and sequence 2B11G2_VH1_Hz1_N55Q respectively.

Human germline sequence A10 (VBASE VKVI A10; IMGT IGKV6-21*01) was selected as acceptor framework for humanizing 2B11G2 VL; CDRs of 2B11G2 VL were grafted into acceptor framework to generate first humanized sequence of 2B11G2 VL named 2B11G2_VK6_Hz0. No additional framework mutations were introduced due to highly conserved frameworks between donor and acceptor sequences.

The nucleotide sequence of each humanized sequence was generated by codon optimization.

Multiple humanized VH sequences and multiple humanized VL sequences were designed; and a panel of humanized antibodies either in IgG1 or Fab can be generated by combining each humanized VH sequence and each humanized VL sequence. The VH sequence and the VL sequence were carried in different plasmids, thus both heavy chain plasmid and light chain plasmid were co-transfected into expression host cells (i.e. HEK293-6E cells) to generate specific antibody. In this humanization study, the chimeric or humanized antibodies were produced in IgG1 form.

Design of 4E10D7 Humanized Antibodies

The humanized antibodies derived from 4E10D7 mouse antibody were designed by CDR grafting as described above.

Human germline sequence 1-02 (VBASE VH1 1-02; IMGT IGHV1-2*02) was selected as acceptor framework for humanizing 4E10D7 VH; CDRs of 4E10D7 VH were grafted into acceptor framework to generate first humanized sequence of 4E10D7 VH named 4E10D7_VH1_Hz0. Positions 71, 73, 94 (in Chothia numbering convention) in heavy chain frameworks were mutated to corresponding mouse donor residue to generate sequence 4E10D7_VH1_Hz1. Potential post-translational modification (PTM) NG site in CDR2 of 4E10D7_VH1_Hz1 was removed by substituting NG to QG in sequence 4E10D7_VH1_Hz1_N55Q.

Human germline sequence L25 (VBASE VKIII L25; IMGT IGKV3/OR2-268*01) was selected as acceptor framework for humanizing 4E10D7 VL; CDRs of 4E10D7 VL were grafted into acceptor framework to generate first humanized sequence of 4E10D7 VL named 4E10D7_VK3_Hz0. Positions 4, 36, 46, 83 and 87 (in Chothia numbering convention) in the light chain frameworks were mutated to the corresponding mouse residues to generate the humanized sequence named 4E10D7_VK3_Hz3.

Humanized VH and VL sequences were carried in different plasmids, and host cells (i.e. HEK293-6E cells) were co-transfected with one heavy chain plasmid and one light chain plasmid to generate specific IgG1 antibodies.

Production and Purification of Humanized Antibodies

HEK293-6E cells were cultured in F17 medium (Invitrogen, 0050092DK), supplemented with 0.1% Pluronic F68 (Invitrogen, 24040-032) and 4 mM L-GlutaMAX (Invitrogen, 35050-061). The cells were processed at the density of $1\times10^6$/ml on the day before transfection and antibiotics was removed from the medium. On the day of transfection, the cell density and viability were measured firstly to assure the density should be within $1.5\text{-}2.0\times10^6$ cells/ml and the viability should be more than 95%. The use amount of plasmid DNA was calculated by the volume of cells, the total plasmid DNA amount was typically 1 ug per $1\times10^6$ cells for antibody expression. The heavy chain (HC) plasmids and the light chain (LC) plasmids (the recommended HC:LC ratio is 1:1.5 for IgG expression and 1.5:1 for Fab expression) were added into sterilized water (Invitrogen, 10977-015), supplemented with transfection enhancer 293 Expression MAX-1 (ACRO Biosystems, Exp-711) with the ratio of enhancer: DNA=1~4 ul:10 ug, consequently followed by adding the transfection reagent PEI (Polyethylenimine, linear, 25 Da, Polysciences, 24885) of 1 mg/ml with the ratio of PEI: DNA=4:1. The mixture was then gently added to the cells. Tryptone (Tryptone N1, Organotechnie, TekniScience Inc., 19553) was added to the cells with the final concentration of 0.5% at 24 hours after the transfection. The transfected cells were harvested at viability of 60%~80% at generally 5 to 7 days after the transfection.

The purification process was conducted by AKTAxpress system (GE Healthcare). In brief, the harvested cells were centrifuged at 10000G for 10 minutes and the supernatant was filtered through 0.22 um membrane to remove small cell debris. It was recommended to add DPBS (GIBCO, A12586-01) of equal volume into the supernatant to improve capture efficiency. For IgG purification, MabSelect column (GE Healthcare) was connected to AKTAxpress instrument and for Fab purification KappaSelect column (GE Healthcare) was used. The column was equilibrated with 10 CV (column volume) of the running buffer (DPBS) before sample loading. After the samples were loaded, the column was washed with 8 CV DPBS. The antibody samples were eluted from the column by citric elution buffer gradient (50 mM citric sodium, 140 mM NaCl, pH2.5), and then gathered into a deep well plate (Thermo Scientific Nunc Plate, Cat No. THM#278743) with neutralization buffer (1 M Tris-HCl, pH9.0). The antibody samples were pooled from the wells and then dialyzed in PBS or processed by filtering through Amicon centrifuge tubes.

Affinity Maturation of Humanized Variants

Humanized antibodies based on 4E10D7 and based on 2B11G2 were assayed for binding affinity, and a single humanized variant derived from each murine antibody was selected for further refinement by affinity maturation both by rational design and by mutagenesis across binding "hot spots" and the CDR regions using yeast display libraries. Variant antibodies were assayed for binding affinity.

A total of 21 heavy chain variants based on parental 4E10D7-derived humanized antibody hz45 were designed (named 4E10D7_AM_H_01 to 4E10D7_AM_H_21), while the light chain from 4E10D7-hz45 (named 4E10D7_AM_L_00) was used in all further variants.

A total of 50 heavy chain variants based on parental 2B11G2-derived humanized antibody hz42 or hz52 VH (named 2B11G2_AM_H_01 to 2B11G2_AM_H_50), and 5 light chain variants based on parental 2B11G2-derived humanized antibody hz52 VL (named 2B11G2_AM_L_01 to 2B11G2_AM_L_05) were designed.

Chains with mutations showing improved affinity were constructed in IgG or Fab format. Derived antibodies were subsequently renamed using the suffix from the heavy and light chain identifiers. For example, the IgG comprising the 4E10D7_AM_H_01 heavy chain and the 4E10D7_AM_L_00 light chain was renamed AM0100; IgG comprising the 4E10D7_AM_H_19 heavy chain and the 4E10D7_AM_L_00 light chain was renamed AM1900; IgG comprising the 2B11G2_AM_H_44 heavy chain and the 2B11G2AM_05 light chain was renamed AM4405.

Constructed antibodies were assayed for binding to huBMP9, and for inhibition of BMP9 signaling using the BRE-Luc assay described herein.

Example 3: Generation of Anti-BMP9 Antibodies by Phage Display Technology

In parallel with efforts to identify anti-BMP9 antibodies by mouse hybridoma and humanization procedures, described above, phage display was used to identify fully human anti-BMP9 antibodies. Briefly, for the selection of antibodies recognizing human BMP9, multiple panning strategies were employed. Therapeutic antibodies against human BMP9 protein were generated by selection of clones having high binding affinities, using as the source of antibody variant proteins a commercially available phage display library, the MorphoSys HuCAL PLATINUM® library. The phagemid library is based on the HuCAL® concept (Knappik et al., (2000) J Mol Biol 296:57-86) and employs the CysDisplay® technology for displaying the Fab on the phage surface (WO01/05950 to Lohning) In order to increase antibody binding affinity whilst maintaining library diversity the second round output of both solution and solid phase pannings were entered into the RapMAT™ process whilst the third round output of the whole cell and differential whole cell panning strategies were entered (Prassler et al., (2009) Immunotherapy; 1: 571-583).

In order to express full length IgG, variable domain fragments of heavy (VH) and light chains (VL) were subcloned from Fab expression vectors into appropriate expression vectors comprising human constant domains. Eukaryotic HKB11 cells were transfected with expression vector DNA encoding both heavy and light chains of IgGs.

Antibodies were assayed for binding affinity, specificity and inhibition of BMP9 binding to its receptors. Anti-BMP9 antibodies were classified into three groups: Type I inhibitors (able to inhibit the binding of ALKI to BMP9), Type II inhibitors (able to inhibit the binding of ActRIIB and/or BMPRII), or Type I+II inhibitors (able to inhibit the binding of ALKI and ActRIIB and/or BMPRII).

Antibodies showing the highest affinity for huBMP9 were subjected to further engineering. Engineering processes were performed using PCR-based strategies. After synthesis and assembly by overlap extension PCR the re-engineered VH and VL fragments were subcloned into the appropriate vector backbones for subsequent Fab or IgG expressions. Engineering processes involved the following aspects: germlining, removal of PTM sites, and/or codon optimization.

Example 4: BMP Receptor Inhibition Assay

Blocking ELISA was used to identify positive clones that can inhibit the interactions between BMP9 and its receptors. Four different recombinant BMP9 receptors can be used: human Alk1-Fc (R&D system, 370-AL-100); human BMPRII-Fc (R&D system, 811-BR-100); human ActRIIA-Fc (R&D system, 340-R2-100); human ActRIIB-Fc (R&D system).

The blocking activity of antibody sample to specific ligand/receptor combination was measured by ELISA. In brief, 50 ul of receptor at a concentration of 1 ug/ml in coating buffer (PBS) was added into 96 well ELISA plates at 4° C. overnight, followed by washing with PBST one time. ELISA plates were blocked with 200 ul blocking buffer (PBST containing 1% BSA) in each well and then incubated at room temperature (RT) for 1 hour, followed by washing with PBST for 3 times. Diluted antibody sample was mixed with biotinylated human BMP9 (bio-hBMP9 of 1 ug/ml) and incubated at RT for 45 minutes. The mixture of antibody and bio-hBMP9 was added to the plates of 50 ul/well and then incubated at RT for 30 minutes, followed by washing with PBST for 3 times. 50 ul Poly-HRP Streptavidin (Thermofisher, 21140) was added to each well of the plates and incubated at RT for 30 minutes, followed by washing with PBST for 5 times. Finally, 50 ul of TMB reagent (Invitrogen 002023) and 50 ul of 1N HCl (Invitrogen SS01100) were added to each well to stop the reaction. Absorbance of each well was read at 450 nm to get readout $OD_{450}$. Antibodies were characterized as "Type I" inhibitors if they inhibited the binding of Alk1 to BMP9 with an IC50<1 nM. Antibodies were characterized as "Type II" inhibitors if they inhibited the binding of ActRIIA, ActRIIB, and/or BMPRII to BMP9 with an IC50<1 nM. Antibodies were characterized as "Type I+II" if they inhibited the binding of Alk1 with an IC50<1 nM and ActRIIA, ActRIIB, and/or BMPRII to BMP9 with an IC50<1 nM Inhibition of binding of each BMP receptor to human BMP9 was measured in a separate assay.

Example 5: Binding Affinity of Anti-BMP9 Antibodies for BMP9

The solution equilibrium titration (SET) assay allows the determination of Fab-antigen interaction affinities (KD) for tight binders (see Friquet, B., Chaffotte, A. F., Djavadi-Ohaniance, L., and Goldberg, M. E. (1985). Measurements of the true affinity constant in solution of antigen-antibody complexes by enzyme-linked immunosorbent assay. J Immnunol Meth 77, 305-319; herein incorporated by reference). This technique does not require immobilization or labeling of either interaction partner and is suitable for strong interactions (from pM to low nM range). Briefly, mixtures of a constant concentration of Fab (concentrations at or below the expected K) were co-incubated with antigen within a suitable concentration range until equilibrium was reached. The amount of free Fab binding sites was determined by transferring the mixtures on antigen-coated plates and a brief incubation. The free Fab was consequently bound to the plate and detected with a detection antibody after a washing step for removing Fab-antigen complexes. The resulting signal was plotted versus the antigen concentration; and the $K_D$ was accurately determined by non-linear curve fitting.

A 22 serial $2^n$ dilution of the antigens (human BMP9 (GD-43-KS00); cyno BMP9, rat BMP9 (R&D Systems 5566-BP) or mouse BMP9 (iPROT101715)) was prepared in incubation buffer (PBS (Teknova Cat#P0195) containing 0.5% BSA (Sigma Cat#A7906-500G) and 0.02% Tween-20 (VWR Cat#437082Q)). A constant concentration of the Fab was added. A volume of 60 ul of each antigen:Fab mix was distributed in duplicates to a 384-well polypropylene microtiter plate (PP MTP, Greiner Cat#781280). Incubation buffer served as negative control and a sample containing no antigen served as positive control ($B_{max}$). The plate was sealed and incubated overnight (O/N) at room temperature (RT).

A 384-well standard MSD array plate (Meso Scale Discovery Cat#L21XA) was coated with 30 ul/well human BMP9 diluted in PBS as capture agent and incubated O/N at 4° C. After washing for 3 times with 70 ul/well washing buffer (TBS (Teknova Cat#T1680) with 0.05% Tween-20), the plate was blocked with 50 ul/well blocking buffer (PBS with 5% BSA) for 1 hour at RT. After washing, a volume of 30 ul/well of the antigen:Fab mix was transferred from the PP MTP to the coated MSD plate and incubated for 20 min at RT. After an additional wash step, 30 ul of detection antibody (Goat anti-human Fab specific (Jackson Immuno Research Cat#109-005-097) conjugated with MSD SULFO-TAG NHS Ester (Meso Scale Discovery Cat#R91AN-1)) diluted 1:1000 in incubation buffer was added to each well and incubated for 30 min at RT. The MSD plate was washed and 35 ul/well of read buffer (MSD Read Buffer T 4×, Meso Scale Discovery Cat#R92TC-1) was added and then incubated for 5 min at RT. ECL signals were measured with the MSD SECTOR Imager 6000. The data was evaluated with XLfit (IDBS) software following a 1:1 fit model for Fab (according to Piehler et al., 1997).

Example 6: Binding Specificity of Anti-BMP9 Antibodies

Binding affinity of anti-BMP9 antibodies to BMP9 was confirmed, and affinities (and specificities) to other antigens was determined via SPR by the Biacore T200 instrument (Biacore, GE healthcare). The antigen (recombinant human (rh) BMP9, or rhBMP2 (R&D Cat#355-BM-010), rhBMP7 (R&D Cat#354-BP-010), or rhBMP10 (R&D Cat#2926-BP-025)) was immobilized on a CM5 sensor chip (Biacore, GE Healthcare) using standard EDC-NHS amine coupling chemistry to reach specific surface density (50 RU for rhBMP9, 800 RU for rhBMP2, 580 RU for rhBMP7, 390 RU for rhBMP10). The running buffer was HBS-EP+ with 30 ul/min. Kinetic measurements were done using six different Fab concentrations of 2-fold serial dilution (31.25 nM, 62.5 nM, 125 nM, 250 nM, 500 nM, 1000 nM). The samples were measured at a flow rate of 30 ul/min with KINJECT for an injection time of 180 s and a dissociation time of 1500 s. After each cycle the sensor chip was regenerated to remove bound analytes with 10 mM glycine pH 1.5 (for rhBMP9) or 50 mM NaOH (for rhBMP2, rhBMP7 or rhBMP10). The raw data was fitted to a 1:1 binding model using Biacore T200 Evaluation Software (Biacore, GE healthcare) to determine $k_{on}$ and $k_{off}$ rate constants and then calculated KD afterwards.

One of ordinary skill in the art will appreciate that other methods may be used to measure the affinity of antibodies for BMP9, including, for example, ELISA or Octet (Forte-Bio Octet). While each technique is expected to produce substantially similar results, binding affinity and KD as measured by MSD-SET is considered to be definitive for antibodies having a KD less than about 10 nM.

Example 7: In Vitro Activity of Anti-BMP9 Antibodies

The ability of antibodies to inhibit BMP9-induced signaling was assayed using HEK293T ID-BRE2-luc cells, which stably express a BRE (BMP9 responsive element)-driven firefly luciferase.

The stably transfected HEK293T ID-BRE2-luc cells were grown in Dulbecco's Modified Eagle Medium (DMEM, high glucose; DMEM Containing GlutaMAX™-II, 4.5 g/l glucose but no sodium pyruvate; Gibco, #31965) and 10% heat inactivated fetal bovine serum (FBS, PAN # P30-1502, heat inactivated by incubation at 56° C. for 30 min), antibiotic free. Cells were incubated at 37° C. in a 5% $CO_2$ atmosphere. For sub-culturing, cells were detached with Accutase solution (PAA, # L11-007) after washing them once in 1×DPBS (without $CaCl_2$ and $MgCl_2$; Gibco, #14190). Cells were sub-cultured twice a week. As a selection antibiotic, Blasticidin S HCL (Invitrogen, # R210-01) was freshly added to the sub-cultured cells at a final concentration of 10 μg/ml.

For the Reporter Gene Assay, cells were detached using Accutase and seeded in a density of $1\times10^4$ cells per well in measurement medium (cultivation medium without selection antibiotic) in 384 well flat bottom white assay plates (Becton Dickinson Labware, #35-3988) and incubated over night at 37° C. and 5% $CO_2$. The next day, purified IgGs were pre-incubated with antigen (final concentration: 300 pM) for 30 min and 37° C. For human BMP9 induced activity, we use recombinant human BMP9 complex (200 ng/ml, purified by AutekBio FTZ Inc.); for human BMP2 induced activity, we use recombinant human BMP2 (100 ng/ml, R&D #355-BM-010/CF); for human BMP7 induced activity, we use recombinant human BMP7 (400 ng/ml, R&D #354-BP-010/CF); for Rat BMP9 induced activity, we overexpress 6 ug pcDNA3.1-rat BMP9 plasmid in 293T cells seeded in 90 mm dish, and 48 hr later, collect the culture medium as rat BMP9 condition medium, and we use 1/16 diluted rat BMP9 condition medium. The pre-incubated antibody-antigen mixture was added to the cells and 18 hours post stimulation, cells were lysed and luciferase activity was detected by addition of Bright-Glo™ (Bright-Glo™ Luciferase Assay System; Promega, # E2620) to the cells according to the manufacturer's protocol. The luminescence was measured in a Tecan reader (Integration time: 250 ms; Attenuation: none; time between move and integration: 3 ms).

Example 8: Smad1/5/8 Phosphorylation Assay

For the HUVEC cell assay, HUVEC cells were purchased from Allcells and cultured in HUVEC medium (Allcells, H-004). 6-well plates were seeded with $3\times10^5$ cells/well and cultured in medium. Cells were then incubated at 37° C. with 5% $CO_2$ overnight. To the cells, BMP9 antibody, with or without BMP9 (recombinant human BMP9 complex, as described above), was added in DMEM plus 0.5% FBS. After 1 hr, harvest cells and denature in SDS sample buffer for 10 min at 95° C. Proteins were separated by SDS-PAGE and blotted onto nitrocellulose membranes (iBlot Gene Transfer Stacks, Life Tech #34095). Membranes were blocked with 5% nonfat dry milk for 1 hr and then incubated with primary antibodies for overnight at 4° C., anti-phosphor-Smad 1/5 Ab (CST #9516, 1:1000), anti-ID1 Ab (Santa Cruz #SC-488, 1:200) or anti-GAPDH Ab (CST #2118, 1:2000). After being washed, membranes were incubated for 1 hr at room temperature by using the appropriate horseradish peroxidase-conjugated secondary antibodies for 1 hr at room temperature, anti-mouse IgG-HRP (CST #7076, 1:2500) or anti-Rabbit IgG-HRP (CST #7074, 1:2500). Results were visualized by BioRed ChemDoc Image machine.

For the CFSC cell assay, CFSC cells were cultured with DMEM plus 10% FBS. On day 0, seed 50 μl/well of $1.0\times10^5$ cells/ml suspension ($5\times10^3$ cells/well) with culture medium in a black-96-well PE plate, incubate overnight at 37° C., 5% $CO_2$. On day 1, prepare antibody dilutions and human BMP9 solutions: recombinant human BMP9 complex (200 ng/ml) and Abs (dilute from 12 ug/ml by 1:3 ratio and 6 times). Mix antibody and BMP9 (1:1), incubate for 30 min at 37° C., then, add 50 μl/well of the BMPs/Abs mixture to the cell plate containing 50 μl of medium from the previous day, incubate at 37° C. with 5% $CO_2$ 1.5 hr later, fix plate in 4% paraformaldehyde for 15 min at room temperature, after washing with PBS, permeabilize the cells with 0.1% TritonX-100 in PBS for another 15 min at room temperature. Wash again, block the cells with 3% BSA in PBS for 1 hr at room temperature. Then incubate with p-Smad1/5/8 antibody (Millipore #AB3848) overnight at 4° C., after wash, incubate with second antibody (Alexa Fluor 488 Donkey anti-rabbit antibody, Life Tech #A21206) plus DAPI dye for another 2 hr at room temperature. Wash thoroughly, then supplied with 100 ul PBS, read by Thermofisher Cellomics ArrayScan HCS System.

Example 9: In Vivo Activity of Anti-BMP9 Antibodies

In vivo efficacy of anti-BMP9 antibodies was measured using a hydrodynamic injection (HDI) mouse model of liver fibrosis.

Male BALB/c mice, specific pathogen free (SPF) and 7-8 weeks old, were supplied by Shanghai Slac Laboratory Animal Co., Ltd. Upon arrival at the facility, mice were allowed for acclimation for at least 7 days. After randomly grouped, mice were treated intravenously once with BMP9 Abs or human control IgG, and followed by hydrodynamic injection (HDI) of BMP9 plasmids or blank vector. 4 days later, after weighing, all the mice were sacrificed to collect blood and liver tissue samples. Under anaesthesia with 100 mg/kg ketamine, cardiac puncture was performed to get as much blood as possible. Whole livers were quickly flushed with saline, blotted up briefly on paper towel, and followed by weighing to measure the liver weight/body weight ratio. And after liver morphology observation, livers were sliced, then pieces of livers were transferred into cryogenic vials and snap-freezed in liquid nitrogen for molecular biology analysis. All the samples were stored at −80° C. before analyzation.

Liver function, including Serum alanine aminotransferase (ALT) and Aspartate aminotransferase (AST) levels, were measured by HITACHI 7020 Automatic Biochemistry Analyzer, using Quick Auto Neo ALT and Quick Auto Neo AST kit (SHINO-TEST CORPORATION, Japan). Liver tissues were subject to gene expression profiling and histology analysis. For gene expression profiling, total RNA was extracted from the tissues with RNeasy mini kit (Qiagen), reverse transcription of purified RNA was performed using the Superscript III reverse transcription kit according to the manufacturer's instructions (Life Technologies), then the quantification of gene transcripts was measured by quantitative real-time PCR using the Power SYBR Green PCR Master Mix (ABI) and the ABI 7500 Fast real-time PCR system. The primer pairs used for mouse ID1 were 5'-CGAGGCGGCATGTGT TCC-3' (SEQ ID NO: 219) and 5'-TCTGGGGAACCGAGAGCAC-3' (SEQ ID NO: 220); for mouse GAPDH, 5'-CGTGCCGCCTG GAGAAACC-3' (SEQ ID NO: 221) and 5'-TGGAAGAGTGGGAGTTGCT-GTTG-3' (SEQ ID NO: 222). Liver tissues were lysed in T-per buffer (Thermo, #78510) to perform ID1 and p-smad1/5 Western-Blot, with anti-phosphor-Smad 1/5 Ab (CST #9516, 1:1000), anti-ID1 Ab (Santa Cruz #SC-488, 1:200), anti-GAPDH Ab (CST #2118, 1:2000), anti-mouse IgG-HRP (CST #7076, 1:2500) and anti-Rabbit IgG-HRP (CST #7074, 1:2500), the western process was the same as In-vitro activity test by smad 1/5 phosphorylation assay experiment.

Example 10: In Vivo $CCl_4$ Mouse Model of Liver Injury

Male BALB/c and C57BL/6 mice, specific pathogen free (SPF) and 7-8 weeks old, were supplied by Shanghai Slac Laboratory Animal Co., Ltd.

Upon arrival at the facility, mice were allowed to acclimatize for at least 7 days. After randomly grouping, mice were treated intraperitoneally twice a week with 4 μl/g 25% $CCl_4$ dissolved in olive oil to induce liver fibrosis for 2 weeks. At the same time of first $CCl_4$ injection, BMP9 Abs were also injected intravenously (10 mg/kg, twice per week) to test their function during liver fibrosis. The mice were sacrificed one week later, and liver tissues were subjected to protein expression profiling and histology analysis.

For histology, liver specimens were fixed with 10% buffered formalin for 16-18 hrs, embedded with paraffin. Immunohistochemistry was conducted by using Ventana Discovery® automated slide stainer (Ventana Medical Systems, Tucson, Ariz., USA). Rabbit polyclonal anti phospho-Smad1/5/8 (Millipore, Billerica, Mass.) antibody, was applied as the primary antibody at appropriate concentration. For protein expression, Western Blot was performed. Materials and methods were the same as in in-vitro activity test by Smad 1/5 phosphorylation assay, described above.

Example 11: Results of Binding Affinity, Specificity and In Vitro Inhibition Assays The binding affinities, specificities and IC50 values (as measured in the BRE-Luc RGA) of humanized hybridoma-generated IgGs are summarized in Table 4 and Table 5.

TABLE 4

| Antibody | Inhibitor Sub-Type | Inhibition of ALKI/ BMP9* | Inhibition of ActRIIB/B MP9* | Inhibition of BMPRII/ BMP9* |
|---|---|---|---|---|
| AM0100 | Type II | − | + | + |
| AM1900 | Type II | − | + | + |
| AM4405 | Type I | + | − | − |

*= based upon inhibition of the receptor subtypes by the parental murine antibody.
+ = inhibition of interaction at an Ab concentration less than about 1 nM.
− = no inhibition of interaction at an Ab concentration less than about 1 nM.

TABLE 5

Kinetic parameters of anti-BMP9 antibodies (averages of at least three independent assays). KD values as measured by MSD-SET.

| Antibody | RGA IC50 [pM] | huBMP9 KD [pM] | cyno BMP9 KD [pM] | rat BMP9 KD [pM] | mouse BMP9 KD [pM] | huBMP10 KD [pM] | huBMP2 KD [pM] | huBMP7 KD [pM] |
|---|---|---|---|---|---|---|---|---|
| AM0100 | 83 | 182 | 128 | 94 | 73 | nb | nb | nb |
| AM1900 | 100 | 54 | n/a | 46 | n/a | nb | 999000 | 108000 |
| AM4405 | 90 | 18 | 48 | 13 | 8 | nb | 177000 | 9170000 |

n/a = not assayed
nb = no binding
nsp = very weak binding, no evaluation possible The binding affinities, specificities and IC50 values (as measured in the BRE-Luc RGA) of phage display-generated fully human antibodies are summarized in Table 6 and Table 7.

TABLE 6

| Antibody | Inhibitor Sub-Type | VH-Type | VL-Type | Inhibition of ALKI/ BMP9 | Inhibition of ActRIIB/ BMP9 | Inhibition of BMPRII/ BMP9 |
|---|---|---|---|---|---|---|
| MOR022928 | Type I | VH3_15 | lambda-3 | + | − | − |
| MOR023787 | Type I | VH3_15 | lambda-3j | + | − | − |
| MOR022962 | Type I + II | VH3_23 | kappa-1 | + | + | + |
| MOR022965 | Type I + II | VH1A | kappa-1 | + | + | + |
| MOR023073 | Type II | VH1B | kappa-1 | − | + | + |
| MOR023793 | Type II | VH1B | kappa-1 | − | + | + |
| MOR023090 | Type II | VH5 | lambda-1 | − | + | + |
| MOR023795 | Type II | VH5 | lambda-1e | − | + | + |
| MOR023093 | Type II | VH1A | lambda-1 | − | + | + |
| MOR023796 | Type II | VH1A | lambda-1e | − | + | + |

+ = inhibition of interaction at an Ab concentration less than about 1 nM.
− = no inhibition of interaction at an Ab concentration less than about 1 nM.

TABLE 7

Kinetic properties of phage display-generated anti-BMP9 antibodies (averages of at least three independent assays). KD values as measured by MSD-SET.

| Antibody | RGA IC50 [pM] | huBMP9 KD [pM] | cyno BMP9 KD [pM] | rat BMP9 KD [pM] | mouse BMP9 KD [pM] | huBMP10 KD [pM] | huBMP2 KD [pM] | huBMP7 KD [pM] |
|---|---|---|---|---|---|---|---|---|
| MOR023787 | 118 | 200 | 350 | n/a | 740 | nb | 2020000 | nsp |
| MOR022962 | 138 | 12 | 18 | 6 | 5 | nb | nsp | nsp |
| MOR022965 | 180 | 32 | 23 | n/a | 69 | nb | 3110000 | nsp |
| MOR023793 | 113 | 120 | 240 | n/a | 440 | nb | 1810000 | 686000 |
| MOR023795 | 167 | 288 | 262 | 69 | 59 | nb | nsp | nsp |
| MOR023796 | 130 | 440 | 130 | n/a | 420 | nb | nsp | nsp |

n/a = not assayed
nb = no binding
nsp = very weak binding, no evaluation possible Taken together these data show the identification of anti-BMP9 antibodies capable of binding to at least three different epitopes of human BMP9. AM4405, MOR022928 and MOR023787 bind to an epitope of huMBP9 where binding is capable of inhibiting the interaction of Type I BMP receptors (e.g., AlkI) with BMP9. In contrast, AM0100, AM1900, MOR023073, MOR023793, MOR023795, MOR023796, MOR023090, and MOR023093 bind to an epitope of huMBP9 where binding is capable of inhibiting the interaction of Type II BMP receptors (e.g., ActIIR, BMPRII) with BMP9. MOR022962 and MOR022965 bind to a separate epitope where binding is capable of inhibiting the interaction of both Type I and Type II BMP receptors with BMP9 Inhibition of either Type I BMP receptor or Type II BMP receptor, or of both Type I and Type II BMP receptor by the antibodies disclosed herein was achieved at an IC50 less than or equal to about 1 nM.

These data also indicate that antibodies, including human and humanized antibodies, have been identified from two different panning sources that are capable of binding huBMP9 with high affinity and specificity. For example, all antibodies identified bind to huBMP9 with a KD less than 1 nM, e.g., less than 500 pm. Many of the antibodies identified bind to huBMP9 with a KD less than 200 pM. As well, the antibodies of the present invention were capable of cross-reacting with cyno-, rat- and/or murine-BMP9, which is beneficial in that these antibodies can be used in animal models of disease. Finally, all antibodies were highly specific for BMP9, having at least 1000-fold specificity for BMP9 over human BMP10, human BMP7 and human BMP2, and in many cases exhibiting no binding to human BMP10, human BMP7 or human BMP2. As well, these antibodies are able to inhibit BMP9 signal induction in a reporter gene assay ("RGA") with an 1050 less than 1 nM, and in many cases, less than 200 pM. Taken together, these results demonstrate that the antibodies of the present invention are highly specific and potent anti-BMP9 antibodies.

Example 12: Crystal Structure of 2B11G2 Fab with huBMP9

The crystal structure of human BMP9 in complex with 2B11G2 chimeric Fab antibody was solved at 2.8 Å, which contains one homo-dimer of two hBMP9 mature domains and two Fab molecules in each asymmetric unit. The structure was deposited into internal database Proasis with accession number 1dpbd (1dpbd is referred as this structure of hBMP9 with 2B11G2 chimeric Fab hereafter).

By overlaying the structure of 1dpbd onto structure of BMP9-Alk1-ActRIIb (PDB: 4FAO), it showed that 2B11G2 and Alk1 share the same binding surface of BMP9 (mature domain), which is aligned to the experimental observation that 2B11G2 can compete with Alk1 for BMP9 binding. The structure also suggested the interaction of ActRIIb with BMP9 is not affected upon 2B11G2 Fab binding to BMP9.

All 6 CDRs of 2B11G2 contribute to the interactions with BMP9; and major binding interfaces are established between BMP9 and HCDR2, HCDR3 and LCDR3. HCDR1 binds to BMP9 through hydrophobic interactions; specifically, Thr28 and Pro30 of HCDR1 interact with Gly21, Ser24 and Trp25 of BMP9 (in numbering for BMP9 mature domain). HCDR2 binds to BMP9 mainly through hydrophobic interactions; specifically, Val50 is surrounded by phenyl groups from BMP9, Tyr52 has H-bond with Trp22 of one BMP9 monomer and hydrophobic interactions with Leu60 and Phe43 of another BMP9 monomer, Val57 and Ser59 have hydrophobic interaction with Phe43 and Pro44 of BMP9. HCDR3 binds to BMP9 mainly through hydrophobic interactions; specifically, Phe102 is packed with Phe43, Ile56 and Leu60 of one BMP9 monomer and with Trp22 and Trp25 of another BMP9 monomer, Tyr103 is stacked with Tyr86 and Trp25 of BMP9. Asn32 in LCDR1 is the only residue in LCDR1 that has interaction with BMP9. Tyr50 in LCDR2 forms H-bond with Asp47 of BMP9. LCDR3 binds to BMP9 through mixed hydrophobic and polar interactions; specifically, Ser91 and Ser93 form H-bonds with Asp47 and Asp48 of BMP9 respectively, His92 main chain forms H-bonds with Asp47 and Asp48 main chains in BMP9, Trp94 and Tyr96 make hydrophobic interactions with Pro44 and Ala46 of BMP9.

Results from the receptor competition inhibition assay indicated that 2B11G2 is a BMP9 Type I receptor inhibitor. The crystal structure confirms this by showing that 2B11G2 binds to an epitope overlapping the Alk1 (a BMP Type I receptor) binding site.

Interactions between 2B11G2 Fab and the mature fragment of huBMP9 (SEQ ID NO: 215) are illustrated in Table 8.

TABLE 8 residual contacts between 2B11G2 Fab and human BMP9 mature domain (SEQ ID NO: 215).

| Region | Residue | Contacts on huBMP9 | Region | Residue | Contacts on huBMP9 |
|---|---|---|---|---|---|
| HCDR1 | T28 | S24, W25 | HCDR3 | Y101 | L45, I56 |
| | P30 | G21 | | F102 | W22, W25, F43, I56, |
| | | | | Y103 | L60 |
| | | | | | W25, Y86, K96 |
| HCDR2 | Y52 | W22, F43, L60 | | G104 | K53 |
| | N55 | F43, L60, L63 | | G105 | K53 |
| | V57 | F43, P44 | | Y107 | L45 |
| | S59 | P44 | LCDR3 | S91 | D47 |
| LCDR1 | N32 | D47 | | H92 | D47, D48 |
| LCDR2 | Y50 | D47 | | S93 | D48 |
| | | | | W94 | P44, A46 |
| | | | | Y96 | A46 |

Example 13: Results of Vitro Activity Assessment of Anti-BMP9 Antibodies

As shown in FIG. 1*a*, and in Table 5, above, hybridoma-derived antibodies 2B11G2-AM4405, 4E10D7-AM0100 could inhibit human BMP9 induced reporter gene activity with relatively low IC50s, while having nearly no effect on human BMP2 or human BMP7 induced reporter gene activity. As well, as shown in FIG. 1*b*, parental antibodies could inhibit rat BMP9-induced reporter gene activity, and fit clear reducing curves, which means these antibodies have similar inhibitory activities on human and rat BMP9 signaling. Together, these results demonstrate that the anti-BMP9 antibodies are able to specifically inhibit BMP9 signaling, and are able to cross react with BMP9 proteins from different species (e.g., can cross-react with human and rat BMP9)

As well, phage display-generated antibodies were also shown to be specific for BMP9, and cross-reactive to BMP9 from different species. As shown in FIG. 2*a* and in Table 7, above, the fully human anti-BMP9 antibodies could inhibit BMP9 signaling at concentrations less than 1 nM, but did not affect signaling of BMP2 or BMP7 at concentrations up to 1 uM. In particular, Mor022962 could inhibit human BMP9 induced reporter gene activity with relatively low IC50s, while having nearly no effect on human BMP2- or human BMP7-induced reporter gene activity. As shown in FIG. 1*b*, Mor022962 antibody could inhibit rat BMP9 induced reporter gene activity, and fit clear reducing curves. Together, these results demonstrate that the phage display generated-BMP9 antibodies are able to specifically inhibit BMP9 signaling, and are able to cross react with BMP9 proteins from different species (e.g., can cross-react with human and rat BMP9).

Example 14: Results of In Vitro Smad 1/5/8 Phosphorylation Assay

The ability of anti-BMP9 antibodies to inhibit BMP9-induced Smad 1/5 phosphorylation and/or Id1 expression was measured in two cell lines: HUVEC and CFSC as described below.

Without being bound by theory, it is believed that, during BMP9 signaling, BMP9 ligand first binds its receptors and phosphorylates Smad1/5/8, then with the help of Co-Smads. Next, phosphorylated Smad1/5/8 enter the nucleus to promote the expression of BMP9 target genes, for example, ID1. Thus, we tested the level of phosphorylated Smad1/5/8

Figure 3B:
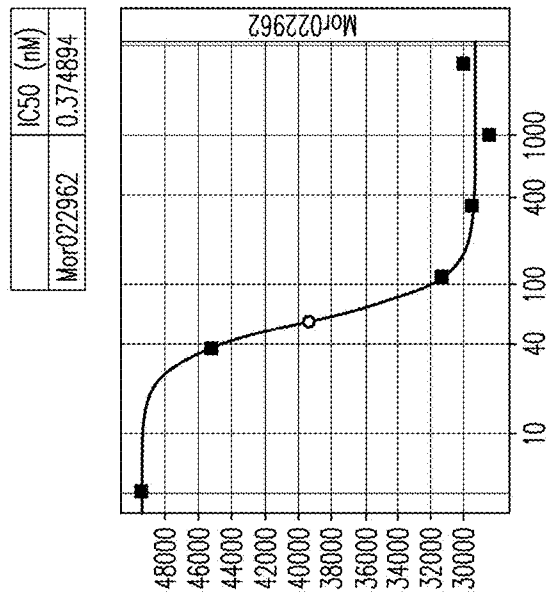
FIG. 3 In vitro activity test by smad 1/5 phosphorylation assay. a. Reducing curves and IC50 of hybridoma-generated BMP9 antibodies on human BMP9 induced phosphorylation of smad 1/5/8 staining in CFSC cells. b. Reducing curves and IC50 of phage display-generated BMP9 antibodies on human BMP9 induced phosphorylation of smad 1/5/8 staining in CFSC cells. c. Western-Bloting of BMP9-induced phosphorylated smad 1/5 and ID1 expression in HUVEC cells in the absence or presence of anti-BMP9 antibody.
Figure 3A:
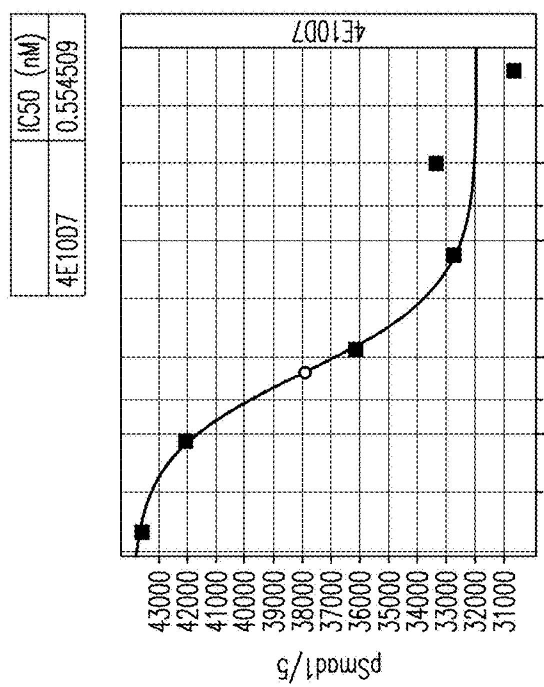
Figure 3C:
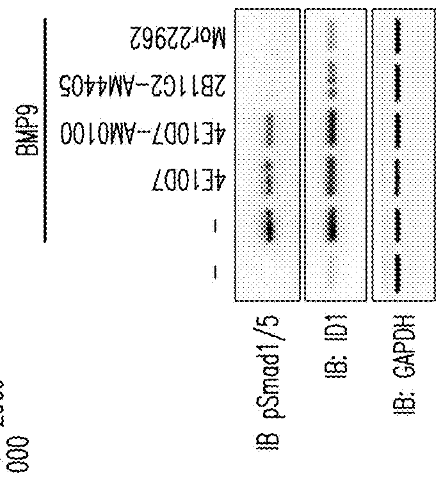

("p-Smad 1/5/8") and ID1 expression as readouts for BMP9 signaling. As shown in FIG. 3*a*, when we treated CFSC cells with BMP9 and hybridoma-generated antibodies, parental 4E10D7 antibody could inhibit the level of p-Smad1/5/8 staining induced by BMP9. As shown in FIG. 3*b*, phage display-generated antibody MOR022962 antibody could inhibit the level of p-Smad 1/5/8 staining induced by BMP9 in CSFC cells. Moreover as shown in FIG. 3*c*, in HUVEC cells, phage display-generated and hybridoma-generated anti-BMP9 antibodies could reduce the level of phosphorylated smad1/5 and ID1 expression induced by BMP9. All of the above data indicate that the anti-BMP9 antibodies inhibit BMP9 signaling.

Example 15: Results of In Vivo Activity of Anti-BMP9 Antibodies

Figure 4A:
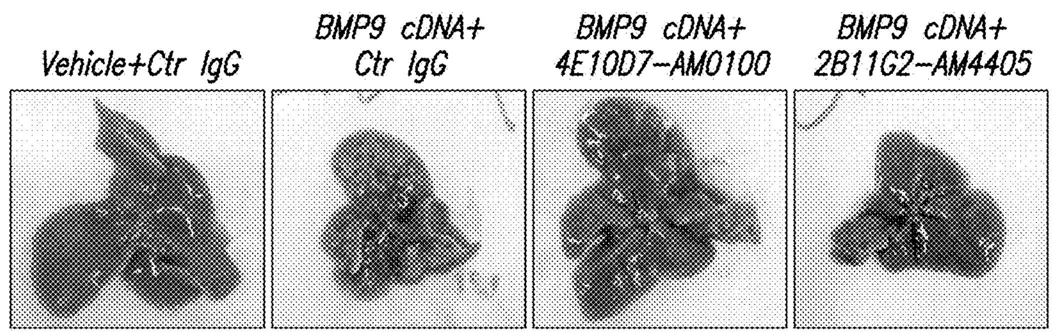
FIG. 4. In vivo efficacy study in BMP9 HDI mouse model with hybridoma-generated anti-BMP9 antibodies. Representative livers (a), liver and body weight (b), liver function (c) of different treatment groups are shown in comparison to untreated and negative controls. d. mRNA expression of ID1 were detected by quantitative PCR. BMP9 cDNA indicates pcDNA3.1-mouse BMP9, which encodes mouse BMP9. *P<0.05, P<0.01, *P<0.001, ****P<0.0001.
Figure 4B:
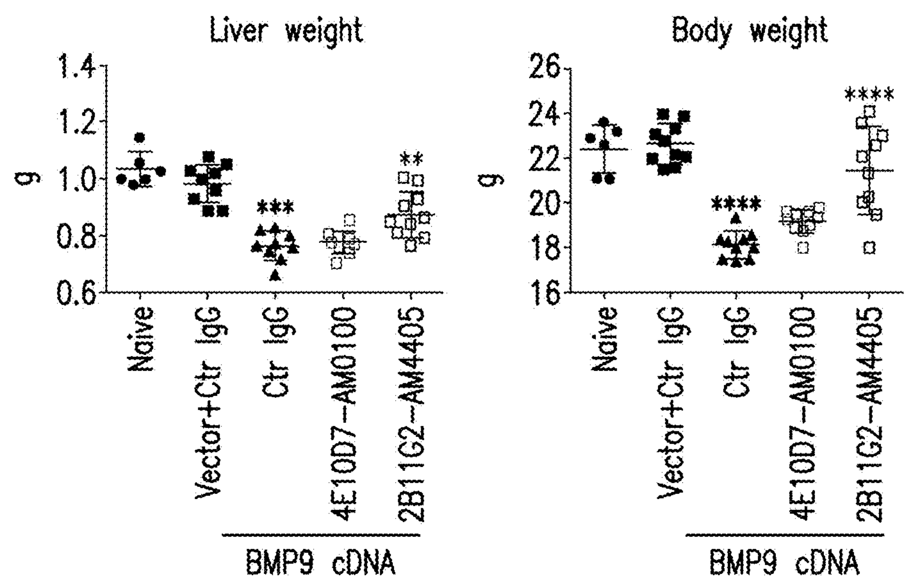
Figure 4C:
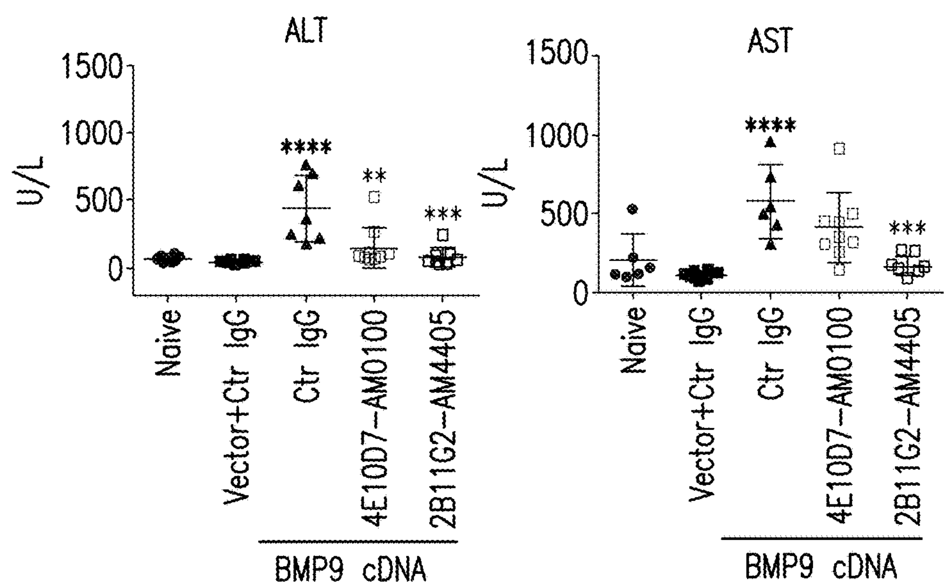
Figure 4D:
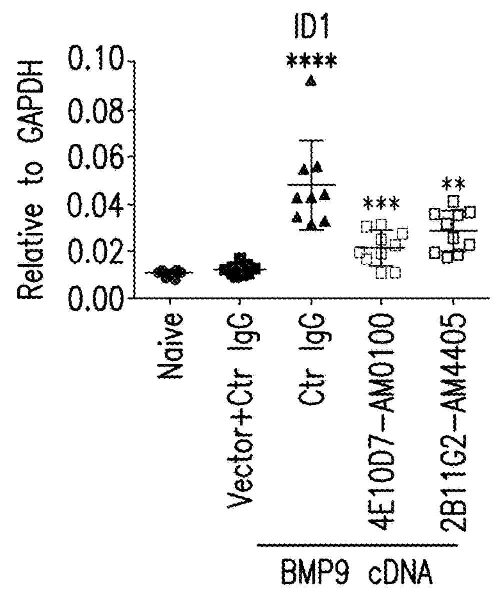
Figure 5A:
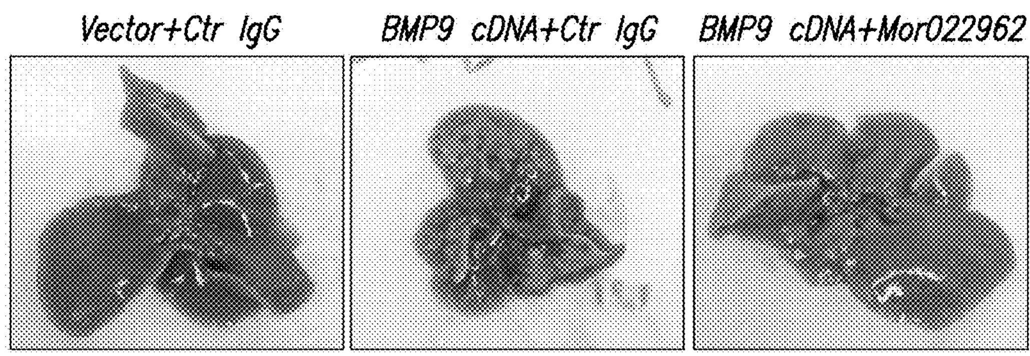
FIG. 5. In vivo efficacy study in BMP9 HDI mouse model with phage display-generated anti-BMP9 antibodies. Representative livers (a), liver and body weight (b), liver functions (c) of different treatment group are shown in comparison to untreated and negative controls. d. mRNA expression of ID1 were detected by quantitative PCR. BMP9 cDNA indicates plasmid pcDNA3.1-mouse BMP9, which encodes mouse BMP9. *P<0.05, P<0.01, *P<0.001, ****P<0.0001.
Figure 5B:
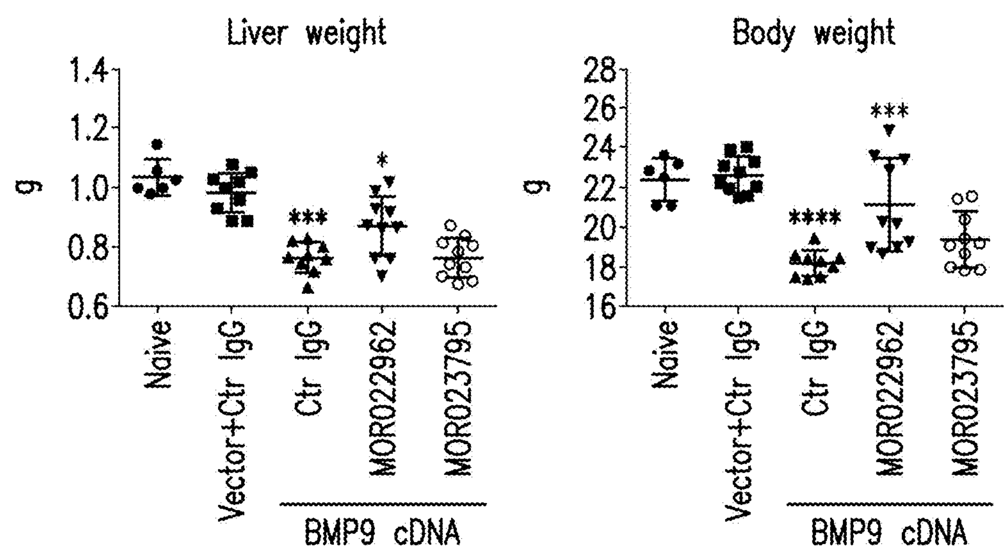
Figure 5C:
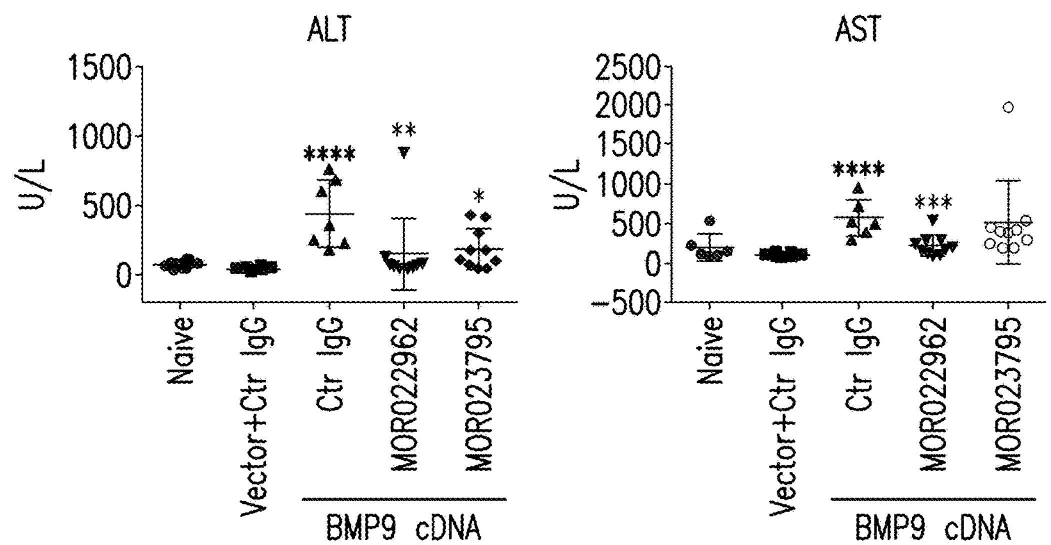
Figure 5D:
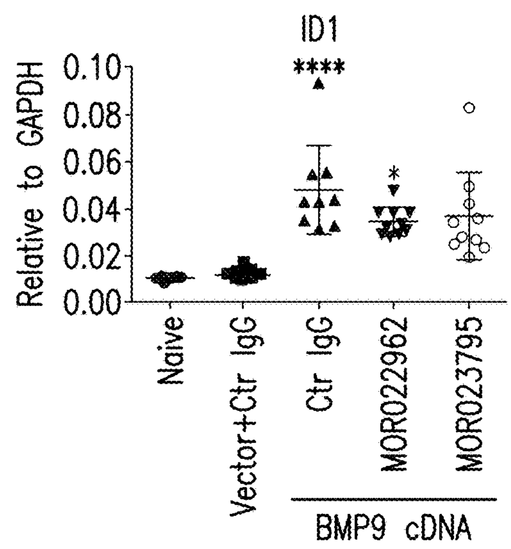

Using liver morphology, liver and body weight, liver functions as readouts for liver injury, we found that hydrodynamic injection of BMP9 expression plasmids could induce severe liver injury in mice. As shown in FIGS. 4 and 5, HDI of BMP9 plasmids could cause severe liver necrosis (FIG. 4*a*/5*a*), accompanied by decreased liver and body weight (FIG. 4*b*/5*b*), and increased ALT, AST levels (FIG. 4*c*/5*c*). When mice were treated with anti-BMP9 antibody at the same time, liver necrosis, ALT and AST levels were decreased, while liver and body weight were improved compared with HDI of BMP9 plasmids only (FIG. 4/FIG. 5). Taken together these results indicate that anti-BMP9 antibodies can effectively block BMP9-induced liver injury in vivo. Moreover, anti-BMP9 antibodies could also inhibit BMP9 induced expression of ID1, a target gene of BMP9 signaling (FIG. 4*d*/5*d*). All of the above data shows that anti-BMP9 antibodies can block both the signaling and function of BMP9 in vivo.

Example 16: Results of In Vivo $CCl_4$ Mouse Model of Liver Injury

Figure 6A:
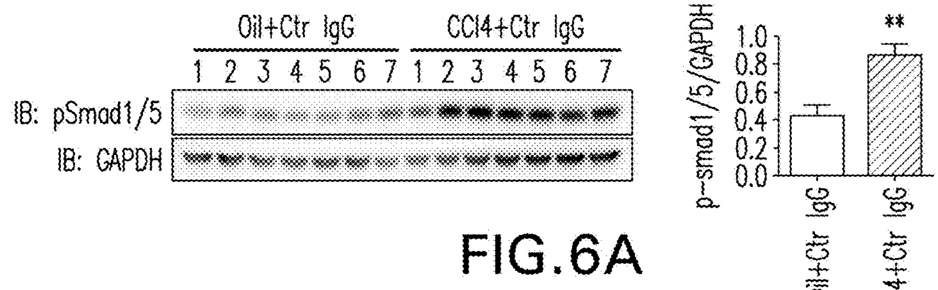
FIG. 6. In vivo efficacy study in $CCl_4$ mouse model. Western blot results of Control IgG plus Oil or $CCl_4$ treated groups (a), Ctr IgG or hybridoma-generated BMP9 Ab plus CCl4 treated groups (b) were shown. The right panels were normalized by GAPDH expression. Significant differences are indicated with: *P<0.05, P<0.01, *P<0.001. c, d. p-Smad 1/5/8 histology results of different groups were shown. c. Data of C57BL/6 mice. d. Data of BALB/c mice.
Figure 6B:
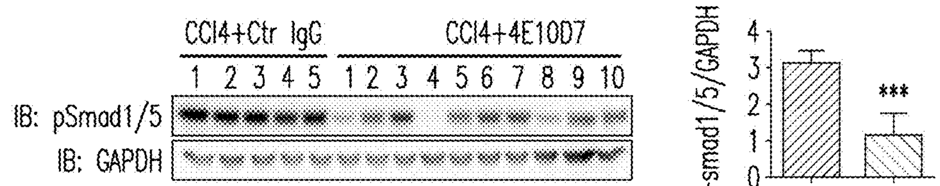
Figure 6B:
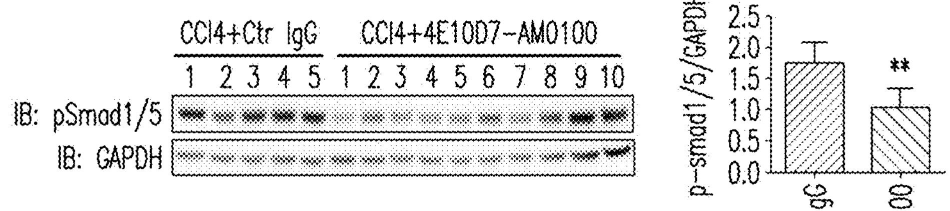
Figure 6C:
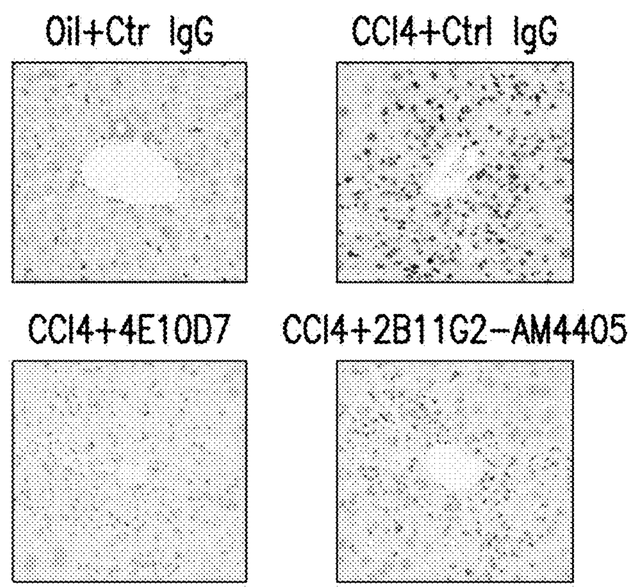
Figure 6D:
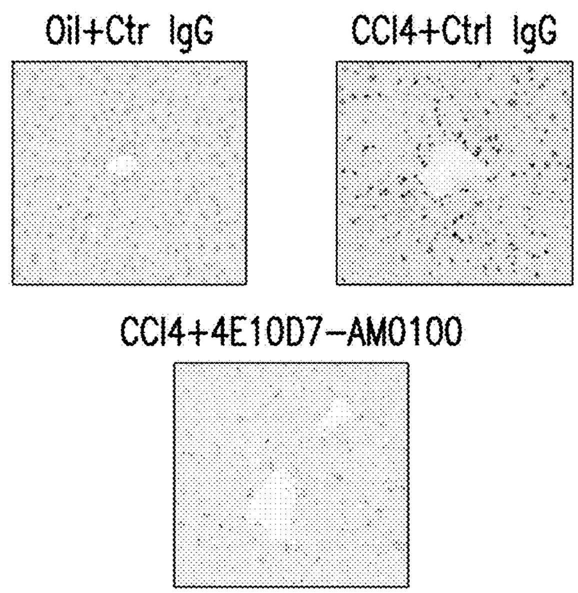
Figure 7A:
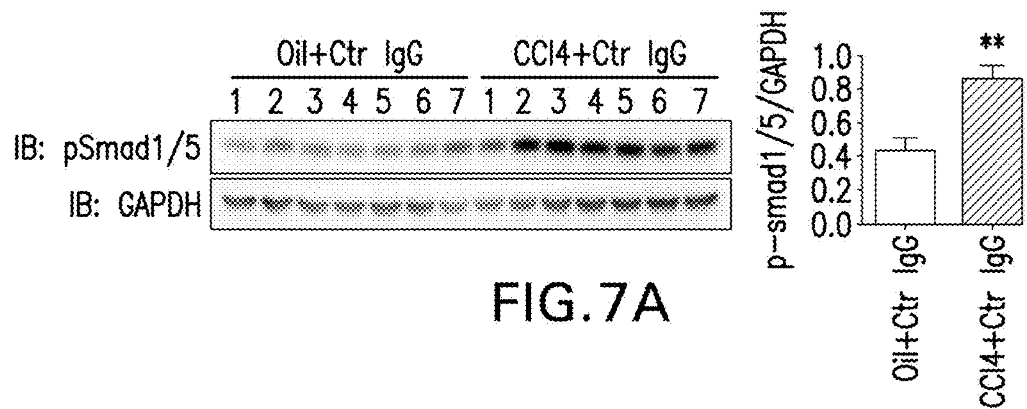
FIG. 7. In vivo efficacy study in $CCl_4$ mouse model. Western blot results of Control IgG plus Oil or CCl4 treated groups (a), Ctr IgG or phage display-generated Ab plus CCl4 treated groups (b) were shown. The right panels were normalized by GAPDH expression. Significant differences are indicated with: *P<0.05, **P<0.01. c. pSmad 1/5/8 histology results of different groups were shown.
Figure 7B:
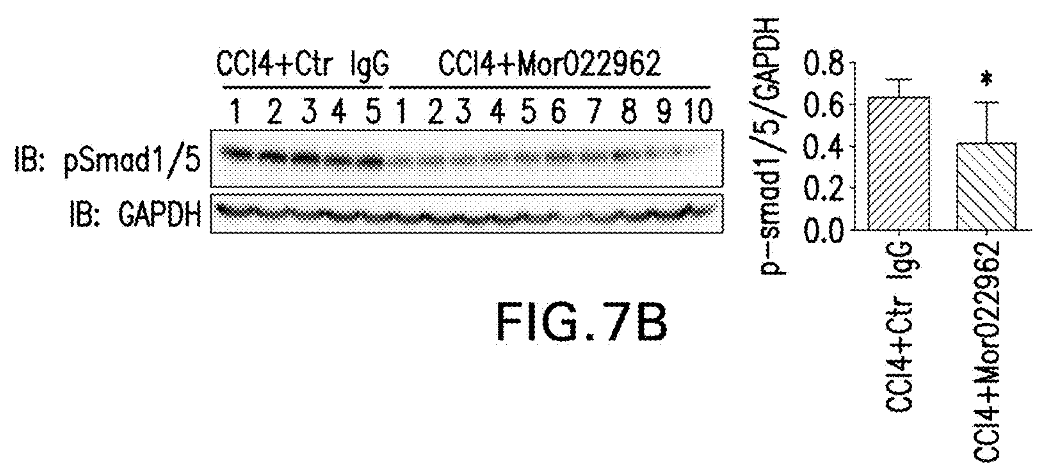
Figure 7C:
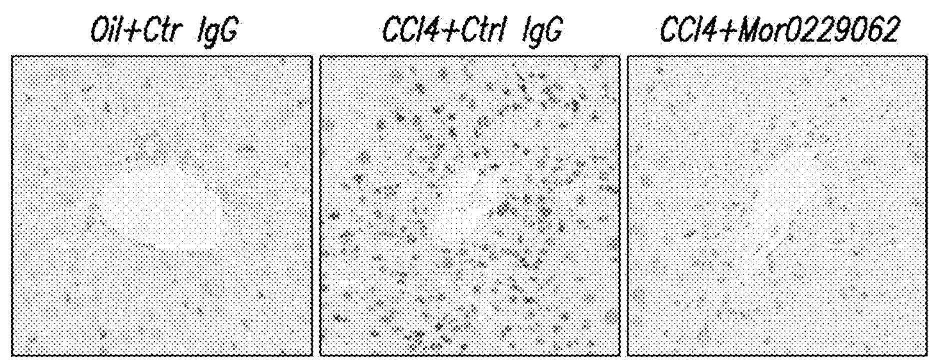

Phosphorylation of smad1/5/8 was upregulated in $CCl_4$-treated mice compared to oil control by both Western Blot and histology (FIGS. 6*a, b* and *c*/FIGS. 7*a, b* and *c*), indicating upreguation of BMP9 and liver damage. When mice were treated with anti-BMP9 antibody, $CCl_4$-induced phosphorylation of smad1/5/8 was inhibited, indicating that BMP9 antibody could effectively inhibit BMP9 signaling in vivo.

Example 17: Long-Term In Vivo CCl4 Mouse Model of Liver Fibrosis

Female BALB/c mice, specific pathogen free (SPF) and 7-8 weeks old, were supplied by Shanghai Slac Laboratory Animal Co., Ltd. After random grouping, mice were injected intravenously (10 mg/kg anti-BMP9 antibody or mouse Control IgG) to test their function during liver fibrosis. 2 hours after antibody injection, mice were treated intraperitoneally with 4 μl/g 25% $CCl_4$ dissolved in olive oil, and were thereafter treated twice per week with the same $CCl_4$ dose for two weeks to induce liver fibrosis.

After two weeks mice were sacrificed to collect blood and liver tissue samples. Under anaesthesia with isoflurane, blood samples were collected. Whole livers were quickly flushed with saline, blotted up briefly on paper towel, and followed by weighing. And after liver morphology observation, livers were sliced, and transferred into cryogenic vials and snap-freezed in liquid nitrogen for molecular biology analysis. All the samples were stored at −80° C. before analysis.

Serum alanine aminotransferase (ALT) level was measured by HITACHI 7020 Automatic Biochemistry Analyzer, using Quick Auto Neo ALT and Quick Auto Neo AST kit (SHINO-TEST CORPORATION, Japan). Liver tissues were subject to gene expression and histology analysis. For gene expression analysis, total RNA was extracted from the tissues with RNeasy mini kit (Qiagen), reverse transcription of purified RNA was performed using the Superscript III reverse transcription kit according to the manufacturer's instructions (Life Technologies), then the quantification of gene transcripts was measured by quantitative real-time PCR using the Power SYBR Green PCR Master Mix (ABI) and the ABI 7500 Fast real-time PCR system. The primer pairs used for mouse ID1 were 5'-CGAGGCGGCATGTGTTCC-3' (SEQ ID NO: 219) and 5'-TCTGGGGAACCGAGAGCAC-3' (SEQ ID NO: 220); for mouse GAPDH, 5'-CGTGCCGCCTGGAGAAACC-3' (SEQ ID NO: 221) and 5'-TGGAAGAGTGGGAGTTGCTGTTG-3' (SEQ ID NO: 222). Liver hydroxyproline content was assayed with modified Hydroxyproline Assay Kit (Sigma). For histology, liver specimens were fixed with 10% buffered formalin for 16-18 hrs, embedded with paraffin, then subject to Sirius red staining and quantification of fibrotic area.

Results of In Vivo $CCl_4$ Mouse Model of Liver Fibrosis.

Using Sirius red staining and liver hydroxyproline content as readouts for liver fibrosis, we found that injection of $CCl_4$ could induce liver fibrosis in mice. As shown in FIG. 8, injection of $CCl_4$ plus control IgG could induce liver fibrosis as determined by positive Sirus red staining and increased liver hydroxyproline content (FIGS. 8*a* & *b*). These were accompanied by increased ALT level (FIG. 8*c*), and increased liver weight (FIG. 8*d*). $CCl_4$ treatment also activated BMP9 signaling by upregulating its target gene, Id1 (FIG. 8*e*). When mice were treated with anti-BMP9 antibody, Id1 gene induction is dramatically decreased, indicating a sufficient blockage of BMP9 signaling by BMP9 antibodies. Meanwhile, $CCl_4$—induced liver fibrosis and ALT level were significantly decreased, while liver weight were improved compared with control IgG group (FIG. 8). Taken together these results from the long-term in vivo model indicate that anti-BMP9 antibodies can effectively block BMP9 signaling and improve $CCl_4$-induced liver fibrosis in a in vivo.

Example 18: Pharmaco-Kinetic (PK) Assays

Mouse PK—Antibody 4E10D7

Male C57BL/6 mice, specific pathogen free (SPF) and 7-8 weeks old, were supplied by Shanghai Laboratory Animal Co., Ltd. (SLAC). Upon arrival at the facility, mice were allowed to acclimatize for at least 7 days. In total, 15 male mice were used in the study, and randomized into 5 groups based on different treatments and various time courses. On day 0, inject (intravenously) Group 1-4 with 10 mg/Kg anti-BMP9 antibody 4E10D7; inject Group 5 with 10 mg/Kg Control IgG, dose volume is 5 ml/kg. Blood were collected at day −1 and 2 h, 6 h, 24 h, 48 h, 72 h, 96 h, 168 h, 336 hr post dose from certain groups (Table 9). Different groups were sacrificed at specific time points. For non-terminal bleeding, blood was collected via orbital bleeding/tail snip under anesthesia. For Terminal bleeding (T), blood was collected via cardiac puncture.

TABLE 9

| | | Bleeding | | | | | | | | | | Sample |
|---|---|---|---|---|---|---|---|---|---|---|---|---|
| Group | Animal | Day −1 | 0 h | 2 h | 6 h | 24 h | 48 h | 72 h | 96 h | 168 h | 336 h | sac |
| Group 1 | 1 | * | | | | *(T) | | | | | | 24 h |
| 4E10D7 | 2 | * | | | | *(T) | | | | | | 24 h |
| | 3 | * | | | | *(T) | | | | | | 24 h |
| Group 2 | 4 | * | | * | | | | *(T) | | | | 72 h |
| 4E10D7 | 5 | * | | * | | | | *(T) | | | | 72 h |
| | 6 | * | | * | | | | *(T) | | | | 72 h |
| Group 3 | 7 | * | | | * | | | | * | *(T) | | 168 h |
| 4E10D7 | 8 | * | | | * | | | | * | *(T) | | 168 h |
| | 9 | * | | | * | | | | * | *(T) | | 168 h |
| Group 4 | 10 | * | | | | | * | | | | *(T) | 336 h |
| 4E10D7 | 11 | * | | | | | * | | | | *(T) | 336 h |
| | 12 | * | | | | | * | | | | *(T) | 336 h |
| Group 5 | 13 | * | | | * | | | * | | *(T) | | 168 h |
| Ctr-IgG | 14 | * | | | * | | | * | | *(T) | | 168 h |
| | 15 | * | | | * | | | * | | *(T) | | 168 h |

The IgG concentrations at various time points were detected by compete Elisa assay. Coat 0.25 μg/mL, 100 μl/well human BMP9 complex on the 96-well plate, incubate overnight at 4° C. After 3 times wishing with washing buffer (1*PBS+0.1% Tween20), add 300 ul/well Blocking buffer (1*PBS+0.1% Tween20+1% BSA), shake at 450 rpm 1 hr at room temperature. Then prepare samples to test: for standard curve, mix 120 μl of Ab (dilute from 100 ug/ml by ratio 1:3 and 7 times in assay buffer containing 8% Naive mouse serum) with 120 μl biotinylated Ab (dilute to 0.067 ug/ml in assay buffer); for serum sample, add 9.6 μl serum sample into 120 μl assay buffer (dilute 12.5 fold), and mix with 120 μl biotinylated Ab (dilute to 0.067 ug/ml in assay buffer). Assay buffer was 1*PBS+0.05% Tween20+1% BSA. Wash the plate 3 times with washing buffer, then add in 100 μl/well prepared samples with duplicate for each point, incubate at room temperature for 2 hr. Subsequently, after another 3 times washing, add 100 μl/well HRP-Streptavidin (1:5000, Pierce #21140) to each well, incubate in dark for 1 hr with shaking at 450 rpm. Then, wash and add TMB Substrate (Life Tech #002023) to each well of the assay plate, seal and incubate at room temperature for about 5 min with shaking at 450 rpm. Stop reaction by adding 100 μl/well 1M HCl, then read OD at 450 nM.

PK Assay in ANIT Rat Model—4E10D7

Male SD rats, 7-8 weeks old, were supplied by Shanghai Slac Laboratory Animal Co., Ltd. Upon arrival at the facility, rats were allowed to acclimatize for at least 7 days. 6 male rats are used in this study, randomized into 2 groups based on different treatments. On day 0, inject (intravenously) Group 1 with 10 mg/Kg anti-BMP9 IgG; inject Group 2 with 10 mg/Kg Control IgG, Group 1 and 2 were fed with ANIT diet (supplied by SLAC). Blood were collected at day −1 and 2 h, 6 h, 8 h, 24 h, 48 h, 72 h, 120 h, 192 h, 336 hr, 504 hr post dose from each rat. All groups were sacrificed 3 weeks later. For non-terminal bleeding, blood was collected via orbital bleeding/tail snip under anesthesia. For Terminal bleeding, blood was collected via cardiac puncture. The IgG concentrations at various time points were detected by compete Elisa assay, similar to the PK assay in normal mice.

Results

Results are shown in FIG. 9. Parental Ab 4E10D7 in both normal mice and ANIT rat model showed similar PK profiles. Ab reaches peak concentration within 2 hours, and begin to decrease and fall by half before 24 hours, then relatively stabilized at 50 ug/ml within 1 week.

Pharmacokinetic (PK) Assay in Cynomolgus Monkey—MOR022962

Single Dose Study:

3 male cynomolgus monkeys (*Macaca fascicularis*), 3 to 4 years old and 2.5 to 4 kg, were administered 10 mg/kg anti-BMP9 antibody MOR022962 (Ab BMP9-2) intravenously. Blood was collected prior to dosing and at 0.25 h, 6 h, 24 h, 48 h, 72 h, 96 h, 120 h, 168 h, 240 h, 336 h, 408 h, 504 h, 576 h, 672 h, 744 h, 840 h, 912 h and 1008 h post dose. Total MOR022962 Ab concentrations at various time points were detected by sandwich ELISA recognizing the Fc domain of the antibody. Total MOR022962 concentrations as a function of time are shown in FIG. 10 for each individual. The maximum concentration was observed at 0.25 h, the first sampling time post-dose, in all individuals. The terminal elimination half-life $t_{1/2}$) was 132 to 145 hours (5.5 to 6.0 days). The apparent accelerated clearance of MOR022962 in one animal beginning at study day 32 (FIG. 10) is consistent with the detection of anti-drug antibodies at the same time.

Repeat Dose Study:

Male cynomolgus monkeys (*Macaca fascicularis*), 2 to 5 years old and 2.3 to 3.8 kg, were administered 10, 30 or 100 mg/kg/week (n=2/group) anti-BMP9 antibody (MOR022962) intravenously for 4 weeks (5 doses). The control animals (n=2) received an equivalent dose volume (1 mL/kg) of vehicle for 4 weeks (5 doses). Blood was collected prior to each dose administration, at 0.25 h after each dose, and 6 h, 24 h, 48 h, 72 h, 96 h, 120 h after the first and the penultimate doses. Total MOR022962 Ab concentrations at various time points were detected by sandwich ELISA recognizing the Fc domain of the antibody. Total MOR022962 Ab concentrations as a function of time are shown in FIG. 11. The maximum concentration ($C_{max}$) was observed at 0.25 h, the first sampling time post-dose, in all treated animals. MOR022962 exposure ($C_{max}$ or $AUC_{0-7d}$) increased dose-proportionally over the dose range of 10-100 mg/kg. Drug accumulation, a ratio of $AUC_{0-7d}$ after the first and penultimate doses, ranged from 1.3-2.3 across the 3 dose groups.

Example 19: Developability

IgG antibodies having good affinity and specificity for huBMP9 (relative to binding to huBMP7, huBMP2 and huBMP10) were assessed for developability using assays known in the art. Briefly, aggregation of antibodies was measured by size exclusion chromatography; melting temperature was assessed at pH=7.5; Hydrophobicity was assessed by hydrophobic interaction chromatography (HIC) in ammonium sulfate $(NH_4)_2SO_4$, Histidine, pH=6; and production titer was measured in a HEK-293T expression system. The results are summarized in Table 11. These results demonstrate that the anti-BMP9 antibodies of the present invention exhibit unexpectedly good developability properties, and are therefore suitable for development as pharmaceutical agents.

TABLE 11

Developability properties of anti-BMP-9 antibodies

| Antibody | Anal. SEC (% monomer) | Production Titer (mg/L) | Tm (° C., pH = 7.4) | Hydrophobicity (M $(NH_4)_2SO_4$) |
|---|---|---|---|---|
| MOR023787 | 96.6 | 78.7 | 71.5 | 0.94 |
| MOR022962 | 99.1 | 67.0 | 74.8 | 0.92 |
| MOR022965 | 96.7 | 74.9 | 74.3 | 0.96 |
| MOR023793 | 98.3 | 29.1 | 68.5 | 0.76 |
| MOR023795 | 97.9 | 56.7 | 69.0 | 0.96 |
| MOR023796 | 96.5 | 95.8 | 72.5 | 0.51 |
| AM0100 | 98.6 | 19.1 | 75.8 | 0.80 |
| AM1900 | 98.4 | 7.2 | 69.0 | 0.80 |
| AM4405 | 99.1 | 28.0 | 73.5 | 1.09 |

Example 20: Crystal Structure of MOR022962 Fv with hBMP9 Dimer

The crystal structure of human BMP9 in complex with MOR022962 Fv domain was solved at 2.2 Å. Each asymmetric unit contains one hBMP9 homodimer and two Fv molecules. The structure was deposited into internal database Proasis with accession number 1ssod (1ssod is thereafter referred as this structure of hBMP9 with MOR022962 Fv).

By superimposing the structure of 1ssod onto structure of BMP9-Alk1-ActRIIb (PDB: 4FAO), it was shown that MOR022962 and ActRIIb share an overlapping contact surface on BMP9 (mature domain), which is in a good agreement with the experimental observations that MOR022962 can compete with ActRIIb binding in BMP9. The structure also shows that the binding surface of MOR022962 to BMP9 does not directly overlap with the binding surface of Alk1 to BMP9.

The crystal structure shows that MOR022962 binds to an epitope in BMP9 that includes L85, L95, Y97, H98 involving hydrophobic interactions, and S83, H98, E100 involving hydrogen bond networks. The detailed interactions between MOR022962 Fv and the mature fragment of huBMP9 (SEQ ID NO: 215) are illustrated in Table 12 below.

Since biochemical experiments show that MOR022962 is unexpectedly able to block the binding of both ActRIIb (a type II BMP receptor) and AlkI (a type I BMP receptor) to BMP9 to a certain degree in biochemical experiments, this indicates that the epitope bound by MOR022962 represents a new binding epitope which results in blocking of both type I and type II BMP9 receptor types, although the mechanism remains unclear.

TABLE 12 residual contacts between MOR022962 Fv and human BMP9 mature domain (SEQ ID NO: 215).

| Residues in huBMP9 | Residues in MOR022962 |
|---|---|
| Hydrogen bond network interactions: | |
| E100 | Y32 in LC |
| H98 | D50, D92 in LC |
| S83 | W103 in HC |
| Hydrophobic interactions: | |
| L85 | L52, H56, H58 in HC |
| L95 | I50, L52, H58,W103 in HC |
| Y97 | W47, I50, W103, S104 in HC and D92, T93, S94, L96 in LC |
| H98 | Y32, D50, S91, D92 in LC and S104, I102 in HC |

HC: heavy chain,
LC: light chain

Thus, in an embodiment, the invention provides an isolated antibody or antigen-binding fragment thereof, which binds to BMP9, and comprises a) the following amino acid residues of the light chain variable region: Y32, D50, S91, D92, T93, S94, and L96; and b) the following amino acid residues in the heavy chain variable region: W47, ISO, L52, H56, H58, 1102, W103, and S104.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Throughout the text of this application, should there be a discrepancy between the text of the specification (e.g., Table 1) and the sequence listing, the text of the specification shall prevail.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

What is claimed is:

1. An isolated antibody or antigen-binding fragment thereof, which binds human bone morphogenetic protein 9 (BMP9) and comprises:
  (a) heavy chain complementarity determining region 1 (HCDR1), heavy chain complementarity determining region 2 (HCDR2), and heavy chain complementarity determining region 3 (HCDR3) sequences of SEQ ID NOs: 1, 2 and 3, respectively, and light chain complementarity determining region 1 (LCDR1), light chain complementarity determining region 2 (LCDR2), and light chain complementarity determining region 3 (LCDR3) sequences of SEQ ID NOs: 11, 12 and 13, respectively; or
  (b) HCDR1, HCDR2, and HCDR3 sequences of SEQ ID NOs: 4, 5 and 6, respectively, and LCDR1, LCDR2, and LCDR3 sequences of SEQ ID NOs: 14, 15 and 16, respectively.

2. The isolated antibody or antigen-binding fragment thereof of claim 1, comprising a heavy chain variable region (VH) sequence of SEQ ID NO: 7.

3. The isolated antibody or antigen-binding fragment thereof of claim 1, comprising a light chain variable region (VL) sequence of SEQ ID NO: 17.

4. The isolated antibody or antigen-binding fragment thereof of claim 1, comprising
  a VH sequence of SEQ ID NO: 7 and a VL sequence of SEQ ID NO: 17.

5. The isolated antibody or antigen-binding fragment thereof of claim 1, comprising:
  (a) a VH sequence having 95%-99% sequence identity to SEQ ID NO: 7; or
  (b) a VH sequence having one, two, three, four or five amino acid mutations relative to SEQ ID NO: 7.

6. The isolated antibody or antigen-binding fragment thereof of claim 1, comprising:
  (a) a VL sequence having 95%-99% sequence identity to SEQ ID NO: 17; or
  (b) a VL sequence having one, two, three, four or five amino acid mutations relative to SEQ ID NO: 17.

7. The isolated antibody or antigen-binding fragment thereof of claim 1, comprising
  a heavy chain sequence of SEQ ID NO: 9.

8. The isolated antibody or antigen-binding fragment thereof of claim 1, comprising
  a light chain sequence of SEQ ID NO: 19.

9. The isolated antibody or antigen-binding fragment thereof of claim 1, comprising
  a heavy chain sequence of SEQ ID NO: 9; and a light chain sequence of SEQ ID NO: 19.

10. The isolated antibody or antigen-binding fragment thereof of claim 1, comprising:
  (a) a heavy chain amino acid sequence having 95%-99% sequence identity to SEQ ID NO: 9;
  (b) a light chain amino acid sequence having 95%-99% sequence identity to SEQ ID NO: 19; or
  (c) a heavy chain amino acid sequence having 95%-99% sequence identity to SEQ ID NO: 9 and a light chain amino acid sequence having 95%-99% sequence identity to SEQ ID NO: 19.

11. The isolated antibody or antigen-binding fragment thereof of claim 1, wherein the isolated antibody or antigen-binding fragment is an IgG.

12. The isolated antibody or antigen-binding fragment thereof of claim 11, wherein the IgG is selected from the group consisting of an IgG1, an IgG2, an IgG3 and an IgG4.

13. The isolated antibody or antigen-binding fragment thereof of claim 1, which has altered effector function through mutation of amino acids within a Fc region.

14. The isolated antibody or antigen-binding fragment thereof of claim 1, wherein the isolated antibody or antigen-binding fragment is selected from the group consisting of: a monoclonal antibody, a chimeric antibody, a single chain antibody, a Fab and a scFv.

15. The isolated antibody or antigen-binding fragment thereof of claim 1, wherein the antibody is a chimeric, humanized or fully human antibody.

16. The isolated antibody or antigen-binding fragment thereof of claim 1, which binds to human BMP9 and inhibits the binding of human BMP9 to a BMP Type II receptor.

17. The isolated antibody or antigen-binding fragment thereof of claim 16, wherein the inhibition of the binding of human BMP9 to said BMP Type II receptor is at an IC50 of less than or equal to about 1 nM.

18. The isolated antibody or antigen-binding fragment thereof of claim 1, wherein the isolated antibody or antigen-binding fragment thereof is a component of an immunoconjugate.

19. A composition comprising the isolated antibody or antigen-binding fragment thereof of claim 1, and a pharmaceutically acceptable carrier.

20. A composition comprising the isolated antibody or antigen-binding fragment thereof of claim 1, and an additional therapeutic agent.

21. An isolated polynucleotide comprising a nucleic acid sequence encoding the antibody or antigen-binding fragment thereof of claim 1.

22. An isolated polynucleotide comprising a nucleic acid sequence encoding a VH or a VL sequence of the antibody or antigen-binding fragment thereof of claim 1, which binds human BMP9.

23. The isolated polynucleotide of claim 22, wherein the nucleic acid sequence encodes a VH sequence comprising SEQ ID NO: 7.

24. The isolated polynucleotide of claim 22, wherein the nucleic acid sequence encodes a VL sequence comprising SEQ ID NO: 17.

25. The isolated polynucleotide of claim 22, comprising a nucleic acid sequence encoding a VH sequence and a nucleic acid sequence encoding a VL sequence, wherein the VH sequence comprising SEQ ID NO: 7 and the VL sequence comprising SEQ ID NO: 17.

26. The isolated polynucleotide of claim 22, wherein the antibody or antigen-binding fragment thereof comprises
  a heavy chain sequence of SEQ ID NO: 9.

27. The isolated polynucleotide of claim 22, wherein the antibody or antigen-binding fragment thereof comprises
  a light chain sequence of SEQ ID NO: 19.

28. The isolated polynucleotide of claim 22, wherein the antibody or antigen-binding fragment thereof comprises
  a heavy chain sequence of SEQ ID NO: 9; and a light chain sequence of SEQ ID NO: 19.

29. The isolated polynucleotide of claim 22, comprising a nucleic acid sequence encoding a heavy chain or a light chain of the antibody or antigen-binding fragment thereof which binds human BMP9, the polynucleotide comprising:
  (a) a VH sequence of SEQ ID NO: 8;
  (b) a heavy chain sequence of SEQ ID NO: 10;
  (c) a VL sequence of SEQ ID NO: 18; or
  (d) a light chain sequence of SEQ ID NO: 20.

30. The isolated polynucleotide of claim 22, comprising a nucleic acid sequence encoding a VH sequence and a VL sequence of the antibody or antigen-binding fragment thereof which binds human BMP9, the polynucleotide comprising a VH sequence of SEQ ID NO: 8 and a VL sequence of SEQ ID NO: 18.

31. The isolated polynucleotide of claim 25, disposed on a single continuous nucleic acid sequence.

32. The isolated polynucleotide of claim 25, disposed on two nucleic acid sequences.

33. A vector comprising the polynucleotide of claim 22.

34. An isolated host cell comprising the vector of claim 33.

* * * * *

SEQUENCE LISTING

<160> NUMBER OF SEQ ID NOS: 222

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Tyr Trp Met His
1 5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Glu Ile Asn Pro Ser Gln Gly Gly Thr Asn Tyr Asn Glu Lys Phe Lys
1 5 10 15

Ser

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Gly Ser Asn Tyr Gly Gly Leu Val Tyr
1 5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gly Tyr Thr Phe Thr Arg Tyr
1 5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Asn Pro Ser Gln Gly Gly
1 5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

```
Gly Ser Asn Tyr Gly Gly Leu Val Tyr
1               5
```

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Trp Met His Trp Val Arg Gln Ala Pro Gly Gln Gly Leu Glu Trp Met
        35                  40                  45

Gly Glu Ile Asn Pro Ser Gln Gly Gly Thr Asn Tyr Asn Glu Lys Phe
    50                  55                  60

Lys Ser Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ile Gly Ser Asn Tyr Gly Gly Leu Val Tyr Trp Gly Gln Gly Thr
            100                 105                 110

Leu Val Thr Val Ser Ser
        115
```

<210> SEQ ID NO 8
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
caagtccagt tggtccaatc gggcgcagaa gtgaaaaagc cgggagcctc agtgaaggtg     60

tcctgcaaag cgtccggcta tactttcacg cgctactgga tgcactgggt cagacaggcc    120

ccgggacagg gtctggaatg gatgggagag attaatccca gccagggagg caccaactac    180

aacgagaagt tcaagtcccg ggtcaccatg accgtggata agagcatcag cactgcctac    240

atggagctgt ccaggctgcg gtcggacgac accgccgtgt actactgcgc catcgggtca    300

aactacggcg gactggtgta ctggggccag gggaccctcg tgactgtgtc ctcg          354
```

<210> SEQ ID NO 9
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Gln Val Gln Leu Val Gln Ser Gly Ala Glu Val Lys Lys Pro Gly Ala
```

-continued

```
1               5                   10                  15

Ser Val Lys Val Ser Cys Lys Ala Ser Gly Tyr Thr Phe Thr Arg Tyr
            20                  25                  30

Trp Met His Trp Val Arg Gln Ala Pro Gly Gln Gly Leu Glu Trp Met
        35                  40                  45

Gly Glu Ile Asn Pro Ser Gln Gly Gly Thr Asn Tyr Asn Glu Lys Phe
    50                  55                  60

Lys Ser Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ile Gly Ser Asn Tyr Gly Gly Leu Val Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445


<210> SEQ ID NO 10
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

caagtccagt tggtccaatc gggcgcagaa gtgaaaaagc cgggagcctc agtgaaggtg     60

tcctgcaaag cgtccggcta tactttcacg cgctactgga tgcactgggt cagacaggcc    120

ccgggacagg gtctggaatg gatgggagag attaatccca gccagggagg caccaactac    180

aacgagaagt tcaagtcccg ggtcaccatg accgtggata agagcatcag cactgcctac    240

atggagctgt ccaggctgcg gtcggacgac accgccgtgt actactgcgc catcgggtca    300

aactacggcg gactggtgta ctggggccag ggaccctcg tgactgtgtc ctcggctagc    360

accaagggcc caagtgtgtt tcccctggcc cccagcagca agtctacttc cggcggaact    420

gctgccctgg gttgcctggt gaaggactac ttccccgagc ccgtgacagt gtcctggaac    480

tctggggctc tgacttccgg cgtgcacacc ttccccgccg tgctgcagag cagcggcctg    540

tacagcctga gcagcgtggt gacagtgccc tccagctctc tgggaaccca gacctatatc    600

tgcaacgtga accacaagcc cagcaacacc aaggtggaca agagagtgga gcccaagagc    660

tgcgacaaga cccacacctg cccccctgc ccagctccag aactgctggg agggccttcc    720

gtgttcctgt tcccccccaa gcccaaggac accctgatga tcagcaggac ccccgaggtg    780

acctgcgtgg tggtggacgt gtcccacgag gacccagagg tgaagttcaa ctggtacgtg    840

gacggcgtgg aggtgcacaa cgccaagacc aagcccagag aggagcagta caacagcacc    900

tacagggtgg tgtccgtgct gaccgtgctg caccaggact ggctgaacgg caaagaatac    960

aagtgcaaag tctccaacaa ggccctgcca gccccaatcg aaaagacaat cagcaaggcc   1020

aagggccagc cacgggagcc ccaggtgtac accctgcccc ccagccggga ggagatgacc   1080

aagaaccagg tgtccctgac ctgtctggtg aagggcttct accccagcga tatcgccgtg   1140

gagtgggaga gcaacggcca gcccgagaac aactacaaga ccaccccccc agtgctggac   1200

agcgacggca gcttcttcct gtacagcaag ctgaccgtgg acaagtccag gtggcagcag   1260

ggcaacgtgt tcagctgcag cgtgatgcac gaggccctgc acaaccacta cacccagaag   1320

tccctgagcc tgagccccgg caag                                          1344


<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Ser Glu Ser Leu Asp Asn Tyr Gly Ile Ser Phe Met Asn
1               5                   10                  15


<210> SEQ ID NO 12
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 12

Ala Ala Ser Asn Gln Gly Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Ser Lys Glu Val Pro Arg Thr
1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Glu Ser Leu Asp Asn Tyr Gly Ile Ser Phe
1               5                   10

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser
1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Lys Glu Val Pro Arg
1               5

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Glu Ser Leu Asp Asn Tyr
            20                  25                  30

Gly Ile Ser Phe Met Asn Trp Phe Gln Gln Lys Pro Gly Gln Ala Pro
        35                  40                  45

Arg Phe Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Thr Ala Val Tyr Phe Cys Gln Gln Ser Lys
                85                  90                  95

Glu Val Pro Arg Thr Phe Gly Gly Gly Thr Lys Val Glu Ile Lys
            100                 105                 110


<210> SEQ ID NO 18
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

gaaattgtgc tgacccagtc ccccgcgacg ctgtcactgt cccctgggga gcgggctacc     60

ttgtcctgcc gcgcctccga atcgctcgac aactacggca tcagcttcat gaactggttc    120

cagcaaaagc cgggacaggc cccacggttc ctgatctacg ccgcatcgaa ccagggttca    180

gggattcccg cgaggttctc gggatctgga tccggcaccg acttcactct gacaatcagc    240

agcctgcagc ctgaagatac cgccgtgtac ttctgccaac agtccaagga ggtcccgcgg    300

acttttggcg gaggcaccaa agtggagatc aag                                 333


<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Leu Asp Asn Tyr
            20                  25                  30

Gly Ile Ser Phe Met Asn Trp Phe Gln Gln Lys Pro Gly Gln Ala Pro
        35                  40                  45

Arg Phe Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Thr Ala Val Tyr Phe Cys Gln Gln Ser Lys
                85                  90                  95

Glu Val Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 20
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
gaaattgtgc tgacccagtc cccgcgacg ctgtcactgt cccctgggga gcgggctacc 60
ttgtcctgcc gcgcctccga atcgctcgac aactacggca tcagcttcat gaactggttc 120
cagcaaaagc cgggacaggc cccacggttc ctgatctacg ccgcatcgaa ccagggttca 180
gggattcccg cgaggttctc gggatctgga tccggcaccg acttcactct gacaatcagc 240
agcctgcagc ctgaagatac cgccgtgtac ttctgccaac agtccaagga ggtcccgcgg 300
acttttggcg gaggcaccaa agtggagatc aagcgtacgg tggccgctcc cagcgtgttc 360
atcttccccc ccagcgacga gcagctgaag agcggcaccg ccagcgtggt gtgcctgctg 420
aacaacttct acccccggga ggccaaggtg cagtggaagg tggacaacgc cctgcagagc 480
ggcaacagcc aggagagcgt caccgagcag gacagcaagg actccaccta cagcctgagc 540
agcaccctga ccctgagcaa ggccgactac gagaagcata aggtgtacgc ctgcgaggtg 600
acccaccagg gcctgtccag ccccgtgacc aagagcttca acaggggcga gtgc 654

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Ser Tyr Ala Met Ser
1 5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ile Thr Leu Gly Thr Gly His Thr His Tyr Ala Asp Ser Val Lys Gly
1 5 10 15

<210> SEQ ID NO 23

<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gly Ser Tyr Ile Ile Trp Ser Ala Leu Asp Tyr
1 5 10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Phe Thr Phe Ser Ser Tyr
1 5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Leu Gly Thr Gly His
1 5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gly Ser Tyr Ile Ile Trp Ser Ala Leu Asp Tyr
1 5 10

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ile Thr Leu Gly Thr Gly His Thr His Tyr Ala Asp Ser Val Lys
50 55 60

Gly Arg Phe Thr Ile Ser Arg Asp Asn Ser Lys Asn Thr Leu Tyr Leu
65 70 75 80

```
Gln Met Asn Ser Leu Arg Ala Glu Asp Thr Ala Val Tyr Tyr Cys Ala
                85                  90                  95

Arg Gly Ser Tyr Ile Ile Trp Ser Ala Leu Asp Tyr Trp Gly Gln Gly
            100                 105                 110

Thr Leu Val Thr Val Ser Ser
        115


<210> SEQ ID NO 28
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

caagtccagc tgctcgaatc tggcggcgga ctggtgcagc ccggaggcag cctgcggctg      60

tcgtgtgccg cctccggatt caccttctca tcctacgcca tgtcctgggt ccgccaggca     120

ccggggaagg gactggaatg ggtgtcgatc accctgggaa ccgggcacac tcattatgcg     180

gactccgtga aagggcgctt caccatttcc cgggacaaca gcaagaacac tctgtacttg     240

caaatgaact ccctgagagc cgaggatacc gctgtgtact actgcgcgag gggctcctac     300

atcatctgga gcgccctgga ctactgggga cagggtactc tcgtgaccgt gtcgagc        357


<210> SEQ ID NO 29
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Thr Leu Gly Thr Gly His Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Tyr Ile Ile Trp Ser Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 30
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
caagtccagc tgctcgaatc tggcggcgga ctggtgcagc ccggaggcag cctgcggctg     60

tcgtgtgccg cctccggatt caccttctca tcctacgcca tgtcctgggt ccgccaggca    120

ccggggaagg gactggaatg ggtgtcgatc accctgggaa ccgggcacac tcattatgcg    180

gactccgtga aagggcgctt caccatttcc cgggacaaca gcaagaacac tctgtacttg    240

caaatgaact ccctgagagc cgaggatacc gctgtgtact actgcgcgag gggctcctac    300

atcatctgga gcgccctgga ctactgggga cagggtactc tcgtgaccgt gtcgagcgct    360

agcaccaagg gcccaagtgt gtttcccctg gcccccagca gcaagtctac ttccggcgga    420

actgctgccc tgggttgcct ggtgaaggac tacttccccg agcccgtgac agtgtcctgg    480

aactctgggg ctctgacttc cggcgtgcac accttccccg ccgtgctgca gagcagcggc    540
```

```
ctgtacagcc tgagcagcgt ggtgacagtg ccctccagct ctctgggaac ccagacctat    600

atctgcaacg tgaaccacaa gcccagcaac accaaggtgg acaagagagt ggagcccaag    660

agctgcgaca agacccacac ctgccccccc tgcccagctc cagaactgct gggagggcct    720

tccgtgttcc tgttcccccc caagcccaag gacaccctga tgatcagcag gacccccgag    780

gtgacctgcg tggtggtgga cgtgtcccac gaggacccag aggtgaagtt caactggtac    840

gtggacggcg tggaggtgca caacgccaag accaagccca gagaggagca gtacaacagc    900

acctacaggg tggtgtccgt gctgaccgtg ctgcaccagg actggctgaa cggcaaagaa    960

tacaagtgca aagtctccaa caaggccctg ccagccccaa tcgaaaagac aatcagcaag   1020

gccaagggcc agccacggga gccccaggtg tacaccctgc cccccagccg ggaggagatg   1080

accaagaacc aggtgtccct gacctgtctg gtgaagggct tctaccccag cgatatcgcc   1140

gtggagtggg agagcaacgg ccagcccgag aacaactaca agaccacccc cccagtgctg   1200

gacagcgacg gcagcttctt cctgtacagc aagctgaccg tggacaagtc caggtggcag   1260

cagggcaacg tgttcagctg cagcgtgatg cacgaggccc tgcacaacca ctacacccag   1320

aagtccctga gcctgagccc cggcaag                                       1347
```

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

```
Arg Ala Ser Gln Asp Ile Arg Ser Tyr Leu Asn
1               5                   10
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

```
Asp Ala Ser Asn Leu Gln Ser
1               5
```

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

```
Gln Gln Ser Asp Thr Ser Pro Leu Thr
1               5
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ser Gln Asp Ile Arg Ser Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Asp Ala Ser
1

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ser Asp Thr Ser Pro Leu
1               5

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Thr Ser Pro Leu
                85                  90                  95

Thr Phe Gly Gln Gly Thr Lys Val Glu Ile Lys
            100                 105

<210> SEQ ID NO 38
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
gacatccaga tgactcagtc accgtcatcg ctgtccgcct ccgtgggaga tcgggtcacc     60

```
attacctgtc gggcatccca agacatcaga agctacctga actggtatca gcagaagcct    120

gggaaggccc ccaagctgct catctacgac gcgagcaacc tccagtctgg agtgcccagc    180

cgcttctccg gttcggggtc cggcactgac tttaccctga ccatttcgtc cctgcaaccg    240

gaggatttcg ctacctacta ctgccagcag tccgacacaa gcccactgac gttcggccag    300

ggcaccaaag tggaaatcaa g                                              321
```

```
<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Thr Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 40
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

gacatccaga tgactcagtc accgtcatcg ctgtccgcct ccgtgggaga tcgggtcacc     60

attacctgtc gggcatccca agacatcaga agctacctga actggtatca gcagaagcct    120

gggaaggccc ccaagctgct catctacgac gcgagcaacc tccagtctgg agtgcccagc    180
```

```
cgcttctccg gttcggggtc cggcactgac tttaccctga ccatttcgtc cctgcaaccg    240

gaggatttcg ctacctacta ctgccagcag tccgacacaa gcccactgac gttcggccag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642


<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Tyr Trp Ile Gly
1               5


<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Ile Tyr Pro Glu Gly Ser Tyr Thr Thr Tyr Ser Pro Ser Phe Gln
1               5                   10                  15

Gly


<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Lys Arg Val Asp Ala Ser Ser Phe Asp Tyr
1               5                   10


<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Tyr Ser Phe Thr Thr Tyr
1               5


<210> SEQ ID NO 45
<211> LENGTH: 6
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 45

```
Tyr Pro Glu Gly Ser Tyr
1               5
```

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

```
Gly Lys Arg Val Asp Ala Ser Ser Phe Asp Tyr
1               5                   10
```

<210> SEQ ID NO 47
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Glu Gly Ser Tyr Thr Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Lys Arg Val Asp Ala Ser Ser Phe Asp Tyr Trp Gly Gln
            100                 105                 110

Gly Thr Leu Val Thr Val Ser Ser
        115                 120
```

<210> SEQ ID NO 48
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gaagtgcagc tcgtgcagtc cggagcggaa gtgaaaaagc cgggagaatc cctgaagatt     60

agctgcaagg ggtcggggta ctcattcacg acttactgga tcggctgggt ccggcagatg    120

cccggaaagg gactggagtg gatgggcatc atctacccgg agggcagcta caccacctac    180

tccccatcgt ttcaaggaca ggtcaccatt tccgccgata agtcaatcag caccgcctac    240

ctccaatggt cgagcctgaa ggcctccgac actgctatgt actattgcgc gagagggaag    300
```

cgcgtggacg cctcctcctt cgactactgg ggccagggca ctctggtcac cgtgtcctcg 360

<210> SEQ ID NO 49
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Glu Gly Ser Tyr Thr Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Lys Arg Val Asp Ala Ser Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 50
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

gaagtgcagc tcgtgcagtc cggagcggaa gtgaaaaagc cgggagaatc cctgaagatt      60

agctgcaagg ggtcggggta ctcattcacg acttactgga tcggctgggt ccggcagatg     120

cccggaaagg gactggagtg gatgggcatc atctacccgg agggcagcta caccacctac     180

tccccatcgt ttcaaggaca ggtcaccatt tccgccgata agtcaatcag caccgcctac     240

ctccaatggt cgagcctgaa ggcctccgac actgctatgt actattgcgc gagagggaag     300

cgcgtggacg cctcctcctt cgactactgg ggccagggca ctctggtcac cgtgtcctcg     360

gctagcacca agggcccaag tgtgtttccc ctggccccca gcagcaagtc tacttccggc     420

ggaactgctg ccctgggttg cctggtgaag gactacttcc ccgagcccgt gacagtgtcc     480

tggaactctg gggctctgac ttccggcgtg cacaccttcc ccgccgtgct gcagagcagc     540

ggcctgtaca gcctgagcag cgtggtgaca gtgccctcca gctctctggg aacccagacc     600

tatatctgca acgtgaacca caagcccagc aacaccaagg tggacaagag agtggagccc     660

aagagctgcg acaagaccca cacctgcccc ccctgcccag ctccagaact gctgggaggg     720

ccttccgtgt tcctgttccc ccccaagccc aaggacaccc tgatgatcag caggaccccc     780

gaggtgacct gcgtggtggt ggacgtgtcc cacgaggacc cagaggtgaa gttcaactgg     840

tacgtggacg gcgtggaggt gcacaacgcc aagaccaagc ccagagagga gcagtacaac     900

agcacctaca gggtggtgtc cgtgctgacc gtgctgcacc aggactggct gaacggcaaa     960

gaatacaagt gcaaagtctc caacaaggcc ctgccagccc caatcgaaaa gacaatcagc    1020

aaggccaagg gccagccacg ggagccccag gtgtacaccc tgccccccag ccgggaggag    1080

atgaccaaga accaggtgtc cctgacctgt ctggtgaagg gcttctaccc cagcgatatc    1140

gccgtggagt gggagagcaa cggccagccc gagaacaact acaagaccac cccccccagtg   1200

ctggacagcg acggcagctt cttcctgtac agcaagctga ccgtggacaa gtccaggtgg    1260

cagcagggca acgtgttcag ctgcagcgtg atgcacgagg ccctgcacaa ccactacacc    1320

cagaagtccc tgagcctgag ccccggcaag                                     1350
```

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

```
Ser Gly Ser Ser Ser Asn Ile Gly Asp Asn Tyr Val Ser
1               5                   10
```

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

```
Arg Asn Asn Lys Arg Pro Ser
1               5
```

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

```
Ser Ser Thr Asp Lys Glu His Leu Val
1               5
```

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

```
Ser Ser Ser Asn Ile Gly Asp Asn Tyr
1               5
```

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

```
Arg Asn Asn
1
```

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

```
Thr Asp Lys Glu His Leu
1               5
```

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asp Asn
            20                  25                  30

Tyr Val Ser Trp Tyr Gln Gln Leu Pro Gly Thr Ala Pro Lys Leu Leu
        35                  40                  45

Ile Tyr Arg Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Thr Asp Lys Glu His
                85                  90                  95

Leu Val Phe Gly Gly Gly Thr Lys Leu Thr Val Leu
            100                 105
```

<210> SEQ ID NO 58
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
caatcagtgc tgacccagcc cccgagcgtg tccggtgccc ctggacagcg ggtcaccatc     60

tcctgttccg gctcctcaag caatattggc gacaactatg tgtcgtggta ccagcagctg    120

ccggggacgg cccctaagct gctgatctac cggaacaaca aaaggccatc cggcgtgccg    180

gatagattct cgggctcgaa gtccggaact agcgccagcc tggcaatcac cgggctgcag    240

gctgaagatg aggcggacta ctactgctcc tctaccgaca aggaacacct ggtgttcgga    300

ggaggaacca agctgactgt gctg                                           324
```

<210> SEQ ID NO 59
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asp Asn
            20                  25                  30

Tyr Val Ser Trp Tyr Gln Gln Leu Pro Gly Thr Ala Pro Lys Leu Leu
        35                  40                  45
```

```
Ile Tyr Arg Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Thr Asp Lys Glu His
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 60
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

caatcagtgc tgacccagcc cccgagcgtg tccggtgccc ctggacagcg ggtcaccatc     60

tcctgttccg gctcctcaag caatattggc gacaactatg tgtcgtggta ccagcagctg    120

ccggggacgg cccctaagct gctgatctac cggaacaaca aaaggccatc cggcgtgccg    180

gatagattct cgggctcgaa gtccggaact agcgccagcc tggcaatcac cgggctgcag    240

gctgaagatg aggcggacta ctactgctcc tctaccgaca aggaacacct ggtgttcgga    300

ggaggaacca agctgactgt gctgggacag cctaaggctg cccccagcgt gaccctgttc    360

ccccccagca gcgaggagct gcaggccaac aaggccaccc tggtgtgcct gatcagcgac    420

ttctacccag gcgccgtgac cgtggcctgg aaggccgaca gcagccccgt gaaggccggc    480

gtggagacca ccacccccag caagcagagc aacaacaagt acgccgccag cagctacctg    540

agcctgaccc ccgagcagtg gaagagccac aggtcctaca gctgccaggt gacccacgag    600

ggcagcaccg tggaaaagac cgtggcccca accgagtgca gc                       642


<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Asn Met His
```

1 5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Leu Ile Tyr Pro Gly Asn Ala Val Thr Ser Tyr Ser Gln Lys Phe Lys
1 5 10 15

Asp

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Asp Asp Tyr Phe Arg Gly Gly Ser Tyr Ala Met Asp Tyr
1 5 10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Gly Tyr Thr Phe Arg Ser Tyr
1 5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Tyr Pro Gly Asn Ala Val
1 5

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Asp Asp Tyr Phe Arg Gly Gly Ser Tyr Ala Met Asp Tyr
1 5 10

<210> SEQ ID NO 67
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Asn Met His Trp Val Arg Gln Ala Pro Gly Gln Gly Leu Glu Trp Met
        35                  40                  45

Gly Leu Ile Tyr Pro Gly Asn Ala Val Thr Ser Tyr Ser Gln Lys Phe
    50                  55                  60

Lys Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Asp Tyr Phe Arg Gly Gly Ser Tyr Ala Met Asp Tyr Trp
            100                 105                 110

Gly Gln Gly Thr Thr Val Thr Val Ser Ser
        115                 120
```

<210> SEQ ID NO 68
<211> LENGTH: 366
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68

```
caagtccagc tcgtccagtc cggggccgaa gtcaagaagc ccggagccag cgtgaaagtg      60

tcctgcaagg cgtcaggcta taccttccgg tcgtacaaca tgcactgggt cagacaggcc     120

ccaggacagg ggctggaatg gatgggcctg atctacccgg gaaacgctgt gactagctac     180

tcccaaaagt tcaaggatcg cgtgacgatg accgtggata agtccacctc aaccgcgtac     240

atggagctgt cctcgctgag gtcggaggac accgcagtgt actactgcgc caaggacgac     300

tacttccggg gcggttccta cgccatggac tactggggac agggcaccac tgtgactgtg     360

tccagc                                                                 366
```

<210> SEQ ID NO 69
<211> LENGTH: 452
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Asn Met His Trp Val Arg Gln Ala Pro Gly Gln Gly Leu Glu Trp Met
        35                  40                  45

Gly Leu Ile Tyr Pro Gly Asn Ala Val Thr Ser Tyr Ser Gln Lys Phe
    50                  55                  60

Lys Asp Arg Val Thr Met Thr Val Asp Lys Ser Thr Ser Thr Ala Tyr
```

```
65                  70                  75                  80

Met Glu Leu Ser Ser Leu Arg Ser Glu Asp Thr Ala Val Tyr Tyr Cys
                85                  90                  95

Ala Lys Asp Asp Tyr Phe Arg Gly Gly Ser Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 70
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
caagtccagc tcgtccagtc cggggccgaa gtcaagaagc ccggagccag cgtgaaagtg     60
tcctgcaagg cgtcaggcta taccttccgg tcgtacaaca tgcactgggt cagacaggcc    120
ccaggacagg ggctggaatg gatgggcctg atctacccgg gaaacgctgt gactagctac    180
tcccaaaagt tcaaggatcg cgtgacgatg accgtggata agtccacctc aaccgcgtac    240
atggagctgt cctcgctgag gtcggaggac accgcagtgt actactgcgc caaggacgac    300
tacttccggg gcggttccta cgccatggac tactggggac agggcaccac tgtgactgtg    360
tccagcgcta gcaccaaggg cccaagtgtg tttcccctgg cccccagcag caagtctact    420
tccggcggaa ctgctgccct gggttgcctg gtgaaggact acttccccga gcccgtgaca    480
gtgtcctgga actctggggc tctgacttcc ggcgtgcaca ccttccccgc cgtgctgcag    540
agcagcggcc tgtacagcct gagcagcgtg gtgacagtgc cctccagctc tctgggaacc    600
cagacctata tctgcaacgt gaaccacaag cccagcaaca ccaaggtgga caagagagtg    660
gagcccaaga gctgcgacaa gacccacacc tgcccccct gcccagctcc agaactgctg    720
ggagggcctt ccgtgttcct gttcccccc aagcccaagg acaccctgat gatcagcagg    780
acccccgagg tgacctgcgt ggtggtggac gtgtcccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaagaat acaagtgcaa agtctccaac aaggccctgc cagcccccat cgaaaagaca   1020
atcagcaagg ccaagggcca gccacgggag ccccaggtgt acaccctgcc ccccagccgg   1080
gaggagatga ccaagaacca ggtgtccctg acctgtctgg tgaagggctt ctaccccagc   1140
gatatcgccg tggagtggga gagcaacggc cagcccgaga acaactacaa gaccaccccc   1200
ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga agtccctgag cctgagcccc ggcaag                             1356
```

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

```
Arg Ala Ser Gln Ser Ile Arg Asn Asn Leu His
1               5                   10
```

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

```
Tyr Ala Ser Gln Ser Ile Arg
1               5
```

```
<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln Ser His Ser Trp Pro Tyr Thr
1               5


<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gln Ser Ile Arg Asn Asn
1               5


<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Ala Ser
1


<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser His Ser Trp Pro Tyr
1               5


<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Arg Asn Asn
            20                  25                  30

Leu His Trp Tyr Gln Gln Lys Pro Asp Gln Ser Pro Lys Leu Leu Ile
        35                  40                  45

Lys Tyr Ala Ser Gln Ser Ile Arg Gly Val Pro Ser Arg Phe Ser Gly
    50                  55                  60
```

```
Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Tyr
                85                  90                  95

Thr Phe Gly Gly Gly Thr Lys Val Glu Ile Lys
            100                 105


<210> SEQ ID NO 78
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

gaaattgtgc tgacccagag cccggacttc caatccgtga ctcccaagga gaaggtcaca      60

atcacgtgca gagcatcgca gtccatccgg aacaacttgc actggtatca acagaagccc     120

gaccagtccc ctaagctgct gattaagtac gccagccagt cgatcagggg ggtgccatca     180

cggtttagcg gatccggatc aggcaccgac ttcactctga ccatcaactc cctggaggct     240

gaagatgcgg ccacctacta ctgccagcag tcccattcgt ggccgtacac tttcggcggc     300

ggtaccaaag tggaaatcaa g                                               321


<210> SEQ ID NO 79
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Arg Asn Asn
            20                  25                  30

Leu His Trp Tyr Gln Gln Lys Pro Asp Gln Ser Pro Lys Leu Leu Ile
        35                  40                  45

Lys Tyr Ala Ser Gln Ser Ile Arg Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 80
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

gaaattgtgc tgacccagag cccggacttc caatccgtga ctcccaagga gaaggtcaca     60

atcacgtgca gagcatcgca gtccatccgg aacaacttgc actggtatca acagaagccc    120

gaccagtccc ctaagctgct gattaagtac gccagccagt cgatcagggg ggtgccatca    180

cggtttagcg gatccggatc aggcaccgac ttcactctga ccatcaactc cctggaggct    240

gaagatgcgg ccacctacta ctgccagcag tcccattcgt ggccgtacac tttcggcggc    300

ggtaccaaag tggaaatcaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642


<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Tyr Trp Met His
1               5


<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Ile Asn Pro Ser Gln Gly Gly Thr Asn Tyr Asn Glu Lys Phe Lys
1               5                   10                  15

Ser


<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 83

Gly Ala Asn Tyr Gly Gly Leu Val Tyr
1 5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Gly Tyr Thr Phe Thr Arg Tyr
1 5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Asn Pro Ser Gln Gly Gly
1 5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gly Ala Asn Tyr Gly Gly Leu Val Tyr
1 5

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Arg Tyr
20 25 30

Trp Met His Trp Val Arg Gln Ala Pro Gly Gln Gly Leu Glu Trp Met
35 40 45

Gly Glu Ile Asn Pro Ser Gln Gly Gly Thr Asn Tyr Asn Glu Lys Phe
50 55 60

Lys Ser Arg Val Thr Met Thr Val Asp Lys Ser Ile Ser Thr Ala Tyr
65 70 75 80

Met Glu Leu Ser Arg Leu Arg Ser Asp Asp Thr Ala Val Tyr Tyr Cys
85 90 95

Ala Ile Gly Ala Asn Tyr Gly Gly Leu Val Tyr Trp Gly Gln Gly Thr
100 105 110

```
Leu Val Thr Val Ser Ser
        115


<210> SEQ ID NO 88
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

caagtccagc tcgtccaatc gggcgccgaa gtgaaaaagc cgggagcctc cgtgaaggtg      60

tcctgcaagg cgtccggtta tactttcacg cgctactgga tgcactgggt cagacaggct     120

ccgggacagg gactggaatg gatgggagag attaacccct cccagggagg caccaactac     180

aacgagaagt tcaagtcccg ggtcaccatg accgtggata agtccatcag cactgcctac     240

atggagctgt cccgcctgcg gtcggacgac accgccgtgt actactgcgc catcggggcg     300

aactacggcg gactggtgta ctggggccag ggactctcg tgactgtgtc ctcg            354


<210> SEQ ID NO 89
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Trp Met His Trp Val Arg Gln Ala Pro Gly Gln Gly Leu Glu Trp Met
        35                  40                  45

Gly Glu Ile Asn Pro Ser Gln Gly Gly Thr Asn Tyr Asn Glu Lys Phe
    50                  55                  60

Lys Ser Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ile Gly Ala Asn Tyr Gly Gly Leu Val Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 90
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
caagtccagc tcgtccaatc gggcgccgaa gtgaaaaagc cgggagcctc cgtgaaggtg      60

tcctgcaagg cgtccggtta tactttcacg cgctactgga tgcactgggt cagacaggct     120

ccgggacagg gactggaatg gatgggagag attaacccct cccagggagg caccaactac     180

aacgagaagt tcaagtcccg ggtcaccatg accgtggata agtccatcag cactgcctac     240

atggagctgt cccgcctgcg gtcggacgac accgccgtgt actactgcgc catcggggcg     300

aactacggcg gactggtgta ctggggccag gggactctcg tgactgtgtc ctcggctagc     360

accaagggcc caagtgtgtt tcccctggcc cccagcagca agtctacttc cggcggaact     420

gctgccctgg gttgcctggt gaaggactac ttccccgagc ccgtgacagt gtcctggaac     480

tctggggctc tgacttccgg cgtgcacacc ttccccgccg tgctgcagag cagcggcctg     540

tacagcctga gcagcgtggt gacagtgccc tccagctctc tgggaaccca gacctatatc     600

tgcaacgtga accacaagcc cagcaacacc aaggtggaca agagagtgga gcccaagagc     660

tgcgacaaga cccacacctg ccccccctgc ccagctccag aactgctggg agggccttcc     720

gtgttcctgt tccccccaa gcccaaggac accctgatga tcagcaggac ccccgaggtg     780
```

```
acctgcgtgg tggtggacgt gtcccacgag gacccagagg tgaagttcaa ctggtacgtg    840

gacggcgtgg aggtgcacaa cgccaagacc aagcccagag aggagcagta caacagcacc    900

tacagggtgg tgtccgtgct gaccgtgctg caccaggact ggctgaacgg caaagaatac    960

aagtgcaaag tctccaacaa ggccctgcca gccccaatcg aaaagacaat cagcaaggcc   1020

aagggccagc cacgggagcc ccaggtgtac accctgcccc ccagccggga ggagatgacc   1080

aagaaccagg tgtccctgac ctgtctggtg aagggcttct accccagcga tatcgccgtg   1140

gagtgggaga gcaacggcca gcccgagaac aactacaaga ccaccccccc agtgctggac   1200

agcgacggca gcttcttcct gtacagcaag ctgaccgtgg acaagtccag gtggcagcag   1260

ggcaacgtgt tcagctgcag cgtgatgcac gaggccctgc acaaccacta cacccagaag   1320

tccctgagcc tgagccccgg caag                                          1344


<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Glu Ser Leu Asp Asn Tyr Gly Ile Ser Phe Met Asn
1               5                   10                  15


<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ala Ser Asn Gln Gly Ser
1               5


<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Ser Lys Glu Val Pro Arg Thr
1               5


<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Glu Ser Leu Asp Asn Tyr Gly Ile Ser Phe
1               5                   10


<210> SEQ ID NO 95
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Ala Ser
1


<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Lys Glu Val Pro Arg
1               5


<210> SEQ ID NO 97
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Leu Asp Asn Tyr
            20                  25                  30

Gly Ile Ser Phe Met Asn Trp Phe Gln Gln Lys Pro Gly Gln Ala Pro
        35                  40                  45

Arg Phe Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Thr Ala Val Tyr Phe Cys Gln Gln Ser Lys
                85                  90                  95

Glu Val Pro Arg Thr Phe Gly Gly Gly Thr Lys Val Glu Ile Lys
            100                 105                 110


<210> SEQ ID NO 98
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

gaaattgtgc tgacccagtc ccccgcgacg ctgtcactgt cccctgggga gcgggctacc      60

ttgtcctgcc gcgcctccga atcgctcgac aactacggca tcagcttcat gaactggttc     120

cagcaaaagc cgggacaggc ccccacggttc ctgatctacg ccgcatcgaa ccagggttca    180

gggattcccg cgaggttctc gggatctgga tccggcaccg acttcactct gacaatcagc     240

agcctgcagc ctgaagatac cgccgtgtac ttctgccaac agtccaagga ggtcccgcgg     300

acttttggcg gaggcaccaa agtggagatc aag                                  333
```

```
<210> SEQ ID NO 99
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Leu Asp Asn Tyr
            20                  25                  30

Gly Ile Ser Phe Met Asn Trp Phe Gln Gln Lys Pro Gly Gln Ala Pro
        35                  40                  45

Arg Phe Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Thr Ala Val Tyr Phe Cys Gln Gln Ser Lys
                85                  90                  95

Glu Val Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 100
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

gaaattgtgc tgacccagtc ccccgcgacg ctgtcactgt cccctgggga gcgggctacc      60

ttgtcctgcc gcgcctccga atcgctcgac aactacggca tcagcttcat gaactggttc     120

cagcaaaagc cgggacaggc ccccacggttc ctgatctacg ccgcatcgaa ccagggttca     180

gggattcccg cgaggttctc gggatctgga tccggcaccg acttcactct gacaatcagc     240

agcctgcagc ctgaagatac cgccgtgtac ttctgccaac agtccaagga ggtcccgcgg     300

acttttggcg gaggcaccaa agtggagatc aagcgtacgg tggccgctcc cagcgtgttc     360

atcttccccc ccagcgacga gcagctgaag agcggcaccg ccagcgtggt gtgcctgctg     420
```

```
aacaacttct acccccggga ggccaaggtg cagtggaagg tggacaacgc cctgcagagc    480

ggcaacagcc aggagagcgt caccgagcag gacagcaagg actccaccta cagcctgagc    540

agcaccctga ccctgagcaa ggccgactac gagaagcata aggtgtacgc ctgcgaggtg    600

acccaccagg gcctgtccag ccccgtgacc aagagcttca acaggggcga gtgc          654
```

```
<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Tyr Ala Ile Ser
1               5
```

```
<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

His Ile Ile Pro His Trp Gly His Ala Arg Tyr Ala Gln Lys Phe Gln
1               5                   10                  15

Gly
```

```
<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Ala Ser Ser Leu Pro His Phe His Trp Phe Asp Tyr
1               5                   10
```

```
<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Thr Phe Ser Ser Tyr
1               5
```

```
<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Pro His Trp Gly His
1               5
```

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

```
Ser Ala Ser Ser Leu Pro His Phe His Trp Phe Asp Tyr
1               5                   10
```

<210> SEQ ID NO 107
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly His Ile Ile Pro His Trp Gly His Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Ser Ser Leu Pro His Phe His Trp Phe Asp Tyr Trp
            100                 105                 110

Gly Gln Gly Thr Leu Val Thr Val Ser Ser
        115                 120
```

<210> SEQ ID NO 108
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
caagtccaac tcgtgcagtc tggagcagaa gtcaagaagc cgggctcaag cgtgaaggtg     60

tcctgcaaag ccagcggagg gaccttctcc tcctatgcca tctcatgggt cagacaggcc    120

ccgggccagg gcctggaatg gatgggtcac atcatccccc attggggaca cgcgcgctac    180

gcccagaagt ttcagggccg cgtgactatt accgcggacg aaagcacttc caccgcctac    240

atggagctgt cctccctgcg gtcggaggac accgcagtgt actactgcgc ccggtcggct    300

tcgtccctgc cacacttcca ctggttcgat tactggggac agggaaccct ggtcactgtg    360

tccagc                                                               366
```

<210> SEQ ID NO 109
<211> LENGTH: 452
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 109

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly His Ile Ile Pro His Trp Gly His Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Ser Ser Leu Pro His Phe His Trp Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 110
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
caagtccaac tcgtgcagtc tggagcagaa gtcaagaagc cgggctcaag cgtgaaggtg     60

tcctgcaaag ccagcggagg gaccttctcc tcctatgcca tctcatgggt cagacaggcc    120

ccgggccagg gcctggaatg gatgggtcac atcatccccc attggggaca cgcgcgctac    180

gcccagaagt ttcagggccg cgtgactatt accgcggacg aaagcacttc caccgcctac    240

atggagctgt cctccctgcg gtcggaggac accgcagtgt actactgcgc ccggtcggct    300

tcgtccctgc cacacttcca ctggttcgat tactggggac agggaaccct ggtcactgtg    360

tccagcgcta gcaccaaggg cccaagtgtg tttcccctgg cccccagcag caagtctact    420

tccggcggaa ctgctgccct gggttgcctg gtgaaggact acttccccga gcccgtgaca    480

gtgtcctgga actctggggc tctgacttcc ggcgtgcaca ccttccccgc cgtgctgcag    540

agcagcggcc tgtacagcct gagcagcgtg gtgacagtgc cctccagctc tctgggaacc    600

cagacctata tctgcaacgt gaaccacaag cccagcaaca ccaaggtgga caagagagtg    660

gagcccaaga gctgcgacaa gacccacacc tgcccccct gcccagctcc agaactgctg     720

ggagggcctt ccgtgttcct gttcccccc aagcccaagg acaccctgat gatcagcagg     780

acccccgagg tgacctgcgt ggtggtggac gtgtcccacg aggacccaga ggtgaagttc    840

aactggtacg tggacggcgt ggaggtgcac aacgccaaga ccaagcccag agaggagcag    900

tacaacagca cctacagggt ggtgtccgtg ctgaccgtgc tgcaccagga ctggctgaac    960

ggcaaagaat acaagtgcaa agtctccaac aaggccctgc cagccccaat cgaaaagaca   1020

atcagcaagg ccaagggcca gccacgggag ccccaggtgt acaccctgcc ccccagccgg   1080

gaggagatga ccaagaacca ggtgtccctg acctgtctgg tgaagggctt ctaccccagc   1140

gatatcgccg tggagtggga gagcaacggc cagcccgaga acaactacaa gaccaccccc   1200

ccagtgctgg acagcgacgg cagcttcttc ctgtacagca agctgaccgt ggacaagtcc   1260

aggtggcagc agggcaacgt gttcagctgc agcgtgatgc acgaggccct gcacaaccac   1320

tacacccaga agtccctgag cctgagcccc ggcaag                             1356
```

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Arg Ala Ser Gln Asp Ile Asn Asn Tyr Leu Asn
1 5 10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Ala Ala Ser Arg Leu Gln Ser
1 5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gln Gln Arg Asp Thr Thr Pro Trp Thr
1 5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Ser Gln Asp Ile Asn Asn Tyr
1 5

<210> SEQ ID NO 115
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Ala Ala Ser
1

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Arg Asp Thr Thr Pro Trp
1 5

<210> SEQ ID NO 117

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Thr Thr Pro Trp
                85                  90                  95

Thr Phe Gly Gln Gly Thr Lys Val Glu Ile Lys
            100                 105
```

<210> SEQ ID NO 118
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118

```
gatatccaga tgactcagtc cccatcctcc ctgtcggcct ccgtgggcga tcgggtcact     60

attacgtgcc gcgccagcca ggacattaac aactacctga actggtatca acagaagccg    120

gggaaggccc ctaagctgct gatctacgct gcaagccggt tgcagtcagg agtgccctca    180

aggttctccg gttccggatc gggcaccgac ttcaccctga ccatcagcag cctccagccg    240

gaggactttg cgacctacta ctgtcagcaa agagacacca ccccctggac attcggacag    300

ggcaccaaag tggaaatcaa g                                              321
```

<210> SEQ ID NO 119
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Arg Asp Thr Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 120
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

```
gatatccaga tgactcagtc cccatcctcc ctgtcggcct ccgtgggcga tcgggtcact     60

attacgtgcc gcgccagcca ggacattaac aactacctga actggtatca acagaagccg    120

gggaaggccc ctaagctgct gatctacgct gcaagccggt tgcagtcagg agtgccctca    180

aggttctccg gttccggatc gggcaccgac ttcaccctga ccatcagcag cctccagccg    240

gaggactttg cgacctacta ctgtcagcaa agagacacca ccccctggac attcggacag    300

ggcaccaaag tggaaatcaa gcgtacggtg gccgctccca gcgtgttcat cttccccccc    360

agcgacgagc agctgaagag cggcaccgcc agcgtggtgt gcctgctgaa caacttctac    420

cccgggagg ccaaggtgca gtggaaggtg gacaacgccc tgcagagcgg caacagccag     480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

```
Ser Ala Trp Met Ser
1               5
```

<210> SEQ ID NO 122
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 122

His Ile Lys Ser Lys Thr Tyr Gly Gly Thr Ile Asp Tyr Ala Ala Pro
1               5                   10                  15

Val Lys Gly


<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Val Gly Gly Tyr Tyr Gly Tyr Gly Tyr Ala Phe Ala Tyr
1               5                   10


<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Phe Thr Phe Ser Ser Ala
1               5


<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Ser Lys Thr Tyr Gly Gly Thr
1               5


<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Gly Gly Tyr Tyr Gly Tyr Gly Tyr Ala Phe Ala Tyr
1               5                   10


<210> SEQ ID NO 127
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Glu Ser Gly Gly Gly Leu Val Lys Pro Gly Gly
```

```
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Gly His Ile Lys Ser Lys Thr Tyr Gly Gly Thr Ile Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Gly Gly Tyr Tyr Gly Tyr Gly Tyr Ala Phe Ala
            100                 105                 110

Tyr Trp Gly Gln Gly Thr Leu Val Thr Val Ser Ser
        115                 120
```

<210> SEQ ID NO 128
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
caagtccagc tcgtcgaatc cggtggcgga ctcgtgaagc cgggaggatc cctgcggctg     60

tcctgcgccg cctccgggtt cactttttcc tccgcatgga tgtcatgggt ccgccaggcc    120

cccgggaagg gtctggaatg ggtcgggcac atcaagtcaa agacctacgg cggcaccatt    180

gactacgccg ccccagtgaa aggaaggttc actatctcgc gggacgacag caagaacacc    240

ctgtatctgc aaatgaacag cctcaagacc gaggatactg cggtgtacta ctgcgcaaga    300

gtgggcggat actacggtta cggctacgct ttcgcgtact ggggacaggg caccctcgtg    360

accgtgtcga gc                                                        372
```

<210> SEQ ID NO 129
<211> LENGTH: 454
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Gly His Ile Lys Ser Lys Thr Tyr Gly Gly Thr Ile Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Gly Gly Tyr Tyr Gly Tyr Gly Tyr Ala Phe Ala
            100                 105                 110
```

```
Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 130
<211> LENGTH: 1362
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
caagtccagc tcgtcgaatc cggtggcgga ctcgtgaagc cgggaggatc cctgcggctg     60
```

```
tcctgcgccg cctccgggtt cactttttcc tccgcatgga tgtcatgggt ccgccaggcc    120
cccgggaagg gtctggaatg ggtcgggcac atcaagtcaa agacctacgg cggcaccatt    180
gactacgccg ccccagtgaa aggaaggttc actatctcgc gggacgacag caagaacacc    240
ctgtatctgc aaatgaacag cctcaagacc gaggatactg cggtgtacta ctgcgcaaga    300
gtgggcggat actacggtta cggctacgct ttcgcgtact ggggacaggg caccctcgtg    360
accgtgtcga gcgctagcac caagggccca agtgtgtttc ccctggcccc cagcagcaag    420
tctacttccg gcggaactgc tgccctgggt tgcctggtga aggactactt ccccgagccc    480
gtgacagtgt cctggaactc tggggctctg acttccggcg tgcacacctt ccccgccgtg    540
ctgcagagca gcggcctgta cagcctgagc agcgtggtga cagtgccctc cagctctctg    600
ggaacccaga cctatatctg caacgtgaac cacaagccca gcaacaccaa ggtggacaag    660
agagtggagc ccaagagctg cgacaagacc cacacctgcc ccccctgccc agctccagaa    720
ctgctgggag gcccttccgt gttcctgttc ccccccaagc ccaaggacac cctgatgatc    780
agcaggaccc ccgaggtgac ctgcgtggtg gtggacgtgt cccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aagaatacaa gtgcaaagtc tccaacaagg ccctgccagc ccccatcgaa   1020
aagacaatca gcaaggccaa gggccagcca cgggagcccc aggtgtacac cctgcccccc   1080
agccgggagg agatgaccaa gaaccaggtg tccctgacct gtctggtgaa gggcttctac   1140
cccagcgata tcgccgtgga gtgggagagc aacggccagc ccgagaacaa ctacaagacc   1200
acccccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagtc cctgagcctg agccccggca ag                      1362
```

```
<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Gly Asp Asn Ile Gly Asp Lys Tyr Val Ser
1               5                   10


<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Asp Asn Lys Arg Pro Ser
1               5


<210> SEQ ID NO 133
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 133

Ser Ser Thr Ala Ser Lys Ser Phe Asn Val
1               5                   10


<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Asn Ile Gly Asp Lys Tyr
1               5


<210> SEQ ID NO 135
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Asp Asn
1


<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Ala Ser Lys Ser Phe Asn
1               5


<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Asp Lys Tyr Val
            20                  25                  30

Ser Trp Tyr Gln Gln Lys Pro Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ser Ser Thr Ala Ser Lys Ser Phe Asn
                85                  90                  95
```

```
Val Phe Gly Gly Gly Thr Lys Leu Thr Val Leu
            100                 105


<210> SEQ ID NO 138
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

agctacgaac tcacccagcc tctgtccgtg tccgtcgcgc tgggacagac tgctcgcatc     60

acttgctccg gcgacaacat cggggacaaa tacgtgtcgt ggtaccagca gaagccgggc    120

caagcccccg tgctggtcat ctatgacgat aacaagcggc catcgggcat tccggagaga    180

ttcagcggtt ccaacagcgg aaacactgcc accctgacca tcagcagggc acaggccggg    240

gatgaggccg actactactg ctcatccacc gcctccaagt cattcaatgt gttcggaggc    300

ggcaccaagc tgaccgtgct c                                              321


<210> SEQ ID NO 139
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Asp Lys Tyr Val
            20                  25                  30

Ser Trp Tyr Gln Gln Lys Pro Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ser Ser Thr Ala Ser Lys Ser Phe Asn
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 140
<211> LENGTH: 639
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
agctacgaac tcacccagcc tctgtccgtg tccgtcgcgc tgggacagac tgctcgcatc     60

acttgctccg gcgacaacat cggggacaaa tacgtgtcgt ggtaccagca gaagccgggc    120

caagcccccg tgctggtcat ctatgacgat aacaagcggc catcgggcat tccggagaga    180

ttcagcggtt ccaacagcgg aaacactgcc accctgacca tcagcagggc acaggccggg    240

gatgaggccg actactactg ctcatccacc gcctccaagt cattcaatgt gttcggaggc    300

ggcaccaagc tgaccgtgct cggtcaacct aaggctgccc ccagcgtgac cctgttcccc    360

cccagcagcg aggagctgca ggccaacaag gccaccctgg tgtgcctgat cagcgacttc    420

tacccaggcg ccgtgaccgt ggcctggaag gccgacagca gccccgtgaa ggccggcgtg    480

gagaccacca cccccagcaa gcagagcaac aacaagtacg ccgccagcag ctacctgagc    540

ctgacccccg agcagtggaa gagccacagg tcctacagct gccaggtgac ccacgagggc    600

agcaccgtgg aaaagaccgt ggccccaacc gagtgcagc                           639
```

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

```
Ser Tyr Tyr Met Asn
1               5
```

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

```
Trp Ile Asn Pro Val Gln Gly Asn Thr Asn Tyr Ala Gln Lys Phe Gln
1               5                   10                  15

Gly
```

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

```
Asn Tyr Phe Asp Val
1               5
```

<210> SEQ ID NO 144

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Tyr Thr Phe Thr Ser Tyr
1               5


<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn Pro Val Gln Gly Asn
1               5


<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asn Tyr Phe Asp Val
1               5


<210> SEQ ID NO 147
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Asn Trp Val Arg Gln Ala Pro Gly Gln Gly Leu Glu Trp Met
        35                  40                  45

Gly Trp Ile Asn Pro Val Gln Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Asn Tyr Phe Asp Val Trp Gly Gln Gly Thr Leu Val Thr Val
            100                 105                 110

Ser Ser


<210> SEQ ID NO 148
<211> LENGTH: 342
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 148

```
caagtccagc tcgtccaatc cggtgctgaa gtcaagaagc cgggagccag cgtgaaagtg     60

tcctgcaagg cctccgggta caccttcacc tcctactaca tgaactgggt cagacaggcc    120

ccgggccagg gcctggagtg gatgggatgg atcaatccag tgcagggaaa cactaactac    180

gcgcagaagt tccagggtcg cgtgaccatg actcgggaca ctagcatttc cacggcctac    240

atggagctgt caaggctgcg gtcggaagat accgcggtgt attactgcgc ccgcaactac    300

ttcgacgtgt ggggacaggg aacccttgtg accgtgtcca gc                       342
```

<210> SEQ ID NO 149
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Asn Trp Val Arg Gln Ala Pro Gly Gln Gly Leu Glu Trp Met
        35                  40                  45

Gly Trp Ile Asn Pro Val Gln Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Asn Tyr Phe Asp Val Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270
```

```
Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 150
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

caagtccagc tcgtccaatc cggtgctgaa gtcaagaagc cgggagccag cgtgaaagtg      60

tcctgcaagg cctccgggta caccttcacc tcctactaca tgaactgggt cagacaggcc     120

ccgggccagg gcctggagtg gatgggatgg atcaatccag tgcagggaaa cactaactac     180

gcgcagaagt tccagggtcg cgtgaccatg actcgggaca ctagcatttc cacggcctac     240

atggagctgt caaggctgcg gtcggaagat accgcggtgt attactgcgc ccgcaactac     300

ttcgacgtgt ggggacaggg aacccttgtg accgtgtcca gcgctagcac caagggccca     360

agtgtgtttc ccctggcccc cagcagcaag tctacttccg gcggaactgc tgccctgggt     420

tgcctggtga aggactactt ccccgagccc gtgacagtgt cctggaactc tggggctctg     480

acttccggcg tgcacacctt ccccgccgtg ctgcagagca gcggcctgta cagcctgagc     540

agcgtggtga cagtgccctc cagctctctg ggaacccaga cctatatctg caacgtgaac     600

cacaagccca gcaacaccaa ggtggacaag agagtggagc ccaagagctg cgacaagacc     660

cacacctgcc ccccctgccc agctccagaa ctgctgggag ggccttccgt gttcctgttc     720

ccccccaagc ccaaggacac cctgatgatc agcaggaccc ccgaggtgac ctgcgtggtg     780

gtggacgtgt cccacgagga cccagaggtg aagttcaact ggtacgtgga cggcgtggag     840

gtgcacaacg ccaagaccaa gcccagagag gagcagtaca acagcaccta cagggtggtg     900

tccgtgctga ccgtgctgca ccaggactgg ctgaacggca aagaatacaa gtgcaaagtc     960

tccaacaagg ccctgccagc ccccatcgaa aagacaatca gcaaggccaa gggccagcca    1020
```

```
cgggagcccc aggtgtacac cctgcccccc agccgggagg agatgaccaa gaaccaggtg   1080

tccctgacct gtctggtgaa gggcttctac cccagcgata tcgccgtgga gtgggagagc   1140

aacggccagc ccgagaacaa ctacaagacc acccccccag tgctggacag cgacggcagc   1200

ttcttcctgt acagcaagct gaccgtggac aagtccaggt ggcagcaggg caacgtgttc   1260

agctgcagcg tgatgcacga ggccctgcac aaccactaca cccagaagtc cctgagcctg   1320

agccccggca ag                                                       1332


<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Ala Ser Gln Thr Ile Ser Asn Phe Leu Ala
1               5                   10


<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Ala Ser Asn Leu Gln Ser
1               5


<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Leu Tyr Ala Glu Ser Ile Thr
1               5


<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Gln Thr Ile Ser Asn Phe
1               5


<210> SEQ ID NO 155
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155
```

Ala Ala Ser
1

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Leu Tyr Ala Glu Ser Ile
1 5

<210> SEQ ID NO 157
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Asp Ile Gln Met Thr Gln Ser Pro Ser Ser Leu Ser Ala Ser Val Gly
1 5 10 15

Asp Arg Val Thr Ile Thr Cys Arg Ala Ser Gln Thr Ile Ser Asn Phe
20 25 30

Leu Ala Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Val Tyr Tyr Cys Gln Gln Leu Tyr Ala Glu Ser Ile
85 90 95

Thr Phe Gly Gln Gly Thr Lys Val Glu Ile Lys
100 105

<210> SEQ ID NO 158
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158
gatatccaga tgacccagag cccatcatcc ctgtcggcct ccgtgggcga cagagtgacc 60
attacttgcc gggcatcaca gacgatctcc aactttctgg cctggtatca gcagaagccg 120
gggaaggcgc ccaagctgct catctacgct gcctccaacc tccaatccgg agtgcctagc 180
cggttcagcg gctcgggatc cgggactgac ttcaccctga ctatctcgag cctgcagccg 240
gaggacttcg cggtgtacta ctgtcagcaa ctgtacgccg aatccatcac attcggacag 300
ggcaccaaag tggagattaa g 321

<210> SEQ ID NO 159
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Phe
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Leu Tyr Ala Glu Ser Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 160
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160

```
gatatccaga tgacccagag cccatcatcc ctgtcggcct ccgtgggcga cagagtgacc      60

attacttgcc gggcatcaca gacgatctcc aactttctgg cctggtatca gcagaagccg     120

gggaaggcgc ccaagctgct catctacgct gcctccaacc tccaatccgg agtgcctagc     180

cggttcagcg gctcgggatc cgggactgac ttcaccctga ctatctcgag cctgcagccg     240

gaggacttcg cggtgtacta ctgtcagcaa ctgtacgccg aatccatcac attcggacag     300

ggcaccaaag tggagattaa gcgtacggtg gccgctccca gcgtgttcat cttccccccc     360

agcgacgagc agctgaagag cggcaccgcc agcgtggtgt gcctgctgaa caacttctac     420

ccccgggagg ccaaggtgca gtggaaggtg gacaacgccc tgcagagcgg caacagccag     480

gagagcgtca ccgagcagga cagcaaggac tccacctaca gcctgagcag caccctgacc     540

ctgagcaagg ccgactacga gaagcataag gtgtacgcct gcgaggtgac ccaccagggc     600

ctgtccagcc ccgtgaccaa gagcttcaac aggggcgagt gc                        642
```

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Asp Tyr Ala Ile His
1 5

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Gly Ile Ile Pro Phe Phe Gly Thr Ala Tyr Tyr Ala Gln Lys Phe Gln
1 5 10 15

Gly

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Arg Ile Val Ser Asp Ser Val Ala Val Gln Tyr Arg His Ala Phe Asp
1 5 10 15

Pro

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Gly Gly Thr Phe Ser Asp Tyr
1 5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Ile Pro Phe Phe Gly Thr
1 5

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

```
Arg Ile Val Ser Asp Ser Val Ala Val Gln Tyr Arg His Ala Phe Asp
1               5                   10                  15

Pro
```

<210> SEQ ID NO 167
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 167

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile His Trp Val Arg Gln Ala Pro Gly Gln Gly Leu Glu Trp Met
        35                  40                  45

Gly Gly Ile Ile Pro Phe Phe Gly Thr Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Val Ser Asp Ser Val Ala Val Gln Tyr Arg His Ala
            100                 105                 110

Phe Asp Pro Trp Gly Gln Gly Thr Leu Val Thr Val Ser Ser
        115                 120                 125
```

<210> SEQ ID NO 168
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 168

```
caagtgcaac tcgtccagtc tggtgccgaa gtcaagaagc caggatcctc ggtgaaagtg     60

tcctgcaagg cctccggggg aaccttttcc gactacgcca tccactgggt ccgccaagca    120

ccgggacagg gcctggaatg gatgggtggc attatcccct tcttcgggac tgcttactat    180

gcgcagaagt tccagggaag agtgacgatt accgccgacg agagcacctc caccgcctac    240

atggaactga gctcactgag gtcggaggat actgcggtgt actactgcgc ccgccggatc    300

gtgtcggatt ccgtggccgt gcagtaccgg catgccttcg acccgtgggg ccagggaacc    360

ctggtcactg tgtcatcc                                                  378
```

<210> SEQ ID NO 169
<211> LENGTH: 456
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 169

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile His Trp Val Arg Gln Ala Pro Gly Gln Gly Leu Glu Trp Met
        35                  40                  45

Gly Gly Ile Ile Pro Phe Phe Gly Thr Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Val Ser Asp Ser Val Ala Val Gln Tyr Arg His Ala
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
```

```
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 170
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 170

```
caagtgcaac tcgtccagtc tggtgccgaa gtcaagaagc caggatcctc ggtgaaagtg     60

tcctgcaagg cctccggggg aaccttttcc gactacgcca tccactgggt ccgccaagca    120

ccgggacagg gcctggaatg gatgggtggc attatcccct tcttcgggac tgcttactat    180

gcgcagaagt tccagggaag agtgacgatt accgccgacg agagcacctc caccgcctac    240

atggaactga gctcactgag gtcggaggat actgcggtgt actactgcgc ccgccggatc    300

gtgtcggatt ccgtggccgt gcagtaccgg catgccttcg acccgtgggg ccagggaacc    360

ctggtcactg tgtcatccgc tagcaccaag ggcccaagtg tgtttcccct ggcccccagc    420

agcaagtcta cttccggcgg aactgctgcc ctgggttgcc tggtgaagga ctacttcccc    480

gagcccgtga cagtgtcctg gaactctggg gctctgactt ccggcgtgca caccttcccc    540

gccgtgctgc agagcagcgg cctgtacagc ctgagcagcg tggtgacagt gccctccagc    600

tctctgggaa cccagaccta tatctgcaac gtgaaccaca agcccagcaa caccaaggtg    660

gacaagagag tggagcccaa gagctgcgac aagacccaca cctgcccccc ctgcccagct    720

ccagaactgc tgggagggcc ttccgtgttc ctgttccccc ccaagcccaa ggacaccctg    780

atgatcagca ggacccccga ggtgacctgc gtggtggtgg acgtgtccca cgaggaccca    840

gaggtgaagt tcaactggta cgtggacggc gtggaggtgc acaacgccaa gaccaagccc    900

agagaggagc agtacaacag cacctacagg gtggtgtccg tgctgaccgt gctgcaccag    960

gactggctga acggcaaaga atacaagtgc aaagtctcca acaaggccct gccagcccca   1020

atcgaaaaga caatcagcaa ggccaagggc cagccacggg agccccaggt gtacaccctg   1080

ccccccagcc gggaggagat gaccaagaac caggtgtccc tgacctgtct ggtgaagggc   1140

ttctacccca gcgatatcgc cgtggagtgg gagagcaacg gccagcccga gaacaactac   1200

aagaccaccc ccccagtgct ggacagcgac ggcagcttct tcctgtacag caagctgacc   1260

gtggacaagt ccaggtggca gcagggcaac gtgttcagct gcagcgtgat gcacgaggcc   1320

ctgcacaacc actacaccca gaagtccctg agcctgagcc ccggcaag                 1368
```

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Ser Gly Ser Ser Ser Asn Ile Gly Ser Asn Tyr Val Tyr
1 5 10

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Gly Asn Asn Asn Arg Pro Ser
1 5

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Asn Ala Trp Asp Thr Lys Ala Tyr Val Trp Val
1 5 10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Ser Ser Ser Asn Ile Gly Ser Asn Tyr
1 5

<210> SEQ ID NO 175
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Gly Asn Asn
1

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Trp Asp Thr Lys Ala Tyr Val Trp
1 5

<210> SEQ ID NO 177
<211> LENGTH: 110
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 177

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Asn Ala Trp Asp Thr Lys Ala
                85                  90                  95

Tyr Val Trp Val Phe Gly Gly Gly Thr Lys Leu Thr Val Leu
            100                 105                 110


<210> SEQ ID NO 178
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178

cagtctgtgc tgactcagcc tccgagcgtg tcaggagcac cgggacagag agtgaccatc     60

tcctgttcgg ggtccagctc gaacattggc tccaactacg tgtactggta tcagcagctc    120

cccggtaccg cgcccaagct gttgatctac ggcaacaaca accggcctag cggcgtgccg    180

gataggttct cgggttcaaa atccgggacg tccgcttccc tggccatcac tggcctgcaa    240

gcggaggacg aagccgacta ctactgcaat gcctgggaca ccaaggccta cgtctgggtg    300

ttcggaggag gcactaagct gaccgtgctg                                     330


<210> SEQ ID NO 179
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Asn Ala Trp Asp Thr Lys Ala
                85                  90                  95

Tyr Val Trp Val Phe Gly Gly Gly Thr Lys Leu Thr Val Leu Gly Gln
```

```
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 180
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

cagtctgtgc tgactcagcc tccgagcgtg tcaggagcac cgggacagag agtgaccatc     60

tcctgttcgg ggtccagctc gaacattggc tccaactacg tgtactggta tcagcagctc    120

cccggtaccg cgcccaagct gttgatctac ggcaacaaca accggcctag cggcgtgccg    180

gataggttct cgggttcaaa atccgggacg tccgcttccc tggccatcac tggcctgcaa    240

gcggaggacg aagccgacta ctactgcaat gcctgggaca ccaaggccta cgtctgggtg    300

ttcggaggag gcactaagct gaccgtgctg ggacagccta aggctgcccc cagcgtgacc    360

ctgttccccc ccagcagcga ggagctgcag gccaacaagg ccaccctggt gtgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga aaagaccgtg gccccaaccg agtgcagc                  648


<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Tyr Asn Met His
1               5


<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 182

Val Ile Tyr Pro Gly Asn Gly Val Thr Ser Tyr Ser Gln Lys Phe Lys
1               5                   10                  15

Asp

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Asp Tyr Phe Tyr Gly Gly Ser Tyr Ala Met Asp Tyr
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Tyr Thr Phe Pro Ser Tyr
1               5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Tyr Pro Gly Asn Gly Val
1               5

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Asp Tyr Phe Tyr Gly Gly Ser Tyr Ala Met Asp Tyr
1               5                   10

<210> SEQ ID NO 187
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Pro Ser Tyr
            20                  25                  30

```
Asn Met His Trp Val Lys Gln Thr Pro Arg Gln Gly Leu Glu Trp Ile
        35                  40                  45

Gly Val Ile Tyr Pro Gly Asn Gly Val Thr Ser Tyr Ser Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Lys Asp Asp Tyr Phe Tyr Gly Gly Ser Tyr Ala Met Asp Tyr Trp
            100                 105                 110

Gly Gln Gly Thr Ser Val Thr Val Ser Ser
        115                 120


<210> SEQ ID NO 188
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188

caggcttatc tacagcagtc tggggctgag ctggtgaggc ctggggcctc agtgaagatg      60

tcctgcaagg cttctggcta cacatttccc agttacaata tgcactgggt aaagcagaca     120

cctagacagg gcctggaatg gattggagtt atttatccag gaaatggtgt tacttcctac     180

agtcagaagt tcaaggacaa ggccacactg actgtagaca aatcttccag cacagcctac     240

atgcagctca gcagcctgac atctgaggac tctgcggtct atttctgtgc aaaagacgat     300

tatttctacg gtggtagcta tgctatggac tactggggtc aaggaacctc agtcaccgtc     360

tcctca                                                                366


<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Ala Ser Gln Ser Ile Ser Asn Asn Leu His
1               5                   10


<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Ala Ser Gln Ser Ile Ser
1               5


<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 191

Gln Gln Ser His Ser Trp Pro Tyr Thr
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Ser Gln Ser Ile Ser Asn Asn
1               5

<210> SEQ ID NO 193
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Tyr Ala Ser
1

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Ser His Ser Trp Pro Tyr
1               5

<210> SEQ ID NO 195
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Ile Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Met Glu Thr
65                  70                  75                  80

Glu Asp Phe Gly Met Phe Phe Cys Gln Gln Ser His Ser Trp Pro Tyr
                85                  90                  95

Thr Phe Gly Gly Gly Thr Lys Leu Glu Ile Lys 100 105

<210> SEQ ID NO 196
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 196
gatattgtgc taactcagtc tccagccacc ctgtctgtga ctccaggaga tagcgtcagt 60
ctttcctgca gggccagcca aagtattagc aacaacctac actggtatca gcaaatatca 120
catgagtctc caaggcttct catcaagtat gcctcccagt ccatctctgg catcccctcc 180
aggttcagtg gcagtggatc agggacagat ttcactctca gtatcaacag tatggagact 240
gaagattttg gaatgttttt ctgtcaacag agtcacagct ggccttacac gttcggaggg 300
gggaccaagc tggaaataaa a 321

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Arg Tyr Trp Met His
1 5

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Glu Ile Asn Pro Ser Asn Gly Gly Thr Asn Tyr Asn Glu Lys Phe Lys
1 5 10 15

Ser

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Gly Ser Asn Tyr Gly Gly Phe Val Tyr
1 5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Gly Tyr Thr Phe Thr Arg Tyr
1 5

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Asn Pro Ser Asn Gly Gly
1 5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Gly Ser Asn Tyr Gly Gly Phe Val Tyr
1 5

<210> SEQ ID NO 203
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

Gln Val Gln Leu Gln Gln Pro Gly Ala Glu Ala Val Lys Pro Gly Ala
1 5 10 15

Ser Val Lys Leu Ser Cys Lys Ala Ser Gly Tyr Thr Phe Thr Arg Tyr
20 25 30

Trp Met His Trp Val Lys Gln Arg Pro Gly Gln Gly Leu Glu Trp Ile
35 40 45

Gly Glu Ile Asn Pro Ser Asn Gly Gly Thr Asn Tyr Asn Glu Lys Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Phe Ala Val Tyr Tyr Cys
85 90 95

Thr Met Gly Ser Asn Tyr Gly Gly Phe Val Tyr Trp Gly Gln Gly Thr
100 105 110

Leu Val Thr Val Ser Ala
115

<210> SEQ ID NO 204
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 204
caggtccaac tgcagcagcc tggggctgag gctgtgaagc ctggggcttc agtgaagttg 60
tcctgcaagg cttctggcta caccttcacc aggtattgga tgcactgggt gaagcagagg 120
cctggacaag gccttgagtg gattggagag attaatccta gcaatggtgg tactaactac 180
aatgagaagt tcaagagcaa ggccacactg actgtagaca aatcctccag cacagcctac 240
atgcaactca gcagcctgac atctgaggat tttgcggtct attactgtac aatggggagt 300
aactacgggg gttttgttta ctggggccaa gggactctgg tcactgtctc tgca 354

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Arg Ala Ser Glu Ser Leu Asp Asn Tyr Gly Ile Ser Phe Met Asn
1 5 10 15

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Ala Ala Ser Asn Gln Gly Ser
1 5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Gln Gln Ser Lys Glu Val Pro Arg Thr
1 5

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Ser Glu Ser Leu Asp Asn Tyr Gly Ile Ser Phe
1 5 10

<210> SEQ ID NO 209
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Ala Ala Ser

1

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Ser Lys Glu Val Pro Arg
1 5

<210> SEQ ID NO 211
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Leu Asp Asn Tyr
20 25 30

Gly Ile Ser Phe Met Asn Trp Phe Gln Gln Lys Pro Gly Gln Pro Pro
35 40 45

Lys Phe Leu Ile Tyr Ala Ala Ser Asn Gln Gly Ser Gly Val Pro Ala
50 55 60

Arg Phe Ser Gly Ser Gly Ser Gly Thr Asp Phe Ser Leu Asn Ile His
65 70 75 80

Pro Leu Glu Glu Asp Asp Thr Ala Met Tyr Phe Cys Gln Gln Ser Lys
85 90 95

Glu Val Pro Arg Thr Phe Gly Gly Gly Thr Lys Leu Glu Ile Lys
100 105 110

<210> SEQ ID NO 212
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212
gacattgtgc tgacccaatc tccagcttct ttggctgtgt ctctagggca gagggccacc 60
atctcctgca gagccagcga aagtcttgat aattatggca ttagttttat gaattggttc 120
caacagaaac caggacagcc acccaaattc ctcatctatg ctgcatccaa ccaaggaagc 180
ggggtccctg ccaggtttag tggcagtggg tctgggacag acttcagcct caacatccat 240
cctttggagg aggatgatac tgcaatgtat ttctgtcagc aaagtaagga ggttcctcgg 300
acgttcggtg gaggcaccaa actggaaatc aaa 333

<210> SEQ ID NO 213
<211> LENGTH: 429
<212> TYPE: PRT
<213> ORGANISM: Homo sapiens

<400> SEQUENCE: 213

```
Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
```

420 425

<210> SEQ ID NO 214
<211> LENGTH: 1942
<212> TYPE: DNA
<213> ORGANISM: Homo sapiens

<400> SEQUENCE: 214
cggtccagcc cggcagcggg tgagagtagg tgctggccaa gacggttcct tcagagcaaa 60
cagcagggag atgccggccc gctccttccc agctcctccc cgtgcccgct aacacagcac 120
ggccgcctgc agtctcctct ctgggtgatt gcgcgggcct aagatgtgtc ctggggcact 180
gtgggtggcc ctgcccctgc tgtccctgct ggctggctcc ctacagggga agccactgca 240
gagctgggga cgagggtctg ctgggggaaa cgcccacagc ccactggggg tgcctggagg 300
tgggctgcct gagcacacct tcaacctgaa gatgtttctg gagaacgtga aggtggattt 360
cctgcgcagc cttaacctga gtggggtccc ttcgcaggac aaaaccaggg tggagccgcc 420
gcagtacatg attgacctgt acaacaggta cacgtccgat aagtcgacta cgccagcgtc 480
caacattgtg cggagcttca gcatggaaga tgccatctcc ataactgcca cagaggactt 540
ccccttccag aagcacatct tgctcttcaa catctccatt cctaggcatg agcagatcac 600
cagagctgag ctccgactct atgtctcctg tcaaaatcac gtggacccct ctcatgacct 660
gaaaggaagc gtggtcattt atgatgttct ggatggaaca gatgcctggg atagtgctac 720
agagaccaaa accttcctgg tgtcccagga cattcaggat gagggctggg agaccttgga 780
agtgtccagc gccgtgaagc gctgggtccg gtccgactcc accaagagca aaaataagct 840
ggaagtgact gtggagagcc acaggaaggg ctgcgacacg ctggacatca gtgtcccccc 900
aggttccaga aacctgccct tctttgttgt cttctccaat gaccacagca gtggaaccaa 960
ggagaccagg ctggagctga gggagatgat cagccatgaa caagagagcg tgctcaagaa 1020
gctgtccaag gacggctcca cagaggcagg tgagagcagt cacgaggagg acacggatgg 1080
ccacgtggct gcggggtcga ctttagccag gcggaaaagg agcgccgggg ctggcagcca 1140
ctgtcaaaag acctccctgc gggtaaactt cgaggacatc ggctgggaca gctggatcat 1200
tgcacccaag gagtatgaag cctacgagtg taagggcggc tgcttcttcc ccttggctga 1260
cgatgtgacg ccgacgaaac acgctatcgt gcagaccctg gtgcatctca agttccccac 1320
aaaggtgggc aaggcctgct gtgtgcccac caaactgagc cccatctccg tcctctacaa 1380
ggatgacatg gaggtgccca ccctcaagta ccattacgag ggcatgagcg tggcagagtg 1440
tgggtgcagg tagtatctgc ctgcggggct ggggaggcag gccaaagggg ctccacatga 1500
gaggtcctgc atgcccctgg gcacaacaag gactgattca atctgcatgc cagcctggag 1560
gaggaaaggg agcctgctct ccctccccac accccaccca aagcatacac cgctgagctc 1620
aactgccagg gaaggctaag gaaatgggga tttgagcaca acaggaaagc ctgggagggt 1680
tgttgggatg caaggaggtg atgaaaagga gacaggggga aaaataatcc atagtcagca 1740
gaaaacaaca gcagtgagcc agaggagcac aggcgggcag gtcactgcag agactgatgg 1800
aagttagaga ggtggaggag gccagctcac tccaaaaccc ttggggagta gagggaagga 1860
gcaggccgcg tgtcacaccc atcattgtat gttatttccc acaacccagt tggaggggca 1920
tggcttccaa tttagagacc cg 1942

<210> SEQ ID NO 215
<211> LENGTH: 110

<212> TYPE: PRT
<213> ORGANISM: Homo sapiens

<400> SEQUENCE: 215

```
Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110
```

<210> SEQ ID NO 216
<211> LENGTH: 414
<212> TYPE: PRT
<213> ORGANISM: Homo sapiens

<400> SEQUENCE: 216

```
Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly
        35                  40                  45

Val Asp Phe Asn Thr Leu Leu Gln Ser Met Lys Asp Glu Phe Leu Lys
    50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Val Ser Ile Pro His His Glu
        115                 120                 125

Glu Val Ile Met Ala Glu Leu Arg Leu Tyr Thr Leu Val Gln Arg Asp
    130                 135                 140

Arg Met Ile Tyr Asp Gly Val Asp Arg Lys Ile Thr Thr Phe Glu Val
145                 150                 155                 160

Leu Glu Ser Lys Gly Asp Asn Glu Gly Glu Arg Asn Met Leu Val Leu
                165                 170                 175

Val Ser Gly Glu Ile Tyr Gly Thr Asn Ser Glu Trp Glu Thr Phe Asp
            180                 185                 190

Val Thr Asp Ala Ile Arg Arg Trp Gln Lys Ser Gly Ser Ser Thr His
        195                 200                 205

Gln Leu Glu Val His Ile Glu Ser Lys His Asp Glu Ala Glu Asp Ala
    210                 215                 220

Ser Ser Gly Arg Leu Glu Ile Asp Thr Ser Ala Gln Asn Lys His Asn
225                 230                 235                 240
```

```
Pro Leu Leu Ile Val Phe Ser Asp Asp Gln Ser Ser Asp Lys Glu Arg
                245                 250                 255

Lys Glu Glu Leu Asn Glu Met Ile Ser His Glu Gln Leu Pro Glu Leu
            260                 265                 270

Asp Asn Leu Gly Leu Asp Ser Phe Ser Ser Gly Pro Gly Glu Glu Ala
        275                 280                 285

Leu Leu Gln Met Arg Ser Asn Ile Ile Tyr Asp Ser Thr Ala Arg Ile
    290                 295                 300

Arg Arg Asn Ala Lys Gly Asn Tyr Cys Lys Arg Thr Pro Leu Tyr Ile
305                 310                 315                 320

Asp Phe Lys Glu Ile Gly Trp Asp Ser Trp Ile Ile Ala Pro Pro Gly
                325                 330                 335

Tyr Glu Ala Tyr Glu Cys Arg Gly Val Cys Asn Tyr Pro Leu Ala Glu
            340                 345                 350

His Leu Thr Pro Thr Lys His Ala Ile Ile Gln Ala Leu Val His Leu
        355                 360                 365

Lys Asn Ser Gln Lys Ala Ser Lys Ala Cys Cys Val Pro Thr Lys Leu
    370                 375                 380

Glu Pro Ile Ser Ile Leu Tyr Leu Asp Lys Gly Val Val Thr Tyr Lys
385                 390                 395                 400

Phe Lys Tyr Glu Gly Met Ala Val Ser Glu Cys Gly Cys Arg
                405                 410


<210> SEQ ID NO 217
<211> LENGTH: 1584
<212> TYPE: DNA
<213> ORGANISM: Homo sapiens

<400> SEQUENCE: 217

ggggagagga agagtggtag ggggagggag agagagagga agagtttcca aacttgtctc     60

cagtgacagg agacatttac gttccacaag ataaaactgc cacttagagc ccagggaagc    120

taaaccttcc tggcttggcc taggagctcg agcggagtca tgggctctct ggtcctgaca    180

ctgtgcgctc ttttctgcct ggcagcttac ttggtttctg gcagccccat catgaaccta    240

gagcagtctc ctctggaaga agatatgtcc ctctttggtg atgttttctc agagcaagac    300

ggtgtcgact ttaacacact gctccagagc atgaaggatg agtttcttaa gacactaaac    360

ctctctgaca tccccacgca ggattcagcc aaggtggacc caccagagta catgttggaa    420

ctctacaaca aatttgcaac agatcggacc tccatgccct ctgccaacat cattaggagt    480

ttcaagaatg aagatctgtt ttcccagccg gtcagtttta atgggctccg aaaatacccc    540

ctcctcttca atgtgtccat tcctcaccat gaagaggtca tcatggctga acttaggcta    600

tacacactgg tgcaaaggga tcgtatgata tacgatggag tagaccggaa aattaccatt    660

tttgaagtgc tggagagcaa aggggataac gagggagaaa gaaacatgct ggtcctggtg    720

tctggggaga tatatggaac caacagtgag tgggagactt ttgatgtcac agatgccatc    780

agacgttggc aaaagtcagg ctcatccacc caccagctgg aggcccacat tgagagcaaa    840

cacgatgaag ctgaggatgc cagcagtgga cggctagaaa tagataccag tgcccagaat    900

aagcataacc ctttgctcat cgtgttttct gatgaccaaa gcagtgacaa ggagaggaag    960

gaggaactga atgaaatgat ttcccatgag caacctccag agctggacaa cttgggcctg   1020

gatagctttt ccagtggacc tggggaagag gctttgttgc agatgagatc aaacatcatc   1080

tatgactcca ctgcccgaat cagaaggaac gccaaaggaa actactgtaa gaggaccccg   1140
```

ctctacatcg acttcaagga gattgggtgg gactcctgga tcatcgctcc gcctggatac 1200
gaagcctatg aatgccgtgg tgtttgtaac taccccctgg cagagcatct cacacccaca 1260
aagcatgcaa ttatccaggc cttggtccac ctcaagaatt cccagaaagc ttccaaagcc 1320
tgctgtgtgc ccacaaagct agagcccatc tccatcctct atttagacaa aggcgtcgtc 1380
acctacaagt ttaaatacga aggcatggcc gtctccgaat gtggctgtag atagaagaag 1440
agtcctatgg cttatttaat aactgtaaat gtgtatattt ggtgttccta tttaatgaga 1500
ttatttaata agggtgtaca gtaatagagg cttgctgcct tcaggaaatg gacaggtcag 1560
tttgttgtag gaaatgcata tttt 1584

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 218

His His His His His His
1 5

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 219
cgaggcggca tgtgttcc 18

<210> SEQ ID NO 220
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 220
tctggggaac cgagagcac 19

<210> SEQ ID NO 221
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 221
cgtgccgcct ggagaaacc 19

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 222
tggaagagtg ggagttgctg ttg 23